(12) United States Patent
Sorrentino et al.

(10) Patent No.: US 12,338,440 B2
(45) Date of Patent: Jun. 24, 2025

(54) INTRACELLULAR KINASE ASSOCIATED WITH RESISTANCE AGAINST ANTI-TUMOUR IMMUNE RESPONSES, AND USES THEREOF

(71) Applicant: iOmx Therapeutics AG, Martinsried (DE)

(72) Inventors: Antonio Sorrentino, Heidelberg (DE); Philipp Beckhove, Regensburg (DE); Tillmann Michels, Heidelberg (DE); Nisit Khandelwal, Martinsried (DE); Michael Boutros, Heidelberg (DE); Marco Breinig, Schriesheim (DE); Peter Sennhenn, Martinsried (DE); Sebastian Meier-Ewert, Martinsried (DE); Valentina Volpin, Regensburg (DE); Ayse Nur Menevse, Regensburg (DE)

(73) Assignee: IOMX THERAPEUTICS AG, Martinsried (DE)

( * ) Notice: Subject to any disclaimer, the term of this patent is extended or adjusted under 35 U.S.C. 154(b) by 274 days.

(21) Appl. No.: 16/316,298

(22) PCT Filed: Apr. 20, 2018

(86) PCT No.: PCT/EP2018/060172
§ 371 (c)(1),
(2) Date: Jan. 8, 2019

(87) PCT Pub. No.: WO2018/193084
PCT Pub. Date: Oct. 25, 2018

(65) Prior Publication Data
US 2021/0040486 A1    Feb. 11, 2021

(30) Foreign Application Priority Data
Apr. 20, 2017  (EP) ..................... 17167295

(51) Int. Cl.
| | | |
|---|---|---|
| *C12N 15/113* | (2010.01) | |
| *A61K 31/506* | (2006.01) | |
| *A61K 31/7088* | (2006.01) | |
| *A61K 45/06* | (2006.01) | |
| *A61P 35/00* | (2006.01) | |
| *C07D 417/12* | (2006.01) | |
| *C07D 417/14* | (2006.01) | |
| *G01N 33/50* | (2006.01) | |
| *G01N 33/574* | (2006.01) | |
| *A61B 10/00* | (2006.01) | |

(52) U.S. Cl.
CPC ........ *C12N 15/1137* (2013.01); *A61K 31/506* (2013.01); *A61K 31/7088* (2013.01); *A61K 45/06* (2013.01); *A61P 35/00* (2018.01); *C07D 417/12* (2013.01); *C07D 417/14* (2013.01); *G01N 33/5047* (2013.01); *G01N 33/57492* (2013.01); *A61B 10/0041* (2013.01); *C12N 2310/122* (2013.01); *C12N 2320/31* (2013.01)

(58) Field of Classification Search
None
See application file for complete search history.

(56) References Cited

U.S. PATENT DOCUMENTS

| | | |
|---|---|---|
| 6,002,008 A | 12/1999 | Wissner et al. |
| 7,125,875 B2 | 10/2006 | Das et al. |
| 8,680,103 B2 | 3/2014 | Lajeunesse et al. |
| 2013/0035301 A1 | 2/2013 | Frattini et al. |
| 2014/0302172 A1 | 10/2014 | Schaab et al. |
| 2016/0081989 A1 | 3/2016 | Vankayalapati et al. |
| 2017/0281766 A1 | 10/2017 | Wiltzius |
| 2018/0243284 A1 | 8/2018 | Sugita et al. |

FOREIGN PATENT DOCUMENTS

| | | |
|---|---|---|
| CN | 1764454 A | 4/2006 |
| EP | 1169038 B9 | 8/2012 |
| WO | 2000/062778 A1 | 10/2000 |

(Continued)

OTHER PUBLICATIONS

Sun et al. Signal Transduction and Targeted Therapy 5:150, pp. 1-15 (Year: 2020).*
Darling et al. Biochemical Journal 478, 1377-1397 (Year: 2021).*
Michels et al. iOmx Therapeutics Satl-inducible kinase 3 faciltates tumor cells resistance against cytotoxic T cell attack by shifting from apoptosis to survival p. 1, publication date unknown (Year: 2022).*
Murray et al. Cancer Discov 9;9:1590-605 (Year: 2019).*
Alfredi et al. "Abstract 749: Highly potent and orally available SIK2 inhibitors block growth of human ovarian cancer cells in culture and xenografts", Oct. 2014, Cancer Research, vol. 74, Issue 19, Supplement, Abstract 749, 2 pages.

(Continued)

*Primary Examiner* — Brian Whiteman
(74) *Attorney, Agent, or Firm* — MH2 Technology Law Group, LLP

(57) ABSTRACT

The invention is based on the surprising finding that SIK3 is associated with resistance against anti-tumour immune responses. In particular, the invention provides methods for treating proliferative diseases using inhibitors of SIK3, especially nucleic acid or small molecule inhibitors of SIK3. Also provided are methods of sensitising cells involved with a proliferative disorder against the cytotoxic effect of certain pro-inflammatory signalling pathways, and/or to kill such cells and/or methods for treating proliferative diseases, using a SIK3 inhibitor together with ligands or agonists of such signalling pathways. Other methods provided by the invention include those involving SIK3 inhibitors to enhance or overcome certain side effects associated with treatments that utilise such signalling pathways, as well as diagnostic, prognostic and monitoring methods and kits based on the detection of SIK3 in a sample obtained from a subject, and screening methods useful for identifying or characterising inhibitors of SIK3.

Figure 1:
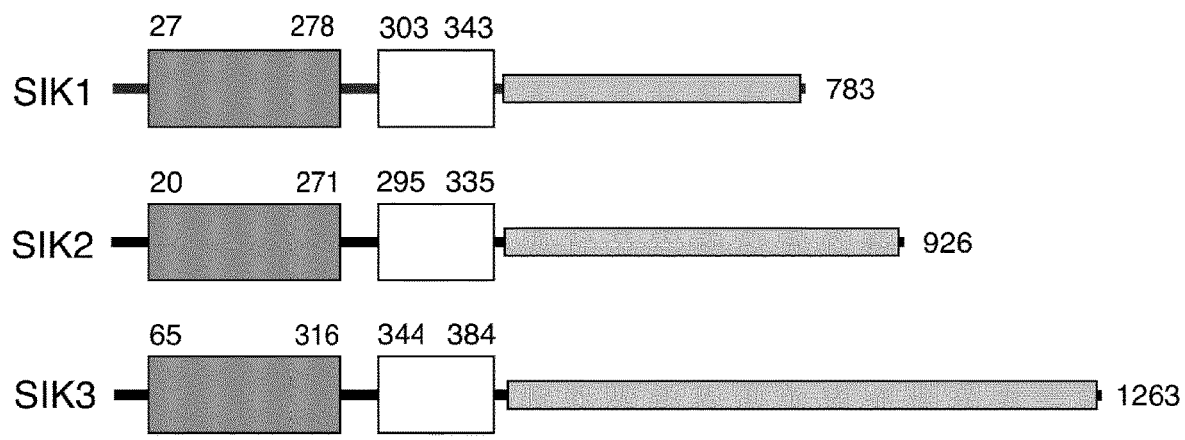

33 Claims, 25 Drawing Sheets
Specification includes a Sequence Listing.

(56) References Cited

FOREIGN PATENT DOCUMENTS

| WO | 2013/136070 A1 | 9/2013 |
|---|---|---|
| WO | 2014/093383 A1 | 6/2014 |
| WO | 2014/140313 A1 | 9/2014 |
| WO | 2015/006492 A1 | 1/2015 |
| WO | 2016/014542 A1 | 1/2016 |
| WO | 2016/014551 A1 | 1/2016 |
| WO | 2016/014552 A2 | 1/2016 |
| WO | 2016/023014 A2 | 2/2016 |
| WO | 2016/172010 A1 | 10/2016 |
| WO | 2017/043633 A1 | 3/2017 |

OTHER PUBLICATIONS

Amara et al., "Critical role of SIK3 in mediating high salt and IL-17 synergy leading to breast cancer cell proliferation", Jun. 28, 2017, PLoS ONE, vol. 12, No. 6, e0180097, 21 pages.
Anastassiadis et al., "Comprehensive assay of kinase catalytic activity reveals features of kinase inhibitor selectivity", 2012, Nat Biotechnology, vol. 29, No. 11, pp. 1039-1045.
Aydin et al., "Plasma levels of IL-6 and TNF-α in patients with esophageal cancer", 2012, Turk J Med Sci, vol. 42, No. 5, pp. 762-767.
Frances Balkwill, "Tumour necrosis factor and cancer", May 2009, Nature Reviews Cancer, vol. 9, pp. 361-371.
Bantscheff et al., "Quantitative chemical proteomics reveals mechanisms of action of clinical ABL kinase inhibitors", Sep. 2007, Nature Biotechnology, vol. 25, No. 9, pp. 1035-1044.
Beutner et al., "TCFH-NMI: Direct Access to N-Acyl Imidazoliums for Challenging Amide Bond Formations", 2018, Org Lett, vol. 20, pp. 4218-4222.
Chen et al., "Salt-inducible kinase 3 is a novel mitotic regulator and a target for enhancing antimitotic therapeutic-mediated cell death", 2014, Cell Death and Disease, vol. 5, e1177, 12 pages.
Christiansson et al., "The Tyrosine Kinase Inhibitors Imatinib and Dasatinib Reduce Myeloid Suppressor Cells and Release Effector Lymphocyte Responses", 2015, Molecular Cancer Therapeutics, vol. 14, No. 5, pp. 1181-1191.
Clark et al., "Phosphorylation of CRTC3 by the salt-inducible kinases controls the interconversion of classically activated and regulatory macrophages", Oct. 16, 2012, PNAS, vol. 109, No. 42, pp. 16986-16991.
Darling et al., "Inhibition of SIK2 and SIK3 during differentiation enhances the anti-inflammatory phenotype of macrophages", 2016, Biochemical Journal, 26 pages.
Das et al., "2-Aminothiazole as a Novel Kinase Inhibitor Template. Structure-Activity Relationship Studies toward the Discovery of N-(2-Chloro-6-methylphenyl)-2-[[6-[4-(2-hydroxyethyl)-1-piperazinyl]-2-methyl-4-pyrimidinyl]amino)]-1,3-thiazole-5-carboxamide(Dasatinib, BMS-354825) as a Potent pan-Src Kinase Inhibitor", 2006, J Med Chem., vol. 49, pp. 6819-6832.
Dobrzycka et al., "Circulating levels of TNF-α and its soluble receptors in the plasma of patients with epithelial ovarian cancer", Sep. 2009, Eur. Cytokine Netw, vol. 20, No. 3, pp. 131-134.
Du et al., "The diverse oncogenic and tumor suppressor roles of salt-inducible kinase (SIK) in cancer", 2015, Expert Opinion Therapeutic Targets, vol. 20, No. 4, 9 pages.
Ota Fuchs, "Transcription Factor NF-kB Inhibitors as Single Therapeutic Agents or in Combination wit Classical Chemotherapeutic Agents for the Treatment of Hematologic Malignancies", 2010, Current Molecular Pharmacology, vol. 3, pp. 98-122.
Hekim et al., "Dasatinib Changes Immune Cell Profiles Concomitant with Reduced Tumor Growth in Several Murine Solid Tumor Models", Feb. 2017, Cancer Immunology Research, vol. 5, No. 2, pp. 157-169.
Kearney et al., "Tumor immune evasion arises through loss of TNF sensitivity", May 18, 2018, Sci Immunol, vol. 3, eaar3451, 14 pages.
Khandelwal et al., "A high-throughput RNAi screen for detection of immune-checkpoint molecules that mediate tumor resistance to cytotoxic T lymphocytes", 2015, EMBO Mol Med, vol. 7, pp. 450-463.
Korneev et al., "TLR-signaling and proinflammatory cytokines as drivers of tumorigenesis", 2017, Cytokine, vol. 89, pp. 127-135.
Kreutzman et al., "Dasatinib promotes Th1-type responses in granzyme B expressing T-cells", 2014, OncoImmunology, vol. 3, No. 5, e28925, 10 pages.
Li et al., "Design and synthesis of novel dasatinib derivatives as inhibitors of leukemia stem cells", 2018, Bioorganic & Medicinal Chemistry Letters, vol. 28, pp. 700-706.
Lizcano et al., "LKB1 is a master kinase that activates 13 kinases of the AMPK subfamily, including MARK/PAR-1", 2004, the EMBO Journal, vol. 23, pp. 833-843.
Lombardi et al., "SIK inhibition in human myeloid cells modulates TLR and IL-1R signaling and induces an anti-inflammatory phenotype", 2016, J. Leukoc. Biol., vol. 99, pp. 711-721.
Lombardo et al., "Discovery of N-(2-Chloro-6-methylphenyl)-2-(6-(4-(2-hydroxyethyl)-piperazin-1-yl)-2-methylpyrimidin-4-ylamino)thiazole-5-carboxamide(BMS-354825), a Dual Src/Abl Kinase Inhibitor with Potent Antitumor Activity in Preclinical Assays", 2004, J. Med. Chem., vol. 47, pp. 6658-6661.
Mustjoki et al., "Clonal expansion of T/NK-cells during tyrosine kinase inhibitor dasatinib therapy", 2009, Leukemia, vol. 23, pp. 1389-1405.
Mustjoki et al., "Rapid mobilization of cytotoxic lymphocytes induced by dasatinib therapy", 2013, Leukemia, vol. 27, pp. 914-924.
Ozanne et al., "The clinically approved drugs dasatinib and bosutinib induce anti-inflammatory macrophages by inhibiting the salt-inducible kinases", 2015, Biochem. J., vol. 465, pp. 271-279.
Pennington et al., "The Necessary Nitrogen Atom: A Versatile High-Impact Design Element for Muliparameter Optimization", 2017, Journal of Medicinal Chemistry, vol. 60, pp. 3552-3579.
Reissfelder et al., "Tumor-specific cytotoxic T lymphocyte activity determines colorectal cancer patient prognosis", Feb. 2015, The Journal of Clinical Investigation, vol. 125, No. 2, pp. 739-751.
Sanosaka et al., "Salt-inducible kinase 3 deficiency exacerbates lipopolysaccharide-induced endotoxin shock accompanied by increased levels of pro-inflammatory molecules in mice", 2015, Immunology, vol. 145, pp. 268-278.
Sasagawa et al., "SIK3 is essential for chondrocyte hypertrophy during skeletal development in mice", 2012, Development, vol. 139, pp. 1153-1163.
Sedger et al., "TNF and TNF-receptors: From mediators of cell death and inflammation to therapeutic giants—past, present and future", 2014, Cytokine Growth Factor Reviews, vol. 25, pp. 453-472.
Sundberg et al., "Development of Chemical Probes for Investigation of Salt-Inducible Kinase Function In Vivo", 2016, ACS Chem Biol, vol. 11, 14 pages.
Uebi et al., "Involvement of SIK3 in Glucose and Lipid Homeostasis in Mice", May 2012, PloS ONE, vol. 7, No. 5, e37803, 15 pages.
Vankayalapati et al., "Abstract LB-296: Discovery of ARN-3261 as a potent, selective, orally available SIK2 inhibitor for treating ovarian, endometrial, primary peritoneal, fallopian tube, and triple negative breast cancers", Jul. 2017, Cancer Research vol. 77, No. 13, Supplement, Abstract LB-296, 2 pages.
Walkinshaw et al., "The Tumor Suppressor Kinase LKB1 Activates the Downstream Kinases SIK2 and SIK3 to Stimulate Nuclear Export of Class IIa Histone Deacetylases", Mar. 29, 2013, the Journal of Biological Chemistry, vol. 288, No. 13, pp. 9345-9362.
Wityak et al., "Discovery and Initial SAR of 2-Amino-5-carboxamidothiazoles as Inhibitors of the Src-family Kinase p56Lck", 2003, Bioorganic & Medicinal Chemistry Letters, vol. 13, pp. 4007-4010.
Wu et al., "Dasatinib promotes the potential of proliferation and antitumor responses of human γdT cells in a long-term induction ex vivo environment", 2014, Leukemia, vol. 28, pp. 206-210.

(56) References Cited

OTHER PUBLICATIONS

Yahara et al., "Pterosin B prevents chondrocyte hypertrophy and osteoarthritis in mice by inhibiting Sik3", 2016, Nature Communications, vol. 7, No. 10959, 14 pages.
Zhou et al., "A Novel Compound ARN-3236 Inhibits Salt-Inducible Kinase 2 and Sensitizes Ovarian Cancer Cell Lines and Xenografts to Paclitaxel", 2016, Clinical Cancer Research, pp. 1-10.
Sohal et al., "Mast Cell Sarcoma Presenting as a Spinal Cord Tumor", Blood, 2006, vol. 108, No. 11, p. 4451 (Abstract).
International Search Report and Written Opinion dated Aug. 29, 2018 from International Application No. PCT/EP2018/060172 (Authorized officer, Eberhard Strack), 32 pages.
Cortes et al., "Long-term bosutinib for chronic phase chronic myeloid leukemia after failure of imatinib plus dasatinib and/or nilotinib", American Journal of Hematology, Dec. 1, 2016, vol. 91, No. 12, pp. 1206-1214.
Charoenfuprasert et al., "Identification of salt-inducible kinase 3 as a novel tumor antigen associated with tumorigenesis of ovarian cancer", Oncogene, Mar. 14, 2011, vol. 30, No. 33, pp. 3570-3584.
Sundberg et al., "Small-molecule screening identifies inhibition of salt-inducible kinases as a therapeutic strategy to enhance immunoregulatory functions of dendritic cells", PNAS, Aug. 26, 2014, vol. 111, No. 34, pp. 12468-12473.
Araujo, J. et al., "Dasatinib: A potent SRC inhibitor in clinical development for the treatment of solid tumors", Cancer Treatment Reviews, 2010, vol. 36, Issue 6, pp. 492-500.
Fraser, C. et al. "Dasatinib inhibits the secretion of TNF-α following TLR stimulation in vitro and in vivo", Experimental Hematology, 2009, vol. 37, Issue 12, pp. 1435-1444.
Chen, Baoan et al. (2013). Apoptosis pathway and tumor multidrug resistance. In Guo, Q. (Ed.), Reversal of Multidrug Resistance in Malignant Tumors, (first ed., pp. 167-168). Southeast University Press. (6 pages including English language translation).
Zheng, Jie (2011). Cellular and Molecular Biology of Tumors (first ed., p. 250). Shanghai Science and Technology Press. (5 pages including English language translation).
Miao, Jianhua and Shu, Yongqian (Eds.). (2016). Analysis of Clinical Application of Malignant Cancer-related Treatment. (first ed., p. 50). Southeast University Press. (5 including English language translation).
E. Day et al., "Inhibition of collagen-induced discoidin domain receptor 1 and 2 activation by imatinib, nilotinib and dasatinib," European Journal of Pharmacology, vol. 599, pp. 44-53, available on line Oct. 11, 2008.
G. Patani et al., "Bioisoterism: A Rational Approach in Drug Design," Chemical Reviews, vol. 96, No. 8, pp. 3147-3176, 1996.
K. Wu et al., "Regulatory perspectives of Type II prodrug development and time-dependent toxicity management: Nonclinical Pham/Tox analysis and the role of comparative toxicology," Toxicology, vol. 236, pp. 1-6, available online Apr. 21, 2007.
A.Sorrentino et al., "Salt- inducible kinase 3 protects tumor cells from cytotoxic T- cell attack by promoting TNF-induced NF-κB activation," Journal for Immuno Therapy of Cancer, vol. 10, pp. 1-18, 2022.

* cited by examiner

E

F

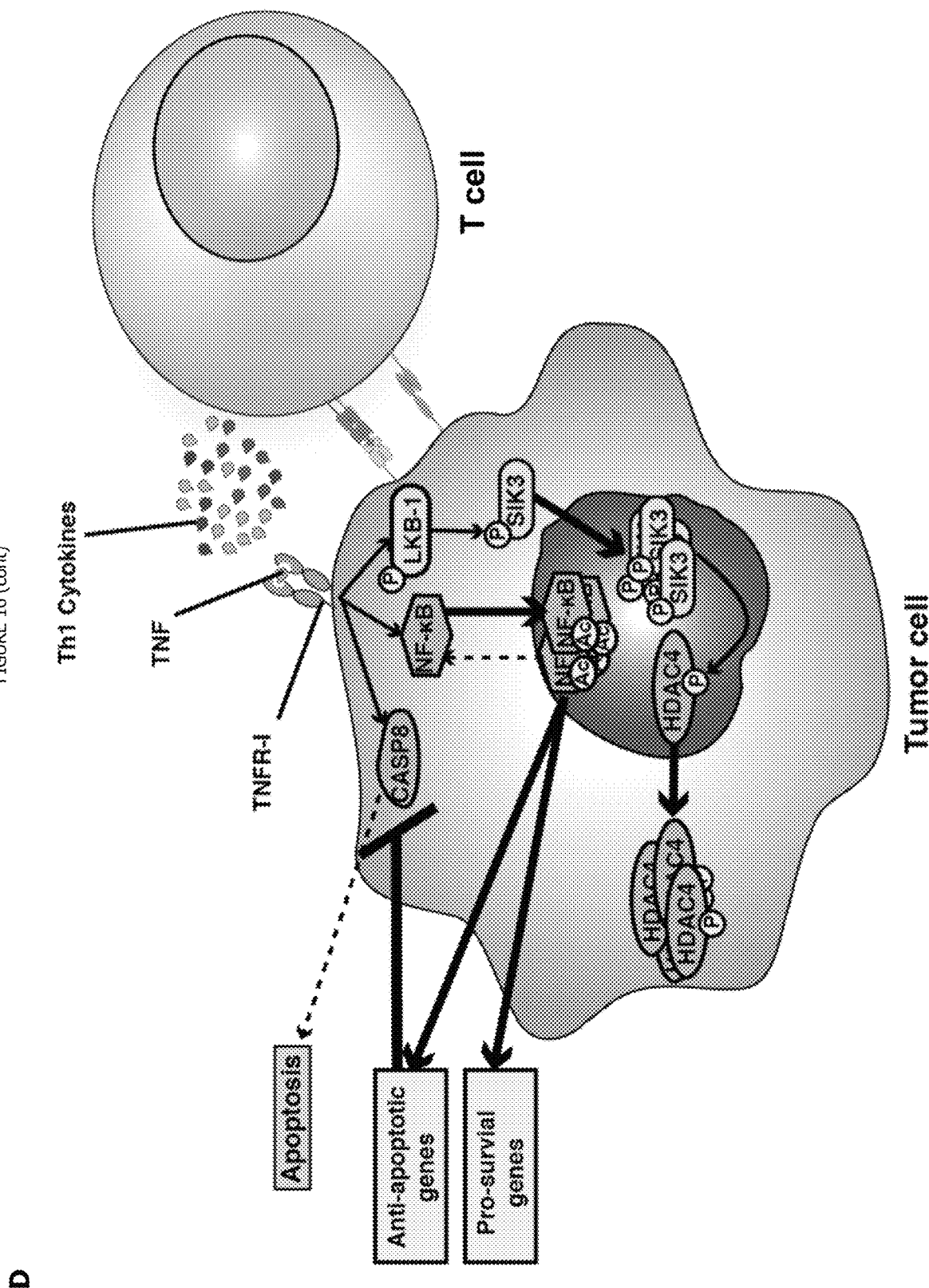

INTRACELLULAR KINASE ASSOCIATED WITH RESISTANCE AGAINST ANTI-TUMOUR IMMUNE RESPONSES, AND USES THEREOF

CROSS-REFERENCE TO RELATED APPLICATIONS

This application is a U.S. National Stage application of PCT/EP2018/060172 filed 20 Apr. 2018, which claims priority to European Patent Application No. 17167295.9 filed 20 Apr. 2017, the entire disclosures of which are herein incorporated by reference.

SEQUENCE LISTING

The instant application contains a Sequence Listing which has been submitted electronically in ASCII format and is hereby incorporated by reference in its entirety. Said ASCII copy, created on 10 Dec. 2018, is named P106_AS1-PCT-SEQ Prot.txt and is 88.3 Kilobytes in size.

The invention is based on the surprising finding that SIK3 is associated with resistance against anti-tumour immune responses. In particular, the invention provides methods for treating proliferative diseases using inhibitors of SIK3, especially nucleic acid or small molecule inhibitors of SIK3. Also provided are methods of sensitising cells involved with a proliferative disorder against the cytotoxic effect of certain pro-inflammatory signalling pathways, and/or to kill such cells and/or methods for treating proliferative diseases, using a SIK3 inhibitor together with ligands or agonists of such signalling pathways. Other methods provided by the invention include those involving SIK3 inhibitors to enhance or overcome certain side effects associated with treatments that utilise such signalling pathways, as well as diagnostic, prognostic and monitoring methods and kits based on the detection of SIK3 in a sample obtained from a subject, and screening methods useful for identifying or characterising inhibitors of SIK3.

In the treatment of cancer there are a number of approaches by which therapies may lead to the elimination of tumour cells, including those that involve or exploit one or more components of the immune system, either directly or indirectly. One of the limitations associated with such therapies is that cancerous cells often exploit immune-checkpoints to evade a patient's immune system, such by preventing immune-recognition or down-regulating a tumour-specific cytotoxic T cell (CTL) response, thereby generating resistance against an immune response (Rabinovich et al 2007, Annu Rev Immunol 25:267; Zitvogel et al 2006, Nat Rev Immunol 6:715). Under normal conditions, such immune-regulatory checkpoints are crucial for the maintenance of self-tolerance under physiological conditions but there is an increasing recognition of the important role that they can also play in cancer (Hanahan and Weinberg 2011, Cell; 144:646); cancerous cells can take over these mechanisms to evade and suppress the immune system in order to develop into a tumour (Drake et al 2006, Adv Immunol 90:51).

Current state of the art cancer therapies include blockade of those few immune-regulatory checkpoints presently known and for which their mechanism of action is understood. For example, blocking antibodies against surface-expressed immune-regulatory proteins, such as CTLA4 and PD-L1 (Chambers et al 2001, Annu Rev Immunol 19:565; Blank et al 2004, Cancer Res 64:1140), can boost anti-tumour immunity and have shown clinical success against many cancer types (Page et al 2014, Annu Rev Med 65:185). However, a large proportion of cancer patients does not respond to such checkpoint blockage therapy (Bu et al 2016, Trends Mol Med 22:448; Hugo et al 2016, Cell 165:35; Topalian et al 2012, New Engl J Med 366:2443), indicating that other immune-checkpoint pathways may be active. Indeed, synergistic cooperation between several immune-regulatory pathways maintains immune tolerance against tumours, which might explain why blocking only one immune-regulatory checkpoint node can still result in tumour escape (Woo et al 2012, Cancer Res 72:917; Berrien-Elliott et al 2013, Cancer Res 73:605). However, little is known about the molecular factors that are central to the mechanism of action of such immune-regulatory pathways. Indeed, successful cancer immunotherapy requires a systematic delineation of the entire immune-regulatory circuit—the 'immune modulatome'—expressed by tumours. Therefore, today, there is still an unmet need for identifying further molecular targets that may serve as immune-regulatory checkpoints and in particular an unmet need for means and methods to modulate, detect and otherwise utilise such possible checkpoint targets, such as in medicine, diagnosis and research.

Salt-inducible kinases (SIKs) constitute a serine tyrosine kinase (STK) subfamily, belonging to the adenosine mono-phosphate-activated kinase (AMPK) family. Three members (SIK1, -2, and -3) have been identified so far. Amino acid homology of SIK1 with SIK2 and SIK3 is 78% and 68%, respectively, in the kinase domain. The cloning of SIK1 (also known as SIK and SNF1LK), abundantly expressed in the adrenal glands of high-salt, diet-fed rats, led to subsequent cloning of SIK2 (also known as QIK, KIAA0781 and SNFLK2), mainly expressed in adipose tissues and the rather ubiquitous SIK3 (also known as QSK, KIAA0999 or L19) (Katoh et al 2004, Mol Cell Endocrinol 217:109). The three SIKs have a similar structure (FIG. 1), with an N-terminal kinase domain (catalytic domain), a middle ubiquitin-associated domain (believed important for phosphorylation by LKB1) and a long C-terminal sequence (believed to be a site for further phosphorylation by PKA). However, there are very diverse roles implicated for the various SIKs. For example, various SIKs have been implicated in biological processes as diverse as osteocyte response to parathyroid hormone (Wein et al 2016, Nature Commun 7:13176) to induction of SIK1 by gastrin and inhibition of migration of gastric adenocarcinoma cells (Selvik et al 2014, PLoS ONE 9:e112485).

In particular, each of SIK2 and SIK3 has been implicated in diverse biological processes. For SIK2 these include (as well as immune suppression as described in more detail below) gluconeogenesis, neuronal survival, melanogenesis, hepatic steatosis, and centrosome splitting, as well as SIK2 being implicated in the progression of cancer, certain ovarian cancers depending on the SIK2 kinase for maintenance of cell proliferation and chemo-resistance, and very recently SIK2 as a centrosome kinase required for mitotic spindle formation and a potential target for ovarian and breast cancer therapy in particular for its role in regulation of sensitisation of ovarian cancer to paclitaxel, including the use of SIK2 inhibitors such as ARN-3236 and its analogues (eg ARN-3261) (Zhou et al 2016, doi: 10.1158/1078-0432.CCR-16-1562, and discussion/references therein; WO2014/093383; AACR abstract LB-296, Washington D.C., 2017). For SIK3 these include (as well as immune suppression as described in more detail below) glucose and lipid homeostasis in mice (Uebi et al 2012, PloS ONE 7:e37803), chondrocyte hypertrophy during skeletal development in mice (Sasagawa et al 2012, Development 139:1153), osteoarthritis in mice (Yahara et al 2016, Nature Commun 7:10959), SIK3 deficiency exacerbating lipopolysaccharide (LPS)-induced endotoxin shock accompanied by increased levels of pro-inflammatory molecules in mice (Sanosaka et al 2015, Immunology 145: 268), SIK3 as a tumour antigen associated with tumourigenesis of ovarian cancer (Chareonfuprasert et al 2011, Oncogene 20:3570) and as a novel mitotic regulator and a target for enhancing antimitotic therapeutic-mediated cell death (Chen et al 2014, Cell Death and Disease 5:e1177), and SIK3 overexpression inducing up-regulation of cyclin D and E leading to acceleration of G1/S cell-cycle progression (Du et al 2015, Exp Opin Therap Targ 4:477).

The cellular signalling pathways implicated as being regulated by SIKs are diverse (Walkinshaw et al 2013, J Biol Chem 288:9345), with not only gluconeogenesis being regulated via CRTC2/CREB and lipogenesis regulated via p300/ChREBP but Walkinshaw et al showed that LKB1 activates SIK2 and SIK3 to phosphorylate class IIa HDACs and promote their cytoplasmic localisation. Yet, under the same experimental conditions, SIK1 was shown to be unable to do so. Different from SIK2, SIK3 was also reported to possess unique properties, such as the ability to promote class IIa HDAC export independent of its kinase activity and to stimulate cytoplasmic localisation of constitutively nuclear mutants of HDAC4 and HDAC7, highlighting the difference among the SIK family members. Moreover, Walkinshaw reported that PKA counteracts LKB1, SIK2, and SIK3 to inhibit the nuclear export of class IIa HDACs.

SIK family members have been identified as a key molecular switch whose inhibition reprograms macrophages to an anti-inflammatory phenotype, with macrophages then showing corresponding changes in cytokine expression (increased expression of interleukin-10 (IL-10), and decrease in expression of tumour necrosis factor alpha (TNF-alpha) upon treatment with the pan-SIK small molecule inhibitors MRT67307, MRT199665, KIN112 and HG-9-91-01 (Clark et al 2012, PNAS 109:16986). Clark reported that HG-9-91-01 appeared to be the most potent SIK family member inhibitor and the most specific for SIK family members, but still showing meaningful inhibition for all three members with most potency against SIK1 and least potency to SIK3, and that these inhibitors elevate IL-10 production by inducing the dephosphorylation of cAMP response element-binding protein (CREB)-regulated transactional coactivator (CRTC) 3. The effects of SIK inhibitors on IL-10 production were lost in macrophages that expressed a drug-resistant mutant of SIK2. Clark proposes that drugs that target SIKs may have potential for treatment of disorders associated with undesired inflammation such as inflammatory bowel disease (eg Crohn's disease and ulcerative colitis) and/or autoimmune disorders (WO 2013/136070).

Sundberg et al 2014 (PNAS 111:12468; WO 2016/023014) further supports the anti-inflammatory role of SIKs in immune cells, describing the use of various small molecule inhibitors similar to HG-9-91-01 (eg, WO 2015/006492; WO 2016/014551; WO 2016/014552) enhances IL-10 production in dendritic cells (DCs) and the conversion of activated DCs to an anti-inflammatory phenotype. This stimulatory effect of SIK inhibition (in particularly, SIK2 inhibition) on IL-10 production was also associated with decreased production of the pro-inflammatory cytokines IL-1-beta, IL-6, IL-12 and TNF-alpha.

Using a phenotypic screen for up-regulation of IL-10 production by activated DCs to test a collection of >150 kinase inhibitors comprising FDA-approved drugs, Sundberg also identified that the approved drugs dasatinib and bosutinib up-regulated such IL-10 production, also by a mechanism involving CRT3/CREB signalling, and that such effect on IL-10 production was correlated with these drugs' potent binding to SIK1 and SIK2. Indeed, Ozanne et al 2015 (Biochem J465:271) confirmed that both dasatinib and bosutinib are pan SIK inhibitors in a biochemical assay (although their potency to inhibition of SIK3 is 3 to 5-fold less than for SIK1 or SIK2) and that these two kinase inhibitors (but not other protein tyrosine kinases inhibitors) elevate IL-10 production in macrophages, and induce a pattern of cytokine production that is characteristic of "regulatory"-like macrophages; in particular inhibition of production of IL6, IL12 and TNF-alpha. This mechanism of IL10 induction in macrophages by bosutinib and dasatinib was also shown to involve CRTC3 dephosphorylation and CREB-dependent gene transcription, and expression of drug-resistant SIK2 mutants in macrophages blocked IL10 production by bosutinib and dasatinib.

Dasatinib (SPRYCEL®), a small molecule inhibitor of Abl and Src family protein tyrosine kinases (in particular of BCR-ABL), is approved for the treatment of Philadelphia chromosome positive (Ph+) chronic myeloid leukaemia (CML) and Ph+acute lymphoblastic leukaemia (ALL). Dasatinib has been or is under investigation for numerous other cancer types, including solid tumours such as breast cancer, melanoma, ovarian cancer and non-small cell lung cancer, and in particular is under clinical testing in combination with the anti-PD-1 monoclonal antibody nivolumab (OPDIVO®) for treating relapsed or refractory Ph+ALL. However, numerous reports have implicated dasatinib with immune suppression, including leading to increased infections and formation of skin cancer in dasatinib-treated CML patients (Sillaber et al 2009, Br J Haematol 144:195); with experimental evidence to support such inhibition of immune responses by dasatinib. For example: (i) Schade et al 2007 (Immunobiology 111:1366) reported that dasatinib inhibits T cell activation and proliferation in peripheral blood T lymphocytes (PBTs) in vitro, as well as using an in vivo mouse model. Such inhibitory activity was not induced by apoptosis, and also led to the inhibition of the production of pro-inflammatory cytokines (eg TNF-alpha); (ii) Fraser et al 2009 (Exp Hematol 37:1435) reported that dasatinib-treated mice had reduced serum levels of TNF-alpha in response to LPS administration, as well as increased serum levels of IL-10; and (iii) Futosi et al 2012 (Blood 119:4981) reported that dasatinib caused inhibition of pro inflammatory functions of mature human neutrophils, leading to inhibition of both TNF-alpha production and neutrophil chemotaxis, and proposed that dasatinib may provide benefit in neutrophil-related inflammatory diseases.

In contrast, some clinical observations from one research group following long-term treatment with dasatinib have suggested a dual role for dasatinib in its effects on the immune system: (i) a subset (n=22) of Ph+ leukaemia patients showed clonal expansion of T/NK cells with adverse effects such as colitis and pleuritis common in such patients (Mustjoki et al 2009, Leukemia 23:1389); and (ii) a rapid mobilisation of cytotoxic lymphocytes induced by dasatinib in certain (n=55) Ph+ leukaemia patients closely mirrored drug plasma concentrations (Mustjoki et al 2013, Leukemia 27:914). Some experimental evidence has supported this contrasting observation of an immune enhancement associated with dasatinib treatment: (i) Wu et al 2014 (Leukemia 28:179) reported the ex-vivo affect of 3 protein tyrosine kinase inhibitors, with only dasatinib showing a proliferation and anti-tumour response of gamma-delta T cells in a long-term induction ex vivo environment; (ii)

Kreutzman et al 2014 (OncoImmunology 3:e28925) reported that dasatinib promotes Th1-type responses in granzyme B expressing T cells using primary samples from CML patients (n=23); and (iii) Hekim et al 2017 (Cancer Immunol DOI: 10.1158/2326-606) very recently reported that dasatinib changes immune cell profiles concomitant with reduced tumour growth in several murine solid tumour models.

Further specificity on the anti-inflammatory role of the various SIKs has been recently elucidated. For example: (i) Darling et al 2016 (Biochem DOI: 10.1042/BCJ20160646) used knock-in mutants of SIK1, SIK2 and SIK3 to show that all SIK family members contributed to a macrophage phenotype characterised by the secretion of high levels of anti-inflammatory cytokines including IL-10. However, SIK2 appears more important than SIK3 for IL-10 production, as while unlike SIK2 a mutant SIK3 knock-in showed an increase in IL-10 mRNA but only a limited effect in actual IL-10 secretion. Importantly however, knock-in of any mutant SIK led to a decrease in TNF-alpha production, as well as in other pro-inflammatory cytokines; (ii) Studying both HG-9-91-01 and another SIK2 inhibitor ARN-3236, Lombardi et al 2016 (J Leuk Biol 99:711) reported SIK inhibition in human myeloid cells modulated TLR and IL-1R signalling and induced an anti-inflammatory phenotype; and (iii) Sundberg et al 2016 (ACS Chem Biol 11:2105) have developed chemical probes for investigation or SIK function in vivo. Using a binding model based on the MARK3/Par-1 kinase domain, they demonstrated that SIK inhibitors could be developed to have increased selectivity towards individual SIKs; such as YKL-05-099 in particular which showed increased selectivity to SIK2. They were able to recapitulate in vivo their previously observed anti-inflammatory phenotypes (including, decreased production of TNF-alpha), and showed that YKL-05-099 treatment led to a dose dependent decrease in phosphorylation of HDAC5 at SIK-regulated Ser25 in total splenic leukocytes.

Tumour necrosis factor (TNF)—previously known as tumour necrosis factor alpha (TNF-alpha)—was first identified in 1975 (and cloned in 1984) for its ability to induce rapid haemorrhagic necrosis of experimental cancers, although its history could be traced back to the work of Coley in the 1890s. The early promise that TNF would be a powerful anticancer cytokine soon faded with the realisation that the recombinant cytokine could induce signs and symptoms of endotoxic shock: the therapeutic index was alarmingly small (Balkwill 2009, Nature Rev Cancer 9:361). Not surprisingly therefore, TNF (tasonermin; BEROMUN®) has since been approved in the EU for only specific application: to prevent or delay amputation for soft tissue sarcoma of the limbs uses in combination with melphalan via mild hypothermic isolated limb perfusion. More recently however, there has been a resurgence of interest in the potential therapeutic uses of TNF, particularly since more is now known about its dual role in both anti- and pro-tumour actions, and the switches between these actions governed inter alia through NF-kappaB, and in particular how to control such switches (such as by using the teaching of the present invention).

In parallel to many of the early anti-cancer trials being conducted on TNF, there was also significant attention being paid to the observation that neutralising antibodies to TNF (induced by passive immunisation) protected mice against lethal TNF-mediated endotoxemia. These studies were instrumental in proving that TNF is both potently tumourocidal, as well as being an essential mediator of inflammation. In fact, what quickly became evident was that TNF was a highly pro-inflammatory agent, both independently, and via its ability to induce expression of IL-6. These early findings represent the seminal studies that directly lead to the opposite approach to that presumed useful for cancer therapy, but of neutralising TNF to inhibit inflammation (Sedger & McDermott 2014, Cytokine & Growth Factor Reviews 25:543). Thereafter, numerous anti-TNF therapeutics have been developed, including antibodies that bind to (and sequester) TNF or fragments of recombinant TNF receptors that likewise bind to (and sequester) TNF, thereby reducing the level of free/active TNF. Examples of anti-TNF agents include: the chimeric mouse Fv and human Fc anti-TNF monoclonal Ig infliximab (IFX), the humanised or fully human Fv) anti-TNF monoclonal Igs adalimumab (ADA), golimumab (GOL) and humicade (HUM); the TNFR2-based human Ig Fc etanercept (ETA) and the pegylated recombinant extracellular TNFR1 onercept (ONE) and pegylated human IgG1 Fab' certolizumab pegol (CET). Such approved products are approved for disorders such as rheumatoid arthritis, psoriatic arthritis, ankylosing spondylitis, plaque psoriasis and Crohn's disease. However, there are also several reports of patients on anti-TNF biologics developing lymphomas and other haematological malignancies. These include reports of lymphomas (Hodgkin's lymphomas, B-cell lymphoma of unknown subtype, peripheral T-cell lymphoma, unspecified lymphomas, and hepatosplenic T cell or gamma-delta T cell lymphoma) and acute leukemias (see references in Sedger & McDermott 2014). As a direct consequence of the perceived increase in haematological malignancy and widespread use of these and other immunosuppressive agents, the WHO classification of tumours now includes the category "iatrogenic immunodeficiency-associated lymphoproliferative disease".

Therefore, there is a need, from one or more of the above perspectives, for novel approaches to render cells involved with a proliferative disorder (such as a tumour) more susceptible to the immune system, and in particular to circumvent tumour immune escape mechanisms. The present invention seeks to provide, in particular, novel therapeutic approaches and methods involving existing or novel compounds; for example compounds that sensitise such cells towards a cytotoxic response of the immune system or components thereof. Furthermore, the invention seeks to provide novel strategies to diagnose, prognose and/or monitor cell resistance to such an immune response or components, as wells as screening approaches for the identification of compounds that are useful in the treatment of proliferative disorders. Accordingly, it is an object of the present invention to provide alternative, improved, simpler, cheaper and/or integrated means or methods that address one or more of these or other problems. Such an object underlying the present invention is solved by the subject matter as disclosed or defined anywhere herein, for example by the subject matter of the attached claims.

Generally, and by way of brief description, the main aspects of the present invention can be described as follows:

In a first aspect, the invention relates to a method for the treatment of a proliferative disorder in a subject by inhibiting SIK3; and/or sensitising cells involved with the proliferative disorder to a cell-mediated immune response, the method comprising administering a SIK3 inhibitor to the subject.

In a second aspect, the invention relates to a method for the sensitisation of cells involved with a proliferative disorder to a cell-mediated immune response, the method comprising exposing the cells involved with the proliferative disorder to a SIK3 inhibitor.

In a third aspect, the invention relates to a method for the killing of cells involved with a proliferative disorder, the method comprising exposing cells involved with the proliferative disorder to: (i) TNF, a TNF variant and/or an agonist of TNFR1- or TNFR2-signalling; and (ii) a SIK3 inhibitor.

In a fourth aspect, the invention relates to a method for the treatment of a proliferative disorder in a subject, the method comprising exposing cells involved with the proliferative disorder to: (i) TNF, a TNF variant and/or an agonists of TNFR2- or TNFR1-signalling; and (ii) a SIK3 inhibitor.

In a fifth aspect, the invention relates to a method for the increase of the therapeutic index of treatment with TNF in a subject being treated therewith for a proliferative disorder, the method comprising administering an inhibitor of SIK3 to the subject.

In a sixth aspect, the invention relates to a method for the sensitisation of a subject suffering from a proliferative disorder to a therapy involving the administration of TNF to the subject, the method comprising administering an inhibitor of SIK3 to the subject.

In a seventh aspect, the invention relates to a method for the reduction in risk of a haematological proliferative disorder in a subject being treated with an anti-TNF agent, the method comprising administering an inhibitor of SIK3 to the subject.

The invention also relates to various determination methods, and to items and kits useful for such determination methods, as well as to various methods for identifying compounds The figures show:

FIG. 1: Pictorial representation of the comparative structural features of SIK1, SIK2 and SIK3. N-terminal kinase domains represented by grey rectangles, middle ubiquitin-associated domains represented by white rectangles and C-terminal sequence represented by light grey bar.

Figure 2:
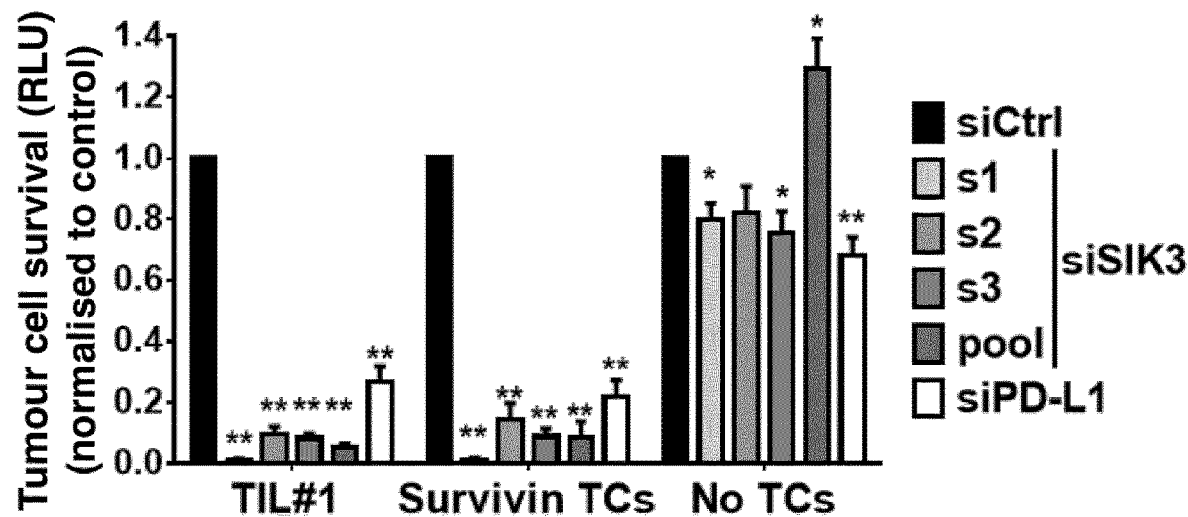

FIG. 2: Luciferase-based cytotoxicity assay for the assessment of T cell-mediated killing of siRNA transfected PANC-1-luc cells. Graph shows remaining luciferase activity (RLU) of tumour cells after 20 h challenge with TIL #1 or survivin-specific T cell clones, normalised to the signal of the scrambled control siRNA (siCtrl).

Figure 3:
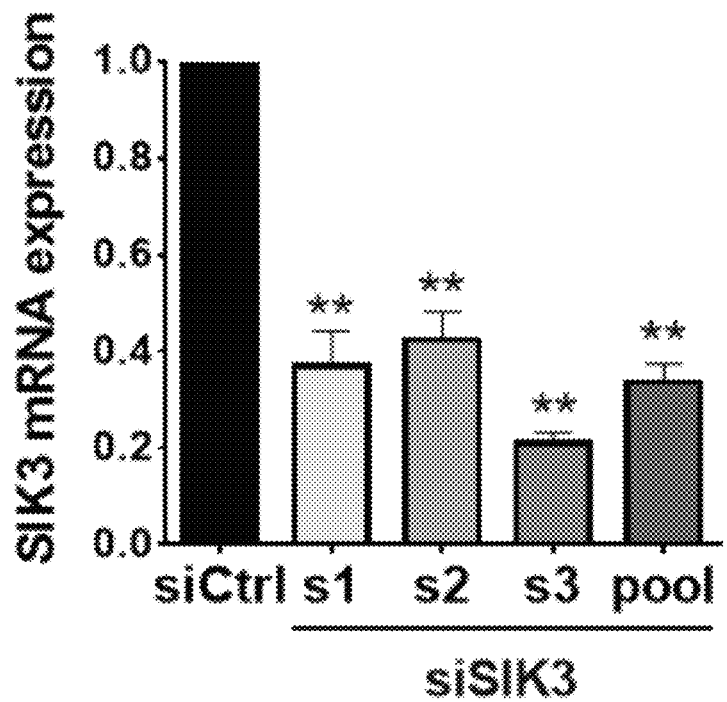
Figure 3:
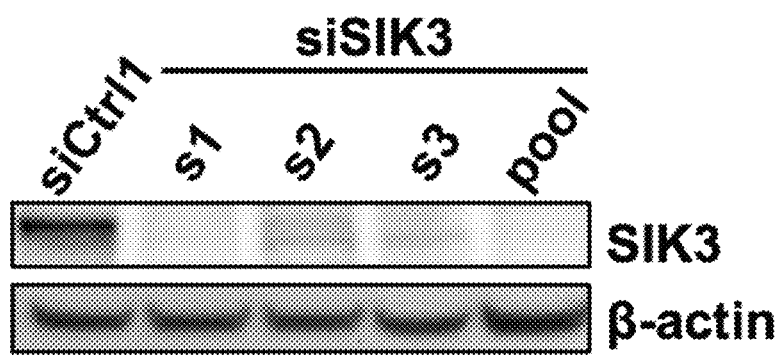
Figure 3:
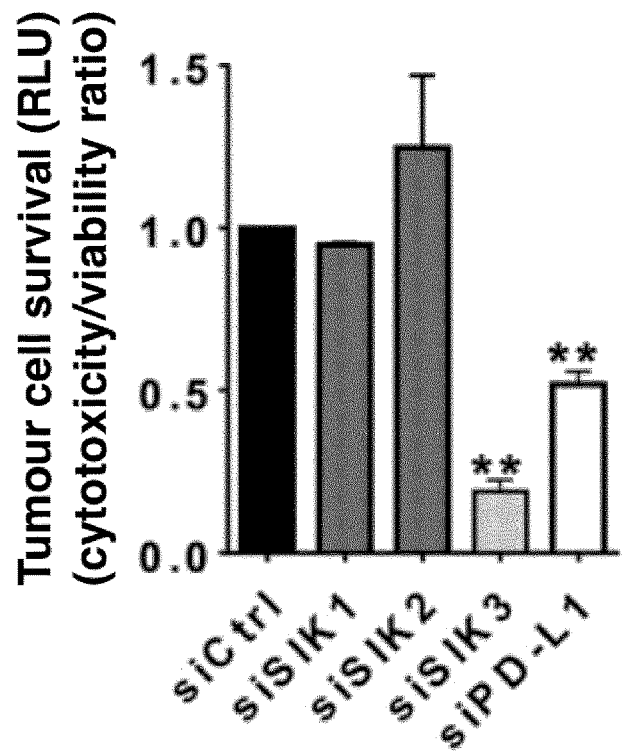
Figure 3:
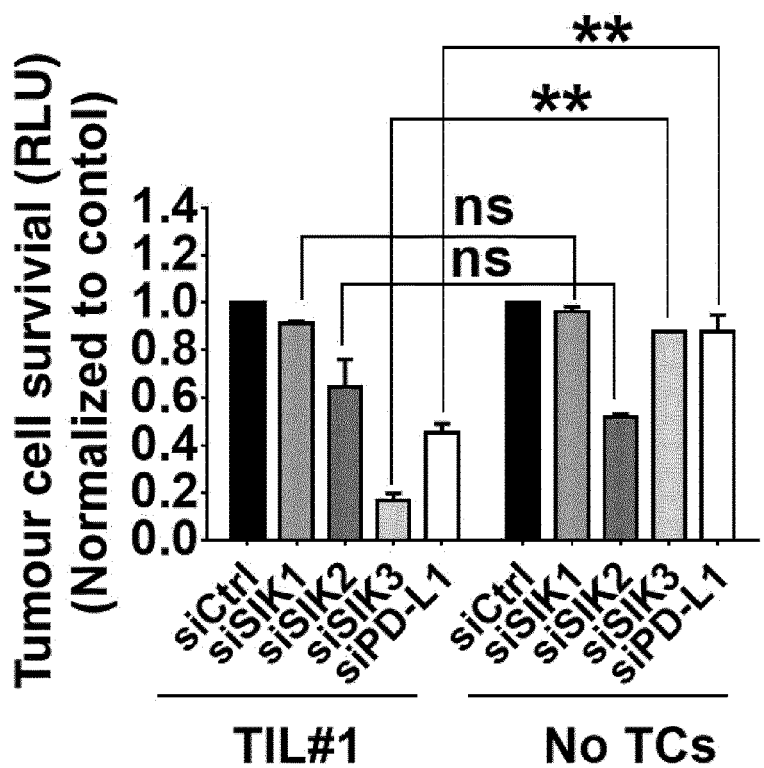

FIG. 3: (A) PANC-1-luc cells were transfected either with single (s1, s2, or s3) or pooled (pool) siRNA sequences targeting SIK3. Scrambled siRNA was used as control (siCtrl). After 72 h, mRNA expression was evaluated using qPCR. Data are normalised to GAPDH. (B) Western blot of SIK3 protein after siRNA knockdown by various siRNAs compared to scrambled controls siRNA (siCtrl). (C) Luciferase-based cytotoxicity assay demonstrating the SIK3-specificity of the effect when PANC-1 cells (having each SIK, or PD-L1 knocked-down by transfection with the indicated siRNA) are exposed to TIL #1 T cells. (D) Normalised RLU values for the two settings (presence vs absence of T cells) of the data presented as a ratio in (C).

Figure 4:
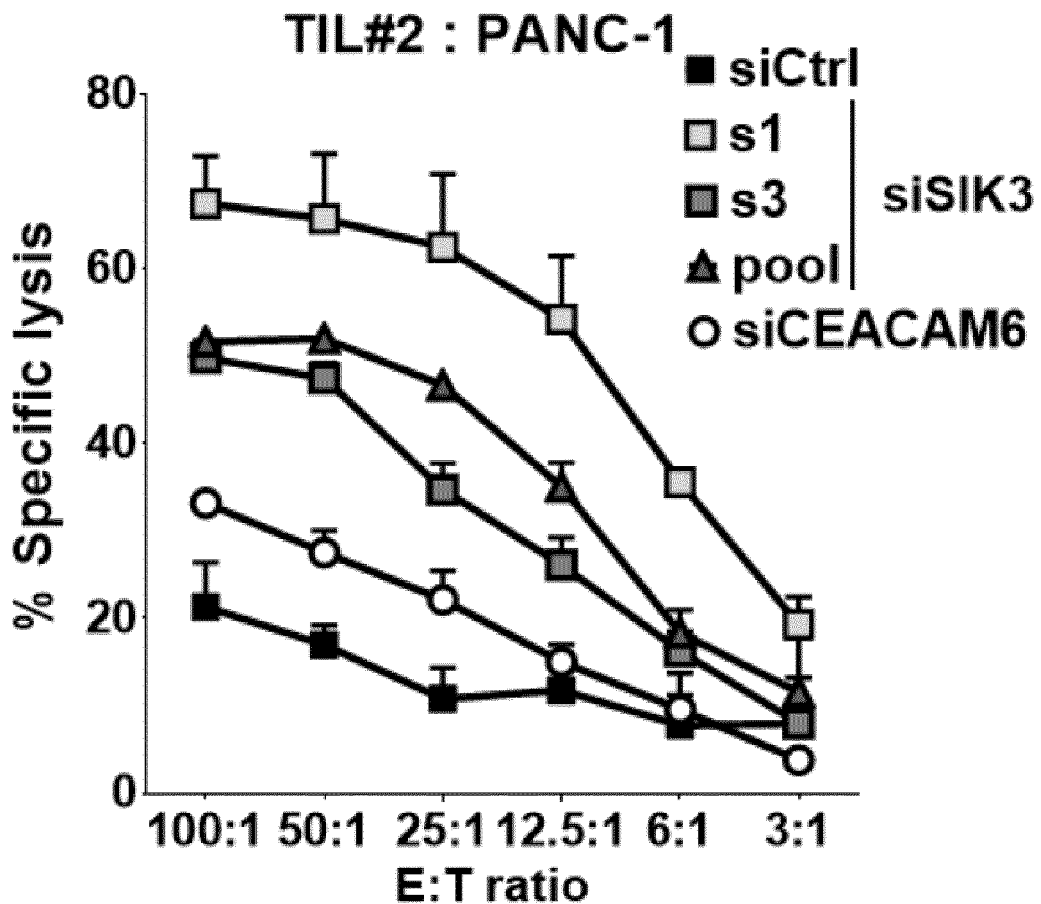
Figure 4:
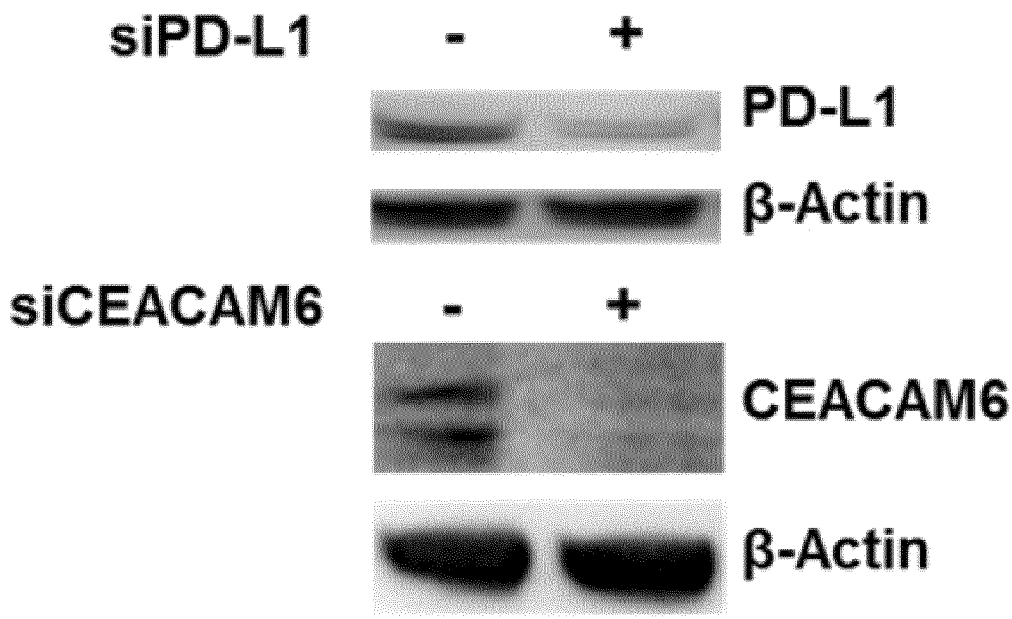

FIG. 4: (A) Chromium release assay for the detection of T-cell mediated cytotoxicity of PANC-1 cells after 6 h co-culture with TIL #2 after transfection with the indicated siRNA. (B) Western blot analysis for the detection of PD-L1 and CEACAM6 protein levels in PANC-1 cells 72 h from the indicated siRNA transfection. Scrambled siRNA was used as negative control.

Figure 5:
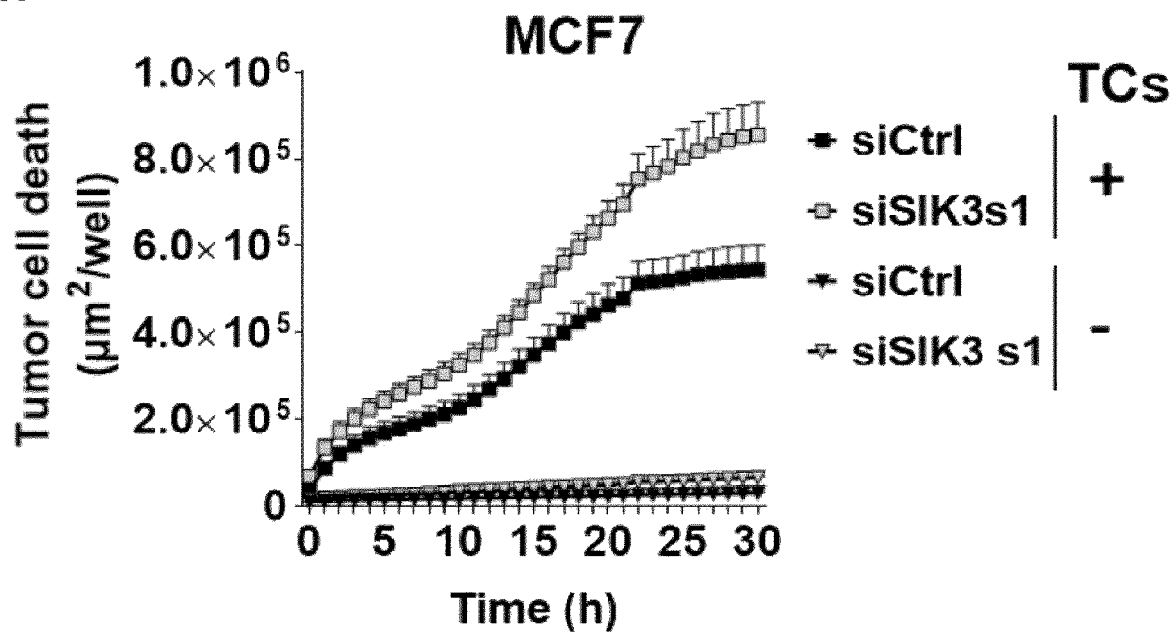
Figure 5:
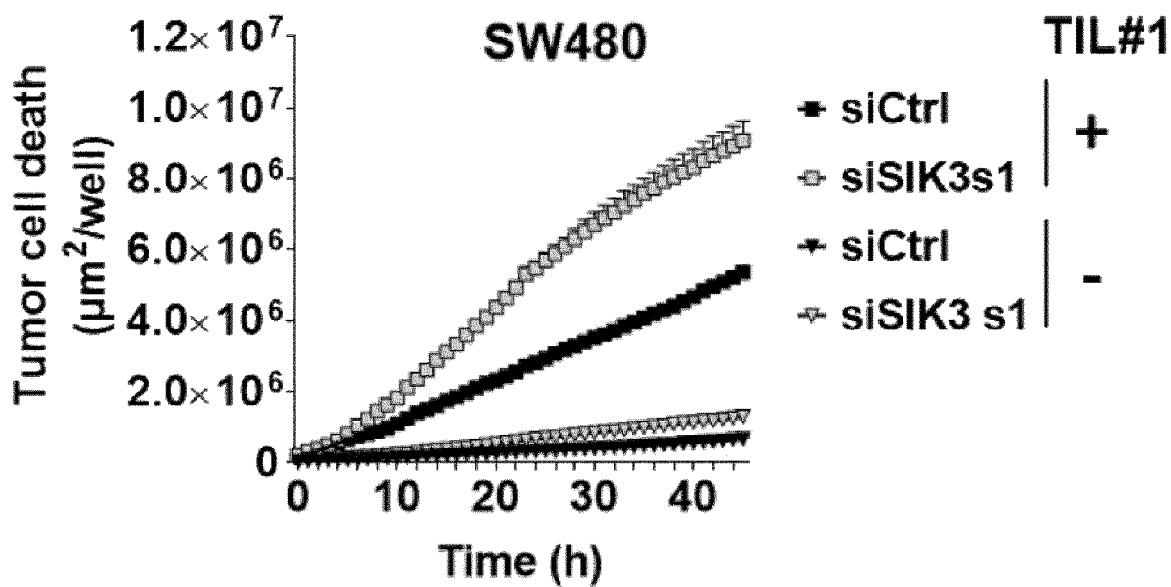

FIG. 5: Real-time live cell microscopy for the evaluation of tumour cell death using YOYO-1 dye. 72 h from transfection with the indicated siRNAs, MCF-7 (A) and SW480 (B) were co-cultured either with survivin-specific T cell clones or with TIL #1, respectively. Graph shows the area of YOYO-1+ cells/well (µm2/well) as a measure of cell death.

Figure 6:
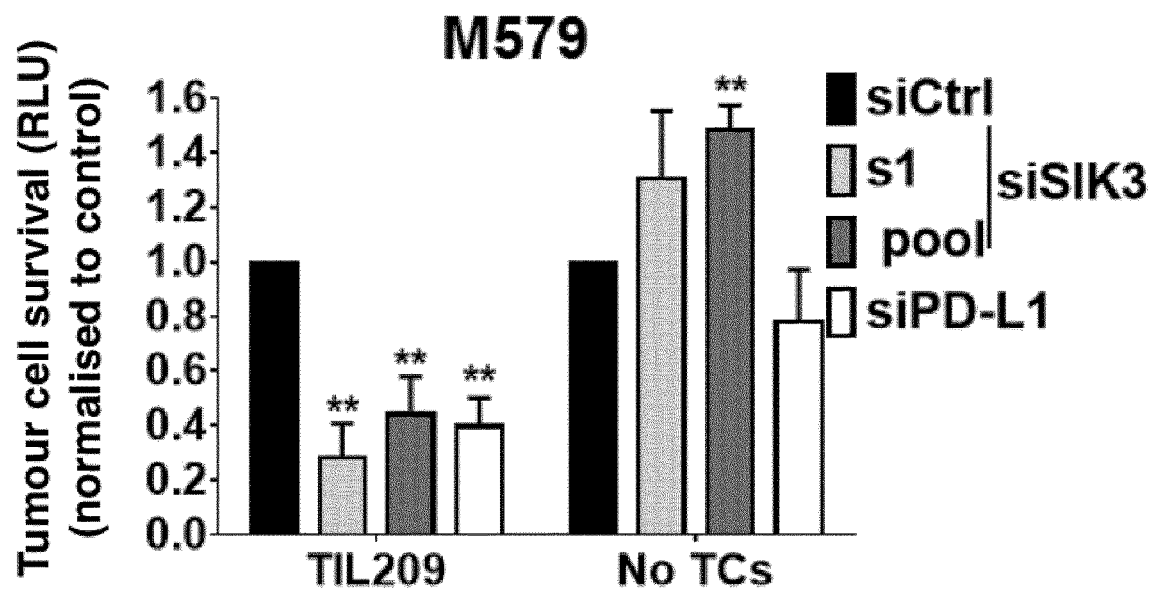
Figure 6:
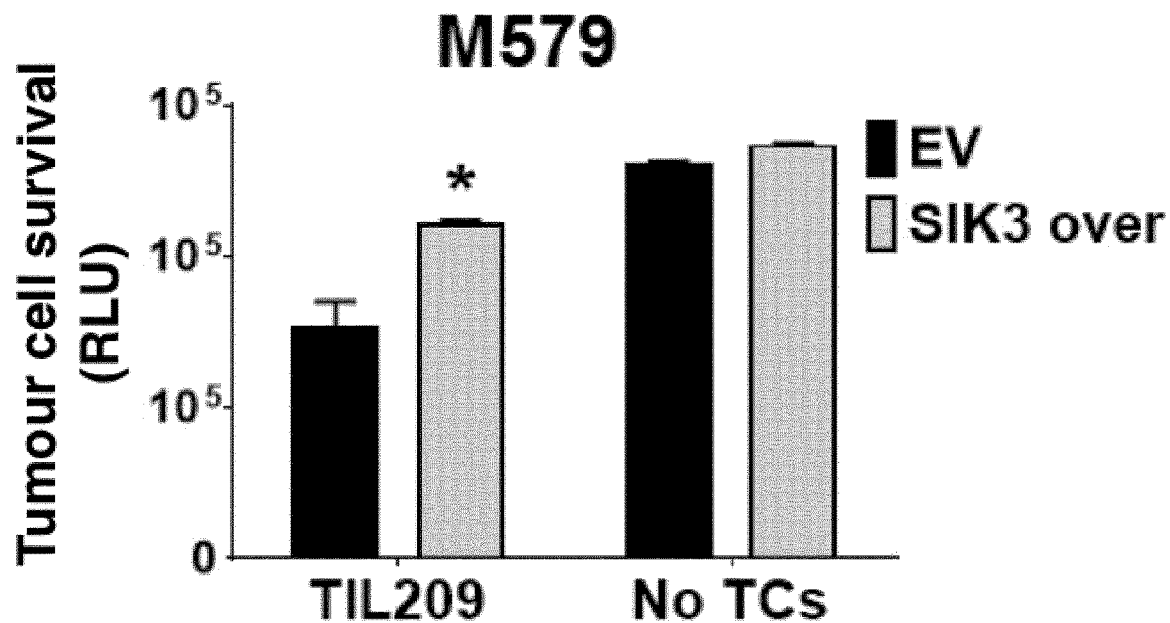

FIG. 6: (A) M579-luciferase expressing melanoma cells (M579-A2-luc) were transfected with the indicated siRNAs, with luciferase-based killing assay performed 20 h after co-culture. (B) M579-A2-luc cells were transfected with SIK3 overexpression vector (SIK3 over) or control vector (EV), with T cell mediated cytotoxicity was assessed as in (A).

Figure 7:
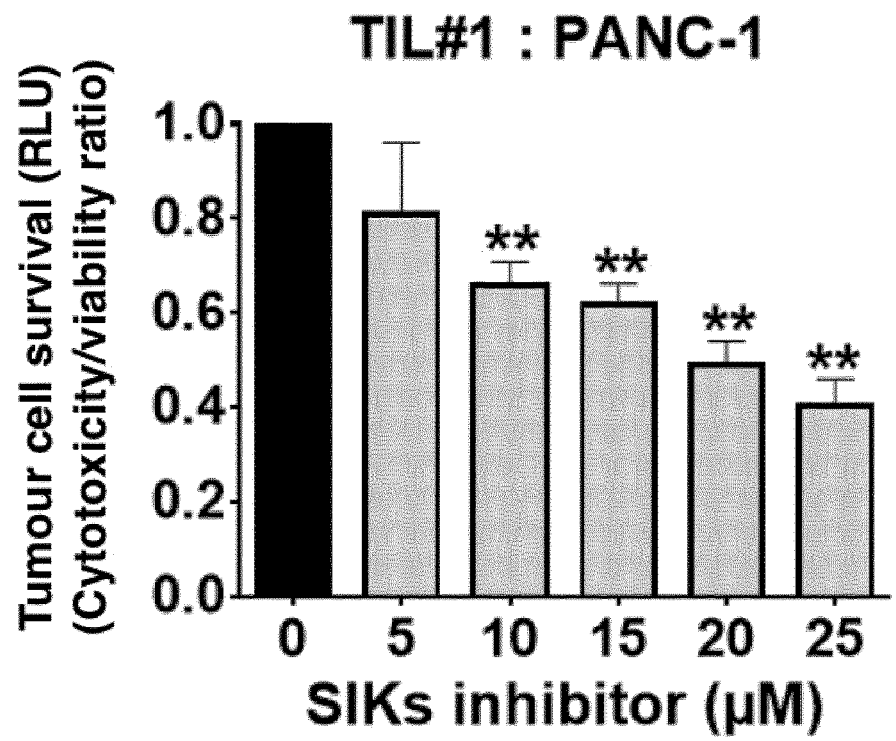
Figure 7:
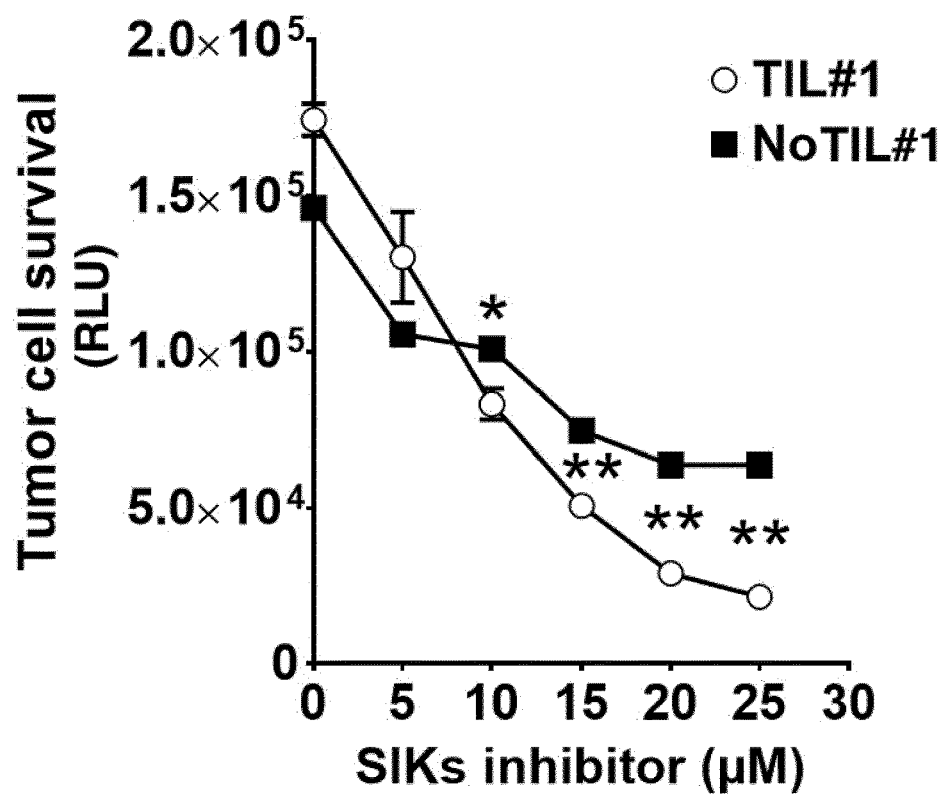
Figure 7:
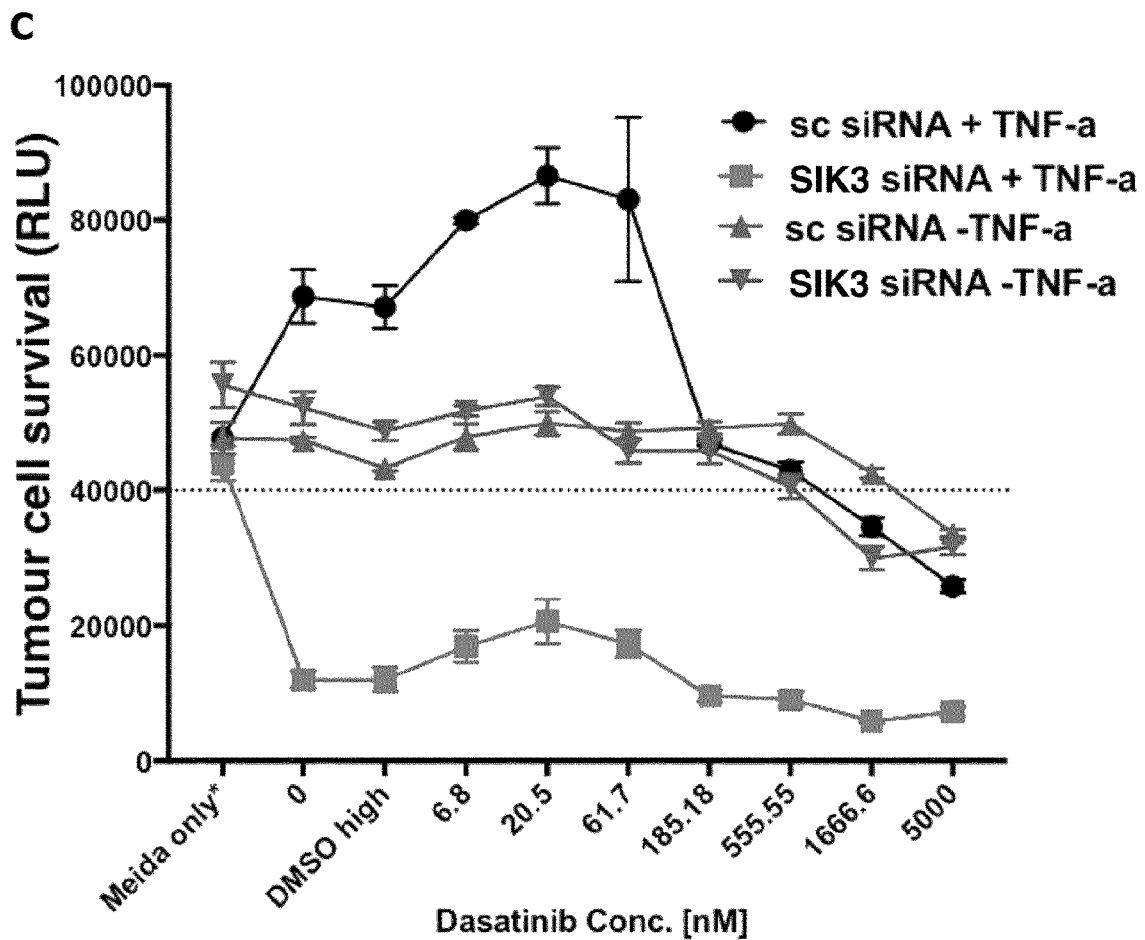
Figure 7:
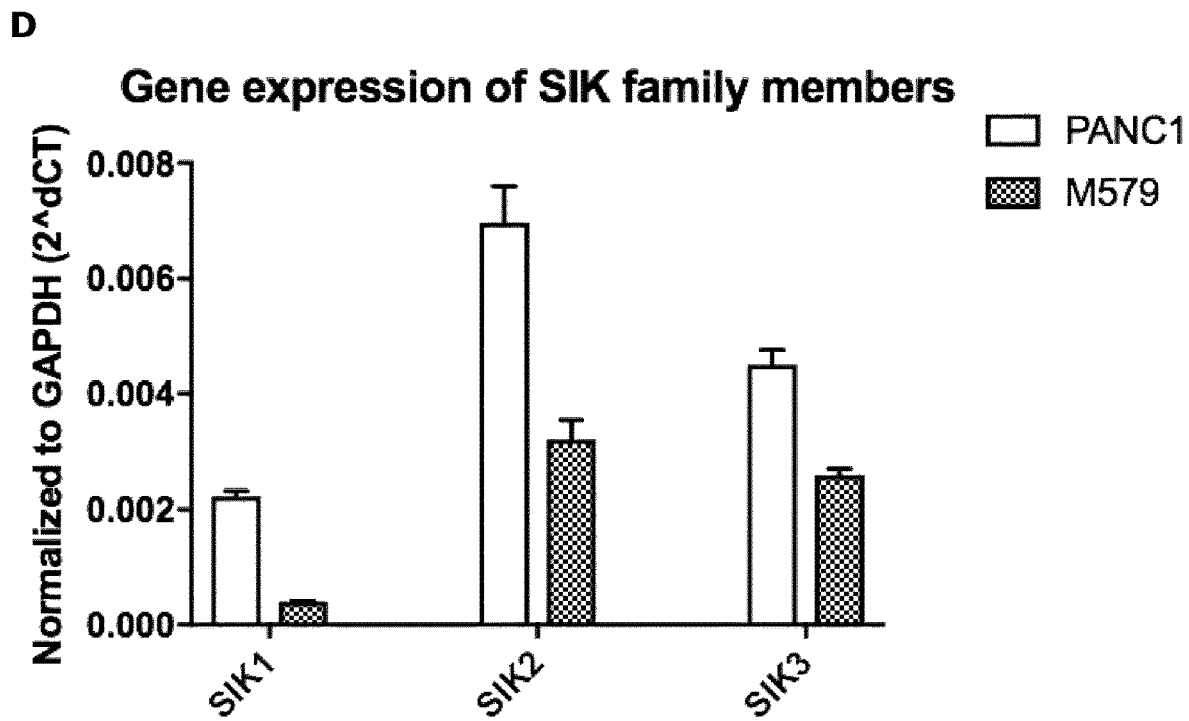
Figure 7:
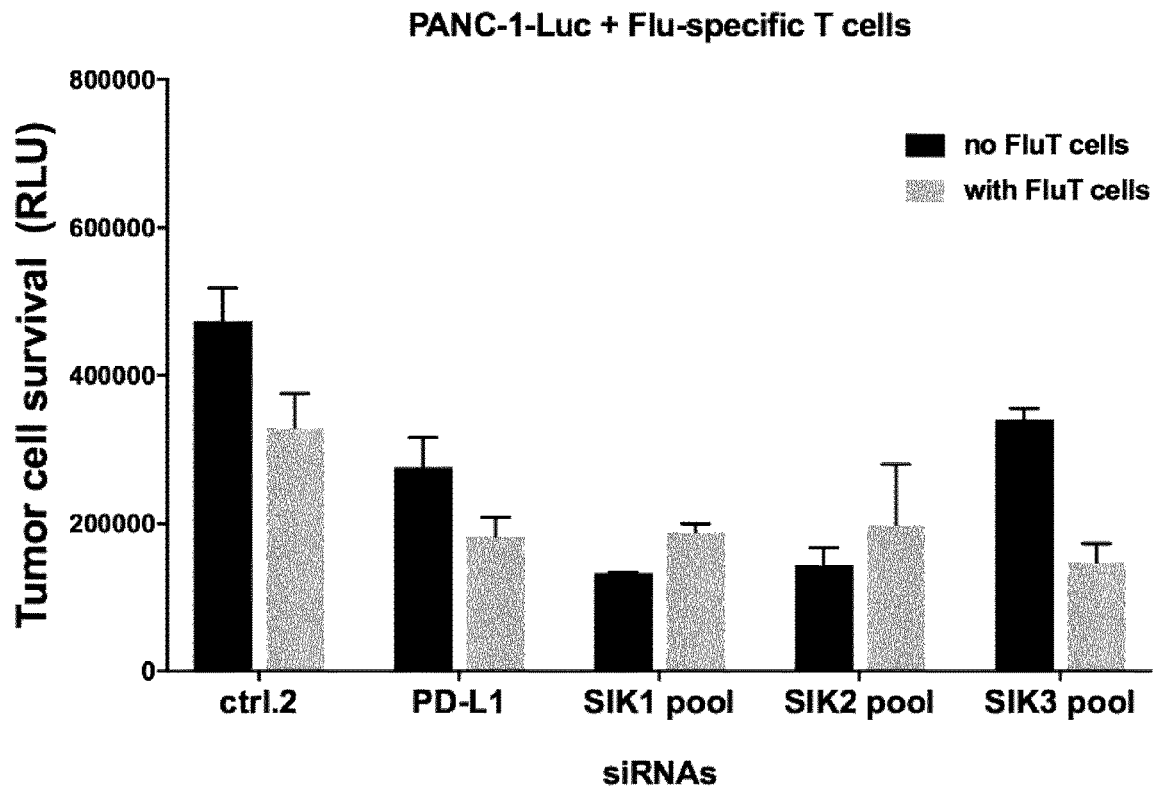
Figure 7:
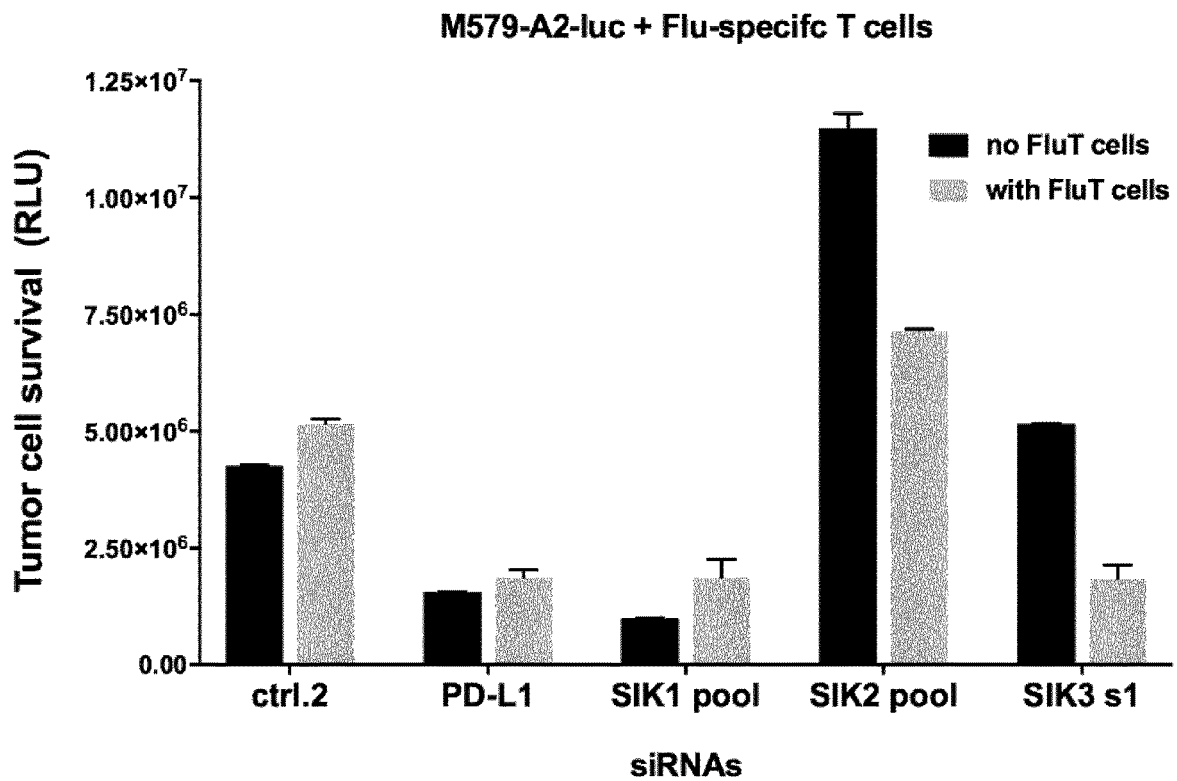
Figure 7:
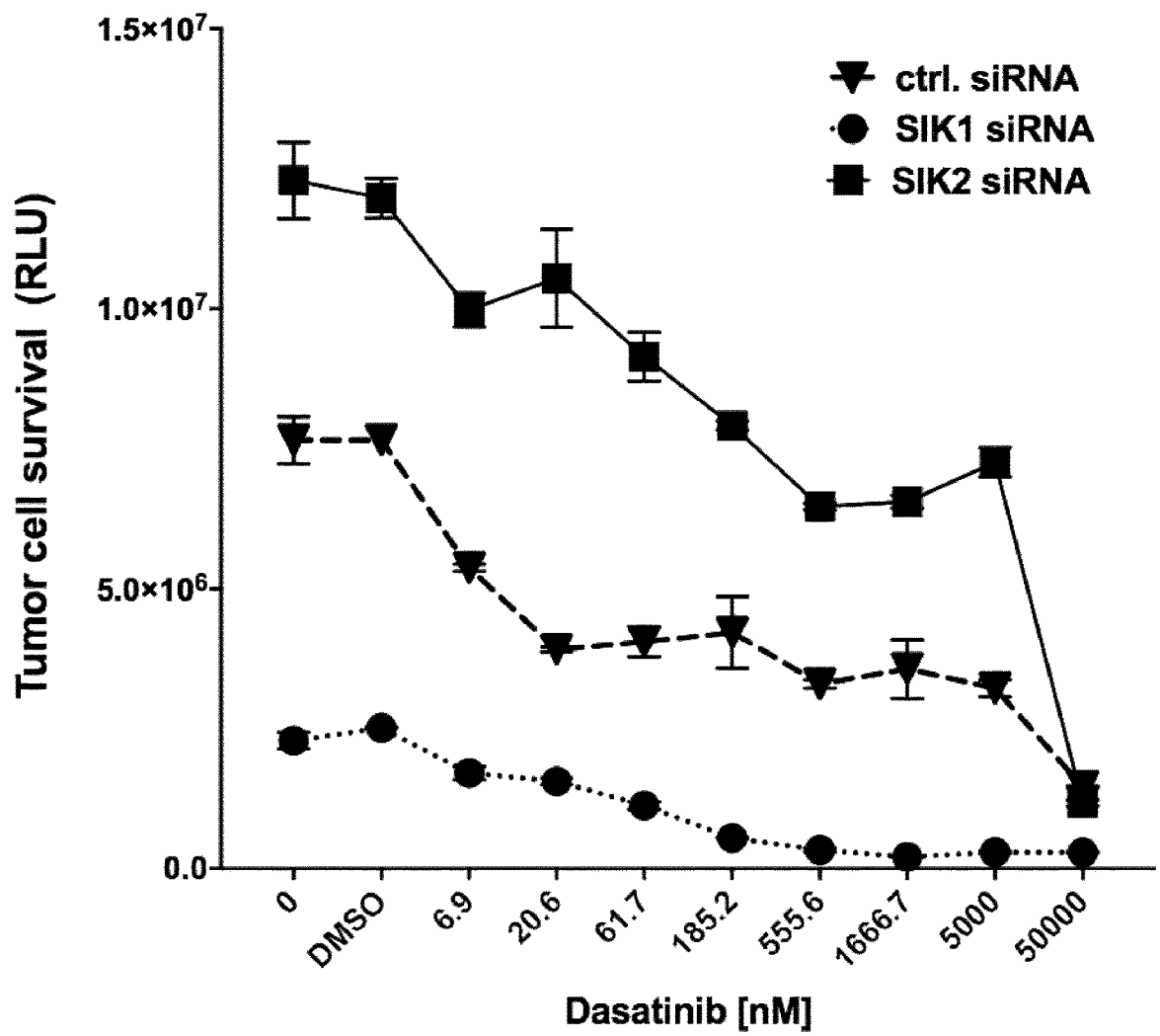

FIG. 7: (A) PANC-1 cells were co-culture with TIL #1 in the presence of increasing concentrations of the SIK inhibitor HG-9-91-01, and T cell mediated cytotoxicity was measured using the luciferase-based killing assay as in FIG. 3C. The signal between cytotoxicity to viability settings is represented as a ratio. (B) Shows the absolute signal for the two settings shown as a ratio in (A). (C) Luciferase-based cytotoxicity assay. PANC-1-luc cells were transfected with the indicated siRNAs for 72 h and then incubated with the stated concentration of dasatinib before stimulation with 100 ng/mL of rHuTNF for 18 h (or no stimulation). (D) Expression of SIK1, SIK2 and SIK3 in PANC1-luc and M579-A1-luc cells lines, as determined by qPCR (normalised to GAPDH expression). (E) Influenza (Flu) antigen-specific T cell-mediated cytotoxicity of PANC1-luc tumour cells after siRNA knock-down of each of the three SIK family members compared to siRNA knock-down of PD-L1 (and scrambled siRNA control). (F) Flu antigen-specific T cell-mediated cytotoxicity of M579-A2-luc tumour cells after siRNA knock-down of each of the three SIK family members compared to siRNA knock-down of PD-L1 (and scrambled siRNA control). (G) Effect of dasatinib on TNF-mediated cytotoxicity of M579-A2-luc tumour cells after siRNA knock-down of SIK1 and SIK2 compared to scrambled siRNA control.

Figure 8:
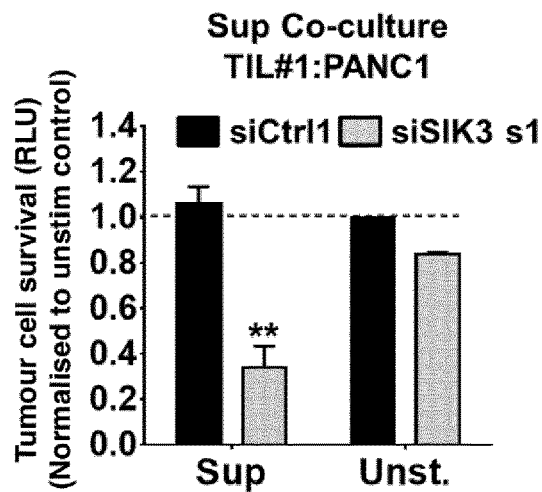
Figure 8:
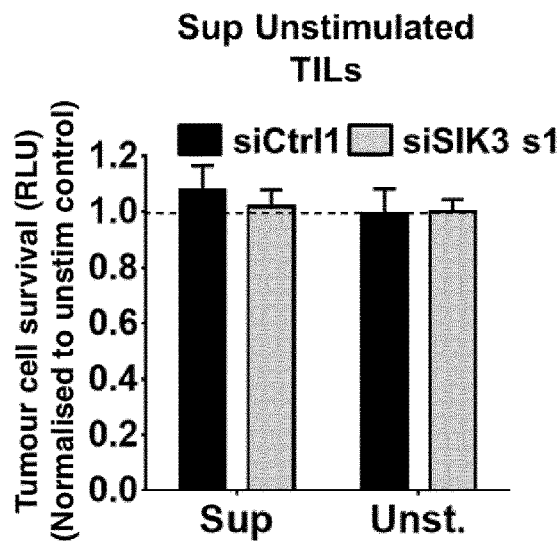
Figure 8:
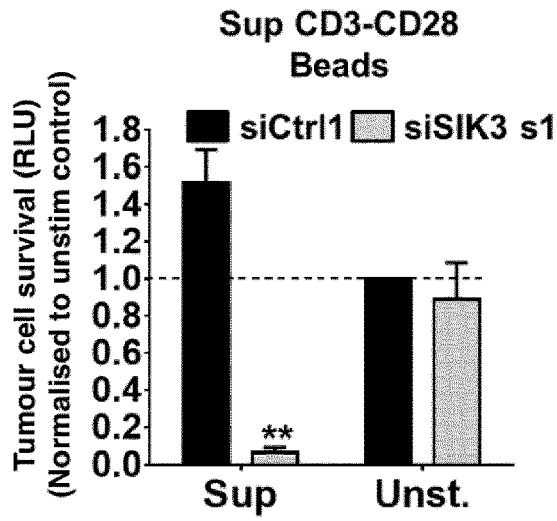
Figure 8:
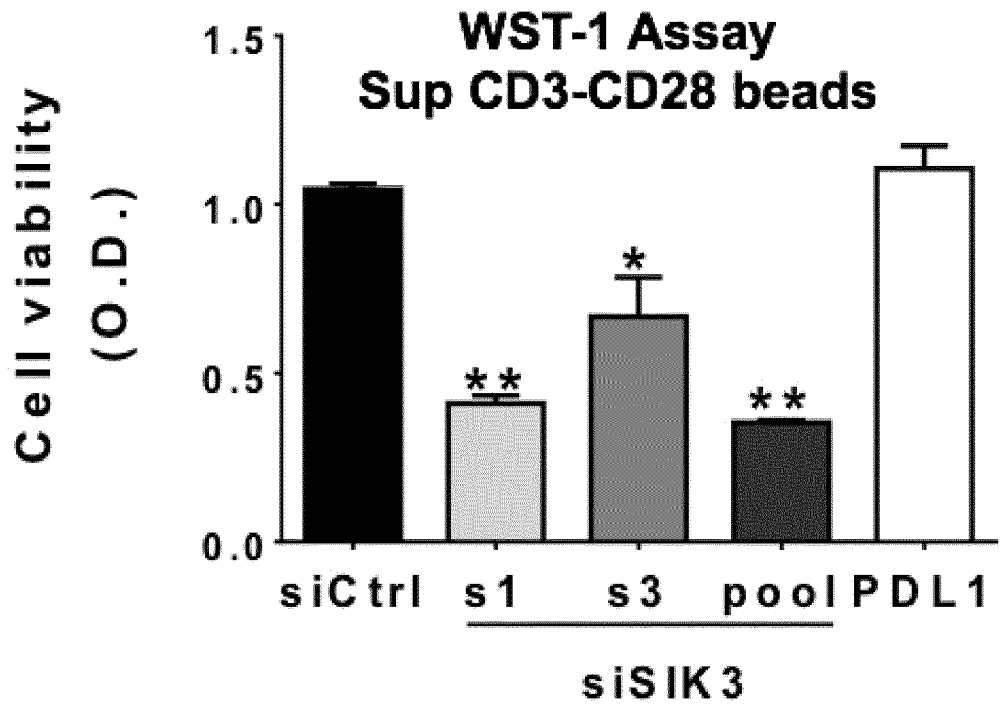
Figure 8:
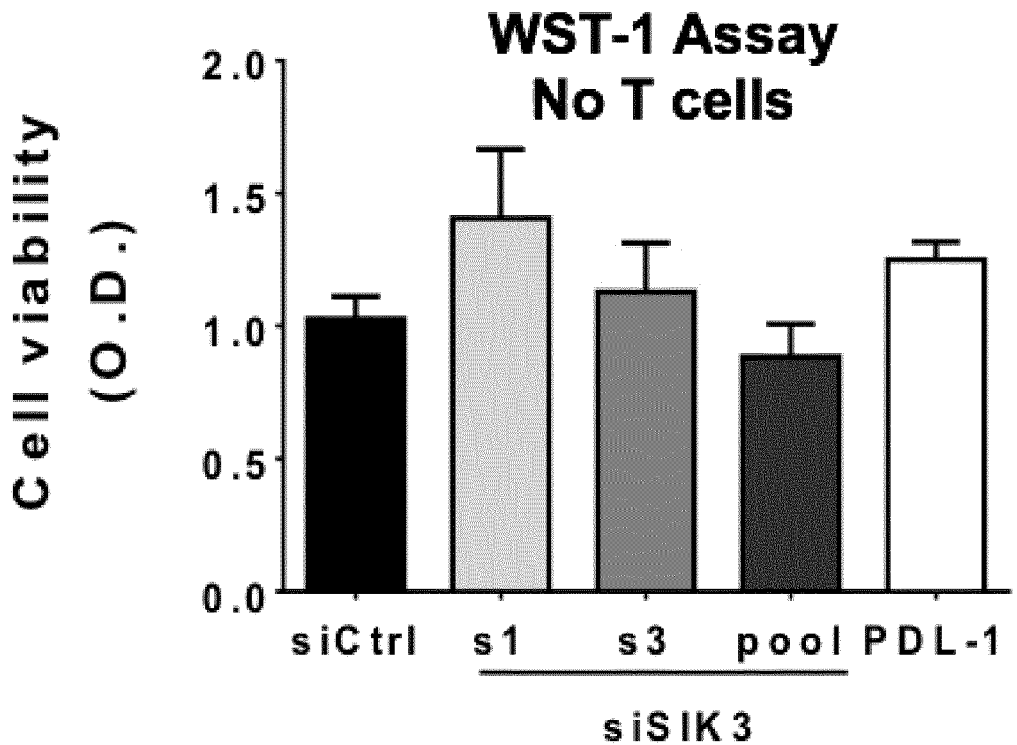

FIG. 8: PANC-1-luc cells were transfected either with single (s1, s2, or s3) or pooled (pool) siRNA sequences targeting SIK3. Scrambled siRNA was used as control (siCtrl). After 72 h, tumour cells were treated with the supernatant (Sup) of tumour-activated (A), unstimulated (B), or CD3-CD28 bead-activated T cells (C). After 20 h, the effect of the supernatant on tumour cell cytotoxicity was measured using luciferase-based killing assay. For each experiment, siRNA transfected tumour cells were treated with culture medium (Unst) as negative control, and no significant changes were observed. Graphs show the remaining luciferase activity (RLU) after stimulation with indicated supernatants represented as fold change luciferase activity compared to unstimulated siCtrl treatment. WST-1 viability assay of PANC-1 cells exposed to supernatant of either polyclonal activated T cells (D), or medium only (E), after transfection with SIK3 siRNAs for 72 h (s1, s3 or pool) compared to scrambled control siRNA (Scr1).

Figure 9:
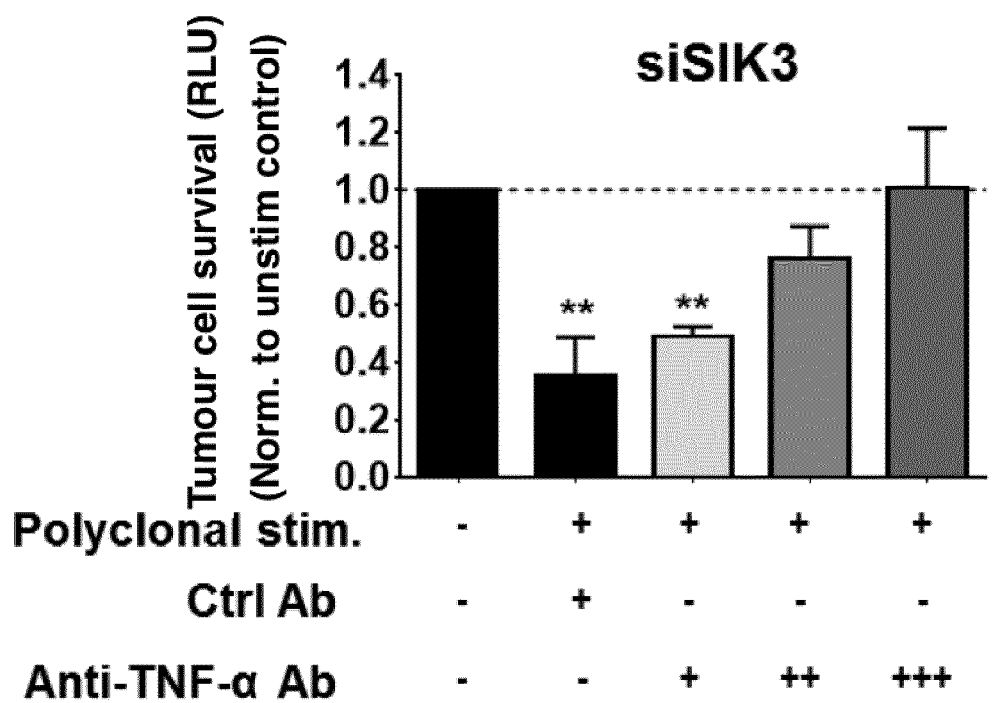
Figure 9:
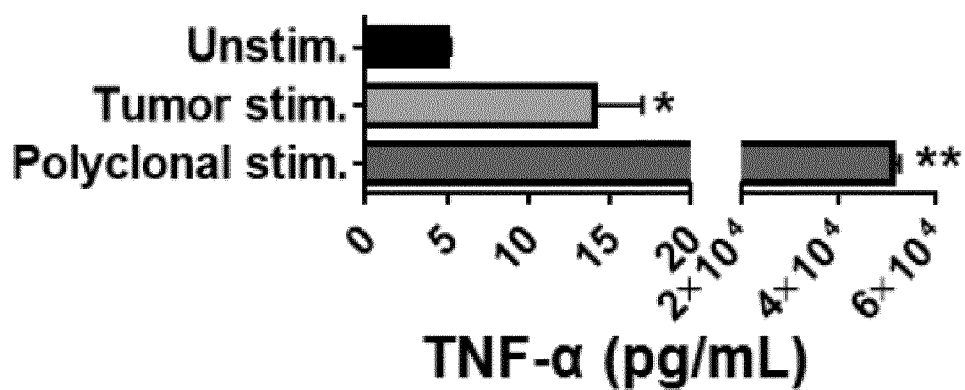
Figure 9:
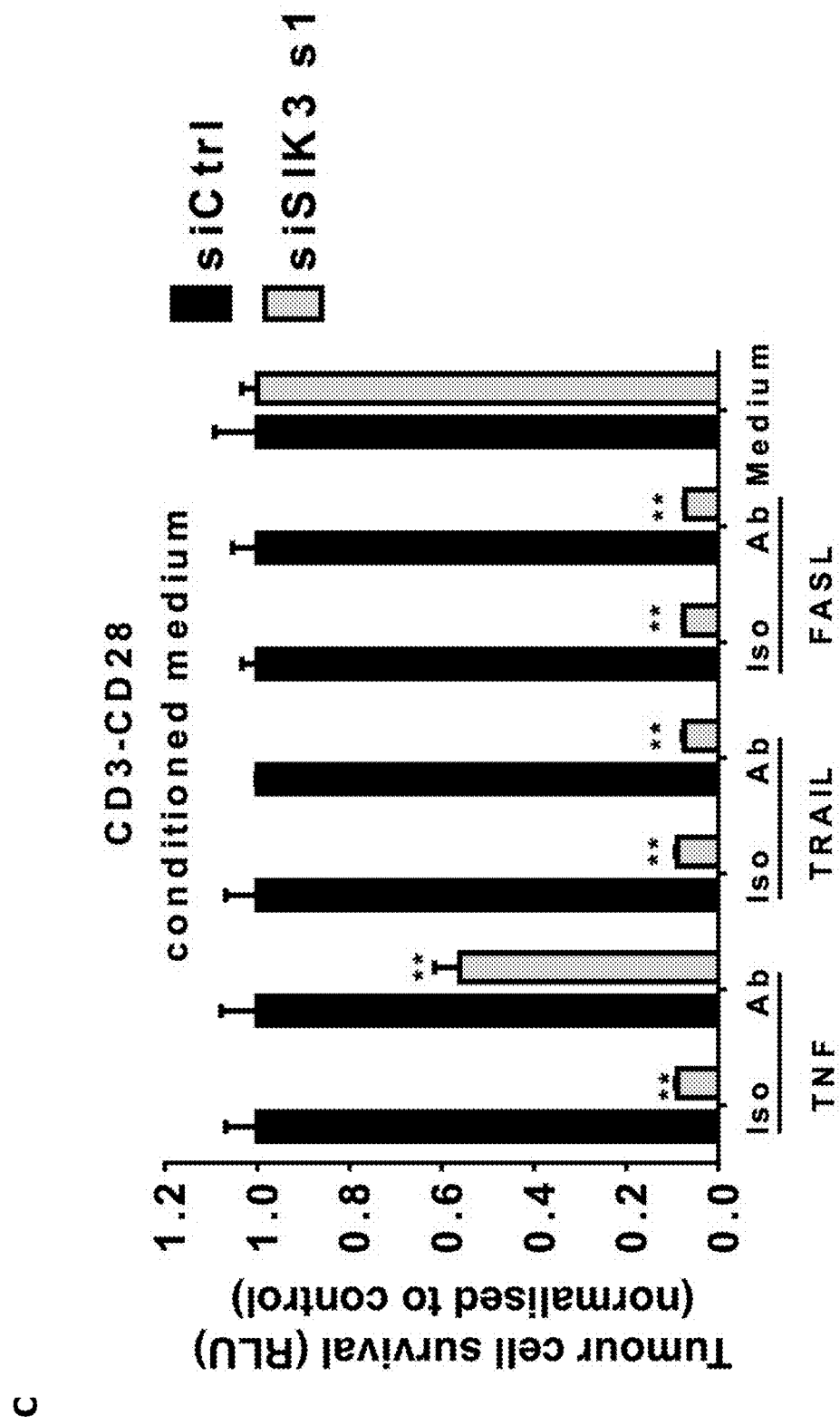

FIG. 9: (A) Supernatant from CD3-CD28 bead-stimulated T cells was incubated with 100 (+), 300 (++) or 900 (+++) ng/mL of anti-TNF neutralising antibody. Isotype control (Ctrl Ab) was used at concentration of 900 ng/mL. Afterwards, siSIK3 transfected PANC-1-luc cells were subjected to the pre-treated supernatant for 24 h and cytotoxicity was measured using luciferase-based killing assay. Graph shows normalised values of remaining luciferase activity (RLU) of tumour cells. (B) Luminex assay for detection of secreted TNF from TIL #1. TIL #1 was co-cultured either with PANC-1 cells or with CD3/CD28 beads (polyclonal stimulation). 24 h after stimulation, supernatant was collected for TNF measurement. (C) Incubation of supernatant from CD3-CD28 bead-stimulated T cells with anti-TRAIL and anti-FASL neutralising antibodies (as per (A)) did not lead to a reduction in cytotoxicity after SIK3 incubation, unlike incubation with the anti-TNF neutralising antibody.

Figure 10:
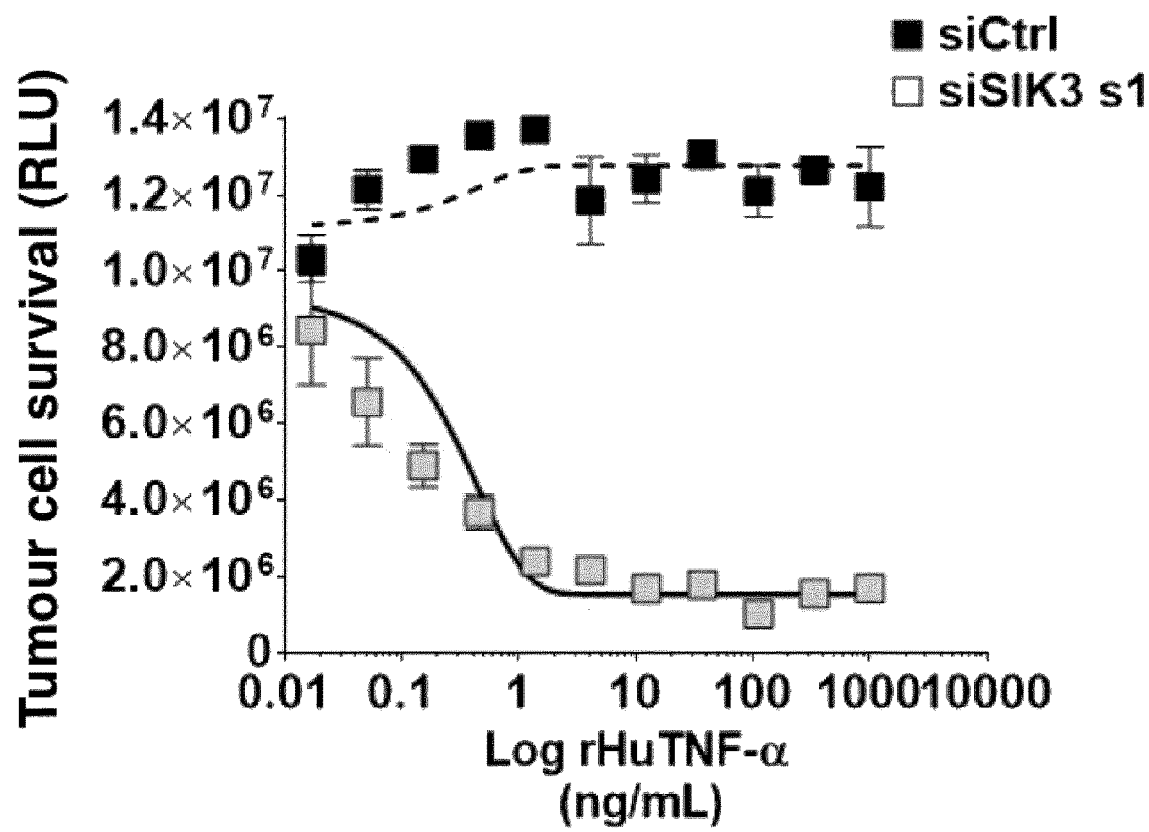
Figure 10:
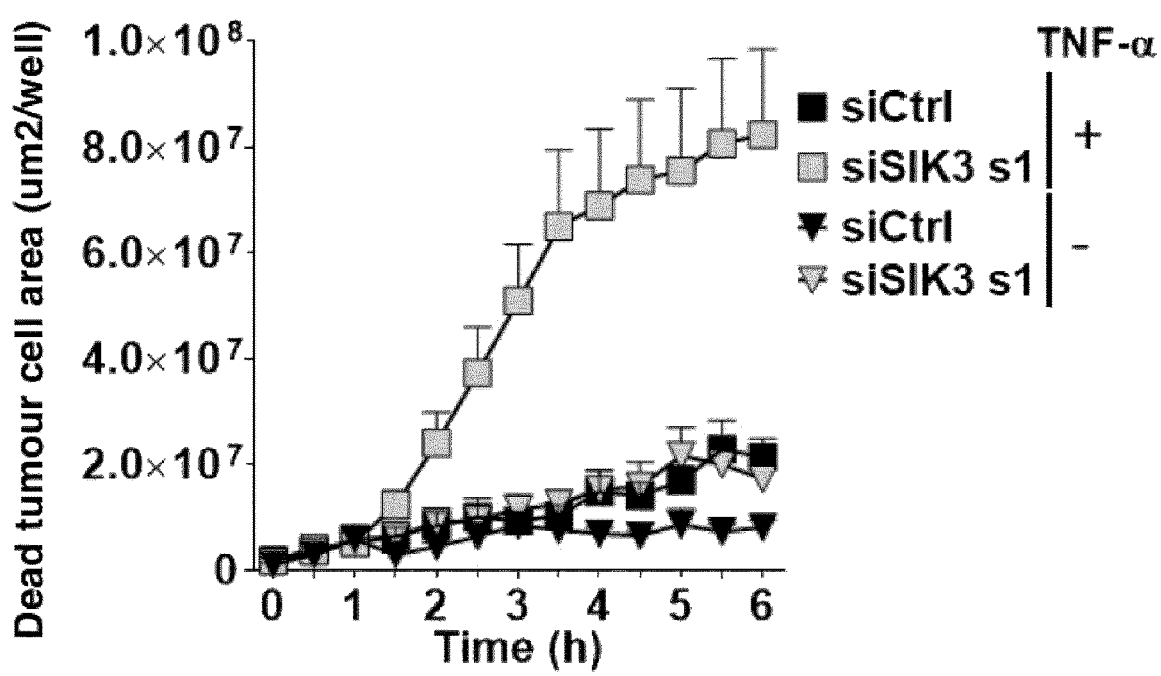

FIG. 10: (A) Dose-response effect of rHuTNF treatment on the viability of the indicated siRNA transfected PANC-1-luc cells. Cytotoxicity was measured as in (FIG. 9A). Graph shows the raw luciferase activity (RLU) of tumour cells after treatment with rHuTNF. (B) Effect of 100 ng/mL TNF treatment on the viability of PANC-1 cells after transfection with the indicated siRNA. Cell death was evaluated using real-time live cell microscopy, measuring the nuclear incorporation of YOYO-1 dye. Graph shows the area of YOYO-1+ cells/well (µm2/well) of images after 6 h stimulation, with cumulative data of 9 different pictures from the same experiment.

Figure 11:
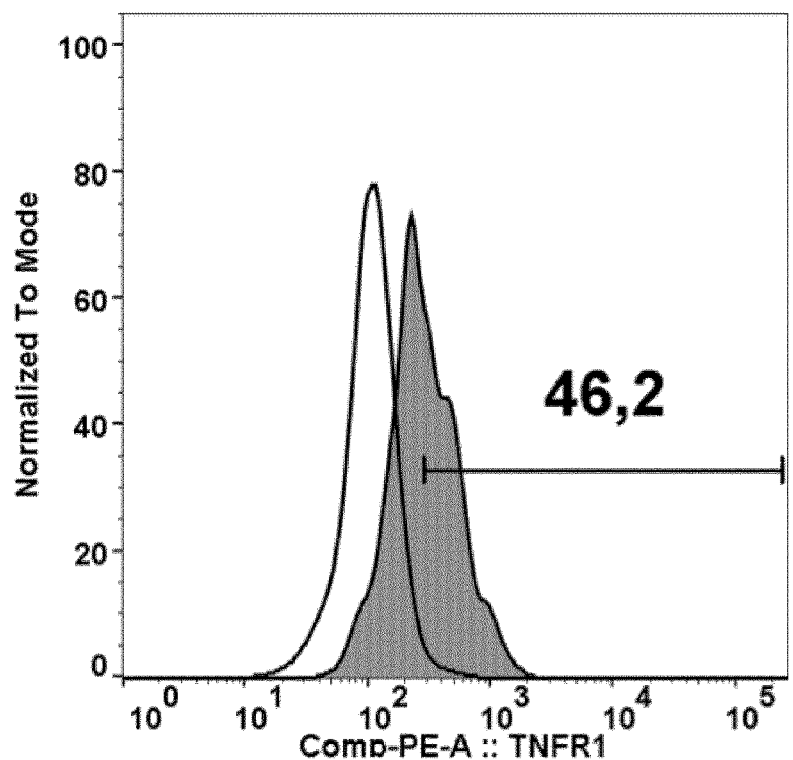
Figure 11:
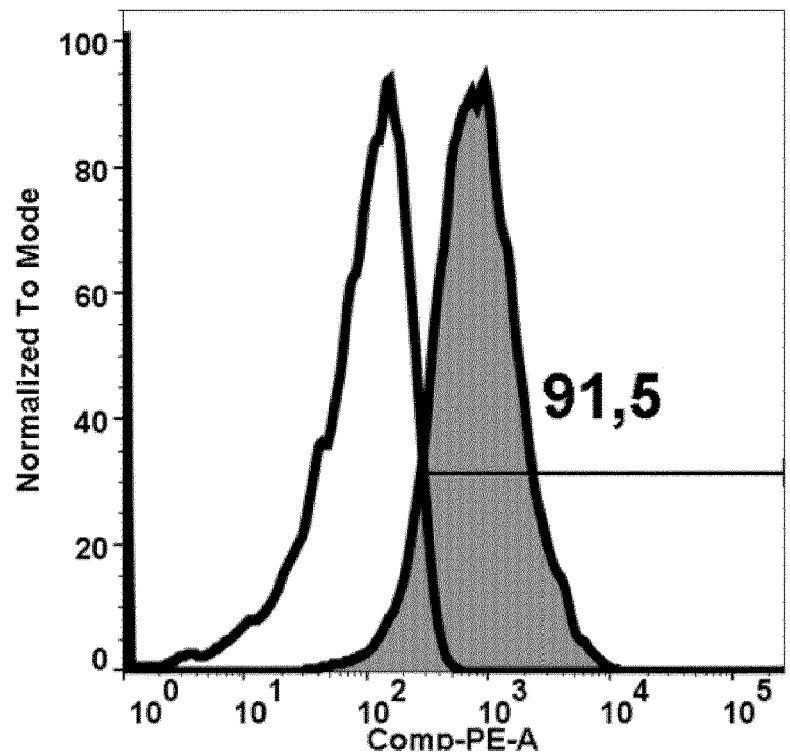
Figure 11:
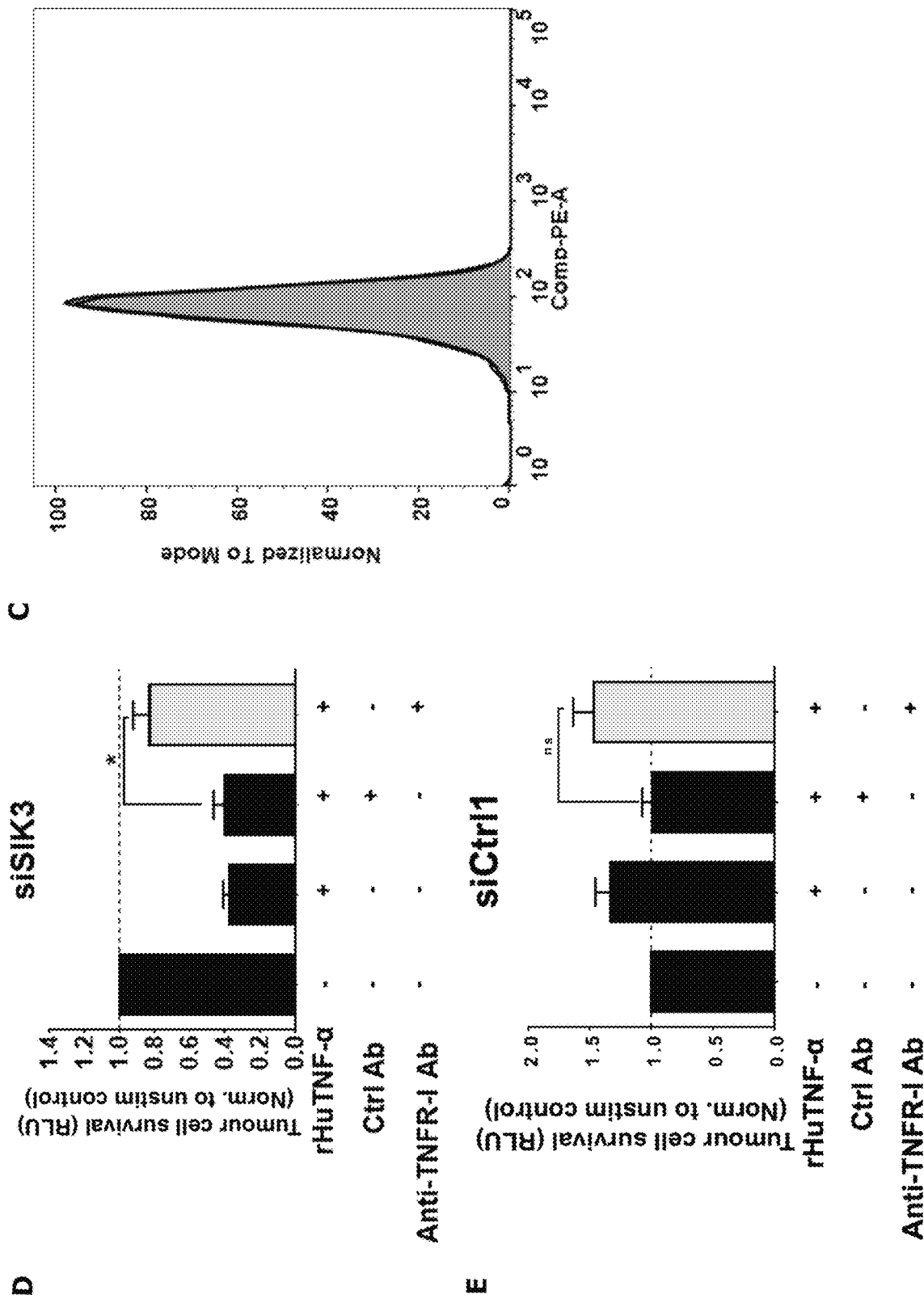

FIG. 11: (A) FACS analysis of PANC-1 cells incubated with anti-TNFR1 antibody (Hyculture GmbH, Cat No: HM2020B) detected with R-Phycoerythrin AffiniPure F(ab')2 Fragment Goat Anti-Mouse IgG (H+L) (Jackson Immuno Research, Cat No: 115-116-146 46), showing significant expression of TNFR1 by PANC-1 cells. FACS analysis of cells incubated with anti-TNFR2 antibody (Acris Antibodies GmbH, Cat No: AM20008AF-N) detected as for the anti-TNFR1 antibody, shows significant expression of TNFR2 by TILS (B), but not by PANC-1 cells (C). (D) Effect of TNF and TNFR1 blockade on SIK3 siRNA transfected PANC-1-luc cells after treatment with the 100 ng/mL of rHuTNF. Luciferase intensity was measured as in FIG. 9A. (E) Effect of TNF and TNFR1 blockade on scrambled control siRNA transfected PANC-1-luc cells after treatment with the 100 ng/mL of rHuTNF. Luciferase intensity was measured as in FIG. 9A.

Figure 12:
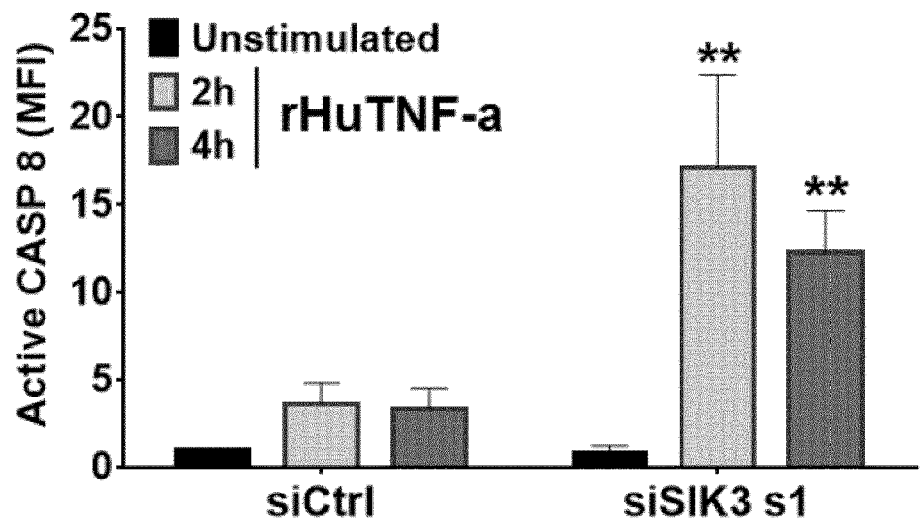
Figure 12:
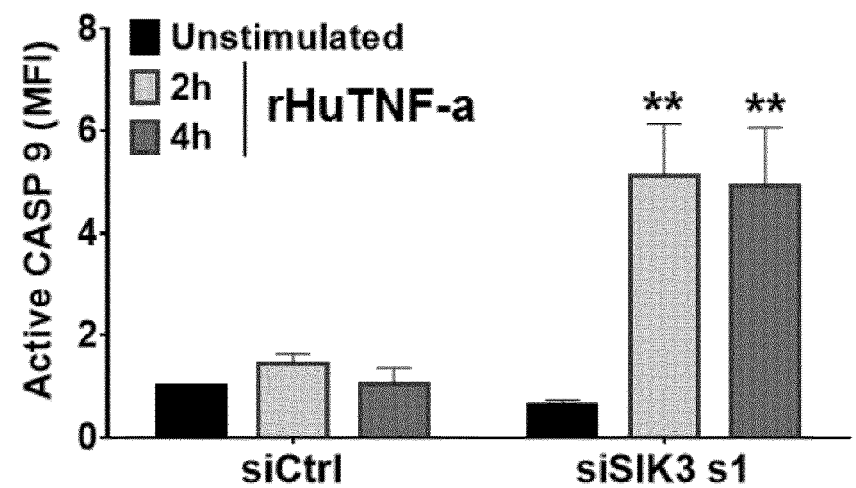
Figure 12:
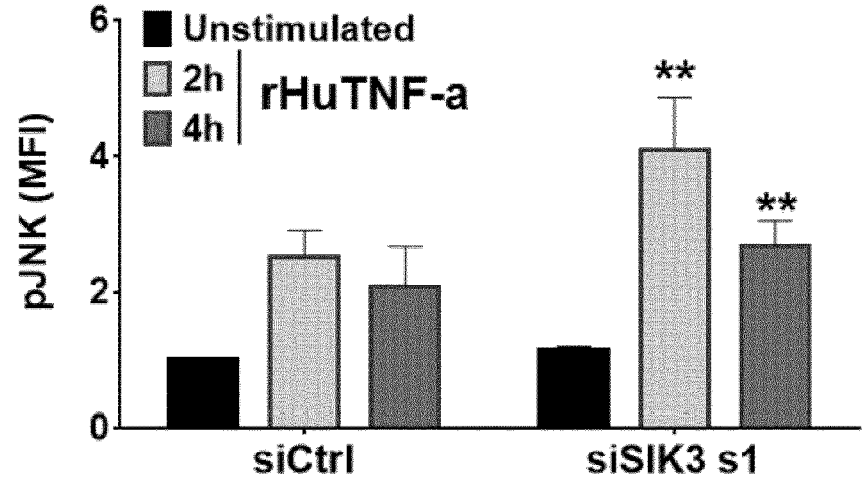

FIG. 12: SIK3 or scrambled control (siCtrl) siRNA transfected PANC-1-luc cells were treated with 100 ng/mL of rHuTNF. After the indicated time points, tumour cells were harvested and total protein fraction was isolated. Luminex assays were performed for active caspase 8 (A), active caspase 9 (B) and pJNK (C). Graphs show median fluorescent intensity (MFI) of analyte-specific beads after normalisation to GAPDH.

Figure 13:
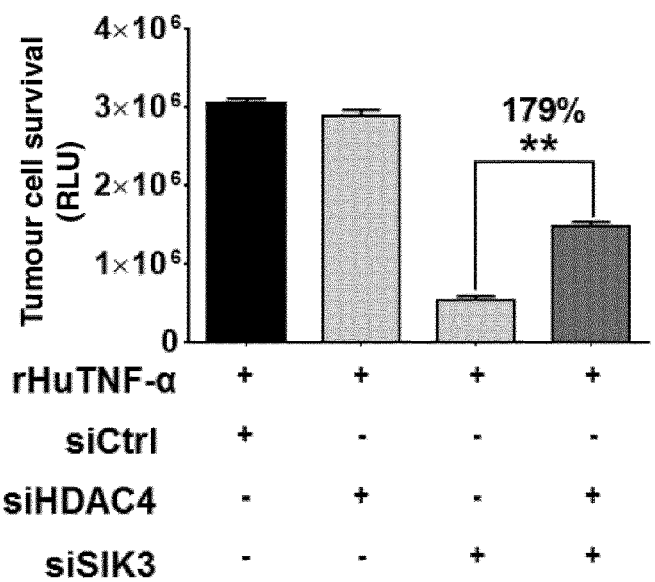
Figure 13:
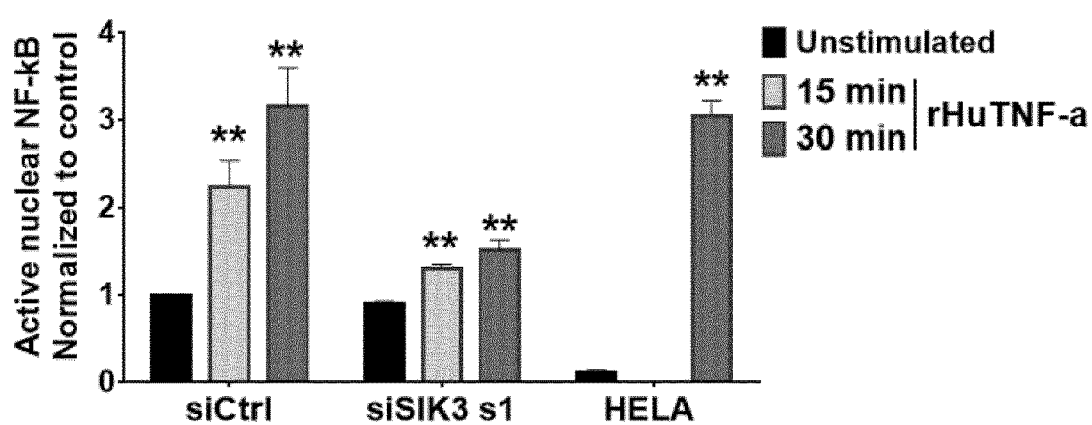
Figure 13:
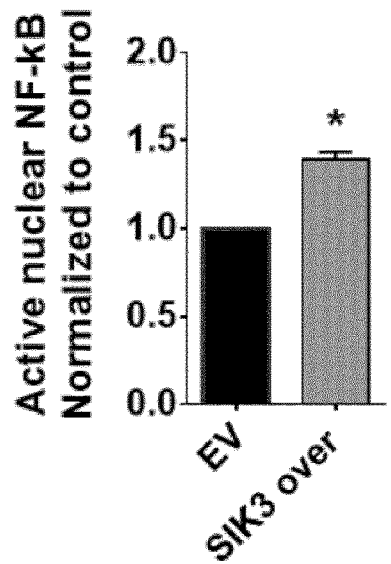

FIG. 13: (A) Luciferase-based cytotoxicity assay. PANC-1-luc cells were transfected with the indicated siRNAs for 72 h and stimulated with 100 ng/mL of rHuTNF for 24 h. Graph shows the remaining luciferase activity of tumour cells. (B) PANC-1 cells were transfected with the indicated siRNAs for 72 h prior to stimulation with 100 ng/mL rHuTNF for the indicated time points. Thereafter, ELISA was performed for detection of nuclear p65 subunit of NF-KB. Graph shows absorbance at lambda 450 nm after normalisation to unstimulated control. (C) PANC-1 cells were transiently transfected either with SIK3 overexpressing vector (SIK3 over) or with control vector (EV) for 48 h. p65 NF-KB ELISA was conducted as in (B).

Figure 14:
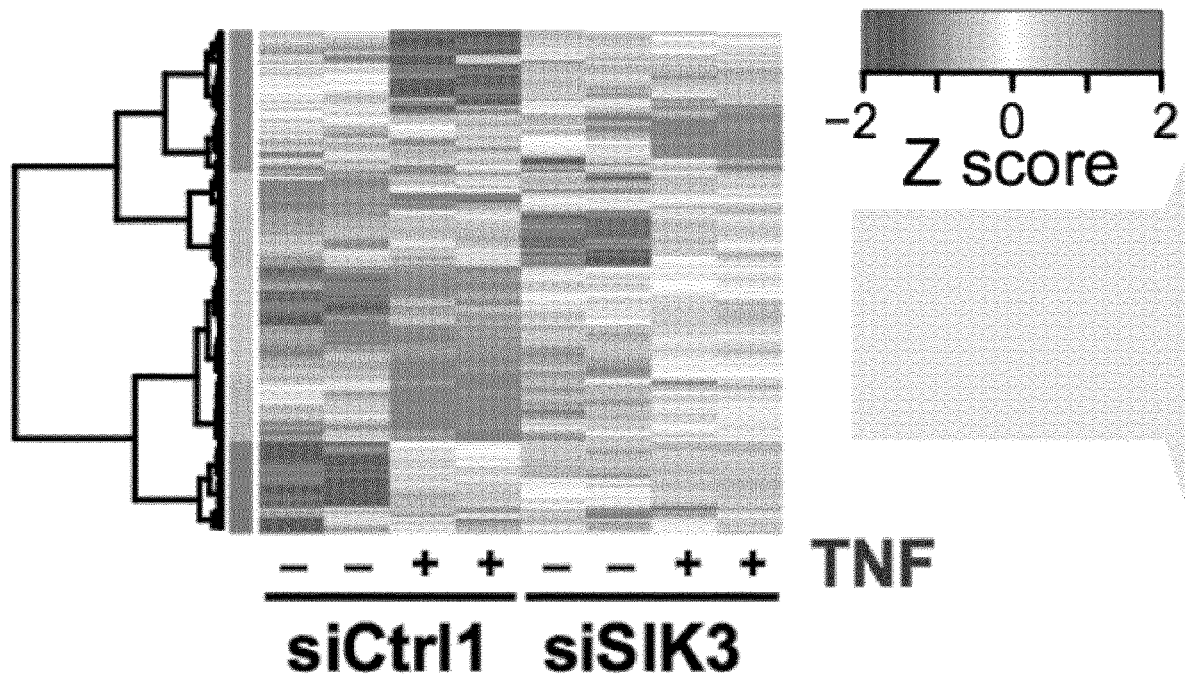

FIG. 14: Two-dimensional hierarchical clustering (Z-score transformed, normalised counts per million; Manhattan distance, Ward method) of 386 genes that were significantly regulated by TNF after 4 h and significantly affected by SIK3 knock-down by siRNA. PANC1 cells depleted of SIK3 by treatment with SIK3 siRNA (siSIK3) and control cells treated with scrambled control siRNA (siCtrl1) in each with and without exposure to TNF (each condition duplicated).

Figure 15:
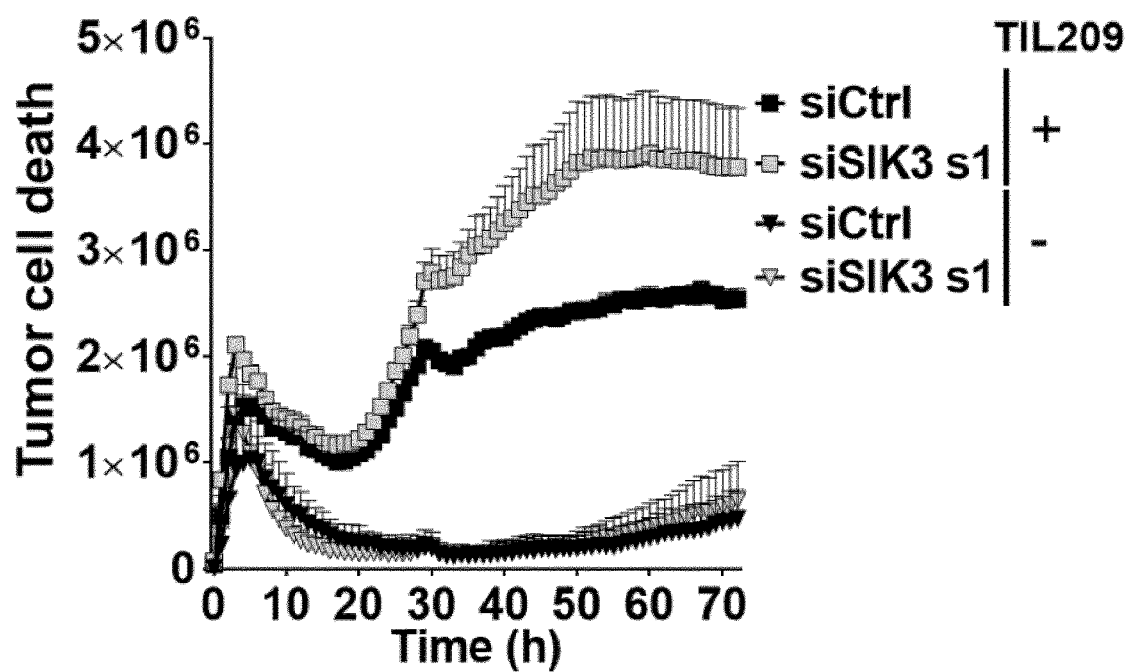

FIG. 15: Real-time live cell microscopy showing mean+/−SEM of TIL209-mediated lysis of M579 cells transduced with shCtrl or shSIK3 lentiviral constructs. The graph indicates the area of YOYO-1+ cells/well (um2/well).

Figure 16:
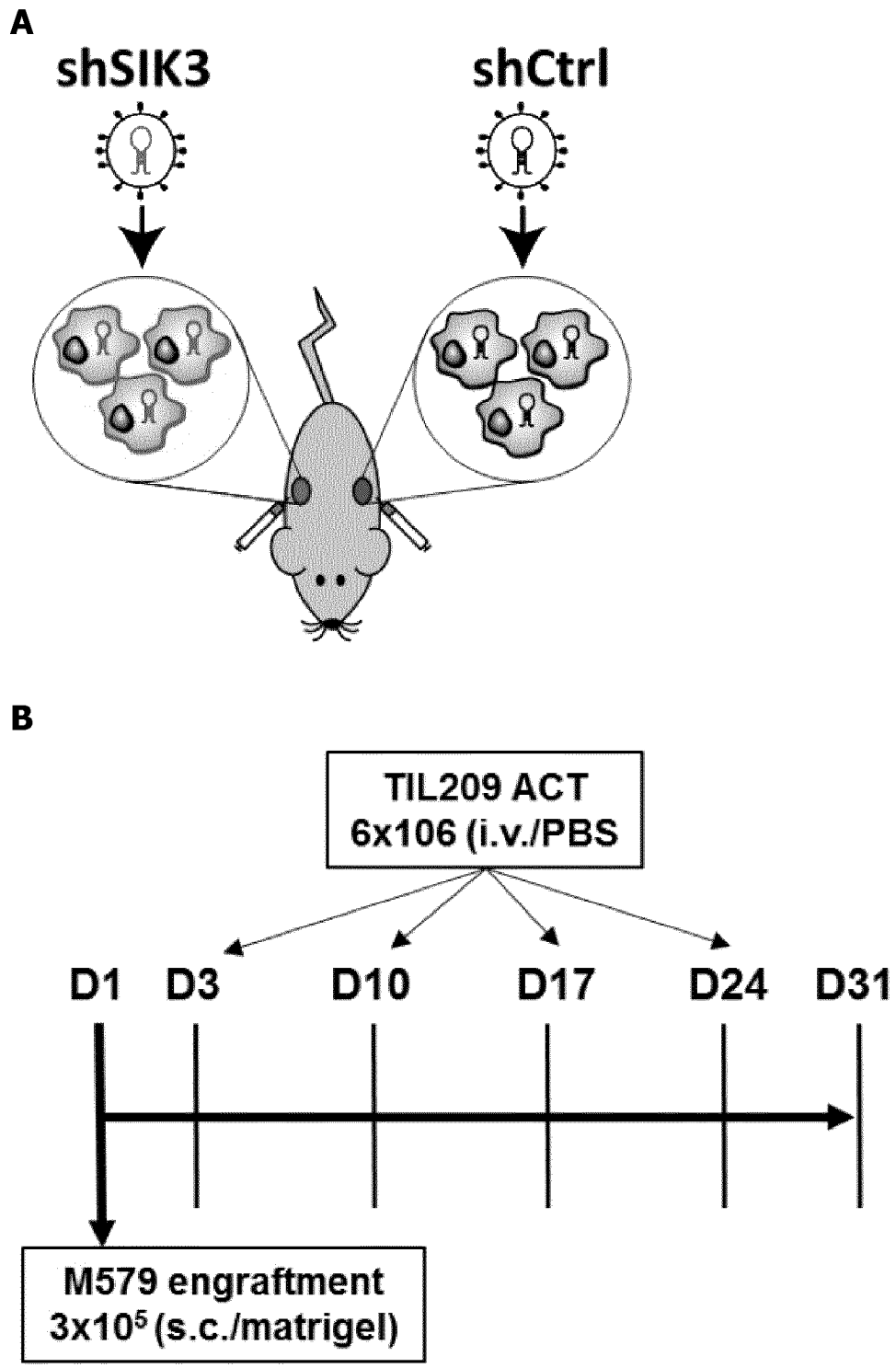
Figure 16:
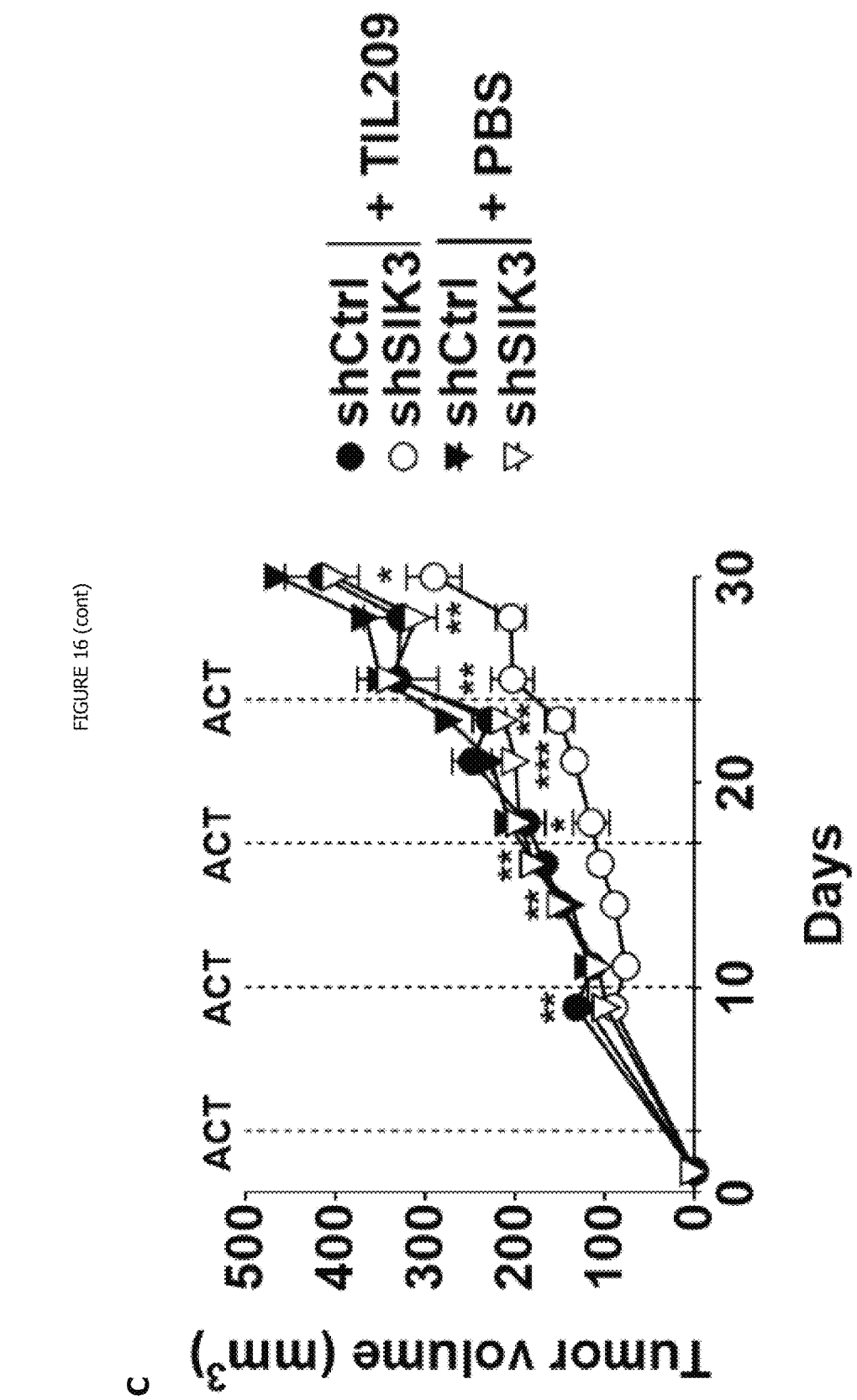

FIG. 16: (A) Schematic representation of the in vivo mouse experiment. Subcutaneous (s.c.) implantation of shCtrl or shSIK3-transduced M579 cells was applied to the left and the right flank of immunodeficient (NOD scid gamma; NSG) mice, respectively. (B) Mice received intravenous (i.v.) injection of TIL209 (n=9) or PBS alone (n=7) at day 3, 10, 17 and 24. (C) Tumour growth curves showing mean+/−SEM of tumour volume (mm3) of shCtrl or shSIK3-engrafted M579 tumours in mice treated with either TIL209 or PBS. Statistical difference was calculated using unpaired one-side Mann-Whitney U-test. (D) Binding of TNF to TNFR1 (TNFR-I) on tumour cells results in downstream signalling cascade that involve caspase 8 cleavage, NF-kappaB nuclear translocation and SIK3 phosphorylation. NF-kappaB nuclear retention is sustained by its acetylation, and HDAC4 deacetylase acts as negative regulator of NF-kappaB. TNF stimulation increases the levels of pLKB1 which in turn results in increased SIK3 activation. SIK3 phosphorylates HDAC4, thereby initiating its shuttling from the nucleus to the cytoplasm. The lack of nuclear HDAC4 sustains NF-kappaB nuclear retention. Nuclear NF-kappaB leads to the transactivation of pro-survival and anti-apoptotic genes, which in turn impede caspase 8 activation.

Figure 17:
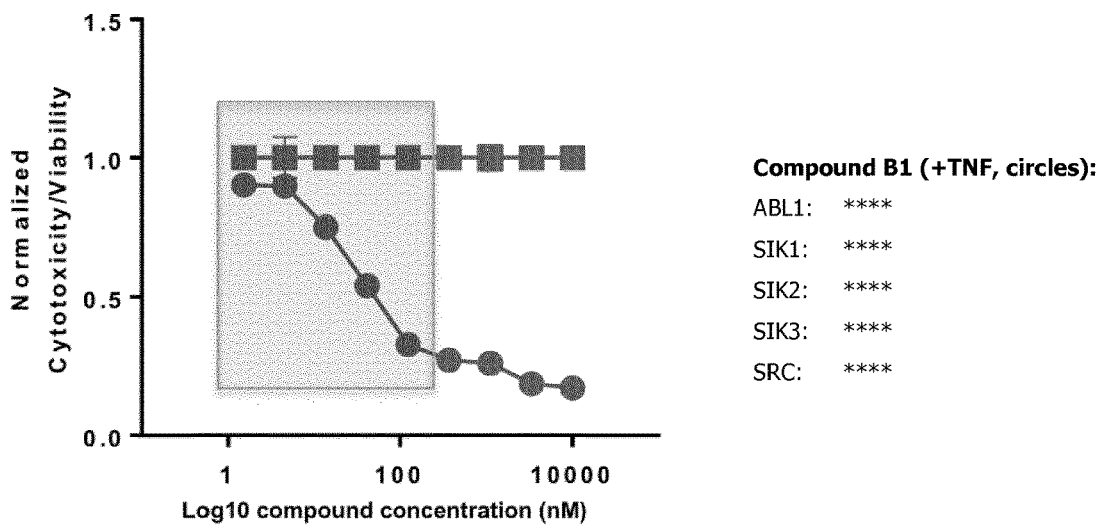
Figure 17:
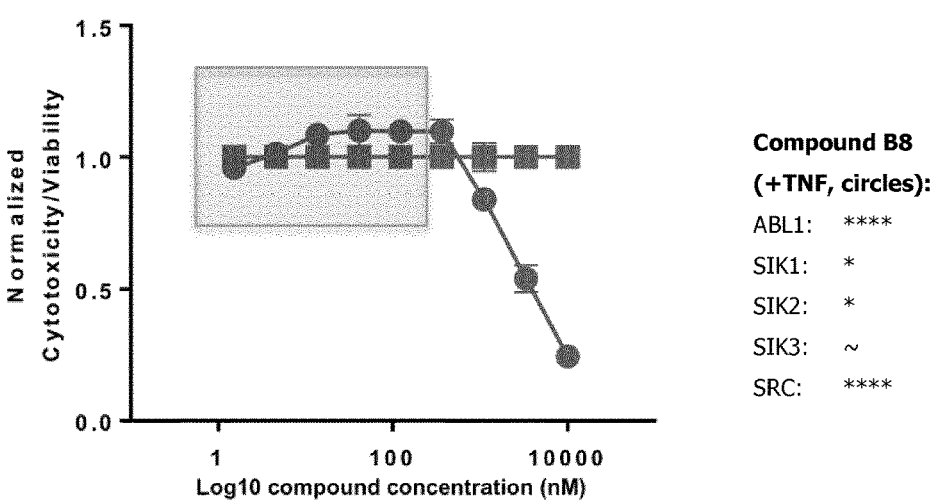
Figure 17:
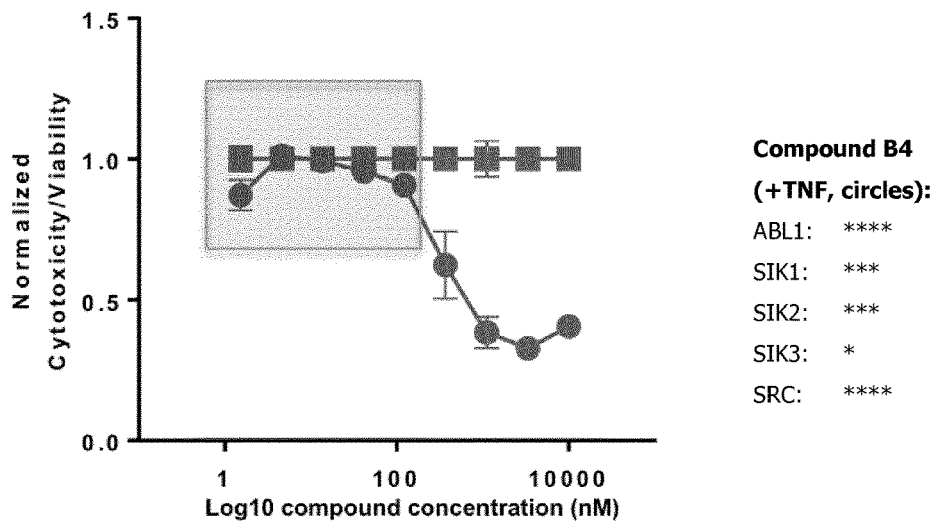

FIG. 17: Relative tumour cell survival (Normalised RLU by cytotoxicity/viability) of certain compounds of general formula 1 in the assay using M579-A1-luc described in Example 9 at various concentrations either alone (squares) or in combination with 10 ng/mL of TNF (circles). Also shown are indicative inhibitory activities of the compound for SIK-family members and for the related kinases ABL1 and SRC, shown with the indicators used for Table 4. (A) The pan-SIK and ABL1 & SRC inhibitor, compound B1; (B) The ABL1 & SRC inhibitor, compound B8. (C) The SIK1, SIK2 and ABL1 & SRC inhibitor, compound B4.

Figure 18:
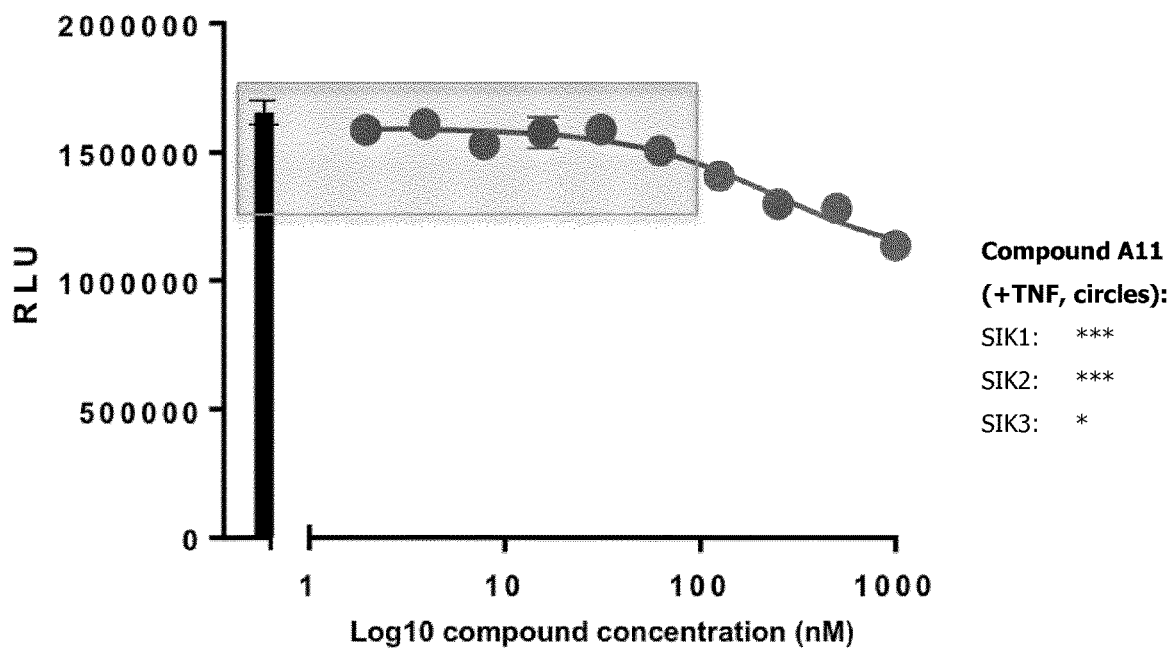
Figure 18:
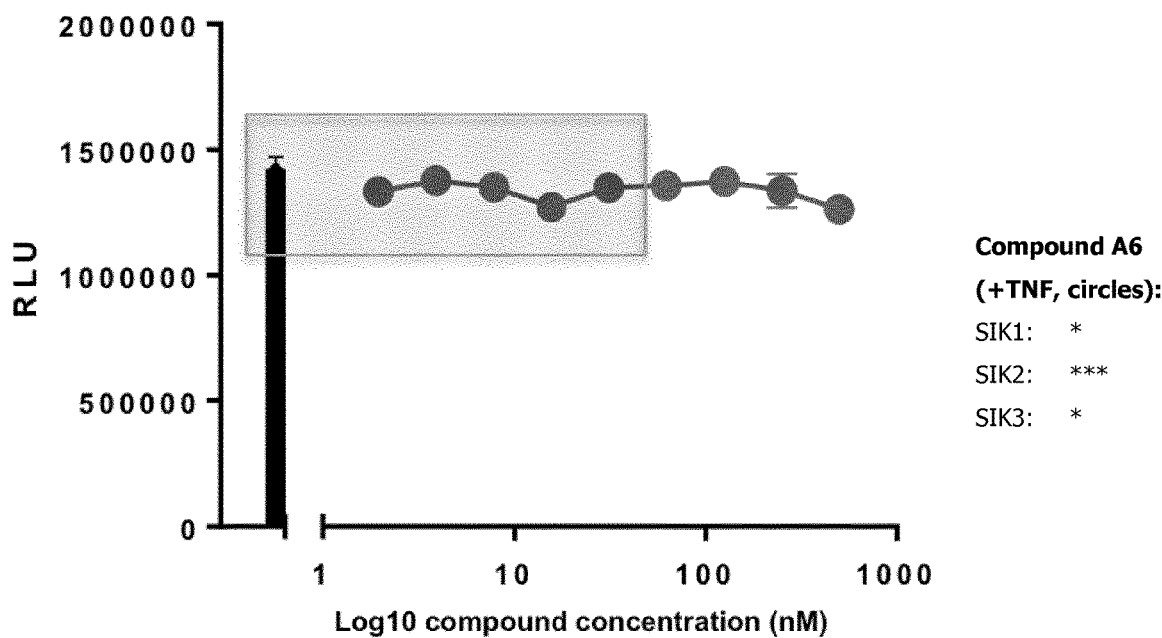

FIG. 18: M579 A2 tumour cell survival (RLU) in the luc assay for SIK-family member selective inhibitors in combination with 10 ng/mL. (A) The strong SIK1 and SIK2 inhibitor but weak SIK3 inhibitor, compound A11. (B) The strong SIK2 inhibitor but weak SIK3 and weak SIK1 inhibitor, compound A6.

The present invention, and particular non-limiting aspects and/or embodiments thereof, can be described in more detail as follows:

In a first aspect, and as may be further described, defined, claimed or otherwise disclosed herein, the invention relates to a method for the treatment of a proliferative disorder in a subject by inhibiting SIK3, the method comprising administering a SIK3 inhibitor to the subject.

In one alternative first aspect, and as may be further described, defined, claimed or otherwise disclosed herein, the invention relates to a method for the treatment of a proliferative disorder in a subject by sensitising cells involved with the proliferative disorder to a cell-mediated immune response, the method comprising administering a SIK3 inhibitor to the subject.

In another alternative first aspect, and as may be further described, defined, claimed or otherwise disclosed herein, the invention relates to a method for the treatment of a proliferative disorder in a subject, by inhibiting SIK3 and (for example, thereby) sensitising cells involved with the proliferative disorder to a cell-mediated immune response, the method comprising administering a SIK3 inhibitor to the subject.

In one related first aspect, and as may be further described, defined, claimed or otherwise disclosed herein, the invention relates to an inhibitor of SIK3 for use in the treatment of a proliferative disorder in a subject, wherein the treatment involves (eg is mediated by): (i) sensitising cells involved with the proliferative disorder to a cell-mediated immune response; and/or (ii) inhibiting SIK3. In another related first aspect, and as may be further described, defined, claimed or otherwise disclosed herein, the invention pertains to a use of a SIK3 inhibitor for the manufacture of a medicament for the treatment of a proliferative disease in a subject, wherein the treatment involves (eg is mediated by): (i) sensitising cells involved with the proliferative disorder to a cell-mediated immune response; and/or (ii) inhibiting SIK3. Preferably the manufacture of the medicament includes a step of preparing, formulating, or otherwise providing, the SIK3 inhibitor in a form suitable for specific delivery of the SIK3 inhibitor to cells involved with the proliferative disorder. In certain embodiments of these related embodiments, in such treatment the inhibitor: (i) sensitises the cells involved with the proliferative disorder to the cell-mediated immune response; and/or (i) inhibits SIK3. In certain of such embodiments, the SIK3 inhibitor is one capable of: (i) sensitising cells involved with the proliferative disorder to a cell-mediated immune response; and/or (ii) inhibiting SIK3.

In a further aspect, and as may be further described, defined, claimed or otherwise disclosed herein, the invention relates to a method for the sensitisation of cells involved with a proliferative disorder to a cell-mediated immune response in the treatment of the proliferative disorder in a subject, the method comprising administering a SIK3 inhibitor to the subject; and in another further aspect, and as may be further described, defined, claimed or otherwise disclosed herein, the invention relates to a method for the inhibition of SIK3 in the treatment of a proliferative disorder in a subject, the method comprising administering an SIK3 inhibitor to the subject.

In a related further aspect, and as may be further described, defined, claimed or otherwise disclosed herein, the invention relates to an inhibitor of SIK3 (eg, a SIK3 inhibitor) for use as a medicament for: (i) sensitising cells involved with a proliferative disorder to a cell-mediated immune response; and/or (ii) inhibiting SIK3.

In yet a related further aspect, and as may be further described, defined, claimed or otherwise disclosed herein, the invention relates to a SIK3 inhibitor for use as a medicament (eg an immuno-oncology medicament) sensitising cells involved with a proliferative disorder (such as a tumour or cancer) to a cell-mediated immune response, for example sensitising cells involved with a proliferative disorder to killing (cell-death) that may be induced by the cell-mediated immune response. An "immune-oncology" medicament is one that would be recognised by the person of ordinary skill, and includes a medicament that is intended to (eg, specifically designed to) enhance one or more components of the immune system of an organism (such as a human) towards cancerous or tumorous cells present in such organism. An immune-oncology medicament may be one (eg an antibody) than binds to an extrinsic immune (inhibitory) checkpoint molecule (such as one described elsewhere herein) and that (eg directly) suppresses T cell function against the cancerous or tumorous cells, or an immune-oncology medicament may be one that inhibits an immune regulator (such as SIK3, as in the present invention) that is intrinsic to the cancerous or tumorous cells where such intrinsic immune regulator does not actively (eg directly) suppress T cells but rather protects the tumour or cancer cells from an immune response via a resistance mechanism.

In particular embodiments of such aspects, the cells involved with a proliferative disorder may be sensitised to killing (cell-death) by (such as induced by) the cell-mediated immune response.

"Salt-inducible kinase 3" or "SIK3" (synonyms QSK and KIAA0999) is a member of a subfamily of serine/threonine protein kinases including SIK1, SIK2, and SIK3 that belong to an AMP-activated protein kinase (AMPK) family. A SIK3 protein in context of the invention is, typically, a protein kinase. Pertinent information on the human SIK3 protein is accessible on UniProt: Q9Y2K2 (Entry version 138 of 15 Mar. 2017) and a SIK3 protein in context of the invention has, preferably, the domain structure shown in FIG. 1, and more preferably comprises an amino acid sequence shown in any of SEQ ID NOs: 1 to 4 (SIK3, Entry version 138 of 15 Mar. 2017) or in any of SEQ ID NOs 13 to 16 (SIK3, Entry version 144 of 28 Mar. 2018), in particular of SEQ ID NOs: 1 or 13. SIK3 is a cytoplasmatic protein with serine/threonine kinase activity which is regulated through phosphorylation of a conserved threonine residue (position 163) in the T-loop of the kinase domain by the LKB1 complex; a phosphorylation which is reported as essential for catalytic activity of SIK3 (Lizcano, J. M. et al.; EMBO J. 23, 833-843 (2004)). For the purposes of the herein disclosed invention the term "phosphorylated SIK3" shall denote a SIK3 protein that is phosphorylated substantially as SIK3 protein can be (eg is) phosphorylated by LKB1, wherein preferably such phosphorylated SIK3 comprising a phosphor-threonine at amino acid position 163. A phosphorylated SIK3 in context of the invention is an SIK3 protein that is activated in its cell-biological context. At least four protein isoforms (SIK3-001 to SIK3-004) generated by alternative splicing of the SIK3 gene product are known. The human SIK3 gene is located at chromosomal position 11q23.3 (HGNC gene Symbol Acc: HGNC:29165), and is conserved in many species such as in chimpanzee, Rhesus monkey, dog, cow, mouse, rat, chicken, zebrafish, and frog. The term SIK3 in some embodiments of the invention may also pertain to variants of the human SIK3 protein having an amino acid sequence that is substantially identical to, or of at least 80%, preferably 85%, more preferably 90, 95, 96, 97, 98, 99, or 100% sequence identity to, the amino acid sequence shown in any of SEQ ID NO: 1 to 4 or in any of SEQ ID NOs 13 to 16, in particular of SEQ ID NOs: 1 or 13, as determined using, e.g., the "Blast 2 sequences" algorithm described by Tatusova & Madden 1999 (FEMS Microbiol Lett 174: 247-250), and which (preferably) retain biological activity identical or substantially identical to the respective reference SIK3 (eg to phosphorylate one or more class II (eg IIa) HDACs, such as HDAC4). Preferred variants of SIK3 protein comprise sequence variants thereof due to sequence polymorphism between and within populations of the respective species, as well as mutations compared to the wild-type sequence of SIK3 which are located in or in close proximity to the activity loop or activation loop (T-loop) of SIK3. A preferred variant of SIK3 protein is a SIK3 T163 mutation, such as a mutation affecting the activation of SIK3. In preferred embodiments a SIK3 protein of the invention is not a SIK (synonyms: SIK and SNF1LK) protein and/or is not a SIK2 (synonyms: QIK, KIAA0781 and SNF1LK2) protein. The amino acid sequence of human SIK1 (UniProt: P57059; entry version 168 of 15 Mar. 2017) and human SIK2 (UniProt: Q9HOK1; entry version 153 of 15 Mar. 2017) are shown in SEQ ID NO: 5 and 6, respectively. The term SIK3 can mean, as applicable to the context (if not more specifically indicated), a SIK3 protein (such as one described above) or an mRNA molecule encoding such a SIK3 protein. The analogous meaning with respect of "SIK1" and "SIK2" is to be understood.

An "inhibitor of SIK3" (or "SIK3 inhibitor") is any moiety that inhibits SIK3, which can mean inhibition of the expression (eg the amount), function, activity and/or stability of SIK3, especially of mRNA and/or protein of SIK3, and in particular of phosphorylated SIK3. A SIK3 inhibitor may impair, suppress, reduce and/or lower the expression of SIK3 (eg SIK3 mRNA or protein) in a cell. The term "expression" means in this context the cellular process of transcribing a gene into an mRNA and the following translation of the mRNA into a protein (and in certain embodiment, the subsequent transport and localisation of such protein). "Gene expression" therefore may thus refer only to the generation of mRNA, irrespectively from the fate of the so produced mRNA, or alternatively/additionally to the translation of the expressed mRNA into a protein (or transport and localisation of such protein). The term "protein expression" on the other hand may refer to the complete cellular process of synthesis of proteins and/or transport/localisation thereof into certain cellular compartments. A SIK3 inhibitor may impair (eg, induces a decrease or reduction in) the efficiency, effectiveness, amount or rate of one or more activities of SIK3 (for example, by impairing the expression of SIK3 protein and/or amount of phosphorylated SIK3 protein), such as one or more of those activities described herein, for example, the activity of SIK3 to phosphorylate class II (eg IIa) HDACs (eg HDAC4) and/or to sensitise a cell involved with a proliferative disorder to a cell-mediated immune response. A SIK3 inhibitor may have a negative effect towards the stability of SIK3 (eg SIK3 mRNA or protein), which shall be understood in its broadest sense, and shall include inhibitors which, for example, interfere with and reduce the SIK3 protein half-life or interfere with and disturb SIK3 protein folding, protein presentation or transport/localisation within the cell.

Such a SIK3 inhibiting moiety can act directly, for example, by binding to SIK3 and decreasing the amount or rate of one or more of the properties of SIK3 such as its expression, function and/or stability, in particular its ability to act as a kinase (eg to phosphorylate HDAC4), for example by reducing the amount or activity of phosphorylated SIK3 in the cell. A SIK3 inhibitor may also decrease the amount or rate of SIK3 function or activity by impairing its expression, stability, for example, by binding to SIK3 protein or mRNA and modifying it, such as by removal or addition of a moiety, or altering its three-dimensional conformation; and by binding to SIK3 protein or mRNA and reducing its stability or conformational integrity. A SIK3 inhibitor may, alternatively, act indirectly, for example, by binding to a regulatory molecule or gene region to modulate such regulatory protein or gene region function and hence consequentially affect a decrease in the amount or rate of SIK3 expression (eg amount), function/activity and/or stability, in particular by impairing one or more activity of SIK3 protein or mRNA (such as by changing the amount or rate of expression and/or stability of SIK3 protein or mRNA). Thus, an SIK3 inhibitor can act by any mechanisms that impair, such as result in a decrease in, the amount or rate of SIK3 expression (eg amount), function/activity and/or stability. Non-limiting examples of SIK3 inhibitors that act directly on SIK3 include: (i) siRNA or shRNA molecules that bind to and reduce expression of SIK3 mRNA; and (ii) small molecule moieties that bind to the catalytic domain of SIK3 and reduce the kinase activity of SIK3. Non-limiting examples of SIK3 inhibitors that act indirectly on SIK3 include: (i) siRNA or shRNA molecules that bind to and reduce expression of LKB1 mRNA; and (ii) small molecule moieties that bind to the catalytic domain of LKB1 and reduce the kinase activity of LKB1, that in each case by reduction in the amount or activity of LKB1 protein, consequential reduce the amount (and hence activity) of phosphorylated SIK3 protein. An indirect SIK3 inhibitor may also be, for example, an antagonist (such as a blocking antibody) to the glucagon receptor (or insulin receptor), which then decreases the amount and/or activity of SIK3 (or phospho-SIK3) protein in the cell.

General and specific examples of SIK3 inhibitors are described elsewhere herein, including those as may be characterised by the applicable functional and/or structural features set out herein.

As used herein, a "subject" includes all mammals, including without limitation humans, but also non-human primates such as cynomolgus monkeys. It also includes dogs, cats, horses, sheep, goats, cows, rabbits, pigs and rodents (such as mice and rats). It will be appreciated that a particularly preferred subject according to the invention is a human subject, such as a human suffering from (or at risk of suffering from) a disorder, disease or condition, for example a human patient.

As used herein, "therapy" is synonymous with treating a disease, disorder or condition, which includes reducing symptoms of the disease, disorder or condition, inhibiting progression of the disease, disorder or condition, causing regression of the disease, disorder or condition and/or curing the disease, disorder or condition.

The term "treatment" in the present invention is meant to include therapy, e.g. therapeutic treatment, as well as prophylactic or suppressive measures for a disease (or disorder or condition). Thus, for example, successful administration of a SIK3 inhibitor prior to onset of the disease results in treatment of the disease. "Treatment" also encompasses administration of a SIK3 inhibitor after the appearance of the disease in order to ameliorate or eradicate the disease (or symptoms thereof). Administration of a SIK3 inhibitor after onset and after clinical symptoms, with possible abatement of clinical symptoms and perhaps amelioration of the disease, also comprises treatment of the disease. Those "in need of treatment" include subjects (such as a human subject) already having the disease, disorder or condition, as well as those prone to or suspected of having the disease, disorder or condition, including those in which the disease, disorder or condition is to be prevented.

The disease, disorder or a condition, in the context of the herein described invention, is a proliferative disorder (including a condition or symptom associated with such disorder).

A "proliferative disorder" refers to a disorder characterised by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "proliferative disorder" is neoplasm or tumour, which is an abnormal growth of tissue or cells. Cancer is art understood, and includes any of various malignant neoplasms characterised by the proliferation of cells that have the capability to invade surrounding tissue and/or metastasise to new colonisation sites. Proliferative disorders include cancer, atherosclerosis, rheumatoid arthritis, idiopathic pulmonary fibrosis and cirrhosis of the liver. Non-cancerous proliferative disorders also include hyperproliferation of cells in the skin such as psoriasis and its varied clinical forms, Reiter's syndrome, *Pityriasis rubra* pilaris, and hyperproliferative variants of disorders of keratinisation (e.g., actinic keratosis, senile keratosis), scleroderma, and the like.

In more particular embodiments, the proliferative disorder is a cancer or tumour, in particular a solid tumour (including a condition or symptom associated with such cancer or tumour). Such proliferative disorders including but not limited to head and neck cancer, squamous cell carcinoma, multiple myeloma, solitary plasmacytoma, renal cell cancer, retinoblastoma, germ cell tumours, hepatoblastoma, hepatocellular carcinoma, melanoma, rhabdoid tumour of the kidney, Ewing Sarcoma, chondrosarcoma, any haemotological malignancy (e.g., chronic lymphoblastic leukemia, chronic myelomonocytic leukemia, acute lymphoblastic leukemia, acute lymphocytic leukemia, acute myelogenous leukemia, acute myeloblasts leukemia, chronic myeloblastic leukemia, Hodgekin's disease, non-Hodgekin's lymphoma, chronic lymphocytic leukemia, chronic myelogenous leukemia, myelodysplastic syndrome, hairy cell leukemia, mast cell leukemia, mast cell neoplasm, follicular lymphoma, diffuse large cell lymphoma, mantle cell lymphoma, marginal zone lymphoma, Burkitt Lymphoma, mycosis fungoides, seary syndrome, cutaneous T-cell lymphoma, peripheral T cell lymphoma, chronic myeloproliferative disorders, myelofibrosis, myeloid metaplasia, systemic mastocytosis), and central nervous system tumours (eg, brain cancer, glioblastoma, non-glioblastoma brain cancer, meningioma, pituitary adenoma, vestibular schwannoma, a primitive neuroectodermal tumour, medulloblastoma, astrocytoma, anaplastic astrocytoma, oligodendroglioma, ependymoma and choroid plexus papilloma), myeloproliferative disorders (eg, polycythemia vera, thrombocythemia, idiopathic myelfibrosis), soft tissue sarcoma, thyroid cancer, endometrial cancer, carcinoid cancer, or liver cancer.

In one preferred embodiment, the various aspects of the invention relate to, for example the SIK3 inhibitors are used in treatments for proliferative disorders that include those described herein. Accordingly, in one embodiment the proliferative disorder can be a tumour, in particular a solid tumour.

The cell that is sensitised to the cell-mediated immune response is one involved with the proliferative disorder (eg, a cell associated with the proliferative disorder), which in certain embodiments such cell is one involved in the proliferative disorder (eg, a cell that is abnormally proliferating, such as one that is over-proliferating). For example, such cell may be a cell characterised by loss of normal controls that affect its growth and cell division, such as a cell of a neoplasm or tumour. In particular embodiments, such cell may be a cancerous cell or one that is derived form or is a cell of a cancer or tumour. In other embodiments, such cell may be skin cell, such as one showing hyperproliferation such as one involved in psoriasis, Reiter's syndrome, *Pityriasis rubra* pilaris or scleroderma.

A cell may be "involved with a proliferative disorder" if, for example, it is associated therewith, such as it being a causative factor in such proliferative disorder or if it is affected by such proliferative disorder. In particular a cell is "involved with a proliferative disorder" if the cell is characterised by an abnormal proliferation such as abnormal cell growth or cell division, and if the abnormal cell growth or cell division is part of the pathology of, or causative for, the proliferative disease. A cell "involved with a proliferative disorder", in those embodiments wherein the proliferative disorder is a tumour or cancer, can as a non-limiting example, be a tumour (or cancer) cell, or a cell of derived from (tissue) of such tumour or cancer; in particular of a solid tumour.

In certain embodiments, the SIK3 inhibitor may inhibit SIK3 in the cell involved with the proliferative disorder (eg the tumour cell). In particular of such embodiments, the SIK3 inhibitor may inhibit SIK3 in such cell preferentially to inhibiting SIK1 and/or SIK2 in such cell; and/or may inhibit SIK3 in such cell preferentially to inhibiting SIK1 and/or SIK2 and/or SIK3 in one or more types of immune cells. For example, the SIK3 inhibitor may inhibit SIK3 in the cell involved with the proliferative disorder (eg the tumour cell) preferentially to inhibiting SIK1 and/or SIK2 and/or SIK3 in macrophages and/or dendritic cells (in particular, those capable of or producing IL-10).

The SIK3 inhibitor may be administered to the subject, in particular in an amount (such as a dose) that is effective to, inhibit SIK3 and/or that is effective to sensitise the cells involved with the proliferative disorder to the cell-mediated immune response. Suitable amounts, formulations and means for such administration are described elsewhere herein.

In particular embodiments, the SIK3 inhibitor is administered in an amount (such as a therapeutically effective amount) that is effective to reduce activity of SIK3, preferably of SIK3 in (of) the cells involved with the proliferative disorder. In such embodiments, a "therapeutically effective amount" of the SIK3 inhibitor can be an amount that is capable to reduce the activity of the SIK3 to an applicable level, but that does not lead to significant (eg intolerable) side effects or over-dosage in respect of other activities of the SIK3 inhibitor.

In such particular embodiments, for example, such an amount of the SIK3 inhibitor may be one that is not effective to reduce the activity of ABL1 and/or SRC kinase, such as ABL1 and/or SRC kinase in (of) the cells involved with the proliferative disorder. By way of example (and with reference to the activities shown in Table 4 herein), if dasatinib was to be administered in an amount effective to inhibit SIK3, its main kinase targets (ABL and SRC) would also be inhibited, and possibly to such a degree that an over-dosage of dasatinib, or other side effects such as those mediated by over inhibition of ABL and/or SRC would occur. Indeed, but without being bound to theory, from biochemical (and/or affinity) perspectives, dasatinib may not be able to inhibit SIK3 in-vivo without inhibiting ABL and/or SRC in the same cell, and any ABL or SRC present in such cell may sequester the (majority of) dasatinib in the cell to such an extent that no dasatinib would remain to (effectively) act as a SIK3 inhibitor. Accordingly, in certain embodiments, dasatinib may be considered not to be a SIK3 inhibitor in the context of the present invention, when acting in vivo, such as in cells involved with a proliferative disorder. In other certain embodiments, a AS1 inhibitor in the context of the present invention may inhibit AS1 more potently than dasatinib and/or may inhibit ABL and/or SRC kinases less potently than dasatinib. For example, a preferred AS1 inhibitor in the context of the present invention may inhibit AS1 with a (biochemical) IC50 of less than about 100 nM, 50 nM, 25 nM or 10 nM (such as less than about 25 nM) and inhibits ABL and SRC each with an IC50 of greater than about 25 nM, 50 nM, 100 nM or 500 nM (such as greater than about 100 nM), in each case where such IC50 may be determined using a method analogous a biochemical kinase assay described in Example 11 or 13).

Preferably, the activity of SIK3 is effectively inhibited (reduced), and/or the activity of ABL and/or SRC is not effectively inhibited (reduced); in each case, preferably referring to the SIK3, ABL and/or SRC kinase in (of) the cells involved with a proliferative disorder. For example, an "effective" inhibition (or reduction) may include one where the activity is lowered by a degree (or to a level) that has a physiological effect (eg to a therapeutically effective level), such as a reduction by about 10%, 20%, 50%, or more than 50% such as 70% or 90% of activity of the respective kinase. In respect of SIK3, one of such reductions may be desirable to elicit a therapeutic response. In respect of ABL and/or SRC, the desired level of reduction may be one that is less than that desired for a reduction in SIK3.

The term "immune cell" is art recognised to describe any cell of an organism involved in the immune system of such organism, in particular of a mammal such as a human. Leukocytes (white blood cells) are immune cells that are involved in the innate immune system, and the cells of the adaptive immune system are special types of leukocytes, known as lymphocytes. B cells and T cells are the major types of lymphocytes and are derived from hematopoietic stem cells in the bone marrow. B cells are involved in the humoral immune response, whereas T cells are involved in cell-mediated immune response. In preferred embodiments of the invention, the immune cell can be a myeloid cell eg a T cell, and in particular (such as when an increase in cell-mediated immune response is required, such as to treat a cancer) the T cell can be a cytotoxic T cell (also known as TC, cytotoxic T lymphocyte, CTL, T-killer cell, cytolytic T cell, CD8+ T-cell or killer T cell). A CTL is a T-cell that is involved in the killing of cancer cells, cells that are infected (particularly with viruses), or cells that are damaged in other ways. Other preferred immune cells for such embodiments can include Tumour-Infiltrating Lymphocytes (TILs). TILs are white blood cells that have left the bloodstream and migrated into a tumour. Typically, TILs are a mix of different types of cells (i.e., T cells, B cells, NK cells, macrophages) in variable proportions, T cells being the most abundant cells. TILs can often be found in the stroma and within the tumour itself, and are implicated in killing tumour cells. The presence of lymphocytes in tumours is often associated with better clinical outcomes.

The term "cell-mediated immune response", as used herein, may include, but is not limited to, a response in a host organism involving, utilising, and/or promoting any one or combinations of T cell maturation, proliferation, activation, migration, infiltration and/or differentiation, and/or the activation/modulation/migration/infiltration of a macrophage, a natural killer cell, a T lymphocyte (or T cell), a helper T lymphocyte, a memory T lymphocyte, a suppressor T lymphocyte, a regulator T lymphocyte, and/or a cytotoxic T lymphocyte (CTL), and/or the production, release, and/or effect of one or more cell-secretable or cell-secreted factor such as a cytokine or autocoid (in particular a pro-inflammatory cytokine such as TNF), and/or one or more components of any of such processes (such as a cytokine or autocoid, particular a pro-inflammatory cytokine such as TNF). The term "cell-mediated immune response," as used herein, may include a cellular response involving a genetically engineered, in-vitro cultured, autologous, heterologous, modified, and/or transferred T lymphocyte, or it may include a cell-secretable or cell-secreted factor (such as a cytokine or autocoid, in particular a pro-inflammatory cytokine such as TNF) produced by genetic engineering. A cell-mediated immune response is preferably not a humoral immune response, such as an immune response involving the release of antibodies. In certain embodiments, in particular when the proliferative disorder is a cancer or tumour, the cell-mediated immune response is an anti-tumour cell-mediated immune response. For example, one that leads to a reduction in tumour (cell) growth, such as a cytotoxic cell-mediated immune response (such as a cytotoxic T cell and/or TNF exposure) that kills cells of the cancer or tumour.

In certain embodiments, the cell mediating the cell-mediated immune response may be mediated by a cell, such as an immune cell, capable of secreting (eg secreting) pro-inflammatory cytokine, such as one selected from the group consisting of: interleukin-1 (IL-1), IL-12, and IL-18, tumour necrosis factor (TNF), interferon gamma (IFN-gamma), and granulocyte-macrophage colony stimulating factor. In particular of such embodiments, the pro-inflammatory cytokine is tumour necrosis factor (TNF) [alpha].

In other embodiments, the cell-mediated immune response may a cell-secretable or cell-secreted factor (such as a cytokine or autocoid), in particular one secretable or secreted by an immune cell. In particular of such embodiments, the cell-mediated immune response is a pro-inflammatory cytokine, in particular tumour necrosis factor (TNF).

The terms "sensitising", "sensitisation" and "to sensitise" (and the like), as used herein in the context of cell(s) being sensitised to a cell-mediated immune response, will be understood by the person of ordinary skill, and include the meaning that such cells can exhibit an increased susceptibility to one or more effect (eg a treatment effect) that the cell-mediated immune response may have on such cells. In particular, cells that are so sensitised may, when in the presence of (eg exposed to) a cell-mediated immune response, be killed more easily (such as more rapidly, a greater proportion of cells dying or being killed and/or upon a lower amount or exposure of the cell-mediated immune response) than analogous cells that have not been so "sensitised". For example, cell(s) so sensitised may be induced into cell-death (eg apoptosis) upon exposure to a lower number of T cells or to a lower concentration of TNF (such as about 10%, 20%, 30% 40%, 50% or more than 50% fewer T cells or lower concentration of TNF). Methods to determine whether such cells have been sensitised (and by which degree) to cell-mediated immune responses are described herein, such as in the examples. Accordingly, in certain embodiments of the present invention, cells involved with the proliferative disorder may be sensitised to cell-death/killing (eg by entry into apoptosis) by a cell-mediated immune response (such as CTL or a proinflammatory cytokine eg TNF).

The terms "tumour necrosis factor" and "TNF" (previously and hence alternatively known as tumour necrosis factor alpha and TNF-alpha) shall, in the context of the herein disclosed invention, be understood to refer to any proteins know under these denotations in the art. In particular, the term TNF encompasses endogenous TNF of any organism where such is present, and preferably of animals or mammals, such as humans. By means of example and not limitation, human TNF may encompass endogenous proteins as disclosed in inter alia Pennica et al. 1984 (Nature 312:724-9) and in the UniProtKB/Swiss-Prot database with the entry No P01375 (for example, entry version 224 of 15 Mar. 2017), as well as any sequence variants thereof due to normal sequence polymorphism between and within human populations. By means of further non-limiting examples, the term may encompass endogenous TNF proteins as annotated in the UniProtKB/Swiss-Prot database for bovine (Q06599), dog (P51742), goat (P13296), guinea pig (P51435), cat (P19101), horse (P29553), mouse (P06804), chimp (Q8HZD9), pig (P23563), rabbit (P04924), rat (P16599) and others, as well as any sequence variants thereof due to sequence polymorphism between and within populations of each respective species. Further, the term TNF particularly encompasses the soluble, secreted cytokine form of TNF, including monomeric as well as, preferably, the typically more active trimeric forms thereof (see, e.g., Smith & Baglioni 1987. J Biol Chem 262:6951-4). The primary amino acid sequences of soluble forms of endogenous TNF are indicated in the above mentioned UniProtKB/Swiss-Prot database entries for the respective exemplified organisms. In addition, the term TNF may also encompass membrane-bound forms of TNF expressed on the surface of some cell types (see, e.g., Kriegler et al. 1988. Cell 53:45-53). Further, the term TNF may also encompass synthetic or recombinant proteins whose primary amino acid sequence is identical or substantially identical ("substantially identical", as used throughout this specification, generally refers to ≥80%, e.g., ≥85%, preferably ≥90%, more preferably ≥95%, even more preferably ≥98% or ≥99% sequence identity) to the sequence of an endogenous TNF, as determined using, e.g., the "Blast 2 sequences" algorithm described by Tatusova & Madden 1999 (FEMS Microbiol Lett 174:247-250), and which (preferably) retain biological activity identical or substantially identical to the respective endogenous TNF, as determined using, e.g., the cytotoxicity tests described by Flick & Gifford 1984 (J Immunol Methods 68:167-75). As will appear from the context of aspects and embodiments of the present invention, the term TNF may, in particular, refer herein to endogenous TNF, soluble and/or membrane bound, preferably soluble, produced by cells, tissues, organs or organisms, preferably human. Nevertheless, also envisioned by the term "TNF" are exogenous forms of tumour necrosis factor, in particular those produced by recombinant technologies and, in certain embodiments, may be administered to subjects, or exposed to or contacted with cells in various aspects and embodiments of the invention. In certain of such embodiments, the TNF may be a recombinant TNF uses as a therapeutic, such as tasonermin (BEROMUN®).

In certain embodiments, the cell-mediated immune response can be mediated by a pro-inflammatory cytokine-secreting cell, such as a lymphocyte (eg a T cell), in particular a cytotoxic T lymphocyte (CTL).

In particular embodiments, the cell-mediated immune response may induce killing (eg cell-death, such via apoptosis) of cells involved with the proliferative disorder. For example, the treatment (method) may comprise (eg may involve) that (or be mediated by) the cell-mediated immune response induces such killing of cells involved with the proliferative disorder.

The cells involved with the proliferative disorder may be killed (eg induced into cell death) by one or more cytotoxic processes, in particular those that are endogenous to such cell such as programmed cell death (PCD). Cell death processes may include, but are not limited to, necrosis (in particular necroptosis), apoptosis, anoikis, autophagy, ferroptosis, mitotic catastrophe and activation-induced cell death. In certain preferred embodiments, the cells involved with the proliferative disorder (eg the tumour cells) are induced into apoptosis by the cell-mediated immune response (eg by TNF). In a further embodiment, the SIK3 inhibitor is administered to not kill such cells in the absence of the cell-mediated immune response (eg in the absence of TNF). In particular of such further embodiments, the SIK3 inhibitor may be administered in an amount (eg in a dose) that is not effective to kill such cells in the absence of the cell-mediated immune response. The examples herein, describe various assays by which an amount of SIK3 inhibitor may be determined that is effective to kill such cells only in the presence of the cell-mediated immune response.

In other particular embodiments, the cell-mediated immune response may involve at least one immune cell effector molecule, in particular an effector molecule that is secretable or secreted by an immune cell. In particular of such embodiments, the effector molecule can be a pro-inflammatory cytokine, preferably tumour necrosis factor (TNF).

In certain embodiments, the effector molecule is not a cell effector molecule selected from Fas ligand (FasL or CD95L) and TNF-related apoptosis-inducing ligand (TRAIL, CD253 or TNFSF10).

In particular embodiments of the invention, the SIK3 inhibitor may be administered to the subject (eg in an amount or dose effective) with the intent to (or so as to) (effectively) sensitise cells involved with the proliferative disorder to killing induced by TNF. For example, the SIK3 inhibitor may be administered in a therapeutically effective amount, such as an amount effective to sensitise the cells involved with the proliferative disorder to killing (cell-death) induced by TNF.

For example, the SIK3 inhibitor may be administered to the subject (for example, in an amount or dose effective) to induce apoptosis of such cells mediated by TNF, such as when such cells are in the presence of or contacted with TNF. In further embodiments, the SIK3 inhibitor may be administered to the subject (eg in an amount or dose effective) to induce a reduced amount of cytotoxicity (eg apoptosis)—such as to not induce killing (eg apoptosis) of such cells—in the absence of TNF; for example the SIK3 inhibitor may be administered in an amount or dose that is—not as effective in cytotoxicity (eg apoptosis)—such as being not effective to induce such killing—in the absence of TNF.

TNF can induce pro-apoptotic processes via binding to and/or signalling via tumour necrosis factor receptor 1 (TNFR1) and or tumour necrosis factor receptor 2 (TNFR2). Accordingly, in certain embodiments the SIK3 inhibitor may be administered to the subject (eg in an amount or dose effective) to (effectively) sensitise cells involved with the proliferative disorder to apoptosis mediated by tumour necrosis factor receptor 1 (TNFR1) signalling and/or tumour necrosis factor receptor 2 (TNFR2) signalling. Preferably, the SIK3 inhibitor can be administered to the subject (eg in an amount or dose effective) to (effectively) sensitise cells involved with the proliferative disorder to apoptosis mediated thereby in particular mediated by TNFR1. For example, the SIK3 inhibitor may be administered in a therapeutically effective amount that is effective to mediate TNFR1- and/or TNFR2-signalling, and/or apoptosis mediated thereby.

For example in certain embodiments, the SIK3 inhibitor may be administered (eg in an amount or dose effective) to induce apoptosis of such cells by TNFR1 and/or TNFR2 signalling, such as upon active TNFR1 signalling. In particular of such embodiments, the SIK3 inhibitor may be administered to the subject (eg in an amount or dose, such as a therapeutically effective amount) to (effectively) induce a reduced amount of cytotoxicity (eg apoptosis)—such as to not induce apoptosis of such cells—in the absence of TNFR1 and/or TNFR2 signalling, such as in the absence of active TNFR1 signalling. For example, the SIK3 inhibitor may be administered in an amount or does that is not as effective in cytotoxicity (eg apoptosis)—such as being not effective to induce such apoptosis—in the absence of such signalling.

Therefore, in certain embodiments, the SIK3 inhibitor may be administered to the subject (eg in an amount or dose) to induce a reduced amount of cytotoxicity (eg apoptosis)—such as to not be cytotoxic—to cells involved with the proliferative disorder in the absence of the cell-mediated immune response.

In particular embodiments, the SIK3 inhibitor may be continued to be administered to the subject even if the tumour of the subject is increased in size during treatment. Without being bound by theory, an increase in tumour size during such treatment may indicate an (enhanced) immune reaction against cells of the tumour (eg, the cells have become sensitised to the cell-mediated immune response), and hence the administration of the SIK3 inhibitor can, in such embodiments, continued to be administered so as to maintain such sensitivity and associated (enhanced) immune reaction.

The inventors herein demonstrate that the inhibition of SIK3 is associated with a number of key biological processes or phenotypes, including those surprisingly involved in the control and/or triggering of cytotoxic process innate to cells, such as apoptosis. For example, the inventors demonstrate in the examples, for the first time, that tumour cells can be sensitised to the apoptotic effects of TNF by the inhibition of SIK3, acting through pathways and components thereof including liver kinase B1 (LKB1, STK11 or NY-REN-19), histone deacetylase 4 (HDAC4), nuclear factor kappa-light-chain-enhancer of activated B cells (NF-kappaB), and pro-apoptotic genes regulated by NF-kappaB such as Caspase 8 and Caspase 9. Also demonstrated, is that c-Jun N-terminal kinase (JNK) is a signalling component associated with sensitisation to the apoptotic effects of TNF by the inhibition of SIK3.

The term "associated with", in the context of this embodiment (and other embodiments, where applicable) can mean that two components, variables, effects or phenotypes are interrelated with each other, and/or that they are related to (eg correlated to) each other, and/or that there is a causative link between a first and a second component, variable, effect or phenotype (such as the second is in response to the first, the second is a consequence of the first, or the second is caused by the first).

Accordingly, in one such embodiment, administration of the SIK3 inhibitor can associate with impairment of NF-kappaB activity (eg, by an enhancement or increase in translocation of NF-kappaB out of the nucleus) in cells involved with the proliferative disorder.

In particular of such embodiments, such impairment of NF-kappaB activity (eg, by an enhancement or translocation of NF-kappaB out of the nucleus) may be associated with (activated) TNF- and/or TNFR1-mediated signalling (or TNFR2-mediated signalling) in such cells.

In certain embodiments, the SIK3 inhibitor may be administered to the subject (eg in an amount or dose effective) to impair or inhibit NF-kappaB activity in the cells involved with the proliferative disorder, for example to enhance or increase translocation of NF-kappaB out of the nucleus of such cells. For example, the SIK3 inhibitor may be administered to the subject in a (eg, therapeutically effective) amount being effective to (effectively) impair NF-kappaB activity in cells involved with the proliferative disorder, in particular in an amount effective to (effectively) enhance or increase translocation of NF-kappaB out of the nucleus of the cells involved with the proliferative disorder.

In alternative or further embodiments, administration of the SIK3 inhibitor may be associated with an increase in (eg, the SIK3 inhibitor is administered, such as in an amount or dose effective, to increase) activity of class II (eg IIa) HDACs, eg HDAC4, in the cells involved with the proliferative disorder, for example its translocation or localisation to or its activity in the nucleus of such cells; and in particular upon TNF- and/or TNFR1-mediated signalling (or TNFR2-mediated signalling) in such cells.

In other alternative or further embodiments, administration of the SIK3 inhibitor may be associated with de-acylation of nuclear NF-kappaB (eg de-acylation at its p65 subunit) and/or decreased transactivation of one or more anti-apoptotic factors, in particular upon TNF- and/or TNFR1-mediated signalling (or TNFR2-mediated signalling) in the cells involved with the proliferative disorder. For example, the SIK3 inhibitor may be administered (such as in an amount or dose effective) to cause de-acylation of nuclear NF-kappaB (eg at its p65 subunit) and/or decreased transactivation of one or more anti-apoptotic factors.

In another alternative or further embodiment, administration of the SIK3 inhibitor may be associated with an increase in (eg the SIK3 inhibitor is administered, such as in an amount or dose effective, to increase) cleavage of Casapse 8 and/or Caspase 9 in the cells involved with the proliferative disorder, in particular upon TNF- and/or TNFR1-mediated (or TNFR2-mediated signalling) signalling in such cells.

In yet other alternative or further embodiments, administration of the SIK3 inhibitor may be associated with a reduction in the transcription of one or more anti-apoptotic factors, in particular upon TNF- and/or TNFR1-mediated signalling (or TNFR2-mediated signalling) in the cells involved with the proliferative disorder, for example the reduction of the transcription of one or more NF-kappaB target genes in such cells. In particular, the SIK3 inhibitor is administered (eg in an amount dose effective) to reduce the transcription of one or more such anti-apoptotic factors, in particular upon TNF- and/or TNFR1-mediated signalling (or TNFR2-mediated signalling) in the cells involved with the proliferative disorder.

In one embodiment the administration of the SIK3 inhibitor may be associated with an increase in (eg the SIK3 inhibitor is administered, such as in an amount or dose effective, to increase) JNK activation (such as by phosphorylation) in the cells involved with the proliferative disorder, in particular upon TNF- and/or TNFR1-mediated signalling (or TNFR2-mediated signalling) in such cells.

In another embodiment, administration of the SIK3 inhibitor may not be associated with a significant change in CREB-pathways signalling and/or a significant change gene expression mediated by CREB and/or CREB-regulation.

In a particular embodiment, the TNF- (TNFR2-) and/or TNFR1-mediated signalling in the cells involved with the proliferative disorder may be associated with increased levels of pLKB1 in such cells.

As will now be apparent to the person of ordinary skill given knowledge of the present invention, the treatment aspects of the invention may further comprise a step of administering one or more other moieties that appropriately modify the expression, activity, function or stability of one or more these other pathway components described above, so as to additively or synergistically contribute to the treatment effect. For example, in one such embodiment, a treatment aspect of the invention may further comprise a step of administering an inhibitor of LKB1 (in particular, when the SIK3 inhibitor is not an inhibitor of LKB1). In another of such embodiments, a treatment aspect of the invention may further comprise a step of administering a compound that promotes, enhances or increases one or more class II (eg IIa) HDACs (histone deacetylases), such as HDAC4, in the nucleus of the cells involved with the proliferative disorder. In yet another of such embodiments, a treatment aspect of the invention may further comprise a step of administering an inhibitor of NF-kappaB (activation). The invention also envisions that combinations of two or more such other moieties may be used in a treatment together with the SIK3 inhibitor and/or using other (eg anti-cancer) therapeutically active agents together with the SIK3 inhibitor.

In a second aspect, and as may be further described, defined, claimed or otherwise disclosed herein, the invention relates to a method for the sensitisation of cells involved with a proliferative disorder to a cell-mediated immune response, the method comprising exposing (eg contacting) the cells involved with a proliferative disorder to a SIK3 inhibitor. Such a method may, typically, be practiced as an in-vitro and/or ex-vivo method.

In a particular embodiment, the cell-mediated immune response comprises killing the cells involved with a proliferative disorder, such as where said killing is involves TNF, TNFR2- and/or TNFR1-mediated signalling. For example, the killing of such cells may involve apoptosis of such cells induced by TNF, TNFR2- and/or TNFR1-mediated signalling. Within this and the other applicable embodiments of the various aspects of the invention, TNFR2- and/or TNFR1-mediated signalling may be triggered (eg activated) by any appropriate triggering molecule, such as TNF, a variant of TNF and or a TNFR2 or TNFR1 agonist; in particular by exposing (eg by contacting) the cells associated with the proliferative disorder to the triggering molecule (eg TNF, TNF variant or TNFR1 agonist). Such exposure can lead to the triggering molecule (eg TNF, TNF variant or TNFR1 agonist) binding to TNFR2 and/or TNFR1 and, in particular the triggering (eg activation) of TNFR1 signalling In a third aspect, and as may be further described, defined, claimed or otherwise disclosed herein, the invention relates to a method for the killing of cells involved with a proliferative disorder, the method comprising exposing (eg contacting) the cell involved with the proliferative disorder to: (i) TNF, a TNF variant and/or an agonist of TNFR1- or TNFR2-signalling (preferably, TNFR1-signalling); and exposing (eg contacting) the cells involved with the proliferative disorder to (ii) a SIK3 inhibitor. As will be appreciated by the person or ordinary skill, such a method may, typically, be practiced as an in-vitro and/or ex-vivo method.

In a related third aspect, the invention relates to a SIK3 inhibitor for use in the treatment of a proliferative disease involving the killing of a cell involved with the proliferative disorder, the treatment comprising exposing such cell to: (i) TNF, a TNF variant and/or a TNFR1 or TNFR2 agonist; and (ii) a SIK3 inhibitor.

In particular embodiments of such third aspects, the killing of the cell involved with the proliferative disorder is mediated by sensitising such cell to a cell-mediated immune response, in particular by inducing sensitivity to apoptosis of such cell that involves TNF, TNFR2 and/or TNFR1-mediated signalling.

The cell(s) involved with the proliferative disorder may be exposed to the TNF, a TNF variant and/or a TNFR1 or TNFR2 agonist by contacting the cell to such triggering molecule; and/or such cell(s) may be exposed to the SIK3 inhibitor by contacting (of introducing into) such cell(s) with the SIK3 inhibitor. The amounts (or dose) of (i) TNF, a TNF variant and/or a TNFR1 or TNFR2 agonist; and/or (ii) a SIK3 inhibitor are, typically, effective amounts; that is amounts (or doses) that are effective in, for example, sensitising the cell(s) to (such as killing such cell(s) by) apoptosis induced by TNF, TNFR2 and/or TNFR1-mediated signalling. Elsewhere are disclosed suitable amounts of these active agents (or ways to determine them) that may be incorporated in these aspects of the invention; as are further particular characteristics of the SKI3 inhibitor. Accordingly, in certain embodiments: (i) TNF, a TNF variant and/or a TNFR1 or TNFR2 agonist; and (ii) a SIK3 inhibitor, can be administered to a subject suffering from the proliferative disorder (eg, the treatment can comprise the administration of: (i) TNF, a TNF variant and/or a TNFR1 or TNFR2 agonist; and (ii) a SIK3 inhibitor, can be administered to the subject).

The cell(s) involved with the proliferative disorder may be one as described elsewhere herein, and in particular such cell(s) may be cancerous or tumour cell. For example, such cell(s) may be one that is of, or derived from, a solid tumour.

In certain embodiments of these second and third aspects, the method is an in vitro (and/or ex-vivo) method. In alternative embodiments of such methods, the cell(s) involved with the proliferative disorder (such as tumour cells) is present in such subject, in particular in a subject in need of treatment thereof.

In further embodiments of the methods of these first, second and third (and their related) aspects, the (treatment) effect of such method (eg, on the cell(s) involved with the proliferative disorder) can be mediated by (eg, the treatment may comprise, involve or be mediated by) inhibiting SIK3; in particular, by inhibiting the expression, amount, function, activity and/or stability of SIK3 mRNA or protein (eg, of phosphorylated SIK3 protein, and/or as described elsewhere herein). In particular, in such embodiments, the SIK3 activity is (eg, effectively) reduced, such as reduced to a therapeutically effective level.

In yet further embodiments of the methods of these first, second and third (and their related) aspects, the (treatment) effect of such method (eg, on the cell(s) involved with the proliferative disorder) may NOT be mediated by (eg, the treatment may NOT comprise, involve or be mediated by) inhibiting Abl and/or SRC kinase; by NOT (effectively) inhibiting the expression, amount, function, activity and/or stability of Abl and/or SRC kinase or protein. In particular of such embodiments, activity of the ABL1 and/or SRC is NOT (effectively) reduced, such as is NOT reduced to a therapeutically effective level.

In certain embodiments of such methods, in the absence of (eg such effective amount or dose of) the SIK3 inhibitor, the cell(s) involved with the proliferative disorder (such as the tumour cell(s)) are not killed or induced to enter apoptosis (for example, they proliferate) upon TNF, TNFR2- and/or TNFR1-mediated signalling and/or exposure to (eg, the effective amount or dose of) TNF, TNF variant, TNFR2 or TNFR1 agonist.

As described above, in certain embodiments of these methods, the SIK3 inhibitor may inhibit SIK3 in (of) the cell(s) involved with the proliferative disorder (eg tumour cells). In particular of such embodiments, the SIK3 inhibitor may inhibit SIK3 in (of) such cell(s) preferentially to inhibiting SIK1 and/or SIK2 in (of) such cell; and/or may inhibit SIK3 in such cell preferentially to inhibiting SIK1 and/or SIK2 and/or SIK3 in (of) one or more types of immune cells. For example, the SIK3 inhibitor may inhibit SIK3 in (of) the cell(s) involved with the proliferative disorder (eg tumour cells) preferentially to inhibiting SIK1 and/or SIK2 and/or SIK3 in (of) macrophages and/or dendritic cells (in particular, those capable of or producing IL-10). In particular embodiments, the (treatment) effect is mediated by (eg, the treatment comprises, involves or is mediated by) inhibition of SIK3 in (of) the cell(s) involved with the proliferative disorder (eg a tumour cell); and in further of such embodiments, the (treatment) effect is not mediated by (or the effect is mediated by not) (eg, the treatment does not comprise, involve or is not mediated by) inhibiting SIK2, in particular SIK2 in/of other cells (such as those involved with the proliferative disorder or immune cells), and/or the (treatment) effect is not mediated by (or the effect is mediated by not) inhibiting SIK1 (eg, the treatment does not comprise, involve or is not mediated by inhibiting SIK1), in particular SIK1 in/of other cells (such as those involved with the proliferative disorder or immune cells).

Accordingly, and as will also be appreciated from the above, in other certain embodiments, the ABL and/or SRC in (of) other cells (in particular in/of the cells involved with the proliferative disorder, or in/of immune cells) may NOT be inhibited.

Accordingly, in one embodiment, the SIK3 of (eg, in) the cell(s) involved with the proliferative disorder is inhibited. In another (or further) embodiment, SIK2, in particular SIK2 of (eg in) immune cells—such as CTLs—is inhibited to a lesser extent than SIK3 (eg in the cell(s) involved with the proliferative disorder). In yet another (or further) embodiment SIK1, in particular SIK1 of (eg in) immune cells—such as CTLs—is inhibited to a lesser extent than such SIK3.

A given SIK (such as SIK1 or SIK2) may be inhibited to a "lesser extent" than another SIK (such as SIK3) if, for example, the other SIK (such as SIK3) is inhibited by an amount greater than about 2 fold more than the given SIK, such as by an amount greater than about 5, 10, 20, 50, 75 or 100-fold more than the given SIK. In particular, the other SIK (such as SIK3) may be inhibited by an amount between about 5 and 20 fold, 20 and 50 or 50 and 100 fold more than the given SIK. For example, the SIK3 may be inhibited between about 20 and 50 fold more than SIK1 and/or SIK2. By way of example, the SIK3 inhibitor may inhibit SIK3 by 80% (ie, to have only 20% of its uninhibited activity) but inhibit SIK1 by only 4% and SIK2 by only 8%. Accordingly, SIK3 is inhibited about 20-fold more than SIK1 and 10-fold more than SIK2. In particular embodiments, the SIK3 may be inhibited to about the same extent as SIK1 (eg between about 2 to 53 fold of each other), and SIK2 is inhibited to a lesser extent that either (or both) of SIK3 and SIK1: For example, in such embodiments, SIK3 and SIK1 are inhibited by between about a 20 and 50 fold more than SIK2 (eg in immune cells) is inhibited.

In contrast to other studies using SIK inhibitors, treatment with the SIK3 inhibitors in accordance with the present invention, in certain embodiments, may not be associated with an (effective) increase in the production of one or more anti-inflammatory cytokines (for example the anti-inflammatory cytokine may be one selected from the list consisting of: IL-1ra, IL-4, IL-10, IL-11, IL-13 and TGF-beta), and in particular may not be associated with an (effective) increase in the production of IL-10. Correspondingly, in other or further embodiments, treatment with the SIK3 inhibitors in accordance with the present invention may not be associated with an (effective) decrease in the production of one or more pro-inflammatory cytokines; for example, one selected from the list consisting of: IL-1-beta, IL-6, IL-12 and TNF, IFN-gamma and granulocyte-macrophage colony stimulating factor, and in particular embodiments may not be associated with an (effective) decrease in the production of TNF. Accordingly, in certain embodiments, the SIK3 inhibitor may be administered to a subject in: (i) a (therapeutically effective) amount NOT effective to (effectively) increase the production of one or more (eg such) anti-inflammatory cytokines; and/or (ii) in a (therapeutically effective) amount NOT effective to (effectively) decrease the production of one or more (eg such) pro-inflammatory cytokines.

Certain cells involved with the proliferative disorder (eg tumour cells) may, in certain embodiments, be expected to be more susceptible to the sensitising effects of the SIK3 inhibitors in the various aspects of the invention. For example, such cells may be those that exhibit (eg are subject to) activation of TNFR2 and/or TNFR1 signalling, in particular an activated TNFR1. In certain embodiments, such cells are those that express TNFR2 and/or TNFR1, in particular tumour cells that express TNFR1. Accordingly, in certain embodiments, such cells are distinguished or characterised by activated TNFR1- and/or TNFR2-signalling (or the subject is distinguished or characterised by having cells involved with the proliferative disorder—eg tumour cells—that are so distinguished or characterised). The person of ordinary skill will know techniques for determining the status of TNFR1- and/or TNFR2-activation in such cells (such as of the subject). For example, by detecting or monitoring one or more down-stream protein in the TNFR1- and/or TNFR2-signalling pathways. Such proteins are described elsewhere herein, and include NF-kappaB and/or HDAC4.

In one related aspect, the invention relates to a method for the treatment of a proliferative disorder (such as a tumour) in a subject, the (treatment) method comprising administering a SIK3 inhibitor to the subject, by inhibiting SIK3, wherein cells involved with the proliferative disorder are characterised by (eg exhibit or are subject to) activated TNFR2 and/or TNFR1 signalling (eg activated TNFR1 signalling). In another related aspect, the invention relates to a SIK3 inhibitor for use in the treatment of a proliferative disorder, wherein cells involved with the proliferative disorder are distinguished or characterised by (eg exhibit or are subject to) activated TNFR2 and/or TNFR1 signalling (eg activated TNFR1 signalling).

In certain embodiments of the various aspects of the invention, cells involved with the proliferative disorder are those exposed to an appropriate triggering or activating molecule, such as TNF, a variant of TNF and or an agonist of TNFR2- or TNFR1-signalling (preferably, an agonist of TNFR1-signalling), in particular are exposed to an effective amount of such triggering or activating molecule.

In particular embodiments, when the triggering or activating molecule is TNF, it is human TNF. In certain of such embodiments, the TNF is recombinant human TNF (rHuTNF). However, in other embodiments the TNF is endogenous TNF, such as that is produced by or otherwise present in the subject (eg the human patient).

Studies have shown that plasma TNF levels are elevated in numerous types of cancers, and that for example, the upper normal limit of total TNF in healthy subjects is 1.8 pg/mL, as measured using; a Quantikine human TNF-alpha Immunoassay PDTA00C, including in ovarian cancer (Dobrzycka et al 2009, Eur Cytokine Netw 20:131). In other cancers and assays (eg, TNF-alpha-EASIA Kit, DIAsource), the TNF plasma levels of oesophageal cancer patients and the control group were 12.35±9.69 and 4.62±3.06 pg/mL, respectively (Aydin et al 2012, Turk J Med Sci 42:762). Accordingly, in other embodiments the cells involved with the proliferative disorder are (for example a tumour is) one present in a subject having a plasma concentration of TNF greater than about 1.5, 2.5 or 4 pg/mL, such as greater than about 5 pg/mL, and in particular greater than about 10 pg/mL (for example, as measured by a Quantikine human TNF-alpha Immunoassay PDTA00C or a TNF-alpha-ELISA Kit, DIAsource).

Accordingly, in one particular embodiment, the subject involved in the treatment methods of the invention may have (that is, such a subject can be distinguished by, such as distinguished as one suitable for the therapeutic methods of the present invention, by showing, possessing or displaying) a plasma concentration of TNF greater than about 2 pg/mL or greater than about 5 pg/mL (eg, the cells involved with the proliferative disorder are one present in a subject having a plasma concentration of TNF greater than about 2 pg/mL or 5 pg/mL).

Indeed, in those embodiments where the proliferative disorder is a tumour, then the intratumoural concentration of TNF may be a characterisation of the tumour, such as when the tumour is a solid tumour and accessible for biopsy (Reissfelder et al 2015, J Clin Inv 125:739). For example, a tumour (such as a solid tumour eg colorectal cancer) can, in some embodiments of the invention, have an intratumoural concentration (eg, within the tumour tissue) of TNF that is greater than about 0.2, 0.5 or 1 pg/mL, such as greater than about 2 pg/mL, and in particular greater than about 5 pg/mL (for example, as measured by a Quantikine human TNF-alpha Immunoassay).

Accordingly, in such embodiments when the proliferative disorder is a tumour (eg a solid tumour), then the solid tumour (eg, within the subject) may have (that is, such a subject can be distinguished by, such as distinguished as one suitable for the therpapeutic methods of the present invention, by showing, possessing or displaying) an intratumoural concentration of TNF greater than (about) 0.5 pg/mL or greater than about 1 pg/mL.

Accordingly, in a related aspect, the invention can relate to a method for the treatment of a proliferative disorder (or a SIK3 inhibitor for use in such a treatment) in a subject distinguished by having: (i) a plasma concentration of TNF greater than about 2 pg/mL (preferably greater than about 5 pg/mL); and/or (ii) an intratumoural concentration of TNF greater than about 0.5 pg/mL preferably greater than about 1 pg/mL), the treatment method comprising administering a SIK3 inhibitor to the subject, wherein the SIK3 inhibitor: (a) inhibits SIK3 in cells involved with the proliferative disorder; and/or (b) sensitises cells in the subject involved with the proliferative disorder to a cell-mediated immune response.

In particular of such embodiments, the amount (or dose) of SIK3 inhibitor that is exposed to cells involved with the proliferative disorder, or that is administered to the subject, is related to (eg correlated to) the plasma or intratumoural concentration of TNF, wherein a greater amount (or dose) of SIK3 inhibitor is exposed to such cells (or administered to such subject) in those cases of a greater plasma or intratumoural concentration of TNF.

In other or further embodiments, the tumour may be present in a subject having tumour-reactive T-cells in peripheral blood or bone marrow, for example as may be determined by INF-gamma ELISPOT. In yet other or further embodiments, the tumour shows infiltration by Tregs, CD4+ Tconv and/or CD8+ T cells.

In other embodiments, the cells involved with the proliferative disorder comprises a single nucleotide polymorphism (SNP) in the promoter region of TNF associated increased expression of TNF and cancer sensitivity, for example with an AA or GA genotype at the −308G/A SNP in the promoter region of TNF; and in alternative embodiments the tumour does not comprise a SNP associated with decreased expression of TNF and reduced cancer risk, such as does not comprise an AA or GA genotype at the −238G/A SNP or a −857T allele, in each case in the promoter region of TNF (Wang and Lin 2008, Acta Pharmacol Sin 28:1275).

The invention hereby provides alternative combination treatment regimens based on the surprising finding of the inventors that SIK3 activity can influence the sensitivity of a cell towards the cytotoxic effects of TNF. Accordingly, in a fourth aspect, and as may be further described, defined, claimed or otherwise disclosed herein, the invention relates to a method for the treatment of a proliferative disorder in a subject, the method comprising exposing (eg contacting) cells involved with the proliferative disorder in the subject to: (i) TNF, a TNF variant and/or an agonist of TNFR2- or TNFR1-signalling; and exposing (eg contacting) the cells involved with the proliferative disorder in the subject to (ii) a SIK3 inhibitor. In certain embodiments, step (i) of such method does not comprise exposing (eg contacting) cells involved with the proliferative disorder in the subject to a TNF variant.

In certain embodiments, the proliferative disorder and/or such cells are those of the tumour, and in other embodiments, component (i) is TNF, in particular human TNF (such as rHuTNF); and/or component (i) is an agonist of TNFR1-signalling.

In particular embodiments, the method comprises (eg the treatment comprises, involves or is mediated by) increasing the amount of TNF exposed to the cells involved with the proliferative disorder in the subject.

In certain embodiments of such aspects, the treatment may comprise (eg, involves or is mediated by) increasing TNFR1- and/or TNFR2-signalling in (of) the cells involved with the proliferative disorder in the subject. Accordingly, in a related aspect the invention relates to a method for the treatment of a proliferative disorder in a subject, the method comprising: (i) increasing TNFR1- and/or TNFR2-signalling in (of) the cells involved with the proliferative disorder; and (ii) exposing (eg contacting) the cells involved with the proliferative disorder in the subject to a SIK3 inhibitor.

In particular the method can, for example, be effected though the consequence(s) of SIK3 inhibition (such as inhibition of the expression, amount, function, activity and/or stability of SIK3, eg of phosphorylated SIK3), in particular in combination with the consequence(s) of activation of TNFR1- and/or TNFR2-signalling, such as upon binding of the TNF, TNF variant and/or TNFR1 agonist to TNFR1 or TNFR2.

Accordingly, the treatment effect can, in certain embodiments, involve, or be mediated (eg, caused) by, inhibiting SIK3, and/or by sensitising the cells involved with the proliferative disorder to the cytotoxic (eg apoptotic) effects of TNFR1- or TNFR2-signalling. In particular of such embodiments, the SIK3 activity may be (effectively) reduced, such as to a therapeutically effective level.

As described above, herein are also envisioned embodiments wherein SIK3 in the tumour cells is inhibited and, optionally, where SIK2 and/or SIK1 are inhibited to a lesser extent, such as SIK2 or SIK1 of immune cells.

Also as described above, herein are also envisioned embodiments wherein: (x) the treatment comprises, involves or is mediated by (eg, the SIK3 inhibitor is administered in an amount, such as a therapeutically effective amount that is effective to) inhibition of SIK3 activity such that it is (eg, effectively) reduced, such as reduced to a therapeutically effective level; and/or (y) the treatment comprises, involves or is mediated by (eg, the SIK3 inhibitor is administered in an amount, such as a therapeutically effective amount that is NOT effective to) inhibition of Abl and/or SRC kinase, such that Abl and/or SRC kinase activity is NOT (eg, effectively) reduced, such as is NOT reduced to a therapeutically effective level.

In certain embodiments of such aspect, the subject can be administered the SIK3 inhibitor and/or can be administered (the) TNF, and/the TNF variant or an/the agonist of TNFR1- or TNFR2-signalling.

In such embodiments, the SIK3 inhibitor and the TNF, TNF variant or TNFR1 or TNFR2 agonist can be exposed to (for example administered in) an effective amount (or dose), including in formulations or administrative routes as described elsewhere herein. In particular are envisioned embodiments where the TNF, TNF variant or TNFR1 or TNFR2 agonist is encapsulated as a liposomal or other nanoparticle formulation.

When the TNF, TNF variant or TNFR1 or TNFR2 agonist is exposed/administered and the SIK3 inhibitor is exposed/administered, then such combination treatment regimen may comprise embodiments where such exposures/administrations are concomitant. In alternative embodiments such exposures/administrations may be sequential; in particular those embodiments where the SIK3 inhibitor is exposed/administered before the TNF, TNF variant or TNFR1 or TNFR2 agonist is exposed/administered. For example the SIK3 inhibitor may be sequentially exposed/administered within about 14 days of (eg before) the other component, such as within about 10 days, 7 days, 5 days, 2 days or 1 day of (eg before) the other component; and further including where the SIK3 inhibitor may be sequentially exposed/administered within about 48 hours, 24 hours, 12 hours, 8 hours, 6 hours, 4 hours, 2 hours, 1 hours, 30 mins, 15 mins or 5 mins of (eg before) the other component.

The TNF or the TNF variant or TNFR1 or TNFR2 agonist may be administered via conventional routes, such as s.c., i.v. or i.m., and on certain embodiments may be administered intratumourally or by isolated limb perfusion (ILP), such as isolated hepatic perfusion (IHP); and/or may be so administered (in particular, rHuTNF may be so administered) at a dose of between about 5 and 500 ug/m2/day. For example, TNF may be administered between about 25 and 250 ug/m2/day, such as between about 50 and 150 ug/m2/day or between about 75 and 100 ug/m2/day; or wherein TNF is administered up to a MTD of about 50 and 75 ug/m2/day when administered s.c. or up to a MTD of about 150 and 200 ug/m2/day when administered i.v. or i.m. Accordingly, in particular of such embodiments, TNF can be administered to the subject at a dose of between about 5 and 500 ug/m2/day, in particular between about 20 and 200 ug/m2/day.

In particular embodiments a variant of TNF, such as a TNF variant having higher anti-tumour activity and lower systemic toxicity that rHuTNF may be exposed/administered. For example, the TNF variant may be one selected from the group consisting of: (i) a —K90R variant of TNF; (ii) a tumour-homing peptide conjugated to TNF; and (iii) a TNF-antibody conjugate.

In those embodiments of the invention involving a TNF variant, it may be a variant form of TNF having higher cytotoxic activity and lower systemic toxicity.

In other embodiments a TNFR1 or TNFR2 agonist, such as the anti-TNFR1 monoclonal antibody htr-9 (Ferrero et al 2001, Am J Physiol Cell Physiol 281:C1173) may be exposed/administered, and in other embodiments lymphotoxin-alpha (Etemadi et al 2013, FEBS J280:5283) or a variant thereof may be exposed/administered.

In alternative embodiments, cells involved with the proliferative disorder (eg tumour cells) may be exposed to TNF (or increased TNFR1- and/or TNFR2-signalling) through the administration of an agent (eg to a subject harbouring such cell) that can lead to the exposure of such cells to (eg endogenous) TNF, or to another triggering molecule such as a variant of TNF or a TNFR1 or TNFR2 agonist. Such an agent may, for example, be one that is capable of inducing (eg induces) the exposure of such cells to (eg an elevated level of) TNF, in particular an agent that induces the exposure of such cells to TNF levels, such as to an effective amount of (eg endogenous) TNF, for example levels of plasma or intratumoural TNF that are greater than one or those levels described elsewhere herein.

Accordingly, the invention includes those embodiments wherein the subject is administered an agent that is capable of inducing (eg induces) the exposure of the cells involved with the proliferative disorder to (the) TNF, an/the TNF variant or an/the agonist of TNFR1- or TNFR2-signalling. The invention also includes those embodiments wherein the subject gets administered an agent that is capable of increasing TNFR1-signalling (and/or TNFR2-signalling) of, and/or increasing the amount of TNF exposed to, cells involved with the proliferative disorder in the subject.

In certain of such embodiments, the agent is a virus, in particular one that has been engineered to produce a triggering molecule being TNF, a TNF variant or the TNFR1 or TNFR2 agonist (especially, a virus engineered to produce human TNF). Further of such embodiments include those where such virus preferentially infects the cell(s) involved with the proliferative disorder (eg tumour cells) and/or preferentially produces the triggering molecule in the context of (eg when it infects) such cells. As will now be apparent, the administration of such a virus can lead to the exposure of the cell(s) involved with the proliferative disorder to such triggering molecule, and in particular to an effective amount of such a triggering molecule such as TNF.

Accordingly, in certain of such methods, the agent may be a virus that is capable of inducing (eg induces) the exposure of the cell(s) involved with the proliferative disorder the TNF, TNF variant or agonist or TNFR1- or TNFR2-signalling.

Such a virus may be any that is suitable for inducing the exposure of the triggering molecule, and in particular may be a recombinant virus; for example one engineered to infect tumour cells and/or to express TNF (eg after infecting a tumour cell). Examples of virus that may be so engineered include oncolytic viruses (eg, those based on an adenovirus, HSV, vaccinia virus, vesicular stomatitis virus or Newcastle disease virus), such as intratumoural injection of adenovirus vectors to increase plasma levels of pro-inflammatory cytokines and chemokines, including TNF (Bernt et al 2005, Cancer Res 65:4343). In particular of such embodiments, the oncolytic virus may be one based on a DNA virus described in Table 1 of Kaufman et al 2015 (Nature Rev Drug Disc 14:642), one based on an RNA virus described in Table 2 of Kaufman et al 2015, preferably, is an oncolytic virus described in Table 3 of Kaufman et al 2015 as being in clinical trials.

In other of such embodiments, the agent that is administered (and that consequentially leads to exposure of the cells involved with the proliferative disorder to a triggering molecule being TNF, a TNF variant or a TNFR1 or TNFR2 agonist) is an immune cell. In certain of such embodiments, the immune cell may not be an IL10-producing macrophage, for example the immune cells can be a pro-inflammatory immune cell. In particular of such embodiments, the immune cell that is administered may be a lymphoid cell, eg a T cell or a natural killer (NK) cell, for example such a cell that produces TNF.

When administered as an agent in such embodiments of the invention, the immune cell may be administered via adoptive cell transfer (ACT); meaning the transfer of the immune cell into the subject (eg, by infusion or other delivery techniques). Such process is, typically, conducted with the goal of improving immune functionality and characteristics in the subject, and while conventionally the transferred immune cells will have originated from the same subject, they may alternatively have been derived from another (suitable) individual.

When used in this embodiment of the invention, the immune cells may be T cells extracted from the subject, genetically modified and cultured in vitro and returned to the same subject, such as in a therapeutic method of the invention. Such genetic modification can include those that enhance the specificity or targeting of the immune cell, such as the targeting of the immune cell (eg increasing its specificity) to the cell(s) involved with the proliferative disorder (eg a tumour cell). For example, a T cell that is used in such embodiments may be modified to alter the specificity of the T cell receptor (TCR) or to introduce antibody-like recognition in chimeric antigen receptors (CARs). CAR immune cells, in particular, are envisioned for use in such embodiments. CAR immune cells are immune cells displaying engineered receptors, which graft an arbitrary specificity (eg to a tumour cell) onto an immune effector cell (eg a T cell). Typically, these receptors are used to graft the specificity of a monoclonal antibody onto a T cell; with transfer of their coding sequence facilitated by retroviral vectors. CAR T cells are a promising therapy for cancer (Song et al 2015, Oncotarget. 6:21533): using ACT, T cells are removed from an individual (typically the subject) and modified so that they express receptors specific to the patient's particular cancer. These T cells, which can then recognise the subject's cancer cells, are (re)introduced into the subject, leading to exposure of TNF (eg produced by the CAR T cells) to the tumour cells and hence killing of such cells, in particular such cells that are sensitised to such TNF-mediate cytotoxicity by exposure to (eg following administration to the subject of) a SIK3 inhibitor. Accordingly, in particular of such embodiments, the immune cells can be a CAR T cell, such as one engineered to have increased specificity to the subject's cells that are involved with the proliferative disorder (such as tumour cells).

In alternative embodiments, the exposure of the cells involved with the proliferative disorder to TNF (eg endogenous TNF) may be induced by other means or procedures. Accordingly, in such embodiments, the exposure of the cells involved with the proliferative disorder to (eg an effective amount of) TNF can be induced by (and/or the increase in TNFR1-signalling (and/or TNFR2-signalling) in/of the cells involved with the proliferative disorder is induced by) a pharmaceutical, therapeutic or other procedure that increases the amount of TNF in the plasma of the subject and/or in the environment of such cells.

In certain embodiments, such induced exposure to TNF may be brought about by the administration of a cancer immunotherapy.

In one example, such induced exposure to TNF is brought about by an anti-tumour vaccine (eg, a cancer vaccine). Such cancer vaccines include those whereby antigens (eg, those specific to or preferentially expressed by cancer cells) are directly or indirectly introduced into the subject so as to raise or increase an immune response (typically, an adaptive immune response) in the subject that is envisioned to be (more) specific to the cancer cell. Cancer vaccine may comprise, for example, attenuated viruses, in particular for use against cancers such as cervical or liver cancers that are caused by such virus (eg HPV or HBV). Cancer vaccines can alternatively represent individual (or combinations) of particular tumour antigens (eg, those specific to or preferentially expressed by cancer cells), such as tumour-associated antigens (TAAs) that are used to immunise the subject so as to also raise or increase the immune response in the subject. The cancer vaccine may comprise recombinant protein representing (eg a peptide from) the TAA(s), or may be a tumour specific carbohydrate antigen, and hence are directly introduced into the subject upon administration. The cancer vaccine may, alternatively, comprise a nucleic acid (such as DNA or mRNA) than encodes the protein (or peptide) TAA, and upon administration of the nucleic acid vaccine into the subject, the encoded TAA is expressed by cellular targets in the subject, and hence are indirectly introduced into the subject. TAAs may be divided into two categories: shared tumour antigens; and unique tumour antigens. Shared antigens are expressed by many tumours. Unique tumour antigens result from mutations induced through physical or chemical carcinogens (also known as neoantigens); they are therefore expressed only by individual tumours. The person skilled in the art will be aware of examples of cancer vaccines in clinical trials, or approved for use, and include PROSTVAC (BavarianNordic), PROVENGE (Dendreon) and CV9104 (CureVac), as well as being aware of various TAAs (including neoantigens) and approaches by such tumour antigens may be utilised in cancer vaccines. As further examples: (1) immunisation with recipient-derived clonal myeloma immunoglobulin, idiotype (Id), as a tumour antigen, conjugated with keyhole limpet hemocyanin (KLH) has been shown to produce substantial amount or pro-inflammatory cytokines including TNF (Foglietta et al 2013, Bone Marrow Transplant 48: 269); and (2) a synthetic micro-consensus SynCon DNA vaccine of WT1 antigens induced new, neo-antigen-like responses that were superior to those induced by native WT1 DNA immunogens, such as strong CD4 and CD8 T cell responses (including IFN-gamma, CD107a, and TNF responses).

In another example, such induced exposure to TNF may be brought about by the administration of ligand (such as an antibody, eg, a monoclonal antibody), for example one that binds to the surface of the cell(s) involved with the proliferative disorder (such as a tumour cell), for example by binding to a TAA or a receptor on the surface of such cell. Cell surface receptors are common targets for such ligand (antibody) therapies and include CD52 and CD20. Once bound to such a cancer antigen, the eg antibodies can induce antibody-dependent cell-mediated cytotoxicity, activate the complement system, or prevent a receptor from interacting with its ligand, all of which can lead to cell death. Approved such ligands that are antibodies include alemtuzumab, ofatumumab and rituximab. In certain embodiments, such ligands used in combination with SIK3 inhibitors can include those that activate T cells or other cell-mediated immune response. For example: (1) anti-CD137 monoclonal antibodies can dramatically promote proliferation of cytokine-induced killer (CIK) cells and expression of TNF (Zhu et al 2009, Biomed Pharmacother 63:509); (2) an agonist anti-OX40 monoclonal antibody can enhance antitumour immune response by augmenting T-cell differentiation (Redmond et al 2014, Cancer Immunol Res. 2014, 2:142)

In yet another example, the ligand that is administered to the subject is one that binds to an immune (inhibitory) checkpoint molecule. For example, such checkpoint molecule may be one selected from the group consisting of: A2AR, B7-H3, B7-H4, CTLA-4, IDO, KIR, LAG3, PD-1 (or one of its ligands PD-L1 and PD-L2), TIM-3 (or its ligand galectin-9), TIGIT and VISTA. In particular of such embodiments, the ligand binds to a checkpoint molecule selected from: CTLA-4, PD-1 and PD-L1. In other more particular embodiments, the ligand is an antibody selected from the group consisting of: ipilimumab, nivolumab, pembrolizumab, BGB-A317, atezolizumab, avelumab and durvaluma; in particular an antibody selected from the group consisting of: ipilimumab (YERVOY®), nivolumab (OPDIVO®), pembrolizumab (KEYTRUDA®) and atezolizumab (TECENTRIQ®). In other embodiments, the ligand that binds to a immune (inhibitory) checkpoint molecule may be a non-antibody peptide, such as a high-affinity PD-1 variant (eg, Maute et al, 2015; PNAS 112: E6506), a peptide targeting the immune checkpoint molecule (such as AUNP-12 of Aurigene Discovery Technologies, US 2011/0318373) or a D peptide blocking an interaction between immune checkpoint molecule (such as the PDL1-PD1 interaction and (D) PPA-1, Chang et al, 2015; Anyeg Chem Int 54:11760). In yet other embodiments, the ligand that binds to a immune (inhibitory) checkpoint molecule may be a small molecule, such as the PDL1-targeting BMS-202 or BMS-8 (Zak et al, 2016; Oncotarget 7:30323), the inhibitors of PDL1/D1 known as BMS-1001 or BMS-1166 (Skalniak et al, 2017; Oncotarget 8:72167), the PDL1 and VISTA antagonist CA-170 of Curis/Aurigen undergoing phase 1 trials (Powderly et al, Ann Onc 28: Issue suppl 5, mdx376.007) or CA-327 of Curis/Aurigen which targets PDL1 and TIM3.

In yet another particular embodiments, such induced exposure to TNF may be brought about by radiotherapy.

Radiotherapy is a method of locoregional treatment of cancers or tumours, using radiation to destroy the cancer cells by blocking their ability to multiply and/or to stimulate an immune reaction against the them (such one raised as a response to the presence of dead or dying cancer cells). Radiotherapy, in the context of the present invention, consists—in particular—of the therapeutic use of ionising radiation. Said radiotherapy and the associated ionising radiation are those commonly used and known to those skilled in the art. Radiotherapy includes in particular the use of ionizing radiation, for example gamma-rays, X-rays and/or radiation emanating from radioisotopes. In the context of the present invention, it is more particularly X-ray radiation. The radiotherapy may be administered in fractionated form during one or more cycles, such as a cycle that can range from 1 to 4 weeks, more particularly 3 weeks. The cycle defines the interval between the beginning and the end of an administration scheme. When the cycle takes three weeks, radiotherapy can be administered over three weeks, with one week between. The radiotherapy may in particular be administered at a rate of one daily irradiation, 5 days out of 7, for the desired number of weeks. The amount of radiation used in (photon) radiation therapy is measured in gray (Gy), and varies depending on the type and stage of cancer being treated. For curative cases, the typical dose for a solid epithelial tumour ranges from 60 to 80 Gy, while lymphomas are treated with 20 to 40 Gy.

When the SIK3 inhibitor is used in combinations treatments together with any of such other procedures (eg, the other agent, the cancer immunotherapy, the cancer vaccine, the antibody or the radiotherapy, in each case as described herein), then such combination treatment regimen may comprise embodiments where such exposures/administrations are concomitant. In alternative embodiments such administrations may be sequential; in particular those embodiments where the SIK3 inhibitor is administered before such other procedure. For example the SIK3 inhibitor may be sequentially administered within about 14 days of (eg before) the other procedure, such as within about 10 days, 7 days, 5 days, 2 days or 1 day of (eg before) the other procedure; and further including where the SIK3 inhibitor may be sequentially administered within about 48 hours, 24 hours, 12 hours, 8 hours, 6 hours, 4 hours, 2 hours, 1 hours, 30 mins, 15 mins or 5 mins of (eg before) the other procedure.

Without being bound to theory, administration of the SIK3 inhibitor (and hence inhibition of the expression, amount, function, activity or stability of SIK3, eg in a tumour cell) prior to administration of the TNF, TNF variant or TNFR1 or TNFR2 agonist, or prior to administration of such other procedures (eg, the other agent, the cancer immunotherapy, the cancer vaccine, the antibody or the radiotherapy, is foreseen to be particularly effective in sensitising the cells involved with the proliferative disorder to the cytotoxic effects of the cell-mediated immune response.

As described above, existing therapies (or those under clinical trials) involving administration of TNF and/or use of anti-TNF molecules suffer certain known disadvantages; and particular side effects. The present invention provides methods that may be used to mitigate (or reduce) such disadvantages and/or particular side effects.

In a fifth aspect, and as may be further described, defined, claimed or otherwise disclosed herein, the invention relates to a method for the increase of the therapeutic index of treatment with TNF in a subject being treated therewith for a proliferative disorder (eg a cancer disease or a tumour), the method comprising administering an inhibitor of SIK3 to the subject.

In a related aspect, the invention relates to a method for supporting TNF therapy in a subject suffering from a proliferative disorder (eg a cancer disease or a tumour), the method comprising administering an inhibitor of SIK3 to the subject.

In a sixth aspect, and as may be further described, defined, claimed or otherwise disclosed herein, the invention relates to a method for the sensitisation of a subject suffering from a proliferative disorder (eg a cancer disease or tumour) to a therapy involving the administration of TNF to the subject, the method comprising administering an inhibitor of SIK3 to the subject. The term "sensitisation" (and the like), as used herein in the context of a subject being sensitised to a therapy (eg one involving the administration of TNF), will be understood by the person of ordinary skill, and includes the meaning that the subject increases susceptibility to one or more (treatment) effect—in particular an efficacy effect—that such therapy may have on the subject. In particular, a subject that is so sensitised may, when undergoing such therapy, show an increased response (such as more rapidly, a greater degree of response and/or upon a lower amount or exposure of such therapy) than an analogous subject that have not been so "sensitised.

In a seventh aspect, and as may be further described, defined, claimed or otherwise disclosed herein, the invention relates to a method for the reduction in risk of (developing) a haematological proliferative disorder (as a secondary disorder) in a subject being treated with an anti-TNF agent, the method comprising administering an inhibitor of SIK3 to the subject. For example, such aspect may alternatively, be considered as a method for the prevention of a haematological proliferative disorder (as a secondary disorder) in a subject being treated with an anti-TNF agent, the method comprising administering an inhibitor of SIK3 to the subject.

This aspect of the invention is based on the observation as described above, that there are reports of patients receiving anti-TNF biologics developing lymphomas and other haematological malignancies. Indeed, such disorders are typically described in package leaflets/prescribing information as possible (but rare) side-effects of treatment with anti-TNF agents. As a direct consequence of the perceived increase in haematological malignancy and widespread use of these and other immunosuppressive agents, the WHO classification of tumours now includes the category "iatrogenic immunodeficiency-associated lymphoproliferative disease".

Therefore, typically in such aspects, the subject is being treated with the anti-TNF agent for an indication other than a proliferative disorder, and in particular of such embodiments the subject does not—upon commencement of the anti-TNF treatment—suffer from a haematological proliferative disorder. Indeed, typically the subject would suffer from, and/or is being treated with the anti-TNF agent for an autoimmune disorder; preferably an autoimmune disorder selected from the group consisting of: rheumatoid arthritis, psoriatic arthritis, ankylosing spondylitis, plaque psoriasis, inflammatory bowel disease, ulcerative colitis, Crohn's Disease, psoriasis, hidradenitis suppurativa and refractory asthma; such as one selected from the group consisting of: rheumatoid arthritis, psoriatic arthritis, ankylosing spondylitis, plaque psoriasis and Crohn's Disease; and in particular rheumatoid arthritis.

In certain embodiments, the anti-TNF agent is one selected from a list consisting of: infliximab, adalimumab, golimumab, humicade, etanercept, onercept and certolizumab pegol, in particular infliximab or humicade.

In certain embodiments, the haematological malignancies proliferative disorder may be a lymphoproliferative disease, in particular an iatrogenic immunodeficiency-associated lymphoproliferative disease.

In certain embodiments of such fifth to seventh aspects, the (treatment) effect (eg the increase in therapeutic index, sensitisation of a subject or reduction in risk) is mediated by (eg, the treatment comprises or involves): (i) inhibiting SIK3 (such as by the inhibition of the expression, amount, function, activity and/or stability of SIK3, for example, of phosphorylated SIK3), in particular by inhibiting SIK3 in cells involved with the proliferative disorder; and/or (ii) sensitising such cells to the killing effects of TNF. In further embodiments, the (treatment) effect may not be mediated by (eg, the treatment may not comprise or involve) inhibiting SIK2 and/or SIK1, in particular not mediated by (eg, the treatment does not comprise or involve) inhibiting SIK2 and/or SIK1 (and/or SIK3) in immune cells.

SIK3 inhibitors of or for use with the invention:

In all aspects of the invention are included embodiments where the SIK3 inhibitor can be specific (eg, selective) for SIK3 (eg a SIK3-specific inhibitor).

In particular of such embodiments, the SIK3 inhibitor may inhibit (eg the expression, amount, function, activity and/or stability of) SIK3 (in particular, the function or activity of phosphorylated SIK3) more potently than it inhibits (eg the expression, amount, function, activity and/or stability of) one or more other kinases, such as SIK2 and/or SIK1 (in particular, the function or activity of phosphorylated SIK2 and/or phosphorylated SIK1), and/or ABL or SRC kinase. Accordingly, in certain embodiments, the SIK3 inhibitor inhibits SIK3 more potently than it inhibits ABL1 and/or SRC kinase.

A SIK3 inhibitor can be considered "specific" (eg, "selective") for SIK3 or to inhibit SIK3 "more potently" if the SIK3 inhibitor inhibits SIK3 preferentially to inhibiting SIK2 and/or than SIK1. In certain of such embodiments, the SIK3 inhibitor inhibits SIK3 preferentially to inhibiting one or more other serine tyrosine kinases (STK), including without limitation Abl, Src and/or Bcr-Abl. For example, a SIK3-specific inhibitor (eg, a selective SIK 3 inhibitor) may inhibit SIK3 with a potency that is greater than about 2 fold more than its potency against the given other SIK (or STK), such as with a potency that is greater than about 5, 10, 20, 50, 100, 200, 500 or 1000 fold more potent than against the given other SIK (or STK). In particular, the SIK3 inhibitor may be more potent against SIK3 by an amount between about 50 and 500 fold, 10 and 200 fold or 50 and 1000 fold more than its potency against the given other SIK (or STK). For example, the SIK3 inhibitor may be more potent against SIK3 by an amount that is between about 20 and 500 fold more potent than against SIK1 and/or against SIK2. In other embodiments, the SIK3 inhibitor shows an IC50 for SIK3 inhibition that is lower than the IC50 for SIK1 and or SIK2 inhibition, such as by a fold-amount (or range thereof) as described in this paragraph. By way of example, the SIK3 inhibitor may inhibit SIK3 with an IC50 of about 2 nM, but inhibit SIK1 with an IC50 of only 100 nM and SIK2 with an IC50 of only 200 nM. Accordingly, such SIK3 inhibitor inhibits SIK3 50-fold more potently than SIK1 and 100-fold more potently than SIK2.

In certain embodiments, the SIK3 inhibitor inhibits SIK3 in cells involved with a proliferative disorder. For example, the SIK3 inhibitor inhibits such SIK3 more potently than it inhibits SIK1 and/or SIK2 in such cells, and/or more potently than it inhibits SIK1 and/or SIK2 and/or SIK3 (in particular, SIK2) in immune cells.

In other embodiments, the SIK3 inhibitor may inhibit SIK3 as well as another SIK; in particular of such embodiments the SIK3 inhibitor may inhibit SIK3 and SIK1 more potently than inhibiting SIK2. For example, the SIK3 inhibitor may inhibit SIK3 and SIK1 at about the same potency (such as within about 2 and 5 fold of each other) but may inhibit SIK3 (and SIK1) more potently than it inhibits SIK2 (such as by an amount greater than about 5, 10, 20, 50, 100, 200, 500 or 1000 fold more). In more particular of such embodiments, the SIK3 inhibitor may inhibit SIK3 and SIK1 in cells involved with a proliferative disorder; optionally, more potently than it inhibits SIK2 in such cells, and/or more potently than it inhibits SIK2 in immune cells.

Such specificity (selectivity or preferential potency) for SIK3 (and optionally, SIK1) or other kinases, such as ABL and/or SRC kinases, can be measured in-vitro, such as in an in vitro biochemical assay, for example as provided by DiscoverX, ProQinase, Reaction Biology or ThermoFisher. Alternatively, the specificity (selectivity or preferential potency) for SIK3 is measured in-vivo, such as in a cell-based or animal model.

Accordingly, in certain embodiments of the invention, in a cell-based of animal model, the SIK3 inhibitor can inhibit (eg the expression, amount, function, activity and/or stability of) SIK3 (in particular, the function or activity of phosphorylated SIK3) in cells involved with a proliferative disorder, more potently than it inhibits (eg the expression, amount, function, activity and/or stability of) ABL and/or SRC kinases, and/or SIK2 (and/or SIK1)—in particular, the function or activity of phosphorylated SIK2 and/or phosphorylated SIK1; and/or SIK3—cells (such as in (of) immune cells, or for ABL, SRC and SIK2, in/of cells involved with the proliferative disorder), preferably SIK2 in immune cells.

In further embodiments, the (treatment) effect may be mediated by (eg, the treatment may comprise, involve or be mediated by) inhibition of (eg the expression, amount, function, activity and/or stability of) SIK3 (such as in cells involved with a proliferative disorder) and not by the inhibition of (eg the expression, amount, function, activity and/or stability of) ABL and/or SRC kinases, and/or SIK2 (and/or SIK3)—such as in an immune cell—in particular, the (treatment) effect may optionally be additionally mediated by (eg, the treatment may comprise, involve or be mediated by) inhibition of SIK1 in such cells.

Accordingly, in certain embodiments, the SIK3 inhibitor inhibits SIK3 in (of) cells involved with the proliferative disorder more potently than it inhibits ABL1 and/or SRC kinase in (of) such cells, and (preferably) more potently than it inhibits SIK2 and/or SIK1 in (of) such cells.

In other embodiments, the SIK3 inhibitor inhibits a kinase target of dasatinib (such as Abl, Src and/or Bcr-Abl with an IC50 that is less than dasatinib inhibits such target, for example by a factor of about 2, 3, 5 or 10-fold less.

Inhibitors of SIK3, are in certain embodiments the following specific molecules and/or molecular classes: the SIK3 inhibitor may be one selected from a polypeptide, peptide, glycoprotein, a peptidomimetic, an antibody or antibody-like molecule (such as an intra-body); a nucleic acid such as a DNA or RNA, for example an antisense DNA or RNA, a ribozyme, an RNA or DNA aptamer, siRNA, shRNA and the like, including variants or derivatives thereof such as a peptide nucleic acid (PNA); a genetic construct for targeted gene editing, such as a CRISPR/Cas9 construct and/or guide RNA/DNA (gRNA/gDNA) and/or tracrRNA; a hetero-bi-functional compound (such as a PROTAC or a HyT molecule); a carbohydrate such as a polysaccharide or oligosaccharide and the like, including variants or derivatives thereof; a lipid such as a fatty acid and the like, including variants or derivatives thereof; or a small organic molecules including but not limited to small molecule ligands, or small cell-permeable molecules.

The SIK3 inhibitor of the invention may be in a prodrug form. Prodrugs forms of a particular compound are those other compounds (such as ester forms of the particular compound) that upon administration to a subject undergo chemical conversion under physiological conditions to provide the particular compound. Additionally, prodrugs can be converted to the particular compound by chemical or biochemical methods in an ex vivo environment. For example, prodrugs can be slowly converted to the particular compound when, for example, placed in a transdermal patch reservoir with a suitable enzyme or chemical reagent. Exemplary prodrugs are esters or amides which are hydrolysable in vivo.

Nucleic Acid SIK3 Inhibitors:

In one particular set of embodiments, the SIK3 inhibitor is a nucleic acid.

The terms "nucleic acid", "polynucleotide" and "oligonucleotide" are used interchangeably throughout and include DNA molecules (e.g., cDNA or genomic DNA), RNA molecules (e.g., mRNA), analogues of the DNA or RNA generated using nucleotide analogues (e.g., peptide nucleic acids and non-naturally occurring nucleotide analogues), and hybrids thereof. The nucleic acid molecule can be single-stranded or double-stranded.

In the case of SIK3 inhibitors being CRISPR/Cas9 constructs and/or guide RNA/DNAs (gRNA/gDNA) and/or tracrRNAs, the basic rules for the design of CRISPR/Cas9 mediated gene editing approaches are known to the skilled artisan and for example reviewed in Wiles M V et al (Mamm Genome 2015, 26:501) or in Savic N and Schwank G (Transl Res 2016, 168:15).

In particular embodiments, the SIK3 inhibitor may be an inhibitory nucleic acid molecule, such as antisense nucleotide molecule including a siRNA or shRNA molecule, for example as described in detail herein below.

In more particular of such embodiments, the inhibitory nucleic acid (such as siRNA or shRNA) can bind to, such as specifically bind to, a nucleic acid (such as mRNA) that encodes or regulates the expression, amount, function, activity or stability of: (i) SIK3 (eg phosphorylated SIK3); or (ii) a gene (such as LKB1 or the glucagon receptor) that controls the expression, amount, function and/or stability of SIK3 and, for example, thereby modulates the expression, amount function, activity and/or stability of SIK3 (eg phosphorylated SIK3).

An inhibitor of SIK3 that is a nucleic acid can be, for example, an anti-sense nucleotide molecule, an RNA, DNA or PNA molecule, or an aptamer molecule. An anti-sense nucleotide molecule can, by virtue of it comprising an anti-sense nucleotide sequence, bind to a target nucleic acid molecule (eg based on sequence complementarity) within a cell and modulate the level of expression (transcription and/or translation) of SIK3, or it may modulate expression of another gene that controls the expression, function and/or stability of SIK3. Similarly, an RNA molecule, such as a catalytic ribozyme, can bind to and alter the expression of the SIK3 gene, or it can bind to and alter the expression of other genes that control the expression, function and/or stability of SIK3, such as a transcription factor for or repressor protein of SIK3 and/or LKB1 or the glucagon receptor. An aptamer is a nucleic acid molecule that has a sequence that confers it an ability to form a three-dimensional structure capable of binding to a molecular target.

An inhibitor of SIK3 that is a nucleic acid can be, for example, can further be a double-stranded RNA molecule for use in RNA interference. RNA interference (RNAi) is a process of sequence-specific gene silencing by post-transcriptional RNA degradation or silencing (prevention of translation). RNAi is initiated by use of double-stranded RNA (dsRNA) that is homologous in sequence to the target gene to be silenced. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3'end (Elbashir et al., Nature 411:494-498 (2001); Bass, Nature 411:428-429 (2001); Zamore, Nat. Struct. Biol. 8:746-750 (2001)). dsRNAs of about 25-30 nucleotides have also been used successfully for RNAi (Karabinos et al., Proc. Natl. Acad. Sci. USA 98:7863-7868 (2001). dsRNA can be synthesised in vitro and introduced into a cell by methods known in the art.

A particularly preferred example of an antisense molecule of the invention is a small interfering RNA (siRNA) or endoribonuclease-prepared siRNA (esiRNA). An esiRNA is a mixture of siRNA oligos resulting from cleavage of a long double-stranded RNA (dsRNA) with an endoribonuclease such as *Escherichia coli* RNase III or dicer. esiRNAs are an alternative concept to the usage of chemically synthesised siRNA for RNA Interference (RNAi). An esiRNAs is the enzymatic digestion of a long double stranded RNA in vitro.

As described above, a modulator of the invention that is an RNAi molecule (such as an siRNA) may bind to and directly inhibit or antagonise the expression of mRNA of SIK3. However, a modulator of the invention that is an RNAi molecule (such as an siRNA) may bind to and inhibit or antagonise the expression of mRNA of another gene that itself controls the expression (or function or stability) of SIK3. Such other genes may include transcription factors or repressor proteins or LKB1 or the glucagon receptor.

The sequence identity of the antisense molecule according to the invention in order to target a SIK3 mRNA (or to target mRNA of a gene controlling expression, function and/or stability of SIK3), is with increasing preference at least 75%, at least 80%, at least 85%, at least 90%, at least 95%, at least 98%, at least 99% and 100% identity to a region of a sequence encoding the SIK3 protein, as disclosed herein (or of such other controlling gene, of which a preferred example is the LKB1 gene). Preferably, the region of sequence identity between the target gene and the modulating antisense molecule is the region of the target gene corresponding to the location and length of the modulating antisense molecule. For example, such a sequence identity over a region of about 19 to 21 bp of length corresponding to the modulating siRNA or shRNA molecule). Means and methods for determining sequence identity are known in the art. Preferably, the BLAST (Basic Local Alignment Search Tool) program is used for determining the sequence identity with regard to one or more SIK3 RNAs as known in the art. On the other hand, preferred antisense molecules such as siRNAs and shRNAs of the present invention are preferably chemically synthesised using appropriately protected ribonucleoside phosphoramidites and a conventional RNA synthesiser. Suppliers of RNA synthesis reagents include Proligo (Hamburg, Germany), Dharmacon Research (Lafayette, CO, USA), Pierce Chemical (part of Perbio Science, Rockford, IL (USA), Glen Research (Sterling, VA, USA), ChemGenes (Ashland, MA, USA), and Cruachem (Glasgow, UK).

The ability of antisense molecules, siRNA, and shRNA to potently, but reversibly, silence genes in vivo make these molecules particularly well suited for use in the pharmaceutical composition of the invention which will be also described herein below. Ways of administering siRNA to humans are described in De Fougerolles et al., Current Opinion in Pharmacology, 2008, 8:280-285. Such ways are also suitable for administering other small RNA molecules like shRNA. Accordingly, such pharmaceutical compositions may be administered directly formulated as a saline, via liposome based and polymer-based nanoparticle approaches, as conjugated or complexation pharmaceutical compositions, or via viral delivery systems. Direct administration comprises injection into tissue, intranasal and intratracheal administration. Liposome based and polymer-based nanoparticle approaches comprise the cationic lipid Genzyme Lipid (GL) 67, cationic liposomes, chitosan nanoparticles and cationic cell penetrating peptides (CPPs). Conjugated or complexation pharmaceutical compositions comprise PEI-complexed antisense molecules, siRNA, shRNA or miRNA. Further, viral delivery systems comprise influenza virus envelopes and virosomes.

The antisense molecules, siRNAs, shRNAs may comprise modified nucleotides such as locked nucleic acids (LNAs). The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers are synthesised chemically and are commercially available. The locked ribose conformation enhances base stacking and backbone pre-organisation. This significantly increases the hybridisation properties (melting temperature) of oligonucleotides. Particularly preferred example of siRNAs is GapmeR (LNA™ GapmeRs (Exiqon)). GapmeRs are potent antisense oligonucleotides used for highly efficient inhibition of SIK3 mRNA (or of mRNA of a gene controlling expression, function and/or sta-bility of SIK3). GapmeRs contain a central stretch of DNA monomers flanked by blocks of LNAs. The GapmeRs are preferably 14-16 nucleotides in length and are optionally fully phosphorothioated. The DNA gap activates the RNAse H-mediated degradation of targeted RNAs and is also suitable to target transcripts directly in the nucleus.

Preferred antisense molecules for targeting SIK3 are antisense molecules or constructs having a sequence complementary to a region (such as one described above) of a nucleic acid sequence of an SIK3 mRNA, preferably a sequence complementary to a region of a sequence encoding the amino acid sequence shown in SEQ ID NO: 1 to 4 or in any of SEQ ID NOs 13 to 16, in particular of SEQ ID NOs: 1 or 13, more preferably, a sequence complementary to a region of between about 15 to 25 bp (such as between about 19 and 21 bp) of a sequence encoding the amino acid sequence shown in SEQ ID NO: 1 to 4 or in any of SEQ ID NOs 13 to 16, in particular of SEQ ID NOs: 1 or 13.

In particular embodiments, an antisense molecule for targeting SIK3 may be an siRNA selected from the SIK3 siRNA molecules identified as "s1", "s2", "s3, or "s4" herein (eg in Table A; SEQ ID NOs: 7, 8, 9 and 10, respectively).

TABLE A1 exemplary siRNA sequences used

| Gene | siRNA ID | siRNA sequence | Order number (Dharmacon/GE Lifesciences) | SEQ ID NO. |
|---|---|---|---|---|
| SIK3 | s1 | GCGCCAGGCUUUAUCUUAU | D-004779-01 | 7 |
| SIK3 | s2 | GAACAGCGACGAUGCUUAU | D-004779-05 | 8 |
| SIK3 | s3 | GCACUAACCUGCUUGGGUA | D-004779-06 | 9 |
| SIK3 | s4 | GGAGCAGGCAGGCGUGUAA | D-004779-020 | 10 |
| SIK3 | Pool | As above: s1, s2, s3 and s4 | As above | N/A |
| SIK1 | Pool | | M-003959-05 | N/A |
| SIK2 | Pool | | M-004778-03 | N/A |
| PD-L1 | Smart Pool | | M-015836-01 | N/A |

TABLE A1-continued exemplary siRNA sequences used

| Gene | siRNA ID | siRNA sequence | Order number (Dharmacon/GE Lifesciences) | SEQ ID NO. |
|---|---|---|---|---|
| CEACAM6 | Smart Pool | | M-015306-01 | N/A |
| HDAC4 | ON-Target plus pool | | J-003497-07 to J-003497-10 | N/A |
| Control | siCtrl/ siCtrl1 | | 4390844 (ThermoScientific) | N/A |

In particular embodiments, an antisense molecule for targeting SIK3 may be an shRNA molecule identified as "shSIK3 herein (eg in Table A2; SEQ ID NO: 11).

TABLE A2 exemplary shRNA sequences used

| Gene | shRNA ID | Sequence | Order number (Sigma) | SEQ ID NO. |
|---|---|---|---|---|
| SIK3 | shSIK3 | CCGGGCCAGGCTT TATCTTATCAAAC TCGAGTTTGATAA GATAAAGCCTGGC TTTTTG | TRCN0000037452 | 11 |
| Control | shCtrl | CCGGGCGCGATAG CGCTAATAATTTC TCGAGAAATTATT AGCGCTATCGCGC TTTTT | SHC016H | 12 |

In one embodiment the antisense molecules of the invention may be isolated. In another embodiment, the antisense molecules of the invention may be recombinant, synthetic and/or modified, or in any other way non-natural or not a product of nature. For example, a nucleic acid of the invention may contain at least one nucleic acid substitution (or deletion) modification such as between 1 and about 5 such modifications, preferably no more than 1, 2 or 3 such modifications) relative to a product of nature, such as a human nucleic acid. As described above, the antisense molecules of the invention may be modified by use of non-natural nucleotides, or may be conjugated to another chemical moiety. For example, such chemical moieties may be a heterologous nucleic acid conferring increased stability or cell/nucleus penetration or targeting, or may be a non-nucleic acid chemical moiety conferring such properties, of may be a label.

Certain preferred embodiments pertain to a genetic construct for gene editing that is used as an inhibitor of expression, function and/or stability of SIK3 in the context of the herein described invention. By using genome editing constructs it is possible to modulate the expression, stability and/or activity of SIK3. Genome editing approaches are well known in the art and may be easily applied when the respective target genomic sequences are known. Preferably, such approaches may be used in gene therapy using e.g. viral vectors, which specifically target tumour cells in accordance with the above descriptions.

In case of genome editing, DNA is inserted, replaced, or removed, from a genome using artificially engineered nucleases, or so called "molecular scissors". The nucleases create specific double-stranded break (DSBs) at desired locations in the genome, and harness the cell's endogenous mechanisms to repair the induced break by natural processes of homologous re-combination (HR) and non-homologous end-joining (NHEJ). For doing so, engineered nucleases such as zinc finger nucleases (ZFNs), Transcription Activator-Like Effector Nucleases (TALENs), the CRISPR/Cas system, and engineered meganuclease re-engineered homing endonucleases are routinely used for genome editing. According to another preferred embodiment, for genome editing approaches for modulating/inhibiting SIK3, the rare-cutting endonuclease is Cas9, Cpf1, TALEN, ZFN, or a homing endonuclease may be used. Also, it may be convenient to engineer using DNA-guided Argonaute interference systems (DAIS). Basically, said Argonaute (Ago) protein is heterologously expressed from a polynucleotide introduced into said cell in the presence of at least one exogenous oligonucleotide (DNA guide) providing specificity of cleavage to said Ago protein to a preselected locus. The TALEN and Cas9 systems are respectively described in WO 2013/176915 and WO 2014/191128. The Zinc-finger nucleases (ZFNs) are initially described in Kim, Y G; Cha, J.; Chandrasegaran, S. ("Hybrid restriction enzymes: zinc finger fusions to Fok I cleavage domain" (1996). Proc Natl Acad Sci USA 93 (3): 1156-60). Cpf1 is class 2 CRISPR Cas System described by Zhang et al. (Cpf1 is a single RNA-guided Endonuclease of a Class 2 CRIPR-Cas System (2015) Cell; 163:759-771). The argonaute (AGO) gene family was initially described in Guo S, Kemphues K J. ("par-1, a gene required for establishing polarity in C. elegans embryos, encodes a putative Ser/Thr kinase that is asymmetrically distributed" (1995) Cell; 81(4):611-20).

The use of the CRISPR/Cas9, CRISPR/Cpf1 or the Argonaute genome-editing systems is particularly adapted to be used in combination with the transfection of guide RNA or guide DNA sequences. In this context the guide-RNAs and a nucleic acid sequence coding for Cas9 nickase (or similar enzymes), is transfected into a target cell (preferably a tumour cell) so that they form a complex able to induce a nick event in double-stranded nucleic acid targets in order to cleave the genetic sequence between said nucleic acid targets.

In certain embodiments, it may be useful to deliver the guide RNA-nanoparticle formulations separately from the Cas9. In such an instance a dual-delivery system is provided such that the Cas9 may be delivered via a vector and the guide RNA is provided in a nanoparticle formulation, where vectors are considered in the broadest sense simply as any means of delivery, rather than specifically viral vectors. Separate delivery of the guide RNA-nanoparticle formulation and the Cas9 may be sequential, for example, first Cas9 vector is delivered via a vector system followed by delivery of sgRNA-nanoparticle formulation) or the sgRNA-nanoparticle formulation and Cas9 may be delivered substantially contemporaneously (i.e., co-delivery). Sequential delivery may be done at separate points in time, separated by days, weeks or even months. In certain embodiments, multiple guide RNAs formulated in one or more delivery vehicles (e.g., where some guide RNAs are provided in a vector and others are formulated in nanoparticles) may be provided with a Cas9 delivery system. In certain embodiments, the Cas9 is also delivered in a nanoparticle formulation. In such an instance the guide RNA-nanoparticle formulation and the Cas9 nanoparticle formulation may be delivered separately or may be delivered substantially contemporaneously (i.e., co-delivery). As will now be apparent to the person of ordinary skill, the gene target of such genome-editing approaches may be the gene of SIK3. Alternatively, the gene target of such editing may be another gene that controls the expression, function and/or stability of SIK3, for example LKB1 or the glucagon receptor.

In preferred embodiments of the invention, the compounds for genome editing approaches according to the invention comprise at least the use of a guide RNA or DNA complementary to a region (such as one described above) of a SIK3 sequence. In some additional embodiments, the compounds for use in genome editing approaches of the invention may include donor sequences homologous to such a region of SIK3, as templates for homology directed repair. The donor sequences comprise a mutated sequence of SIK3 that when used in the CRISPR induced repair mechanism in a target cell, is by homologous recombination inserted/copied into the SIK3 genomic locus, and therefore yields into a mutated SIK3 gene which is characterised by a reduced expression, function and/or stability of the expressed SIK3. CRISPR/Cas9 genome editing in cancer therapy is reviewed for ex-ample in Khan F A et al: "CRISPR/Cas9 therapeutics: a cure for cancer and other genetic diseases." (Oncotarget. 2016 May 26. doi: 10.18632/oncotarget.9646; incorporated by reference in its entirety).

Hetero-Bi-Functional Compounds

In particular embodiments, inhibitors of SIK3 may be a hetero-bi-functional compound that contains two ligands connected by a linker, wherein one ligand binds to the target protein (in this case, SIK3 or a gene that controls the expression, amount, function, activity and/or stability of SIK3) and the other ligand binds to and/or recruits a component of the cellular protein degradation machinery such as binding to a ubiquitin ligase protein (eg E3 ubiquitin ligase) or such as recruiting a chaperone protein. Examples of such hetero-bi-functional compounds include PROTACs ("PROteolysis TAgeting Chimera) or HyT ("hydrophobic tagging") molecules, in each case designed to bind to the target protein for the present invention. The general principles of PROTACs and HyT molecules are reviewed in Huang & Dixit 2016 (Cell Research 26:484) and exemplified specifically in, for example, WO 2016/146985A1.

A PROTAC that binds to the target protein (eg SIK3) with one ligand and with the other ligand to an E3 ubiquitin ligase protein thereby brings the ligase and the target into close proximity. Without being bound by any particular theory it is generally understood that it is this close proximity which in turn triggers the poly-ubiquitination and subsequent proteasome-dependent degradation of the target protein of interest. Supporting evidence for a PROTAC approach on a general level is provided by known proof-of-concept examples where alternative PROTACs have been used to degrade: the Estrogen-receptor (Cyrus et al 2010, Chem Bio Chem 11:1531); the Androgen-receptor (Sakamoto et al 2003, Mol Cell Proteomics 2:1350); methionine aminopeptidase-2 (Sakamoto et al 2001, PNAS 98:8554); as well as the Aryl Hydrocarbon Receptor (Lee et al 2007, Chem Bio Chem 8:2058).

The concept of hydrophobic tagging is similar to that of PROTAC, but instead of using a ligand to recruit a specific E3 ligase, a synthetic hydrophobic group, such as adamantane, linked to a chemical moiety that specifically recognizes the target protein (eg SIK3), assumes the role of "recruiter" for the degradation machinery. Upon binding to the target protein, the hydrophobic tag mimics or induces a misfolded state. Without being bound by any particular theory it is generally understood that modification of the target protein with a bulky hydrophobic side-group attracts the chaperone machinery, the primary goal of which is to help refold misfolded proteins. Since the covalent modification cannot be easily removed, the target protein remains unfolded and is eventually cleared by ubiquitin-proteasome mediated degradation.

In certain embodiments of such a hetero-bi-functional compound in the context of the present invention, the ligand contained therein that binds to the target protein (eg SIK3) may be a peptide that binds (preferably, specifically) to such target protein; and in alternative embodiments the ligand that binds to the target protein (eg SIK3) may be a small molecule such as small molecule SIK3 inhibitor that binds (preferably, specifically) to such target protein. Exemplary small molecule SIK3 inhibitors are described elsewhere herein, and as well as such small molecule SIK3 inhibitors having utility as inhibitors per-se (that is, not contained in a hetero-bi-functional compound, may—in certain embodiments—be comprised in a hetero-bi-functional compound.

Small Molecule SIK3 Inhibitors:

In another particular set of embodiments, the SIK3 inhibitor may be a small molecule (in particular, a small molecule ligand or a small cell-permeable molecule).

In more particular of such embodiments, a small molecule SIK3 inhibitor can bind to: (i) SIK3 and inhibit the function or activity of SIK3 (eg phosphorylated SIK3); or (ii) a gene (such as LKB1 or the glucagon receptor) that controls the expression, amount function, activity and/or stability of SIK3 and, example, thereby modulates the expression, amount, function, activity and/or stability of SIK3 (eg phosphorylated SIK3).

An inhibitor of SIK3 that is a small molecule can be, for example, any chemical structure or compound (molecule) having a SIK3 inhibitory activity as described herein and a molecular weight of, for example, less than 3000 dalton (Da), preferably less than 1500 Da, most preferably less than 1000 Da Typically, a small molecule is a compound having a molecular mass of less than about 750 Da, such as less than about 650 or 600 Da, (and in certain embodiments, a small molecule may be less than about 550 or 500 Da). Furthermore, (in particularly for a cell-permeable compound, and especially for an orally active compound), the small molecule can have, in certain embodiments: (i) no more than 5 hydrogen bond donors (the total number of nitrogen-hydrogen and oxygen-hydrogen bonds); (ii) no more than 10 hydrogen bond acceptors (all nitrogen or oxygen atoms); and/or (iii) an octanol-water partition coefficient log P not greater than 5. Accordingly, in some embodiments the SIK3 inhibitor can be a cell-permeable small organic molecule, such as one that binds to and inhibits the function or activity of SIK3 (in particular, of phosphorylated SIK3).

In one particular embodiment of all aspects of the invention, the SIK3 inhibitor is dasatinib.

Dasatinib (or BMS-354825) is a cancer drug produced by Bristol-Myers Squibb and sold under the trade name SPRYCEL®. The chemical name for dasatinib is N-(2-chloro-6-methylphenyl)-2-[6-[4-(2-hydroxyethyl)-1-piperazinyl]-2-methyl-4-pyrimidinyl]amino]-5-thiazolecarboxamide, especially the monohydrate form thereof. The molecular formula of dasatinib (monohydrate) is $C_{22}H_{26}ClN_7O_2S \cdot H_2O$, which corresponds to a formula weight of 506.02 (monohydrate), and dasatinib (monohydrate) has the following chemical structure:

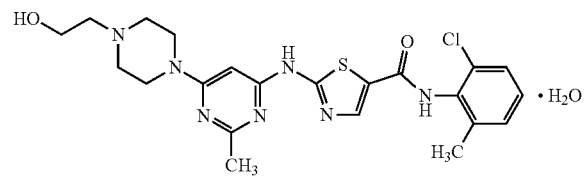 [SMILES: Cc1nc(Nc2ncc(C(=O)Nc3c(C)cccc3Cl)s2)cc(N2CCN(CCO)CC2)n1 ; "· H2O"]

In an alternative particular embodiment of all aspects of the invention, the SIK3 inhibitor is not dasatinib. For example, in one particular embodiment of all aspects of the invention, the SIK3 inhibitor is a variant of dasatinib. A "variant" in the context of a small molecule (such as a SIK3 inhibitor, eg dasatinib) means another small molecule that has a different chemical structure to the reference small molecule (ie, the variant is a different small molecule), wherein the different chemical structure retains one more structural features of the core structure of the reference small molecule. The chemical structure of a variant may differ from that of the reference small molecule by the addition, removal or substitution of at least one atom, or addition, modification, removal or substitution of at least one atomic or group substituent, or a change of at least one chemical bond between atoms, compared to the reference small molecule. For example, two, three, four, five, or more than five such atomic or group substituents may be added, removed or substituted on the chemical structure of the reference small molecule to provide such a variant of the reference small molecule (eg of dasatinib).

Accordingly, the invention in particular includes those embodiments where the SIK3 inhibitor a variant of dasatinib.

For example, in some embodiments, the SIK3 inhibitor is the monohydrate of the cyclic compound of claim 3 of EP 1 169 038 B9, or is a salt (or is a solvate, salt, complex, polymorph, crystalline form, racemic mixture, diastereomer, enantiomer, tautomer, isotopically labelled form, prodrug, and combination) thereof.

In one certain embodiments, the SIK3 inhibitor is (eg a variant of dasatinib being) a cyclic compound of "formula I" or "formula II" as defined on pages 3 to 13 of WO 00/62778A1 (herein, formula I and formula II$_{WO}$, respectively), in particular the "Preferred Compounds" thereof as defined on pages 13 and 14 of WO 00/62778A1, and salts thereof. In certain of such embodiments the compound is not dasatinib (or is not a monohydrate or salt of dasatinib), such as the compound is not the cyclic compound of claim 3 of EP 1 169 038 B9, or a salt thereof (or not a solvate, salt, complex, polymorph, crystalline form, racemic mixture, diastereomer, enantiomer, tautomer, isotopically labelled form, prodrug, and combination thereof). Such disclosures of WO 00/62778A1 are incorporated, solely for such specific purpose by reference herein.

Accordingly, in particular embodiments of the invention, the SIK3 inhibitor is a cyclic compound of the following formula I (eg a variant of dasatinib) and salts, prodrugs, solvates and stereoisomers (or solvates, salts, complexes, stereoisomers, polymorphs, crystalline forms, racemic mixtures, diastereomers, enantiomers, tautomers, isotopically labelled forms, prodrugs, and combinations thereof) thereof:

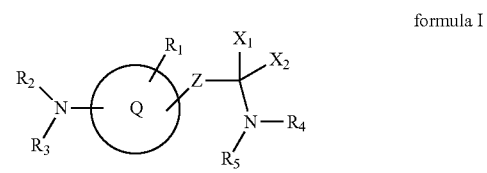

formula I where
Q is:
(1) a 5-membered heteroaryl ring;
(2) a 6-membered heteroaryl ring; or
(3) an aryl ring;
optionally substituted with one or more groups $R_1$;
Z is:
(1) a single bond;
(2) —$R_{16}$C=CH—; or
(3) —$(CH_2)_m$—, where m is 1 to 2;
$X_1$ and $X_2$ are each hydrogen, or together form =O or =S;
$R_1$ is:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$;
(2) —OH or —$OR_6$;
(3) —SH or —$SR_6$;
(4) —$C(O)_2H$, —$C(O)_qR_6$, or —O—$C(O)_qR_6$, where q is 1 or 2;
(5) —$SO_3H$ or —$S(O)_qR_6$;
(6) halo;
(7) cyano;
(8) nitro;
(9) —$Z_4$—$NR_7R_8$,
(10) —$Z_4$—$N(R_9)$—$Z_5$—$NR_{10}R_{11}$;
(11) —$Z_4$—$N(R_{12})$—$Z_5$—$R_6$;
(12) —$P(O)(OR_6)_2$;
$R_2$ and $R_3$ are each independently:
(1) hydrogen or $R_6$;
(2) —$Z_4$—$R_6$; or
(3) —$Z_3$—$NR_7R_8$;
$R_4$ and $R_5$:
(1) are each independently hydrogen or $R_6$;
(2) —$Z_4$—$N(R_9)$—$Z_5$—$NR_{10}R_{11}$;
(3) —$N(R_9)Z_4R_6$; or
(4) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;
$R_7$, $R_8$, $R_9$, $R_{10}$, $R_{11}$ and $R_{12}$:
(1) are each independently hydrogen or $R_6$;
(2) $R_7$, and $R_8$ may together be alkylene, alkenylene or heteroalkyl, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$ is:
(1) cyano;
(2) nitro;
(3) —$NH_2$;
(4) —NHOalkyl;
(5) —OH;
(6) —NHOaryl;
(7) —NHCOOalkyl;
(8) —NHCOOaryl;
(9) —$NHSO_2$alkyl;
(10) —$NHSO_2$aryl;
(11) aryl;
(12) heteroaryl;
(13) —Oalkyl; or
(14) —Oaryl;

$R_{14}$ is:
(1) —$NO_2$;
(2) —COOalkyl; or
(3) —COOaryl;

$R_{15}$ is:
(1) hydrogen;
(2) alkyl;
(3) aryl;
(4) arylalkyl; or
(5) cycloalkyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —C(O)H, —C(O)$Z_6$, or —O—C(O)$Z_6$;
(5) —$SO_3$H, —$S(O)_qZ_6$; or $S(O)_qN(Z_9)Z_6$;
(6) halo;
(7) cyano;
(8) nitro;
(9) —$Z_4$—$NZ_7Z_8$;
(10) —$Z_4$—N($Z_9$)—$Z_5$—$NZ_7Z_8$;
(11) —$Z_4$—N($Z_{10}$)—$Z_5$—$Z_6$;
(12) —$Z_4$—N($Z_{10}$)—$Z_5$H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_r$—O—, where r is 1 to 5, completing a 4- to 8-membered saturated or unsaturated ring together with the atoms to which they are attached;

$Z_4$ and $Z_5$ are each independently:
(1) a single bond;
(2) —$Z_{11}$—$S(O)_q$—$Z_{12}$—;
(3) —$Z_{11}$—C(O)—$Z_{12}$;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$; or
(8) —$Z_{11}$—C(O)—O—$Z_{12}$—;

$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$Z_{11}$ and $Z_{12}$ are each independently:
(1) a single bond;
(2) alkylene;
(3) alkenylene; or
(4) alkynylene; and $Z_{13}$ is:
(1) a single bond;
(2) —$Z_{11}$—$S(O)_q$—$Z_{12}$—;
(3) —$Z_{11}$—C(O)—$Z_{12}$;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—;
(8) —$Z_{11}$—C(O)—O—$Z_{12}$—;
(9) —C($NR_{13}$)—;
(10) —C($CHR_{14}$)—; or
(11) —C(C($R_{14}$)$_2$)—.

Preferred compounds of (or for use in) the present invention are compounds of the formula I, and salts thereof, wherein Q is thiazole and wherein one or more, and especially all, of Z, $X_1$, $X_2$ $R_1$, $R_2$, $R_3$, $R_4$, and $R_5$ are selected from the following definitions: Z is a single bond; $R_1$ is selected from hydrogen, halo, alkyl, aryl, alkoxy, alkoxycarbonyl, or aryloxycarbonyl and is more preferably hydrogen; $X_1$ and $X_2$ together form =O or =S and more preferably form =O; $R_2$ is hydrogen; $R_3$ is selected from —$Z_4$—$R_6$ or —$Z_{13}$—$NR_7R_8$ and is more preferably —$Z_4$—$R_6$, wherein $Z_4$ is a single bond and R is aryl or heteroaryl which is unsubstituted or substituted with $Z_1$, $Z_2$ and one or more (preferably, one or two) groups $Z_3$; $R_4$ is hydrogen; and $R_5$ is selected from aryl groups or heteroaryl groups which are substituted with $Z_1$, $Z_2$ and one or more (such as one or two) groups $Z_3$.

Compounds within formula I include compounds of the following formula $II_{WO}$ (eg a variant of dasatinib) and salts thereof:

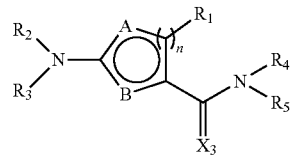

formula $II_{WO}$ where
n is 1 or 2
A is selected from carbon and nitrogen;
B is selected from nitrogen, oxygen and sulphur;

$X_3$ is oxygen or sulphur; and $R_1$, $R_2$, $R_3$, $R_4$ and $R_5$ are as described above.

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. The expression "lower alkyl" refers to alkyl groups of 1 to 4 carbon atoms.

The term "alkenyl" refers to straight or branched chain hydrocarbon groups of 2 to 10, preferably 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, preferably 2 to 4, carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e.g., —(CH$_2$)$_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —CH$_2$—CH=CH—, —CH$_2$—CH=CH—CH$_2$—, —C(CH$_3$)$_2$CH=CH— and —CH(C$_2$H$_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —CH$_2$—C≡C—, —CH(CH$_3$)—C≡C— and —C≡C—CH(C$_2$H$_5$)CH$_2$—.

The terms "ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

The terms "cycloalkyl" and "cycloalkenyl" refer to cyclic hydrocarbon groups of 3 to 12 carbon atoms.

The terms "halogen" and "halo" refer to fluorine, chlorine, bromine and iodine.

The term "unsaturated ring" includes partially unsaturated and aromatic rings.

The terms "heterocycle", "heterocyclic" or "heterocyclo" refer to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulphur atoms, where the nitrogen and sulphur heteroatoms may optionally be oxidised and the nitrogen heteroatoms may optionally be quaternised. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

The term "heteroaryl" refers to aromatic heterocyclic groups.

Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, pyridazinyl, triazolyl, triazinyl, and the like.

Where q is 1 or 2, "—C(O)$_q$H" denotes —C(O)—H or —C(O)—OH; "—C(O)$_q$R$_6$" or "—C(O)$_q$Z$_6$" denote, respectively, —C(O)—R$_6$ or —C(O)—OR$_6$, or —C(O)—Z$_6$ or —C(O)—OZ$_6$; "—O—C(O)$_q$R$_6$" or "—O—C(O)$_q$Z$_6$" denote, respectively, —O—C(O)—R$_6$ or —O—C(O)—OR$_6$, or —O—C(O)—Z$_6$ or —O—C(O)—OZ$_6$; and "—S(O)$_q$R$_6$" or "—S(O)$_q$Z$_6$" denote, respectively, —SO—H$_6$ or —SO$_2$—H$_6$, or —SO—Z$_6$ or —SO$_2$—Z$_6$.

Compounds of the formula I may in some cases form salts. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilisation.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulphuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternised with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of compounds of formula I are also contemplated herein. The term "Prodrug", as employed in this context, denotes a compound which, upon administration to a subject, undergoes chemical conversion by metabolic or chemical processes to yield a compound of formula I, or a salt and/or solvate thereof. Solvates of the compounds of formula I are preferably hydrates.

All stereoisomers of the present compounds, such as those which may exist due to asymmetric carbons on the R substituents of the compound of formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Throughout the specification, groups and substitutions thereof are chosen to provide stable moieties and compounds.

In certain of such embodiments, the SIK3 inhibitor is a compound of formula I (eg a variant of dasatinib) where R2 of formula I or formula II$_{WO}$ is hydrogen, and R3 of formula I or formula II$_{WO}$ is Rx, wherein Rx has the following formula X:

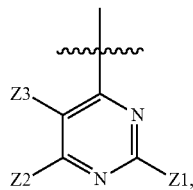

formula X and solvates, salts, complexes, polymorphs, crystalline forms, racemic mixtures, diastereomers, enantiomers, tautomers, isotopically labelled forms, prodrugs, and combinations thereof, wherein Z1, Z2 and Z3 of formula X are as defined herein or in WO 00/62778A1. Preferably in formula X:

Z1 is methyl; and/or

Z2 is —$Z_4$—$NZ_7Z_8$, —$Z_4$—$N(Z_9)$—$Z_5$—$NZ_7Z_8$ or $Z_4$—$N(Z_{10})$—$Z_5$—H (where $Z_4$ and $Z_5$ to $Z_{10}$ are as defined herein or in WO 00/62778A1, in particular where $Z_4$ is a single bond); and/or Z3 is hydrogen.

In particular of such embodiments, Z2 in formula X is a substituent selected from the group consisting of:

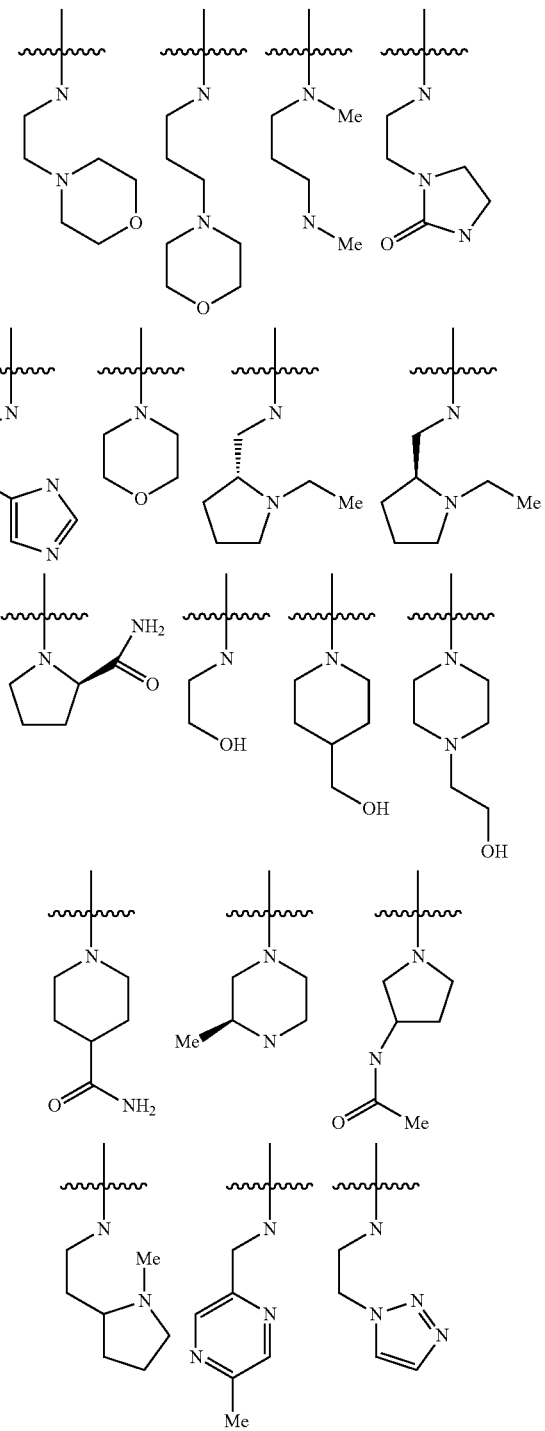

In other particular embodiments, in formula X Z1 is (preferably) methyl, Z3 is hydrogen and Z2 is (preferably) a substituent selected from the group consisting of:

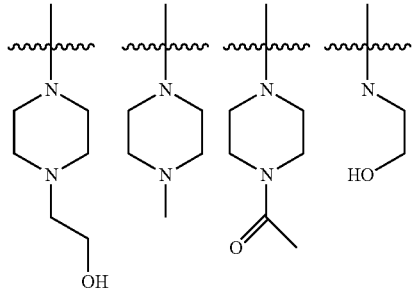

In other embodiments, particularly when in formula X Z1 is methyl and Z3 is hydrogen, Z2 may not be:

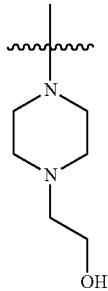

In certain particular of such embodiments, the SIK3 inhibitor is a compound of formula I (eg a variant of dasatinib) where R2 of formula I or formula II$_{WO}$ is hydrogen, and R3 of formula I or formula II$_{WO}$ is Rdas, wherein Rdas has the following formula Y:

formula Y

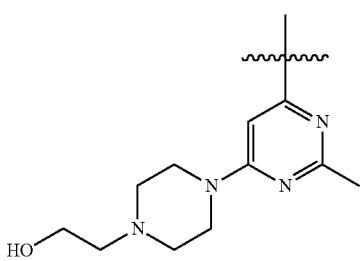

and solvates, salts, complexes, polymorphs, crystalline forms, racemic mixtures, diastereomers, enantiomers, tautomers, isotopically labelled forms, prodrugs, and combinations thereof.

In further of any of such embodiments, X1 and X2 of formula I together form (or X3 of formula II$_{WO}$ is) =O or =S (preferably, =O), Z of formula I is (preferably) a bond, n of of formula II$_{WO}$ is (preferably) 1, R1 of formula I or formula II$_{WO}$ is (preferably) hydrogen, one of R4 or R5 of formula I or formula II$_{WO}$ is (preferably) hydrogen and one of R4 or R5 of formula I or formula II$_{WO}$ is R6, in particular wherein R$_4$ of formula II$_{WO}$ is hydrogen and R$_5$ of formula II$_{WO}$ is R$_6$, where R6 is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with Z1, Z2 and one or more (preferably, one or two) groups Z3 (where Z1, Z2 and Z3 are as defined herein or in WO 00/62778A1). In particular of such further embodiments, such R6 is aryl, aralkyl, heterocyclo, or heterocycloalkyl (preferably aryl or heteroaryl), each of which is unsubstituted or substituted with Z1, Z2 and one or more (preferably, one or two) groups Z3 (where Z1, Z2 and Z3 are as defined herein or in WO 00/62778A1). Preferably in such embodiments, R6 is a monocyclic aryl or heteroaryl (in particular, a 6 membered monocyclic aryl or heteroaryl, preferably a 6 membered heteroaryl) substituted with one, two or three Zx (in particular with at least one, or two, at an ortho-position on the monocyclic aryl or heteroaryl), where each Zx may be, independently: (i) Zy, where Zy is a C1-5 (in particular, a C1, C2 or C3) alkyl, alkenyl or alkynyl; (ii) —OH or —OZy; (iii) —SH or —SZy; (iv) halo; or (v) —SO2-Zy or —SO2-N—(Zy)(Zy). In particular of such embodiments, Zx may be a non-polar substituent. The monocyclic aryl or heteroaryl R$_6$ (when R$_5$ of formula II$_{WO}$ is R$_6$,) is, preferably, phenyl or pyridinyl (eg, a pyridin-2-yl, or more preferably pyridin-3-yl), optionally substituted with one, two or three (preferably two) Zx, in particular where one Zx is substituted at the ortho position of the phenyl or pyridinyl, and/or in particular where each Zx is independently selected from the group consisting of: —Cl, —F, —Br, —Me, —OMe, —OEt and —CN (preferably, selected from —Cl, —F, —Me and —Br). In particular, a substituted phenyl or pyridinyl such R$_6$, where at least one (or both) of the meta positions is not hydrogen (such as is a Zx as defined herein), and/or where the para position is hydrogen.

In certain particular of such embodiments the SIK3 inhibitor may be (eg, a variant of dasatinib being) a cyclic compound of any one of claims 1 to 21 of WO 00/62778A1, and salts (or solvates, salts, complexes, polymorphs, crystalline forms, racemic mixtures, diastereomers, enantiomers, tautomers, isotopically labelled forms, prodrugs, and combinations) thereof. In certain of such embodiments, R2, R3, X1, X2, R4, R5 and/or R6 are as defined herein. In particular of such embodiments, the variant of dasatinib is selected from the group of cyclic compounds consisting of claim 22 of WO 00/62778A1, and salts thereof. Such disclosures of WO 00/62778A1 are incorporated by reference herein, solely for such specific purpose.

In other particular of such embodiments the SIK3 inhibitor may be (eg, a variant of dasatinib being) a compound of "formula III" as defined in claim 23 of WO 00/62778A1, in particular is a compound as set forth in claim 23 or 53 of WO 00/62778A1 and salts thereof. Such disclosures of WO 00/62778A1 are incorporated by reference herein, solely for such specific purpose. In certain of such embodiments, R2, R3, R4, R5 and/or R6 are as defined above, and/or X3 is (preferably) oxygen.

In yet other particular of such embodiments the SIK3 inhibitor may be (eg, a variant of dasatinib being) a compound as set forth in claim 59 of WO 00/62778A1 and salts thereof. Such disclosure of WO 00/62778A1 is incorporated by reference herein, solely for such specific purpose. In certain of such embodiments, R2, R3, R4, R5 and/or R6 are as defined above, and/or X3 is (preferably) oxygen.

In further particular of such embodiments the SIK3 inhibitor may be (eg, a variant of dasatinib being) a cyclic compound of "formula II" of claim 1 of EP 1169038B9 (formula II$_{EP}$ herein), and salts thereof. Such disclosure, together with paragraphs [0010] to [0032] of EP 1169038B9, is incorporated by reference herein, solely for such specific purpose.

Accordingly, in such embodiments, a SIK3 inhibitor may be a compound (eg a variant of dasatinib) where within formula I being a cyclic compound of the following formula II$_{EP}$ or a salt thereof:

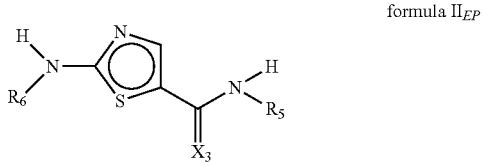

formula II$_{EP}$ wherein
$X_3$ is oxygen or sulphur;
$R_5$ is an aryl group which is substituted with one or more groups selected from alkyl and halo;
$R_6$ is: aryl or heteroaryl which is substituted with $Z_1$, $Z_2$ and one or more groups $Z_3$, wherein
  (a) said aryl is substituted with at least one group $Z_3$ where $Z_3$ is —$Z_4$—$NZ_7Z_8$ where $Z_4$ is a bond, $Z_7$ is hydrogen or alkyl, and $Z_8$ is heterocyclo-substituted alkyl; or
  (b) said heteroaryl is substituted with at least one group $Z_3$ where $Z_3$ is —$Z_4$—$NZ_7Z$\$ where $Z_4$ is a bond, $Z_7$ is hydrogen or alkyl, and $Z_8$ is heterocyclo-substituted alkyl; or
  (c) said heteroaryl is substituted with at least one group $Z_3$ where $Z_3$ is alkyl;
$Z_1$, $Z_2$ and $Z_3$ are each independently:
  (1) hydrogen or $Z_6$, where $Z_6$ is (i) alkyl, alkenyl, alkynyl, cycloalkyl, cyctoalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
  (2) —OH or —OZ;
  (3) —SH or —$SZ_6$;
  (4) —C(O)$_q$H, —O(O)$_q Z_6$, or —O—C(O)$_q Z_6$, where q is 1 or 2;
  (5) —SO$_3$H, —S(O)$_q Z_6$; or S(O)$_q$N($Z_9$)$Z_6$;
  (6) halo;
  (7) cyano;
  (8) nitro;
  (9) —$Z_4$—$NZ_7Z_8$;
  (10) —$Z_4$—N($Z_9$)—$Z_5$—$NZ_7Z_8$;
  (11) —$Z_4$—N($Z_{10}$)—$Z_5$—$Z_6$;
  (12) —$Z_4$—N($Z_{10}$)—$Z_5$—H;
  (13) oxo;
  (14) —O—C(O)—$Z_6$;
  (15) any two of $Z_1$, $Z_2$, and $Z_3$ may together be alkylene or alkenylene completing a 3- to 8-membered saturated or unsaturated ring together with the atoms to which they are attached; or
  (16) any two of $Z_1$, $Z_2$, and $Z_3$ may together be —O—(CH$_2$)$_r$—O—, where r is 1 to 5, completing a 4- to 8-membered saturated ring together with the atoms to which they are attached;

$Z_4$ and $Z_5$ are each independently:
  (1) a single bond;
  (2) —$Z_{11}$—S(O)$_q$—$Z_{12}$—;
  (3) —$Z_{11}$—C(O)—$Z_{12}$—;
  (4) —$Z_{11}$—C(S)—$Z_{12}$—;
  (5) —$Z_{11}$—O—$Z_{12}$—;
  (6) —$Z_{11}$—S—$Z_{12}$—;
  (7) —$Z_{11}$—O—C(O)—$Z_{12}$; or
  (8) —Z—C(O)—O—$Z_{12}$—;
$Z_7$, $Z_8$, $Z_9$ and $Z_{10}$:
  (1) are each independently hydrogen or $Z_6$;
  (2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
  (3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;
$Z_{11}$ and $Z_{12}$ are each independently:
  (1) a single bond;
  (2) alkylene;
  (3) alkenylene; or
  (4) alkynylene.

In certain of such embodiments, R6 of formula II$_{EP}$ may be Rdas and/or X3 is (preferably) oxygen and/or R5 of formula II$_{EP}$ may be R6 as defined herein. In particular of such embodiments, the SIK3 inhibitor may be (eg, a variant of dasatinib being) a compound is selected from the group of cyclic compounds consisting of claim 2 of EP 1169038B9, and salts thereof. Such disclosure is incorporated by reference herein solely for such specific purpose.

In one particular aspect, the invention also relates to a variant of dasatinib of any of the general (or specific) formula or structures disclosed herein (eg, of formula I, II$_{WO}$ or II$_{EP}$), and salts (or solvates, salts, complexes, polymorphs, crystalline forms, racemic mixtures, diastereomers, enantiomers, tautomers, isotopically labelled forms, prodrugs, and combinations) thereof.

In certain embodiments of the invention, the SIK3 inhibitor can be a variant of dasatinib (that is not dasatinib); ie, that in such embodiments the SIK3 inhibitor is one having the general formula I (or II$_{WO}$ or II$_{EP}$), with the proviso that the SIK3 inhibitor is not compound A8.

The SIK3 inhibitors formula I, II$_{WO}$ or II$_{EP}$ may be synthesised following the disclosure, in particular Schemes A to XI (and/or the procedures in Examples 1 to 580), of WO 00/62778A1. Such disclosure is incorporated by reference herein solely for such specific purpose. Alternatively, the SIK3 inhibitors that are a variant of dasatinib may be synthesised according to the procedures described in Example 10 herein.

In certain embodiments the SIK3 inhibitor is, and in a certain aspect the invention relates to, a (cyclic) compound as set forth in Table A3 or Table A4 (in particular, compound B3, B2 or A6), and solvates, salts, stereoisomers, complexes, polymorphs, crystalline forms, racemic mixtures, diastereomers, enantiomers, tautomers, isotopically labelled forms, prodrugs, and combinations thereof.

TABLE A3 small molecule compounds of the invention

| Compound Number | Structure | Name |
|---|---|---|
| A1 | 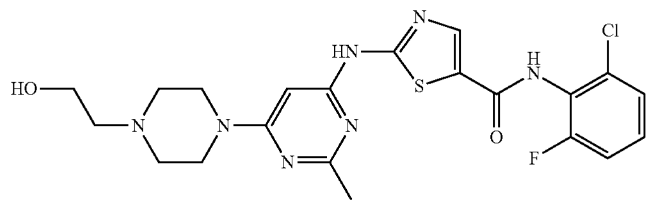 | N-(2-chloro-6-fluorophenyl)-2-((6-(4-(2-hydroxyethyl)piperazin-1-yl)-2-methylpyrimidin-4-yl)amino)thiazole-5-carboxamide |
| A2 | 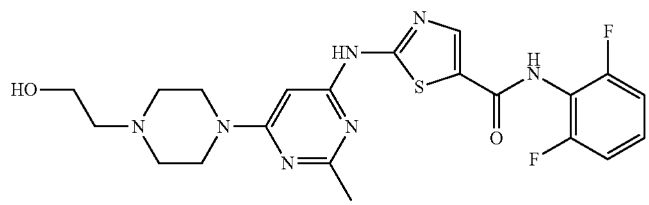 [SMILES: Cc1nc(Nc2ncc(C(=O)Nc3c(F)cccc3F)s2)cc(N2CCN(CCO)CC2)n1] | N-(2,6-difluorophenyl)-2-((6-{4-(2-hydroxyethyl)piperazin-1-yl)-2-methylpyrimidin-4-yl)amino)thiazole-5-carboxamide |
| A3 | 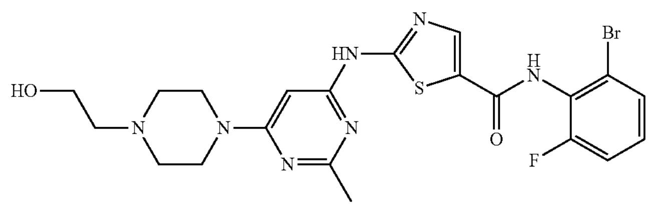 [SMILES: Cc1nc(Nc2ncc(C(=O)Nc3c(F)cccc3Br)s2)cc(N2CCN(CCO)CC2)n1] | N-(2-bromo-6-fluorophenyl)-2-((6-(4-(2-hydroxyethyl)piperazin-1-yl)-2-methylpyrimidin-4-yl)amino)thiazole-5-carboxamide |
| A4 | 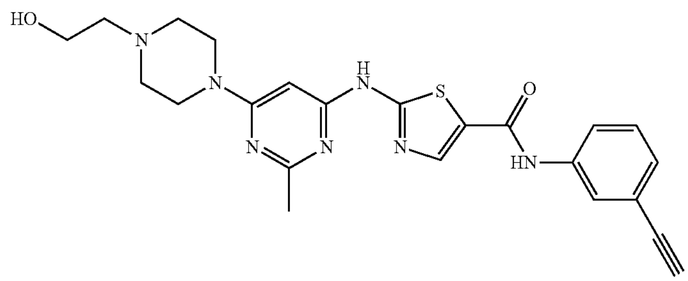 [SMILES: C#Cc1cccc(NC(=O)c2cnc(Nc3cc(N4CCN(CCO)CC4)nc(C)n3)s2)c1] | N-(3-ethynylphenyl)-2-((6-(4-(2-hydroxyethyl)piperazin-1-yl)-2-methylpyrimidin-4-yl)amino)thiazole-5-carboxamide |
| A5 | 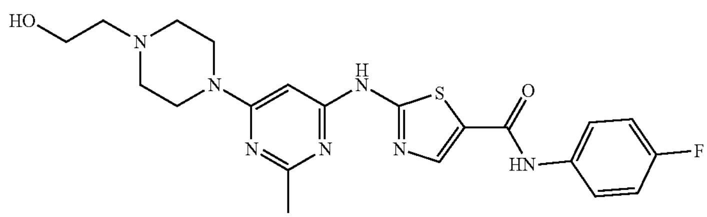 [SMILES: Cc1nc(Nc2ncc(C(=O)Nc3ccc(F)cc3)s2)cc(N2CCN(CCO)CC2)n1] | N-(4-fluorophenyl)-2-((6-(4-(2-hydroxyethyl)piperazin-1-yl)-2-methylpyrimidin-4-yl)amino)thiazole-5-carboxamide |
| A6 | 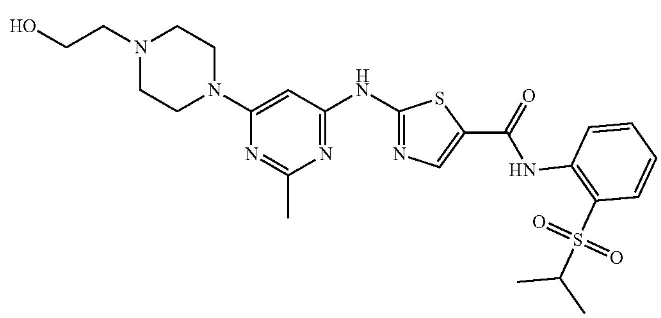 [SMILES: Cc1nc(Nc2ncc(C(=O)Nc3ccccc3S(=O)(=O)C(C)C)s2)cc(N2CCN(CCO)CC2)n1] | 2-((6-(4-(2-hydroxyethyl)piperazin-1-yl)-2-methylpyrimidin-4-yl)amino)-N-(2-(propane-2-sulfonyl)phenyl)thiazole-5-carboxamide |

TABLE A3-continued small molecule compounds of the invention

| Compound Number | Structure | Name |
|---|---|---|
| A7 | 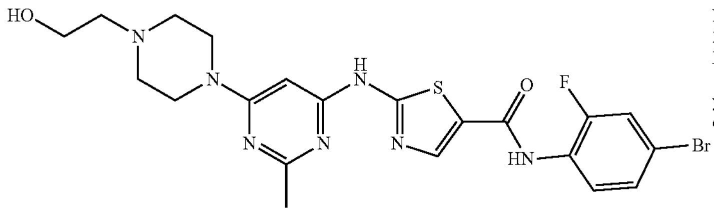 [SMILES: Cc1nc(Nc2ncc(C(=O)Nc3ccc(Br)cc3F)s2)cc(N2CCN(CCO)CC2)n1] | N-(4-bromo-6-fluorophenyl)-2-((6-(4-(2-hydroxyethyl)piperazin-1-yl)-2-methylpyrimidin-4-yl)amino)thiazole-5-carboxamide |
| A8 (dasatinib) | 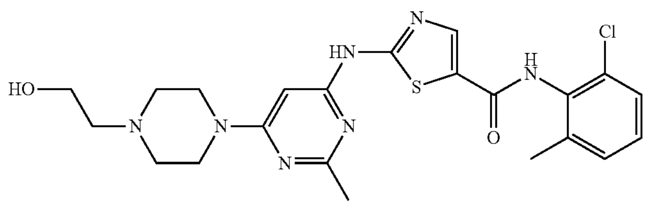 | N-(2-chloro-6-methylphenyl)-2-((6-(4-(2-hydroxyethyl)piperazin-1-yl)-2-methylpyrimidin-4-yl)amino)thiazole-5-carboxamide |
| A9 | 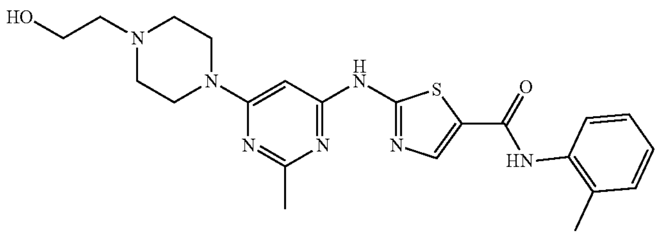 [SMILES: Cc1nc(Nc2ncc(C(=O)Nc3ccccc3C)s2)cc(N2CCN(CCO)CC2)n1] | 2-((6-(4-(2-hydroxyethyl)piperazin-1-yl)-2-methylpyrimidin-4-yl)amino)-N-(o-tolyl)thiazole-5-carboxamide |
| A10 | 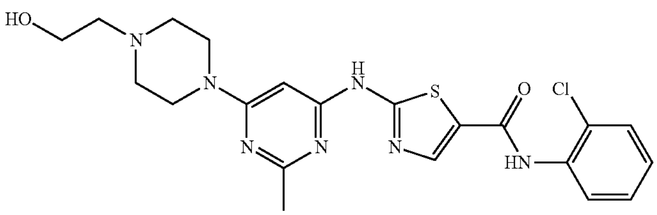 [SMILES: Cc1nc(Nc2ncc(C(=O)Nc3ccccc3Cl)s2)cc(N2CCN(CCO)CC2)n1] | N-(2-chlorophenyl)-2-((6-(4-(2-hydroxyethyl)piperazin-1-yl)-2-methylpyrimidin-4-yl)amino)thiazole-5-carboxamide |
| A11 | 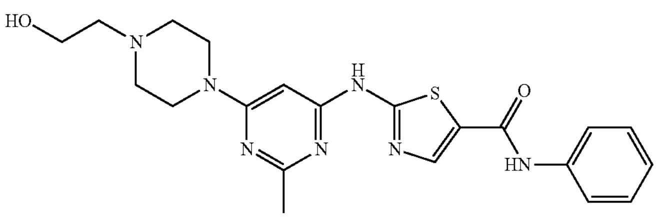 [SMILES: Cc1nc(Nc2ncc(C(=O)Nc3ccccc3)s2)cc(N2CCN(CCO)CC2)n1] | ((6-(4-(2-hydroxyethyl)piperazin-1-yl)-2-methylpyrimidin-4-yl)amino)-N-phenylthiazole-5-carboxamide |
| A12 | 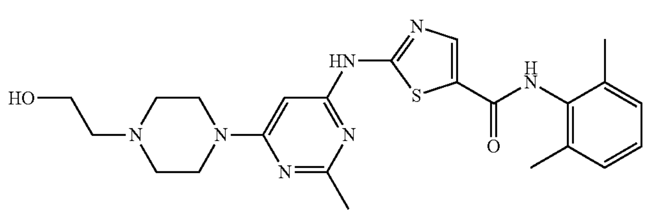 | N-(2,6-dimethylphenyl)-2-((6-(4-(2-hydroxyethyl)piperazin-1-yl)-2-methylpyrimidin-4-yl)amino)thiazole-5-carboxamide |
| A13 | 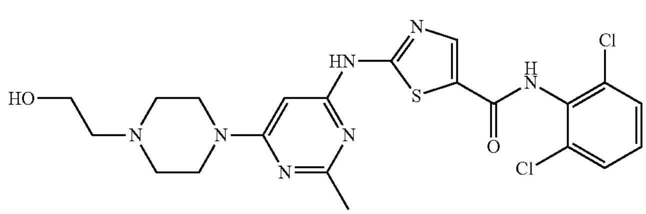 | N-(2,6-dichlorophenyl)-2-((6-(4-(2-hydroxyethyl)piperazin-1-yl)-2-methylpyrimidin-4-yl)amino)thiazole-5-carboxamide |

TABLE A4 other compounds of formula I/of the invention.

| Compound Number | Structure | Name |
|---|---|---|
| B1 | 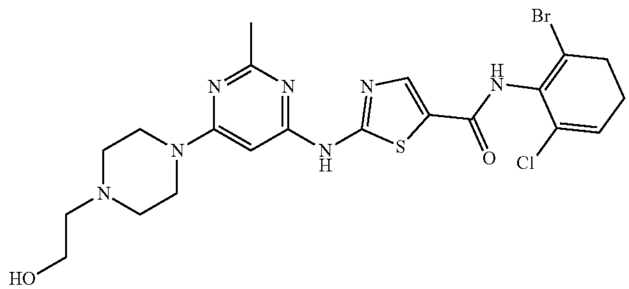 [SMILES: Cc1nc(Nc2ncc(C(=O)NC3=C(Br)CCC=C3Cl)s2)cc(N2CCN(CCO)CC2)n1] | N-(2-bromo-6-chlorophenyl)-2-((6-(4-(2-hydroxyethyl)piperazin-1-yl)-2-methylpyrimidin-4-yl)amino)thiazole-5-carboxamide |
| B2 | 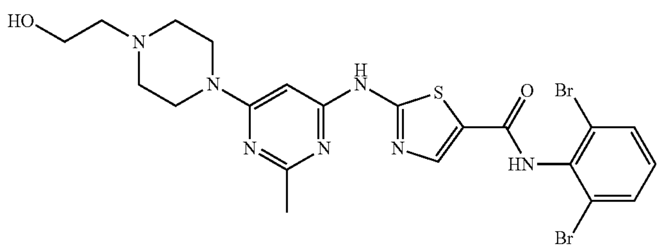 [SMILES: Cc1nc(Nc2ncc(C(=O)Nc3c(Br)cccc3Br)s2)cc(N2CCN(CCO)CC2)n1] | N-(2,6-dibromophenyl)-2-((6-(4-(2-hydroxyethyl)piperazin-1-yl)-2-methylpyrimidin-4-yl)amino)thiazole-5-carboxamide |
| B3 | 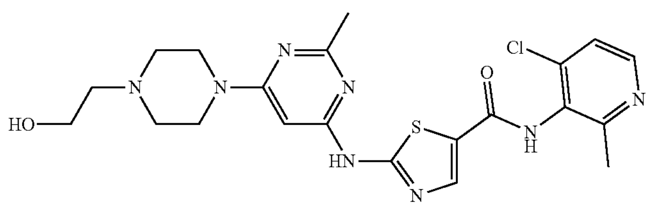 [SMILES: Cc1nc(Nc2ncc(C(=O)Nc3c(Cl)ccnc3C)s2)cc(N2CCN(CCO)CC2)n1] | N-(4-chloro-2-methylpyridin-3-yl)-2-((6-(4-(2-hydroxyethyl)piperazin-1-yl)-2-methylpyrimidin-4-yl)amino)thiazole-5-carboxamide |
| B4 | 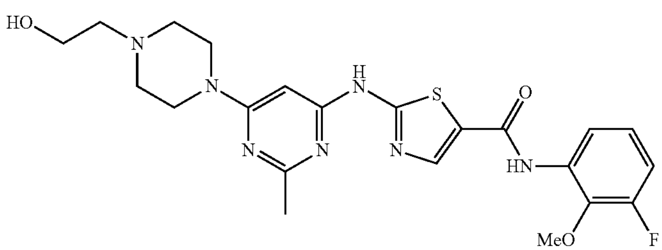 [SMILES: COc1c(F)cccc1NC(=O)c1cnc(Nc2cc(N3CCN(CCO)CC3)nc(C)n2)s1] | N-(3-fluoro-2-methoxyphenyl)-2-((6-(4-(2-hydroxyethyl)piperazin-1-yl)-2-methylpyrimidin-4-yl)amino)thiazole-5-carboxamide |
| B5 | 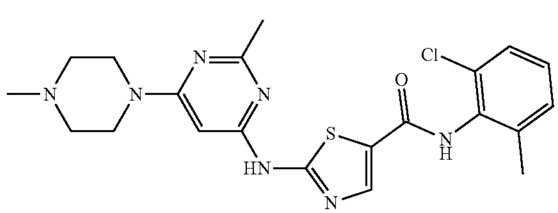 [SMILES: Cc1nc(Nc2ncc(C(=O)Nc3c(C)cccc3Cl)s2)cc(N2CCN(C)CC2)n1] | N-(2-chloro-6-methylphenyl)-2-((2-methyl-6-(4-methylpiperazin-1-yl)pyrimidin-4-yl)amino)thiazole-5-carboxamide |

TABLE A4-continued other compounds of formula I/of the invention.

| Compound Number | Structure | Name |
|---|---|---|
| B6 | 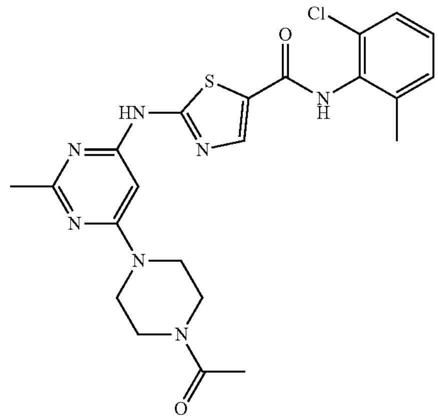 [SMILES: CC(=O)N1CCN(c2cc(Nc3ncc(C(=O)Nc4c(C)cccc4Cl)s3)nc(C)n2)CC1] | 2-((6-(4-acetylpiperazin-1-yl)-2-methylpyrimidin-4-yl)amino)-N-(2-chloro-6-methylphenyl)thiazole-5-carboxamide |
| B7 | 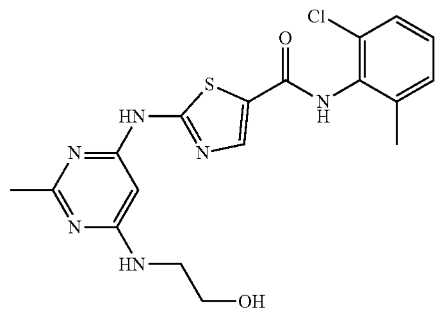 [SMILES: Cc1nc(NCCO)cc(Nc2ncc(C(=O)Nc3c(C)cccc3Cl)s2)n1] | N-(2-chloro-6-methylphenyl)-2-((6-((2-hydroxyethyl)amino)-2-methylpyrimidin-4-yl)amino)thiazole-5-carboxamide |
| B8 | 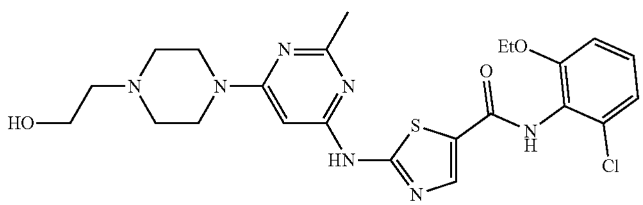 [SMILES: CCOc1cccc(Cl)c1NC(=O)c1cnc(Nc2cc(N3CCN(CCO)CC3)nc(C)n2)s1] | N-(2-chloro-6-ethoxyphenyl)-2-((6-(4-(2-hydroxyethyl)piperazin-1-yl)-2-methylpyrimidin-4-yl)amino)thiazole-5-carboxamide |
| B9 | 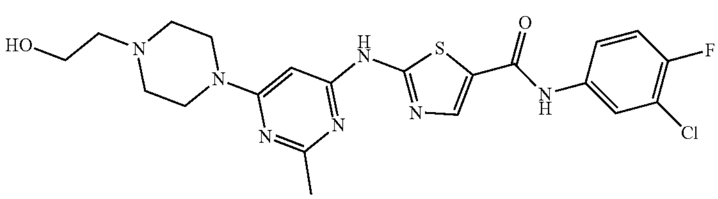 [SMILES: Cc1nc(Nc2ncc(C(=O)Nc3ccc(F)c(Cl)c3)s2)cc(N2CCN(CCO)CC2)n1] | N-(3-chloro-4-fluorophenyl)-2-((6-(4-(2-hydroxyethyl)piperazin-1-yl)-2-methylpyrimidin-4-yl)amino))thiazole-5-carboxamide |

In certain embodiments the SIK3 inhibitor is, and in a certain aspect the invention relates to, a compound as set forth in Table A3 or Table A4, and solvates, salts, complexes, polymorphs, crystalline forms, racemic mixtures, diastereomers, enantiomers, tautomers, isotopically labelled forms, prodrugs, and combinations thereof, with one or more (preferably all) of the provisos that the SIK3 inhibitor or the compound is not compound A9, B8 and/or B9. Accordingly, in other embodiments the SIK3 inhibitor is, and in a certain aspect the invention relates to, a compound of any of the general (or specific) formula or structures disclosed herein (eg, of formula I, $II_{WO}$), and salts (or solvates, salts, complexes, polymorphs, crystalline forms, racemic mixtures, diastereomers, enantiomers, tautomers, isotopically labelled forms, prodrugs, and combinations) thereof, with one or more (preferably all) of the proviso that when, in general formula $II_{WO}$, X3 is oxygen, n is 1, $R_1$ is hydrogen, $R_2$ is hydrogen, $R_3$ is Rdas and one of $R_4$ or $R_5$ is hydrogen, then the other of $R_4$ or $R_5$ is an $R_6$ that is (i) not 2-chloro-6-ethoxyphenyl; and/or (ii) not 3-chloro-4-fluorophenyl.

In other embodiments, the SIK3 inhibitor is, and in a certain aspect the invention relates to, a compound of any of the general (or specific) formula or structures disclosed herein (eg, of formula I, $II_{WO}$), and salts (or solvates, salts, complexes, polymorphs, crystalline forms, racemic mixtures, diastereomers, enantiomers, tautomers, isotopically labelled forms, prodrugs, and combinations) thereof, with one or more (preferably all) of the proviso that when, in general formula $II_{WO}$, n is 1, A is nitrogen, B is sulphur, X3 is oxygen, $R_1$ is hydrogen, $R_2$ is hydrogen, $R_4$ is hydrogen, $R_3$ is formula Y and $R_5$ is $R_6$, then $R_6$ is not 2-chloro-6-methylphenyl.

In yet other embodiments, the SIK3 inhibitor is, and in a certain aspect the invention relates to, a compound of any of the general (or specific) formula or structures disclosed herein (eg, of formula I, $II_{WO}$), and salts (or solvates, salts, complexes, polymorphs, crystalline forms, racemic mixtures, diastereomers, enantiomers, tautomers, isotopically labelled forms, prodrugs, and combinations) thereof, with one or more (preferably all) of the proviso that when, in general formula $II_{WO}$, n is 1, A is nitrogen, B is sulphur, $X_3$ is oxygen, $R_1$ is hydrogen, $R_2$ is hydrogen, $R_4$ is hydrogen, $R_5$ is $R_6$ and $R_6$ is:

(i) a phenyl substituted at an ortho position with a —Cl, then either (x) the other ortho position is hydrogen, or a Zx (as defined above) that is not methyl (such as, a Zx that is —Cl, —F, —Br, —OMe, —OEt, or —CN), and preferably at least one of the meta or the para positions is substituted with Zx as defined above; or (y) the other ortho position is methyl and at least two of the ortho or para positions are substituted with Zx (as defined above); or (z) R3 is not Rdas; or (ii) a phenyl substituted at an ortho position with a methyl, then either (x) the other ortho position is hydrogen, or a Zx (as defined above) that is not —Cl (such as, a Zx that is —F, —Br, —Me, —OMe, —OEt or —CN), and preferably at least one of the meta or the para positions is substituted with Zx as defined above; or (y) the other ortho is —Cl and at least two of the meta or para positions are substituted with Zx (as defined above); or (z) R3 is not Rdas.

In yet another aspect, the invention also relates to a method for the treatment or prevention of a disease, disorder or condition (such as a proliferative disorder eg cancer or a tumour) in a subject (such as one in need thereof), comprising administering to said subject at least once an effective amount of (i) a variant of dasatinib of any of the general (or specific) formula or structures disclosed herein (formula I, $II_{WO}$ or $II_{EP}$), or (ii) a compound as set forth in Table A3 or Table A4 (in particular, compound is B3, B2 or A6), or a salt (or a solvate, salts, complex, polymorph, crystalline form, racemic mixture, diastereomer, enantiomer, tautomer, isotopically labelled form, prodrug, and combination) of (i) or (ii), or comprising administering to said subject at least once an effective amount of the pharmaceutical composition as described above. In a related other aspect, the invention also relates to (i) a variant of dasatinib of any of the general (or specific) formula or structures disclosed herein (formula I, $II_{WO}$ or $II_{EP}$), or (ii) a compound as set forth in Table A3 or Table A4, or a salt (or a solvates salt, complex, polymorph, crystalline form, racemic mixture, diastereomer, enantiomer, tautomer, isotopically labelled form, prodrug, and combination) of (i) or (ii), for use in medicine, such as in the treatment or the prevention of a disease, disorder or condition (such as a proliferative disorder eg cancer or a tumour) in a subject (such as one in need thereof). In particular of such embodiments, the compound is B3, B2 or A6. In other particular of such embodiments, the compound has formula $II_{WO}$, n is 1, A is nitrogen, B is sulphur, $X_3$ is oxygen, $R_1$ is hydrogen, $R_2$ is hydrogen, $R_4$ is hydrogen, $R_5$ is $R_6$ and $R_6$ is a monocyclic heteroaryl substituted with one, two or three Zx, with at least one Zx at an ortho-position on the monocyclic aryl or heteroaryl; wherein each Zx may be, independently: (i) Zy, where Zy is a C1, C2 or C3 alkyl, alkenyl or alkynyl; (ii) —OH or —OZy; (iii) —SH or —SZy; (iv) halo; or (v) —SO2-Zy or —SO2-N—(Zy)(Zy).

In another particular embodiment of all aspects of the invention, the SIK3 inhibitor is bosutinib.

Bosutinib (SKI-606), marketed under the trade name BOSULIF®, is a tyrosine kinase inhibitor or use in the treatment of cancer. The chemical name for bosutinib (monohydrate) is 3-Quinolinecarbonitrile, 4-[(2,4-dichloro-5-methoxyphenyl) amino]-6-methoxy-7-[3-(4-methyl-1-piperazinyl) propoxy]-, hydrate (1:1). Its chemical formula is $C26H29Cl2N5O3.H2O$ (monohydrate); its molecular weight is 548.46 (monohydrate), equivalent to 530.46 (anhydrous). Bosutinib (monohydrate) has the following chemical structure:

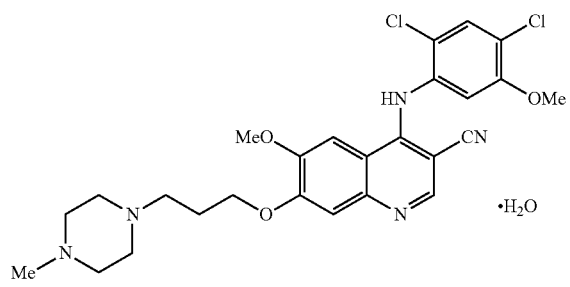 [SMILES: COc1cc(Nc2c(C#N)cnc3cc(OCCCN4CCN(C)CC4)c(OC)cc23)c(Cl)cc1Cl ; O]

In an alternative particular embodiment of all aspects of the invention, the SIK3 inhibitor is not bosutinib. Froe example, in one particular such embodiment of all aspects of the invention, the SIK3 inhibitor is a variant of bosutinib, in particular, a compound claim of any one of claims 1 to 20, or defined in any one of claims 21 to 29 of U.S. Pat. No. 6,002,008, the disclosure of which is hereby incorporated by reference herein, solely for such specific purpose.

General formula (and specific chemical structures) of other SIK-selective inhibitors have been described by others, in particular for use in distinct indications (for example, for treating inflammatory and/or immune disorders such as inflammatory bowel disease and graft-versus-host disease (for example, WO 2013/136070A1, WO 2014/093383A1, WO 2014/140313A1 and WO 2016/023014A2,).

In a different particular embodiment of all aspects of the invention, the SIK3 inhibitor may be one selected from:

A compound as defined in any one of claims 5 to 19 and 24 of WO 2013/136070A1, the disclosure of which is hereby incorporated by reference herein, solely for such specific purpose;

A compound as claimed by any one of claims 1 to 28 or one defined in claim 49, or a pharmaceutically acceptable salt thereof, of WO 2014/093383A1, the disclosure of which is hereby incorporated by reference herein, solely for such specific purpose;

A compound as claimed by any one of claims 1 to 9, or stereoisomer, tautomer, racemic, metabolic, pro- or pre-drug, salts, hydrate, N-oxide form or solvate thereof, of WO 2014/140313A1, the disclosure of which is hereby incorporated by reference herein, solely for such specific purpose; and A compound as defined in any one of claims 1 to 230, or a pharmaceutically acceptable salt thereof, of WO 2016/023014A2, the disclosure of which is hereby incorporated by reference herein, solely for such specific purpose.

Accordingly, in other embodiments, the SIK3 inhibitor may be a compound within a general formula of I, IA or IB of WO 2014/093383A1, or is as one claimed by any one of claims 1 to 28 or one defined in claim 49 of WO 2014/

093383A1, or a pharmaceutically acceptable salt thereof. In yet other embodiments, the SIK3 inhibitor may be a compound within a general formula of I, II or III-A of WO 2016/023014A2, or is one defined in any one of claims 1 to 230 of WO 2016/023014A2, or a pharmaceutically acceptable salt thereof. In particular of such embodiments, such SIK3 inhibitor can be a cell-permeable small molecule that binds to and inhibits the function or activity of SIK3, in particular phosphorylated SIK3.

Pharmaceutical Compositions:

To be used in therapy, the SIK3 inhibitor may be formulated into a pharmaceutical composition appropriate to facilitate administration to animals or humans. The term "composition" means a mixture of substances. The term "pharmaceutical composition" means a mixture of substances including a therapeutically active substance (such as a SIK3 inhibitor) for pharmaceutical use.

Accordingly, in another aspect, herein provided is a pharmaceutical composition comprising a SIK3 inhibitor (of, or for use with the invention), and a pharmaceutically acceptable excipient, stabiliser or carrier. In a preferred embodiment, the pharmaceutical composition comprises a SIK3 inhibitor of Table A3 or Table A4.

In another particular aspect, the invention also relates to a pharmaceutical composition including: (i) a variant of dasatinib of any of the general (or specific) formula or structures disclosed herein (formula I, $II_{WO}$ or $II_{EP}$), or (ii) a compound as set forth in Table A3 or Table A4 (in particular, compound B3, B2 or A6), or a salt (or a solvate, salt, complex, polymorph, crystalline form, racemic mixture, diastereomers, enantiomer, tautomer, isotopically labelled form, prodrug, and combination) of (i) or (ii), and a pharmaceutically acceptable excipient, stabiliser or carrier.

By way of example, the pharmaceutical composition of the invention may comprise between 0.1% and 100% (w/w) active ingredient (for example, a SIK3 inhibitor), such as about 0.5%, 1%, 2%, 3%, 4%, 5%, 6%, 8% 10%, 15%, 20%, 25%, 30%, 40%, 50%, 60%, 70%, 80%, 90%, 95%, 96%, 97%, 98% or 99%, preferably between about 1% and about 20%, between about 10% and 50% or between about 40% and 90%.

As used herein the language "pharmaceutically acceptable" excipient, stabiliser or carrier is intended to include any and all solvents, solubilisers, fillers, stabilisers, binders, absorbents, bases, buffering agents, lubricants, controlled release vehicles, diluents, emulsifying agents, humectants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

The pharmaceutical composition of (or for use with) the invention is, typically, formulated to be compatible with its intended route of administration. Examples of routes of administration include oral, parenteral, e.g., intrathecal, intra-arterial, intravenous, intradermal, subcutaneous, oral, transdermal (topical) and transmucosal administration.

Solutions or suspensions used for parenteral, intradermal, or subcutaneous application, as well as comprising a compound of (or for use with) the invention (eg SIK3 inhibitor), can include the following components: a sterile diluent such as water for injection, saline solution, fixed oils, polyethylene glycols, glycerine; propylene glycol or other synthetic solvents; anti-bacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Kolliphor® EL (formerly Cremophor EL™; BASF, Parsippany, N.J.) or phosphate buffered saline (PBS). In all cases, the injectable composition should, typically, be sterile and be fluid to the extent that easy syringability exists. It should, typically, be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the compound of (or for use with) the invention (e.g., a SIK3 inhibitor) in the required amount in an appropriate solvent with one or a combination of ingredients described herein, as required, followed by filtered sterilisation. Generally, dispersions are prepared by incorporating the active compound into a sterile vehicle which contains a basic dispersion medium and the required other ingredients from those described herein. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, as well as comprising a compound of (or for use with) the invention (eg a SIK3 inhibitor), generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide; a sweetening agent such as sucrose or saccharin; or a flavouring agent such as peppermint, methyl salicylate, or orange flavouring.

Furthermore, the compounds of (or for use with) the invention (eg a SIK3 inhibitor) can be administrated rectally. A rectal composition can be any rectally acceptable dosage form including, but not limited to, cream, gel, emulsion, enema, suspension, suppository, and tablet. One preferred dosage form is a suppository having a shape and size designed for introduction into the rectal orifice of the human body. A suppository usually softens, melts, or dissolves at body temperature. Suppository excipients include, but are not limited to, theobroma oil (cocoa butter), glycerinated gelatin, hydrogenated vegetable oils, mixtures of polyethylene glycols of various molecular weights, and fatty acid esters of polyethylene glycol.

For administration by inhalation, the compounds of (or for use with) the invention (eg a SIK3 inhibitor) are typically delivered in the form of an aerosol spray from pressured container or dispenser which contains a suitable propellant, e.g., a gas such as carbon dioxide, or a nebuliser.

Cells, such as immune cells (eg CAR T cells) for use with the invention can be included in pharmaceutical formulations suitable for administration into the bloodstream or for administration directly into tissues or organs. A suitable format is determined by the skilled person (such as a medical practitioner) for each patient, tissue, and organ, according to standard procedures. Suitable pharmaceutically acceptable carriers and their formulation are known in the art (see, e.g. Remington's Pharmaceutical Sciences 16th edition, Osol, A. Ed., 1980). Such cells, when formed in a pharmaceutical composition, are preferably formulated in solution at a pH from about 6.5 to about 8.5. Excipients to bring the solution to isotonicity can also be added, for example, 4.5% mannitol or 0.9% sodium chloride, pH buffered with art-known buffer solutions, such as sodium phosphate. Other pharmaceutically acceptable agents can also be used to bring the solution to isotonicity, including, but not limited to, dextrose, boric acid, sodium tartrate, propylene glycol, polyols (such as mannitol and sorbitol) or other inorganic or organic solutes. In one embodiment, a media formulation is tailored to preserve the cells while maintaining cell health and identity. For example, a premixture including an aqueous solution of anticoagulant (ACD-A), an equal amount of dextrose (50%), and phosphate buffered saline (PBS), or the like is pre-mixed and aliquoted in a volume to typically match or approximate the cellular matrix or environment from which the cell was extracted from the tissue or organ.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions can be formulated into ointments, salves, gels, or creams as generally known in the art.

In certain embodiments, the pharmaceutical composition is formulated for sustained or controlled release of a compound of (or for use with) the invention (eg a SIK3 inhibitor). Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially (including liposomes targeted to infected cells with monoclonal antibodies to viral antigens) can also be used as pharmaceutically acceptable carriers. These can be prepared according to methods known to those skilled in the art.

It is especially advantageous to formulate oral, rectal or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In some embodiments, the pharmaceutical composition comprising a SIK3 inhibitor is in unit dose form of between 10 and 1000 mg SIK3 inhibitor. In some embodiments, the pharmaceutical composition comprising an SIK3 inhibitor is in unit dose form of between 10 and 200 mg SIK3 inhibitor. In some embodiments, the pharmaceutical composition comprising an ABP is in unit dose form of between 200 and 400 mg SIK3 inhibitor. In some embodiments, the pharmaceutical composition comprising an SIK3 inhibitor is in unit dose form of between 400 and 600 mg SIK3 inhibitor. In some embodiments, the pharmaceutical composition comprising an SIK3 inhibitor is in unit dose form of between 600 and 800 mg SIK3 inhibitor. In some embodiments, the pharmaceutical composition comprising an SIK3 inhibitor is in unit dose form of between 800 and 1000 mg SIK3 inhibitor.

Exemplary unit dosage forms for pharmaceutical compositions comprising SIK3 inhibitors are tablets, capsules (eg as powder, granules, microtablets or micropellets), suspensions or as single-use pre-loaded syringes. In certain embodiments, kits are provided for producing a single-dose administration unit. The kit can contain both a first container having a dried active ingredient and a second container having an aqueous formulation. Alternatively, the kit can contain single and multi-chambered pre-loaded syringes.

Toxicity and therapeutic efficacy (eg effectiveness) of such active ingredients can be determined by standard pharmaceutical procedures in cell cultures or experimental animals, eg, for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Active agents which exhibit large therapeutic indices are preferred. While compounds that exhibit toxic side effects may be used, care should be taken to design a delivery system that targets such compounds to the site of affected tissue in order to minimise potential damage to uninfected cells and, thereby, reduce side effects.

The data obtained from the cell culture assays and animal studies can be used in formulating a range of dosage of the active ingredients (eg a SIK3 inhibitor or TNF, variant of TNF or an agonist of TNFR1 or TNFR2), such as for use in humans. The dosage of such active ingredients lies preferably within a range of circulating concentrations that include the ED50 with little or no toxicity. The dosage may vary within this range depending upon the dosage form employed and the route of administration utilised. For any active ingredients used in the therapeutic approaches of the invention, the (therapeutically) effective dose can be estimated initially from cell culture assays. A dose may be formulated in animal models to achieve a circulating plasma concentration range that includes the IC50 (ie, the concentration of the active ingredients which achieves a half-maximal inhibition of symptoms) as determined in cell culture. Such information can be used to more accurately determine useful (eg effective) amounts or doses, such as for administration to humans. The pharmaceutical compositions can be included in a container, pack, or dispenser together with instructions for administration.

In the context of the invention, an effective amount of the SIK3 inhibitor or the pharmaceutical composition can be one that will elicit the biological, physiological, pharmacological, therapeutic or medical response of a cell, tissue, system, body, animal, individual, patient or human that is being sought by the researcher, scientist, pharmacologist, pharmacist, veterinarian, medical doctor, or other clinician, eg, lessening the effects/symptoms of a disorder, disease or condition, such as a proliferative disorder, for example, a cancer or tumour, or killing or inhibiting growth of a cell involved with a proliferative disorder, such as a tumour cell. The effective amount can be determined by standard procedures, including those described below.

In accordance with all aspects and embodiments of the medical uses and methods of treatment provided herein, the effective amount administered at least once to a subject in need of treatment with a SIK3 inhibitor is, typically, between about 0.01 mg/kg and about 100 mg/kg per administration, such as between about 1 mg/kg and about 10 mg/kg per administration. In some embodiments, the effective amount administered at least once to said subject of a SIK3 inhibitor is between about 0.01 mg/kg and about 0.1 mg/kg per administration, between about 0.1 mg/kg and about 1 mg/kg per administration, between about 1 mg/kg and about 5 mg/kg per administration, between about 5 mg/kg and about 10 mg/kg per administration, between about 10 mg/kg and about 50 mg/kg per administration, or between about 50 mg/kg and about 100 mg/kg per administration.

For the prevention or treatment of disease, the appropriate dosage of a SIK3 inhibitor (or a pharmaceutical composition comprised thereof) will depend on the type of disease to be treated, the severity and course of the disease, whether the SIK3 inhibitor and/or pharmaceutical composition is administered for preventive or therapeutic purposes, previous therapy, the patient's clinical history, age, size/weight and response to the SIK3 inhibitor and/or pharmaceutical composition, and the discretion of the attending physician. The SIK3 inhibitor and/or pharmaceutical composition is suitably administered to the patient at one time or over a series of treatments. If such SIK3 inhibitor and/or pharmaceutical composition is administered over a series of treatments, the total number of administrations for a given course of treatment may consist of a total of about 2, 3, 4, 5, 6, 7, 8, 9, 10 or more than about 10 treatments. For example, a treatment may be given once every day (or 2, 3 or 4 times a day) for a week, a month or even several months. In certain embodiments, the course of treatment may continue indefinitely.

The amount of the SIK3 inhibitor and/or pharmaceutical composition administered will depend on variables such as the type and extent of disease or indication to be treated, the overall health, age, size/weight of the patient, the in vivo potency of the SIK3 inhibitor and/or pharmaceutical composition, and the route of administration. The initial dosage can be increased beyond the upper level in order to rapidly achieve the desired blood-level or tissue level. Alternatively, the initial dosage can be smaller than the optimum, and the daily dosage may be progressively increased during the course of treatment. Human dosage can be optimised, e.g., in a conventional Phase I dose escalation study designed to run from relatively low initial doses, for example from about 0.01 mg/kg to about 20 mg/kg of active ingredient. Dosing frequency can vary, depending on factors such as route of administration, dosage amount and the disease being treated. Exemplary dosing frequencies are once per day, once per week and once every two weeks. Formulation of an SIK3 inhibitor of (or for use with) the present is within the ordinary skill in the art. In some embodiments of the invention such SIK3 inhibitor is lyophilised and reconstituted in buffered saline at the time of administration. The SIK3 inhibitor and/or pharmaceutical composition of may further result in a reduced relapsing of the disease to be treated or reduce the incidence of drug resistance or increase the time until drug resistance is developing; and in the case of cancer may result in an increase in the period of progression-free survival and/or overall survival.

Characteristics of Proliferative Disorders for Treatment (or Diagnosis) in the Context of the Invention:

The invention is based on the surprising finding that SIK3 is associated with resistance against anti-tumour immune responses, and the inventors herein describe various aspects related to the treatment of proliferative disorders (eg cancers or tumours), in particular by overcoming the resistance of cells involved with the proliferative disorder to a cell-mediated immune response.

A disorder treatable by the subject matter of the invention is preferably one characterised by a resistance of one or more cells involved in (eg affected by) the disorder (such as the proliferative disorder) against a defence response of the host organism, such as resistance that is associated with a pathological phenotype. A particular example is a resistance of such cells (eg cells of a tumour or cancer) against one or more immune responses, in particular a cell-mediated immune response, mounted by the subject/patient suffering from the disorder.

The term "resistance" refers to an acquired or natural resistance of a cell involved with (eg of or affected by) a proliferative disease, such as tumour or cancer cell, to a patient's own immune response (such as a cell-mediated immune response, including TNF), or to immune responses aided by immune therapy/immunotherapy such as adoptive T-cell transfer or treatment with checkpoint blockers. Therefore, a resistant cell (eg a resistant tumour or cancer cell) is more likely to escape and survive humoural and/or cellular immune defence mechanisms in a subject having the disorder (such as the tumour or cancer). A treatment of a resistant proliferative disease, such as tumour/cancer resistance, in context of the invention shall be effective if, compared to a non-treated control, the cell involved with the proliferative disease (such as a cell of the tumour of cancer) becomes more sensitive or susceptible to an immune response (such as a cell-mediated immune response or TNF)—in other words will be more likely to be recognised and/or neutralised (for example by cytotoxic processes such as apoptosis) by the subject's immune response.

Accordingly, in particular embodiments of the invention, cell(s) involved with the proliferative disorder may be resistant against (to) a cell-mediated immune response; and/or such cell(s) may have or display a resistant phenotype.

In preferred embodiments of the invention, the terms "cellular resistance", "cell resistance" and the like refers to a resistance of the subject cell(s) (such as a tumour or cancer cell) to a cell-mediated immune response, such as a cytotoxic T lymphocyte (CTL) response or TNF exposure (eg, the tumour or tumour cell being nonresponsive to, or having reduced or limited response to a CTL targeting a tumour cell or to exposure the TNF). A tumour cell may show a reduced or limited response when contacted with a CTL specific for an antigen expressed on that tumour cell or when contacted with TNF. A reduced or limited response is a reduction to a 90% cytotoxic T cell or TNF response, preferably a reduction to 80%, 70%, 60%, 50% or more preferably a reduction to 40%, 30%, 20% or even less. In this case, 100% would denote the state wherein the CTLs or TNF can kill all of the subject cells involved with the proliferative disorder in a sample. Whether or not a subject cell (eg a tumour cell) is resistant to a patient's (cell-mediated or TNF) immune response may be tested in-vitro by contacting a sample of the subjects such cells (eg autologous tumour cells) with (eg autologous) T-cells or (eg recombinant) TNF and thereafter quantifying the survival/proliferation rate of the (eg) tumour cells. As an alternative, the reduction in (cell-mediated) immune response is determined by comparing cancer samples of the same cancer before and after the resistance is acquired (for example induced by therapy), or by comparing with a cancer sample derived from a different cancer which is known to have no resistance to the CTL or to TNF. On the other hand, the treatments of the present invention include the sensitisation of cells involved with the proliferative disorder against CTL and/or TNF and therefor to decrease resistance of such cells. A decrease of (eg tumour) cell resistance against CTL and/or TNF is preferably a significant increase of CTL or TNF-mediated toxicity, preferably a 10% increase, more preferably 20%, 30%, 40%, 50%, 60%, 70%, 80% or more, even more preferably 2 fold increase, 3 fold, 4 fold, 5 fold or more.

In particular embodiments, a resistant phenotype of the cells involved with the proliferative disorder is displayed by such cells when a subject suffering from the proliferative disorder (eg a cancer or tumour) has been previously treated with an (immune)therapy and, for example, such proliferative disorders has progressed despite such prior (immune) therapy. Accordingly, in certain embodiments, the subject may be distinguished (characterised) as having been previously treated with an immunotherapy and whose tumour has progressed, in particular whose tumour relapsed, recurred or did not respond. For example, a class of subject suitable for the various therapeutic methods of the invention can be those whose tumour (or cancer) has progressed (such as has relapsed or recurred, or has not responded to) after prior treatment with a cancer immunotherapy. Therefore, in certain embodiments, the prior immunotherapy comprised administration of an immune checkpoint inhibitor, such as a prior immunotherapy comprising (administration of) an antibody binding to an immune checkpoint molecule, a non-antibody peptide or a small molecule (in each case, such as described elsewhere). In certain embodiments, such prior treatment may be any immunotherapy as described elsewhere herein, including adoptive immune cell transfer (eg TCR or CAR T cell therapy), an anti-tumour vaccine, an antibody binding to an immune checkpoint molecule (such as CTLA-4, PD-1 or PD-L1), or a non-antibody peptide or small molecule ligand of an immune (inhibitory) checkpoint molecule (in each case, such as described elsewhere. Other immunotherapy (such as may be a a prior treatment of a subject) may include: (x) administration of a drug that activates STING protein, which may lead to stimulation of the innate immune system of the subject. Drugs that agonise STING can include cyclic dinucleotides (CDNs), such as compounds Aduro Biotech's ADU-S100, an analogue of 2'3'-cGAMP (Fu et al, 2015; Sci Transl Med 7; 283:ra52); (y) administration of A2aR antagonists such as SCH58261, SYN115, ZM241365 or FSPTP (as reviewed by Leone et al, 2015; Comp Struct Biotech J 13:265); and/or (z) targeting IDO1/TDO and their downstream effectors, such as administration of indoleamine-2,3-dioxygenase which is in clinical trials with the aim at reverting cancer-induced immunosuppression (as reviewed by Platten et al, 2015; Front Immun 5:673).

In other (or further) embodiments, the subject may suffer from a tumour or cancer, and such cancer may have progressed (such as has relapsed or recurred, or has not responded to) after prior radiotherapy. Accordingly, in other embodiments, the subject may be distinguished (characterised) as having a tumour that progressed, in particular relapsed, recurred or did not respond to, prior radiotherapy.

Accordingly, the invention also includes those embodiments where cells involved with the proliferative disorder have been subjected to prior immunotherapy. As one example of such embodiments, the subject may have received (eg treatment by) prior immunotherapy (eg one described elsewhere herein), such as by administration with (a ligand to) an immune checkpoint molecule (eg administration of an immune checkpoint inhibitor), and/or any other prior immunotherapy such as described elsewhere herein.

In other embodiments, the subject may be distinguished (characterised) as having been previously treated with an anti-TNF agent for an autoimmune disorder (eg rheumatoid arthritis). In particular, the subject may be suffering from a malignancy that had arisen during (eg as a consequence) of such treatment with an anti-TNF agent. For example, the subject may suffer from a haematological malignancy that had arisen during (eg as a consequence of) such treatment with an anti-TNF agent, such as a subject suffering from an iatrogenic immunodeficiency-associated lymphoproliferative disease.

A disorder treatable by the subject matter of the invention is, in certain embodiments, one characterised by expression of SIK3; in particular, one characterised by such expression that is aberrant, for example over- (or under-) expression or representation or activity of SIK3 (in particular of phosphorylated SIK3) in a given cell or tissue (such as those cells or tissues involved with the proliferative disease of the subject) compared to that in a healthy subject or a normal cell.

Accordingly, the invention includes those embodiments wherein cells involved with the proliferative disorder (eg cells of the tumour) are characterised by expression and/or activity of SIK3 (in particular, such cells express mRNA and/or protein of SIK3, and/or are positive for such SIK3 expression and/or activity). In particular of such embodiments, the subject is distinguished (eg, can be characterised)—such as being suitable for the treatment methods of the present invention, by having cells involved with the proliferative disorder characterised by expression and/or activity of SIK3, in particular such cells express mRNA and/or protein of SIK3, and/or are positive for such SIK3 expression and/or activity.

A disorder treatable by the subject matter of the invention may, in other certain embodiments, be one characterised by (such as a disorder that is further characterised by) one or more applicable biomarkers.

The term "applicable biomarker" means any one (or more) of the genes (as well as SIK3) expressed by the cell involved with the proliferative disorder that the inventors have surprisingly found are involved in the SIK3-mediated cellular resistance against an immune response (eg a cell-mediated immune response such as TNF). Such genes include (as well as SIK3, in particular phosphorylated SIK3):
  (a) TNFR1 (or TNFR2), such as the presence of (or an amount of) or expression and/or activity of TNFR1 (or TNFR2), in particular TNFR1;
  (b) LKB1, such as the presence of (or an amount of) or expression and/or activity of LKB1, in particular increased amount or activity of LKB1 or pLKB1;
  (c) one or more class II (eg IIa) HDACs, eg HDAC4, such as the presence of (or an amount of) or expression and/or activity of such HDAC, in particular increased amount or activity of such HDAC or pHDAC, especially in the cytoplasm of cells of the tumour;
  (d) Expression of NF-kappa-B, in particular, constitutive expression of NF-kappa-B;
  (e) NF-kappa-B, such as the presence of (or an amount of) or expression and/or activity of NF-kappa-B, in particular increased amount or activity of NF-kappa-B or acetylated NF-kappa-B, especially in the nucleus of cells of the tumour; and/or
  (f) one or more anti-apoptotic genes, such as the presence of (or an amount of) or expression and/or activity of one or more anti-apoptotic genes, in particular one or more of such genes under transcriptional control by NF-kappa-B.

In certain embodiments of all aspects of the invention, the proliferative disorder may be a tumour selected from the group consisting of: head and neck cancer, squamous cell carcinoma, multiple myeloma, solitary plasmacytoma, renal cell cancer, retinoblastoma, germ cell tumours, hepatoblastoma, hepatocellular carcinoma, melanoma, rhabdoid tumour of the kidney, Ewing Sarcoma, chondrosarcoma, any haemotological malignancy (e.g., chronic lymphoblastic leukemia, chronic myelomonocytic leukemia, acute lymphoblastic leukemia, acute lymphocytic leukemia, acute myelogenous leukemia, acute myeloblasts leukemia, chronic myeloblastic leukemia, Hodgekin's disease, non-Hodgekin's lymphoma, chronic lymphocytic leukemia, chronic myelogenous leukemia, myelodysplastic syndrome, hairy cell leukemia, mast cell leukemia, mast cell neoplasm, follicular lymphoma, diffuse large cell lymphoma, mantle cell lymphoma, marginal zone lymphoma, Burkitt Lymphoma, mycosis fungoides, seary syndrome, cutaneous T-cell lymphoma, peripheral T cell lymphoma, chronic myeloproliferative disorders, myelofibrosis, myeloid metaplasia, systemic mastocytosis), and central nervous system tumours (eg, brain cancer, glioblastoma, non-glioblastoma brain cancer, meningioma, pituitary adenoma, vestibular schwannoma, a primitive neuroectodermal tumour, medulloblastoma, astrocytoma, anaplastic astrocytoma, oligodendroglioma, ependymoma and choroid plexus papilloma), myeloproliferative disorders [e.g., polycythemia vera, thrombocythemia, idiopathic myelfibrosis), soft tissue sarcoma, thyroid cancer, endometrial cancer, carcinoid cancer, and liver cancer; in particular one or the forgoing that is a solid tumour; or the cell(s) involved with the proliferative disorder is(are) one of or derived from one of such tumours.

In particular of such embodiments, the proliferative disorder may be a tumour selected from the group consisting of: pancreatic cancer, breast cancer, melanoma, ovarian cancer, oesophageal cancer, sarcomoa and colorectal cancer; or the cells involved with the proliferative disorder are those of or derived from one of such tumours.

In yet other embodiments of the therapeutic methods of the invention, administration of, exposure to or cell contact with the SIK3 inhibitor, when in a subject, may be associated with one or more of:
  an increase in TIL activity in said subject;
  an increase in TIL survival in said subject;
  an increase in TIL number in said subject;
  an increase in TNF production in said subject;
  a decrease in IL10 production in said subject;
  an increase in the ratio of anti-tumour and tumour-suppressive immune cells (eg, the ratio of CD8 T cells/Tregs or the ratio of Teff/MDSC);
  an increase in infiltration of TILs into the tumour of said subject;
  an increase in INF-gamma production in said subject;
  an increase in IL2 production in said subject;
  a decrease in production of TGF-beta in said subject:
  a decrease in production of IL6 in said subject and/or
  a decrease in production of IDO (indoleamine-pyrrole 2,3-dioxygenase) in said subject.

In yet further embodiments of the therapeutic methods of the invention, administration of, exposure to or cell contact with the SIK3 inhibitor, when in a subject, may enhance a cell-mediated immune response in the subject; in particular wherein said enhancement is associated with one or more of the features (a) to (f) as set forth above.

In yet other embodiments of the therapeutic methods of the invention, administration of, exposure to or cell contact with the SIK3 inhibitor, when in a subject, may not be associated with one or more of:
  an increase in the production of one or more anti-inflammatory cytokines, in particular IL-10; and/or
  a decrease in the production of one or more pro-inflammatory cytokines, in particular TNF.

Detection/Diagnostic/Monitoring Methods:

SIK3 can be used for diagnostic purposes to detect, diagnose, or monitor diseases and/or conditions associated with cellular resistance against a cell-mediated immune response; and in particular aberrant and/or localised expression/activity of SIK3 (in particular phosphorylated SIK3) can be so used. In preferred embodiments of the detection and diagnosis methods of the invention, the diseases, disorders or conditions is a cancer or tumour (such as a solid tumour), including one or more of those described elsewhere herein; more preferably one or more of the disorders described elsewhere herein, such as pancreatic cancer, breast cancer, melanoma, ovarian cancer, oesophageal cancer, sarcomoa and colorectal cancer.

Accordingly, in an eighth aspect, the use of one or more other certain genes (applicable biomarkers that are related to the SIK3-mediated resistance as described above) is envisioned in a method for determining whether a subject, such as a mammalian subject (eg a human), has a phenotype, or is at risk of developing a phenotype, that is associated with (eg a disease, disorder or condition, in particular a proliferative disorder such as a cancer or tumour, including a solid tumour, associated with) cellular resistance against a cell-mediated immune response and/or that is associated with (aberrant) expression or activity of SIK3 (eg SIK3 of a cell involved with the proliferative disorder), the method comprising the step of:

detecting (eg protein or mRNA of) an applicable biomarker (as described above, such as SIK3 and/or HDAC4) in a biological sample from said subject (such as the applicable biomarker of the cancer or tumour cell);

wherein the detection of the applicable biomarker in (eg cancer or tumour cells of) the sample indicates a/the phenotype (or a/the risk of developing a phenotype) that is associated with cellular resistance against the cell-mediated immune response, and/or that is associated with (aberrant) expression or activity of SIK3, in the subject.

In certain embodiments of such aspect, the detection of the applicable biomarker may comprise determining the presence or an amount of SIK3 (and in particular phosphorylated SIK3), or activity thereof, in the sample, in particular such SIK3 associated with or of tumour cells of the subject. In other (alternative or further) embodiments, the detection of the applicable biomarker may comprise determining the presence or an amount of one or more of the other applicable biomarkers as described above.

In a related aspect, the in invention relates to a method for determining the presence or an amount of SIK3 (and in particular phosphorylated SIK3) in a biological sample from a subject, the method comprising the steps of:
contacting said sample with an ABP capable of binding to SIK3 (and in particular phosphorylated SIK3); and
detecting binding between SIK3 (and in particular phosphorylated SIK3) in the biological sample and the ABP.

In certain embodiments, a biological sample will (preferably) comprise cells or tissue of the subject, or an extract of such cells or tissue, in particular where such cells are those (usually, typically; or in the case or a specific subject as suspected to be) involved with the proliferative disorder (eg tumour cells such as cells of a solid tumour). The tumour or cell thereof, may be one or, or derived from, one of the tumours described elsewhere herein.

In particular embodiments of such aspect, the method will also comprise a step of:
providing (such as by obtaining) the biological sample from the subject, in particular where such step is conducted prior to the detection step.

In particular embodiments, such detection and/or determination methods can be practiced as a method of diagnosis, such as a method of diagnosis whether a mammalian subject (such as a human subject or patient) has a disease, disorder or condition, in particular (the presence of) a proliferative disorder such as a cancer or tumour (or has a risk of developing such a disease, disorder or condition) that is associated with cellular resistance against a cell-mediated immune response and/or that is associated with (aberrant) expression or activity of SIK3; in particular a (solid) tumour, such as one having cellular resistance against a cell-mediated immune response.

In certain embodiments of these detection, determination and/or diagnostic methods, the cellular resistance against a cell-mediated immune response is cellular resistance against a T cell-mediated immune response, in particular cellular resistance to the killing effect of TNF and/or of TNFR1 or TNFR2 signalling.

Accordingly, particular embodiments of these detection and/or diagnostic methods may also comprise a step of determining the presence or amount of TNF in the sample, wherein the presence of (or an amount of) TNF in the sample indicates a/the phenotype (or a/the risk of developing a phenotype) that is associated with cellular resistance against the cell-mediated immune response, and/or associated with (aberrant) expression or activity of SIK3, in the subject. In particular of such embodiments, amount of TNF in the sample is determined qualitatively. Preferably, the subject is distinguished as having: (i) a plasma concentration of TNF greater than about 2 pg/mL or 5 pg/mL in a plasma sample from the subject; and/or (ii) an intratumoural concentration of TNF greater than about 0.5 pg/mL or 1 pg/mL plasma from a tissue sample from the subject, indicates the (presence of the) phenotype (or the proliferative disorder or a risk of developing the proliferative disorder) that is associated with cellular resistance against the cell-mediated immune response, and/or associated with expression or activity of SIK3, in the subject.

Methodologies to determine the presence or amount of TNF in a sample are described elsewhere herein (in particular, quantitative detection of TNF using ELISA assays such as a Quantitkine TNF-alpha Immunoassay; as are amounts of TNF that, if are exceeded by the TNF present in the sample, indicate that a phenotype associated with cellular resistance against the cell-mediated immune response, and/or associated with (aberrant) expression or activity of SIK3, in the subject.

In certain embodiments, the biological sample is one obtained from a mammalian subject like a human patient. The term "biological sample" is used in its broadest sense and can refer to a bodily sample obtained from the subject (eg, a human patient). For example, the biological sample can include a clinical sample, i.e., a sample derived from a subject. Such samples can include, but are not limited to: peripheral bodily fluids, which may or may not contain cells, e.g., blood, urine, plasma, mucous, bile pancreatic juice, supernatant fluid, and serum; tissue or fine needle biopsy samples; tumour biopsy samples or sections (or cells thereof), and archival samples with known diagnosis, treatment and/or outcome history. Biological samples may also include sections of tissues, such as frozen sections taken for histological purposes. The term "biological sample" can also encompass any material derived by processing the sample. Derived materials can include, but are not limited to, cells (or their progeny) isolated from the biological sample, nucleic acids and/or proteins extracted from the sample. Processing of the biological sample may involve one or more of, filtration, distillation, extraction, amplification, concentration, fixation, inactivation of interfering components, addition of reagents, and the like.

In some embodiments, these detection, determination and/or diagnostic methods may be a computer-implemented method, or one that is assisted or supported by a computer. In some embodiments, information reflecting the presence or an amount of the applicable biomarker (eg SIK3) to be determined (or activity thereof) in a sample is obtained by at least one processor, and/or information reflecting the presence or an amount of such marker (or activity thereof) in a sample is provided in user readable format by another processor. The one or more processors may be coupled to random access memory operating under control of or in conjunction with a computer operating system. The processors may be included in one or more servers, clusters, or other computers or hardware resources, or may be implemented using cloud-based resources. The operating system may be, for example, a distribution of the Linux™ operating system, the Unix™ operating system, or other open-source or proprietary operating system or platform. Processors may communicate with data storage devices, such as a database stored on a hard drive or drive array, to access or store program instructions other data. Processors may further communicate via a network interface, which in turn may communicate via the one or more networks, such as the Internet or other public or private networks, such that a query or other request may be received from a client, or other device or service. In some embodiments, the computer-implemented method of detecting the presence or an amount of the applicable biomarker (or activity thereof) in a sample is provided as a kit.

Such detection, determination and/or diagnosis methods can be conducted as an in-vitro (eg ex-vivo) method, and can be, for example, practiced using the kit of the present invention (or components thereof). An in-vitro method may use, involve or be practised on immortalised cell lines (such as those replicated, cultured or indefinitely maintained outside of the body of an animal or human), or it may be use, involve or be practised in-vitro using cells (such as primary cells) directly or freshly obtained from the body of an animal of human (eg, practised as a so-called "ex-vivo" method).

In some embodiments of these detection, determination and/or diagnosis methods, the biological sample is a tissue sample from the subject, such as a sample of a tumour or a cancer from the subject. As described above, such tissue sample may be a biopsy sample of the tumour or a cancer such as a needle biopsy sample, or a tumour biopsy section or an archival sample thereof. Such a tissue sample may comprise living, dead or fixed cells, such as from the tumour or a cancer, and such cells may be suspected of expressing (e.g. aberrantly or localised) the applicable biomarker to be determined.

In some embodiments, determination and/or diagnosis method of the invention can comprise, such as in a further step, comparing the detected amount (or activity of) of (eg protein or mRNA of) the applicable biomarker (eg SIK3, and in particular phosphorylated SIK3) with a standard or cut-off value; wherein a detected amount greater than the standard or cut-off value indicates a phenotype (or a risk of developing a phenotype) that is associated with cellular resistance against the cell-mediated immune response in the subject and/or is associated with is associated with (aberrant) expression or activity of SIK3 in the subject. Such a standard or cut-off value may be determined from the use of a control assay, or may be pre-determined from one or more values obtained from a study or a plurality of samples having known phenotypes. For example, a cut-off value for a diagnostic test may be determined by the analysis of samples taken from patients in the context of a controlled clinical study, and determination of a cut-off depending on the desired (or obtained) sensitivity and/or specificity of the test.

Examples of methods useful in the detection of (such as the presence or absence of, or an amount of) the applicable biomarker (such as SIK3, and in particular phosphorylated SIK3) include immunoassays, such as the enzyme linked immunosorbent assay (ELISA) and the radioimmunoassay (RIA), which employ an antigen binding protein ("ABP") such as an antibody or an antigen-binding fragment thereof, that specifically binds to such applicable biomarker.

An "antigen binding protein" ("ABP") as used herein includes the meaning of a protein that specifically binds one or more epitope(s) displayed by or present on a target antigen. Typically, an antigen binding protein is an antibody (or a fragment thereof), however other forms of antigen binding protein are also envisioned by the invention. For example, the ABP may be another (non-antibody) receptor protein derived from small and robust non-immunoglobulin "scaffolds"; such as those equipped with binding functions for example by using methods of combinatorial protein design (Gebauer & Skerra, 2009; Curr Opin Chem Biol, 13:245). Particular examples of such non-antibody ABPs include: Affibody molecules based on the Z domain of Protein A (Nygren, 2008; FEBS J 275:2668); Affilins based on gamma-B crystalline and/or ubiquitin (Ebersbach et al, 2007; J Mo Biol, 372:172); Affimers based on cystatin (Johnson et al, 2012; Anal Chem 84:6553); Affitins based on Sac7d from Sulfolobus acidcaldarius (Krehenbrink et al, 2008; J Mol Biol 383:1058); Alphabodies based on a triple helix coiled coil (Desmet et al, 2014; Nature Comms 5:5237); Anticalins based on lipocalins (Skerra, 2008; FEBS J275:2677); Avimers based on A domains of various membrane receptors (Silverman et al, 2005; Nat Biotechnol 23:1556); DARPins based on an ankyrin repeat motif (Strumpp et al, 2008; Drug Discov Today, 13:695); Fynomers based on an SH3 domain of Fyn (Grabulovski et al, 2007; J Biol Chem 282:3196); Kunitz domain peptides based on Kunitz domains of various protease inhibitors (Nixon et al, Curr opin Drug Discov Devel, 9:261) and Monobodies based on a 10th type III domain of fibronectin (Koide & Koide, 2007; Methods Mol Biol 352:95).

An antigen binding protein is "specific" when it binds to one antigen (such as the applicable biomarker, eg SIK3, and in particular phosphorylated SIK3) more preferentially (eg, more strongly or more extensively) than it binds to a second antigen. The term "specifically binds" (or "binds specifically" and the like) used herein in the context of an ABP means that said ABP will preferentially bind to the applicable biomarker to be determined than to bind to other proteins (or other molecules), such as preferentially binding to such SIK3 compared to one or more of SIK2 and/or SIK1 and/or other kinase. Therefore, preferably, the binding affinity of the ABP to the one antigen (e.g. SIK3) is at least 2-fold, 5-fold, at least 10-fold, at least 20-fold, at least 50-fold, at least 100-fold, at least 200-fold, at least 500-fold, at least 1000-fold, at least 2000-fold, at least 5000-fold, at least 10000-fold, at least $10^5$-fold or even at least $10^6$-fold, most preferably at least 2-fold, compared to its affinity to the other targets (e.g. paralogues of SIK3, such as SIK2 and/or SIK1).

In certain embodiments, the antigen binding protein binds to phosphorylated SIK3 preferentially to binding to un-phosphorylated SIK3.

As used herein, the term "antibody" may be understood in the broadest sense as any immunoglobulin (Ig) that enables binding to its epitope. An antibody as such is a species of an ABP. Full length "antibodies" or "immunoglobulins" are generally heterotetrameric glycoproteins of about 150 kDa, composed of two identical light and two identical heavy chains. Each light chain is linked to a heavy chain by one covalent disulphide bond, while the number of disulphide linkages varies between the heavy chain of different immunoglobulin isotypes. Each heavy and light chain also has regularly spaced intrachain disulphide bridges. Each heavy chain has an amino terminal variable domain (VH) followed by three carboxy terminal constant domains (CH). Each light chain has a variable N-terminal domain (VL) and a single C-terminal constant domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to cells or factors, including various cells of the immune system (e.g., effector cells) and the first component (C1q) of the classical complement system. Other forms of antibodies include heavy-chain antibodies, being those which consist only of two heavy chains and lack the two light chains usually found in antibodies. Heavy-chain antibodies include the hcIgG (IgG-like) antibodies of camelids such as dromedaries, camels, llamas and alpacas, and the IgNAR antibodies of cartilaginous fishes (for example sharks). And yet other forms of antibodies include single-domain antibodies (sdAb, called Nanobody by Ablynx, the developer) being an antibody fragment consisting of a single monomeric variable antibody domain. Single-domain antibodies are typically produced from heavy-chain antibodies, but may also be derived from conventional antibodies.

An antibody may, in certain embodiments be a polyclonal antibody, and in other embodiments may be a monoclonal antibody.

The term "polyclonal antibody" as used herein refers to a mixture of antibodies which are genetically different since produced by plasma cells derived from multiple somatic recombination and clonal selection events and which, typically, recognise a different epitope of the same antigen.

The term "monoclonal antibody" or "mAb" as used herein refers to an antibody obtained from a population of substantially homogeneous antibodies based on their amino acid sequence. Monoclonal antibodies are typically highly specific. Furthermore, in contrast to conventional (polyclonal) antibody preparations which typically include different antibodies directed against different determinants (e.g. epitopes) of an antigen, each mAb is typically directed against a single determinant on the antigen. In addition to their specificity, mAbs are advantageous in that they can be synthesised by cell culture (hybridomas, recombinant cells or the like) uncontaminated by other immunoglobulins. The mAbs herein include for example chimeric, humanised or human antibodies or antibody fragments.

The term "chimeric antibody" refers to an antibody whose light and/or heavy chain genes have been constructed, typically by genetic engineering, from immunoglobulin variable and constant regions which are identical to, or homologous to, corresponding sequences of different species, such as mouse and human. Alternatively, heavy chain genes derive from a particular antibody class or subclass while the remainder of the chain derives from another antibody class or subclass of the same or a different species. It covers also fragments of such antibodies. For example, a typical therapeutic chimeric antibody is a hybrid protein composed of the variable or antigen-binding domain from a mouse antibody and the constant or effector domain from a human antibody, although other mammalian species may be used.

The term "humanised antibody" refers to specific chimeric antibodies, immunoglobulin chains or fragments thereof (such as Fab, Fab', F(ab')$_2$, Fv, or other antigen-binding sub-sequences of antibodies), which contain minimal sequence (but typically, still at least a portion) derived from non-human immunoglobulin. For the most part, humanised antibodies are human immunoglobulins (the recipient antibody) in which CDR residues of the recipient antibody are replaced by CDR residues from a non-human species immunoglobulin (the donor antibody) such as a mouse, rat or rabbit having the desired specificity, affinity and capacity. As such, at least a portion of the framework sequence of said antibody or fragment thereof may be a human consensus framework sequence. In some instances, Fv framework residues of the human immunoglobulin need to be replaced by the corresponding non-human residues to increase specificity or affinity. Furthermore, humanised antibodies can comprise residues which are found neither in the recipient antibody nor in the imported CDR or framework sequences. These modifications are made to further refine and maximise antibody performance. In general, the humanised antibody will comprise substantially all of at least one, and typically at least two, variable domains, in which all or substantially all of the CDR regions correspond to those of a non-human immunoglobulin and all or substantially all of the framework regions are those of a human immunoglobulin consensus sequence. The humanised antibody optimally also will comprise at least a portion of an immunoglobulin constant region, typically that of a human immunoglobulin.

Antibody fragments include "Fab fragments", which are composed of one constant and one variable domain of each of the heavy and the light chains, held together by the adjacent constant region of the light chain and the first constant domain (CH1) of the heavy chain. These may be formed by protease digestion, e.g. with papain, from conventional antibodies, but similar Fab fragments may also be produced by genetic engineering. Fab fragments include "Fab-SH", which are Fab fragments containing at least one free sulfhydryl group.

Fab' fragments differ from Fab fragments in that they contain additional residues at the carboxy terminus of the first constant domain of the heavy chain including one or more cysteines from the antibody hinge region. Fab' fragments include "Fab"-SH, which are Fab' fragments containing at least one free sulfhydryl group.

Further, antibody fragments include F(ab')$_2$ fragments, which contain two light chains and two heavy chains containing a portion of the constant region between the CH1 and CH2 domains, such that an interchain disulphide bond is formed between the two heavy chains. A F(ab')$_2$ fragment thus is composed of two Fab' fragments that are held together by a disulphide bond between the two heavy chains. F(ab')$_2$ fragments may be prepared from conventional antibodies by proteolytic cleavage with an enzyme that cleaves below the hinge region, e.g. with pepsin, or by genetic engineering.

An "Fv region" comprises the variable regions from both the heavy and light chains, but lacks the constant regions. "Single-chain antibodies" or "scFv" are Fv molecules in which the heavy and light chain variable regions have been connected by a flexible linker to form a single polypeptide chain, which forms an antigen binding region.

An "Fc region" comprises two heavy chain fragments comprising the CH2 and CH3 domains of an antibody. The two heavy chain fragments are held together by two or more disulphide bonds and by hydrophobic interactions of the CH3 domains.

Alternatively, the presence of the applicable biomarker (eg SIK3, and in particular phosphorylated SIK3) may be detected by detection of the presence of mRNA that encodes such applicable biomarker, or fragments of such mRNA. Methods to detect the presence of such mRNA (or fragments) can include, PCR (such as quantitative RT-PCR), hybridisation (such as to Illumina chips), nucleic-acid sequencing etc. Such methods may involve or comprise steps using one or more nucleic acids as described herein, such as PCR primers or PCR probes, or hybridisation probes, that bind (eg specifically) to such mRNA.

For such detection, determination or diagnostic applications, the ABP or nucleic acid, typically, will be labelled with a detectable labelling group. In general, labelling groups fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, beta-galactosidase, luciferase, alkaline phosphatase); e) biotinylated groups; and f) predetermined polypeptide epitopes recognised by a secondary reporter (e.g., leucine zipper pair sequences, binding sites for secondary antibodies, metal binding domains, epitope tags, etc.). Suitable labelling groups include, but are not limited to, the following: radio-isotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, beta-galactosidase, luciferase, alkaline phosphatase), chemiluminescent groups, biotinyl groups, or predetermined polypeptide epitopes recognised by a secondary reporter (eg, leucine zipper pair sequences, binding sites for secondary antibodies, metal binding domains, epitope tags). In some embodiments, the labelling group is coupled to the ABP or nucleic acid via spacer arms of various lengths to reduce potential steric hindrance. Various methods for labelling proteins are known in the art and may be used. For example, the ABP or nucleic acid may be labelled with a secondary reporter (e.g., leucine zipper pair sequences, binding sites for secondary antibodies, metal binding domains, epitope tags, etc.).

Accordingly, in particular embodiments of the detection/diagnostic methods (or the kits therefor), the means (eg ABP or nucleic acid) for the detection of protein or mRNA of the applicable biomarker (eg SIK3), is labelled, for example is coupled to a detectable label. The term "label" or "labelling group" refers to any detectable label, including those described herein.

In certain embodiments, the detection/diagnostic methods of the invention involve an immunohistochemistry (IHC) assay or an immunocytochemistry (IC) assay. The terms "IHC" and "ICC" are art recognised, and include the meanings of techniques employed to localise antigen expression that are dependent on specific epitope-antibody interactions. IHC typically refers to the use of tissue sections, whereas ICC typically describes the use of cultured cells or cell suspensions. In both methods, positive staining is typically visualised using a molecular label (eg, one which may be fluorescent or chromogenic). Briefly, samples are typically fixed to preserve cellular integrity, and then subjected to incubation with blocking reagents to prevent non-specific binding of the antibodies. Samples are subsequently typically incubated with primary (and sometimes secondary) antibodies, and the signal is visualised for microscopic analysis.

Accordingly, such embodiments of the detection/diagnostic methods of the invention may include a step of preparing a subject IHC or ICC preparation tissue or cells (such as those present in the biological samples obtained from a subject); and preferably wherein the detection of binding of an ABP to the applicable biomarker (eg SIK3, and in particular phosphorylated SIK3) expressed by the tissues of cells said IHC or ICC preparation indicates: (i) a phenotype (or a risk of developing a phenotype) that is associated with cellular resistance against the cell-mediated immune response in the subject; and/or (ii) said subject has or has a risk of developing disease, condition or disorder that is associated with (aberrant) expression or activity of SIK3.

In such IHC/ICC methods is used an ABP that binds to (preferably specifically to) the applicable biomarker (eg SIK3, and in particular phosphorylated SIK3) and that does not bind (eg does not detectably bind) to a validation IHC or ICC preparation of mammalian tissues or cells other than to (detectably) bind to the applicable biomarker (eg such SIK3), that is expressed by the tissue cells or of said validation IHC or ICC preparation.

In certain of such embodiment, said validation and/or subject IHC or ICC preparation is one selected from the list consisting of: a frozen section, a paraffin section, and a resin section, in each case of the tissues and/or cells; and/or wherein the tissues and/or cell comprised in either (or both) said IHC or ICC preparations are fixed. The tissues and/or cells or such IHC or ICC preparation(s) may be fixed by an alcohol, an aldehyde, a mercurial agent, an oxidising agent or a picrate.

In one preferred of such embodiments, said validation and/or subject IHC or ICC preparation is a formalin-fixed paraffin embedded (FFPE) section of said tissues and/or cells; and/or wherein said validation and/or subject IHC or ICC preparation is subjected to antigen retrieval (AR). Such AR may comprise protease-induced epitope retrieval (PIER) or heat-induced epitope retrieval (HIER).

The ABP used in such methods is, preferably, validated. For example, the ABP is validated to (detectably) binds to the applicable biomarker (eg SIK3, and in particular phosphorylated SIK3) expressed by the cells and/or tissues of said validation IHC or ICC preparation, but does not (detectably) bind to a control IHC or ICC preparation of control cells and/or tissues that do not express the applicable biomarker (eg such as SIK3). Preferably, said control cells are gene knock-down or gene knock-out cells and/or tissues for the applicable biomarker (eg SIK3); more preferably, wherein said gene knock-down or gene knock-out cells and/or tissues are siRNA or shRNA gene knock-down or gene knock-out for such applicable biomarker. Such control cells may comprise cells from a cell-line selected from the list consisting of PANC1 and said control cells and/or tissues that do not express such applicable biomarker (eg SIK3) comprise cells of said cell line that have been transfected with a SIK3 siRNA or shRNA selected from those of Tables A1 and A2; and/or said validation IHC or ICC preparation comprises cells from M579 cells transduced with shSIK3 lentiviral vectors (such as described in Example 8).

In such IHC/ICC methods, the ABP is used with said validation and/or subject IHC or ICC preparation at a working concentration of less than about 50 ug/mL, 25 ug/mL, 20 ug/mL, 15 ug/mL, 10 ug/mL, 7.5 ug/mL, 5 ug/mL, 2.5 ug/mL, 1 ug/mL, 0.5 ug/mL, 0.2 ug/ml or 0.1 ug/ml, in particular less than about 5 ug/mL, and more particularly at less than 2.5 ug/mL; preferably, at a concentration that is about 2-fold, 5-fold, 10-fold, 20-fold or 50-fold higher than said working concentration, said ABP does not (detectable) bind to said validation immunohistochemistry (IHC) preparation of mammalian cells or tissues other than to (detectably) bind to the applicable biomarker (eg SIK3, and in particular phosphorylated SIK3) expressed by the mammalian cells or tissue of said IHC preparation, in particular at a concentration that is about 2-fold higher than said working concentration, and more particularly at a concentration that is about 5-fold higher than said working concentration In the detection/diagnostic methods of the invention, the ABP used may be a polyclonal antibody; and preferably may be a rabbit antibody.

In a ninth aspect, the invention relates to a method for determining (or diagnosing) (eg, by in-vitro and/or ex-vivo methods) whether a subject (such as a human subject or patient) has (or has a risk of developing) a disease, disorder or condition that is associated with cellular resistance against a cell-mediated immune response and/or that is associated with (aberrant) expression or activity of SIK3; in particular a proliferative disorder (eg a cancer or tumour), such as one having cellular resistance against a cell-mediated immune response (eg a T cell-mediated immune response); wherein said determination/diagnosis is made with the involvement of a functional assay measuring a biological response, such as one described elsewhere herein. For example, one such method can comprise the steps of:
  contacting cells (eg tumour cells) of the subject (eg, cell suspected to be) involved with the disease, disorder or condition with a SIK3 inhibitor in the presence of a cell-mediated immune response, such as: (i) (an effective amount of) immune cells selected from the group consisting of: lymphocytes, T-cells, CTLs and TILs, or (ii) (an effective amount of) a pro-inflammatory cytokine such as TNF; and
  determining the cell-mediated immune response against such cells of the subject;
  wherein an enhancement of the cell-mediated immune response against such cells of the subject (in the presence of the SIK3 inhibitor) indicates that the subject has (or has a risk of developing) such disease, disorder or condition. One or more of such steps may be in-vitro steps.

In a related aspect, the invention relates to a method for determining (eg, by in-vitro and/or ex-vivo methods) the resistance of a cell involved with a proliferative disease (eg a cancer or tumour) to a cell-mediated immune response, the method comprising the steps or:
  contacting such cells with a SIK3 inhibitor in the presence of a cell-mediated immune response, such as: (i) immune cells selected from the group consisting of: lymphocytes, T-cells, CTLs and TILs, or (ii) (an effective amount of) a pro-inflammatory cytokine such as TNF; and
  determining the cell-mediated immune response against such cells;
  wherein an enhancement of the cell-mediated immune response against such cells (in the presence of the SIK3 inhibitor) indicates that such cells have a resistance to a cell-mediated immune response. One or more of such steps may be in-vitro steps.

In certain embodiments, the cells involved with a proliferative disorder are provided as a biological sample obtained from a subject (such as a human subject or patient) that has (or has a risk of developing) a disease, disorder or condition that is associated with cellular resistance against a cell-mediated immune response and/or that is associated with (aberrant) expression or activity of SIK3.

The enhancement of the cell-mediated immune response can be determined by, for example, increased cytotoxicity of the cells of the subject, increased Caspase 8 and/or Caspase 9 cleavage, decreased expression and/or activity of NF-kappa-B (in particular decreased amount or activity of NF-kappa-B or acetylated NF-kappa-B, especially in the nucleus of cells of the tumour) and/or decreased expression and/or activity of one or more anti-apoptotic genes (in particular one or more of such genes under transcriptional control of NF-kappa-B). Methods to determine such biological responses are described elsewhere herein, for example including the chromium-release cytotoxicity assay described above.

In certain embodiments, the cells of the subject contacted with the cell-mediated immune response are provided (such as by obtaining) a biological sample from the subject, wherein the sample comprises cells of the subject (such as cells of a tumour or cancer of the subject). Particular embodiments of such method also comprise a step of providing (such as by obtaining) a biological sample from the subject, in particular where such step is conducted prior to the contacting step.

In a related aspect, the detection, a determination and/or diagnostic method may be used as a method for monitoring (or prognosing) the success (or likelihood of success or risk or remission) of treatment of a subject being treated, or intended to be treated, with a treatment method of the invention. For example: (1) if the sample from the subject is determined to contain the presence of (or an indicative amount of) one or more of the above applicable biomarkers (eg SIK3, and in particular phosphorylated SIK3), and/or the presence of (or an indicative amount of) TNF, then this indicates that (a future) treatment with a method of the invention (eg administration of a SIK3 inhibitor) may be successful, or more likely to be successful, for such subject; and/or (2) if, during the course of such treatment (eg administration of a SIK3 inhibitor), a reduction in (such as less than an indicative amount of), or the absence of, one or more of the above applicable biomarkers (eg such SIK3) (or Caspase 8 and/or Caspase 9) or expression (or activity) thereof, is determined in the sample from the subject, then this indicates that such treatment with a method of the invention (eg administration of a SIK3 inhibitor) is or was successful, or is more likely to be successful if continued, for such subject.

The person of ordinary skill will now readily recognise how the detection, determination and/or diagnostic methods of the present invention (and any embodiments thereof) may be practiced or modified so as to use them as part of the monitoring or prognostic methods of the invention.

In another aspect, the invention relates to a method of diagnosing and treating a disease, disorder or condition characterised by the presence of or an amount of, and/or characterised by (aberrant) expression or activity of, SIK3 (such as a proliferative disorder, eg a tumour or cancer) in a subject, such as a human patient, comprising:
  conducting a detection, determination and/or diagnostic method of the invention (such as one described above), thereby diagnosing if the subject is suffering from such a disease, disorder or condition; and
  administering an effective amount of a SIK3 inhibitor (and/or a pharmaceutical composition comprising such inhibitor) to the so diagnosed subject, in particular practicing a treatment method of the invention on the subject.

Further embodiments of the administering (or treatment) step of this method of diagnosis and treatment are described in more details above; as are particular embodiments of the methods of the detection, determination or diagnostic method step of this method. Particular of such embodiments include those where the amount of SIK3 inhibitor administered to the subject is correlated to the plasma or intratumoural concentration of TNF (in the subject), wherein a greater amount (or dose) of SIK3 inhibitor administered to such subject in those cases of a greater plasma or intratumoural concentration of TNF.

In yet another aspect, the invention relates to an ABP binding to (preferably specifically to) protein of the applicable biomarker (eg SIK3, and in particular phosphorylated SIK3, or HDAC4 or phosphorylated HDAC4), or a nucleic acid that can bind to (such as specifically to) mRNA of such applicable biomarker, for use in (eg, in-vitro and/or ex-vivo) diagnosis, such as in the detection of (or determination of the risk of developing) a disease, disorder or condition in a (mammalian) subject, such as a human patient, in particular of a disease, disorder or condition that is associated with cellular resistance against a cell-mediated immune response (such as a proliferative disorder, eg a tumour or cancer), and/or that is associated with (aberrant) expression or activity of SIK3.

Accordingly, one embodiment of such aspect provides a use of an ABP that is capable of binding to or binds to (eg specifically to) SIK3 (and in particular to phosphorylated SIK3, or HDAC4 or phosphorylated HDAC4) for/in (eg, in-vitro and/or ex-vivo) diagnosis. In particular is provided an ABP (such as a monoclonal antibody) that binds to (eg specifically to) SIK3 (and in particular to phosphorylated SIK3) for use in the diagnosis of a disease, disorder or condition in a subject that is associated with cellular resistance against a cell-mediated immune response (such as a cancer), and/or that is associated with (aberrant) expression or activity of SIK3.

The ABP or nucleic acid for use for such detection may be any as described elsewhere herein.

Detection/Diagnostic/Monitoring Kits:

In a tenth aspect, herein provided is a kit, such as one for performing the diagnostic methods or the determination methods or the detection methods (or the monitoring or prognostic methods) of the invention, eg, for determining the presence, absence, amount, function, activity and/or expression of the applicable biomarker (eg SIK3, and in particular to phosphorylated SIK3, or HDAC4 or phosphorylated HDAC4) in a sample (eg a biological sample), such as on cells in a sample. The kit comprises an ABP and/or a nucleic acid as described above and, optionally one or more additional components.

In certain embodiments of the kit, an additional component may comprise instructions describing how to use the ABP or a nucleic acid or kit, for detecting the presence of the applicable biomarker in the sample, such as by detecting binding between the ABP and protein such applicable biomarker, and/or detecting binding between the nucleic acid and mRNA of such applicable biomarker. Such instructions may consist of a printed manual or computer readable memory comprising such instructions, or may comprise instructions as to identify, obtain and/or use one or more other components to be used together with the kit.

In other certain embodiments of the kit, the additional component may comprise one or more other item, component, reagent or other means useful for the use of the kit or practice of a detection method of the invention, including any such item, component, reagent or means disclosed herein useful for such practice. For example, the kit may further comprise reaction and/or binding buffers, labels, enzymatic substrates, secondary antibodies and control samples, materials or moieties etc.

In a particular such embodiment, the additional component may comprise means of detecting the presence of protein of the applicable biomarker (eg SIK3, and in particular the phosphorylated SIK3), such as detecting binding between the ABP and such protein.

Various means for indicating the binding of an ABP can be used. For example, fluorophores, other molecular probes, or enzymes can be linked to the ABP and the presence of the ABP can be observed in a variety of ways. A method for screening for diseases, disorders or conditions can involve the use of the kit, or simply the use of one of the disclosed ABPs and the determination of the extent to which ABP binds to the protein of the applicable biomarker (eg SIK3, and in particular the phosphorylated SIK3), in a sample. As will be appreciated by one of skill in the art, high or elevated levels of protein of the applicable biomarker (eg such SIK3), will result in larger amounts of the ABP binding thereto in the sample. Thus, degree of ABP binding can be used to determine how much of the applicable biomarker (eg such SIK3) is in a sample. Subjects or samples with an amount of such applicable biomarker that is greater than a predetermined amount (eg, an amount or range that a person without a disorder related to the applicable biomarker (eg such SIK3) would have) can be characterised as having a disease, disorder or condition mediated by SIK3 (such as one mediated by the (aberrant) expression, function, activity and/or stability of SIK3), in particular SIK in tumour cells.

In some embodiments, the kit further comprises one or more of the following: standards of protein or mRNA of the applicable biomarker (eg SIK3, and in particular phosphorylated SIK3), positive and/or negative controls for ABP or nucleic acid binding, a vessel for collecting a sample, materials for detecting binding of the ABP or nucleic acid to protein or mRNA (as applicable) of the applicable biomarker in said sample, and reagent(s) for performing said detection.

In another aspect herein provided is the use of a kit as described above for performing the (eg in vitro) diagnostic or detection methods of the invention; and, in a related other aspect the invention related to a kit as described above for use in a (eg in vitro and/or ex-vivo) determination/diagnostic method of the present invention.

In another aspect herein provided is a kit for use in a diagnostic method for determining whether a subject has, or has a risk of developing, a disease, disorder or condition that is associated with cellular resistance against a cell-mediated immune response and that is associated with expression or activity of SIK3; wherein:

the diagnostic method comprises a step of surgically obtaining a (eg, tissue) sample from the subject; and the kit comprises: (a) either (x) a nucleic acid capable of binding specifically to an applicable biomarker (as described above, such as SIK3 or HDAC4), or (y) an ABP binding specifically to applicable biomarker (as described above, such as SIK3 or HDAC4); and (b) optionally (i) instructions describing how to use the ABP or a nucleic acid or kit for detecting SIK3 activity in the (tissue) sample; and/or (ii) one or more other item, component, reagent or other means useful for the use of the kit or the detection of SIK3 activity in the (tissue) sample.

In such diagnostic methods, "surgically" refers to a step that may comprise a significant intervention practiced on the animal or human body, such as taking a biopsy sample, for example a tissue sample of a solid tumour. However, other less less significant steps may include taking of, or sampling, blood, for example by venous puncture or skin-prick. In certain embodiments, it does not include sampling blood by venous puncture or skin-prick, or other non- (or less-) significant method of diagnosis practiced on the human or animal body.

As described above, kits of the invention may be accompanied by instructions, including those to use them for determining the amount, activity and/or expression of the applicable biomarker (eg SIK3, and in particular phosphorylated SIK3, or HDAC4 or phosphorylated HDAC4), such as in tumour cells in a sample.

The various determination(screening)/diagnostic aspects of the invention may be used to identify (eg, to distinguish) wherein the disease, disorder or condition is, and/or is determined to be, (or the subject having such disease, disorder or condition is distinguished to be) one suitable for treatment with a SIK3 inhibitor.

In particular embodiments of such diagnostic aspects of the invention, the subject (eg, from whom the sample was obtained) had been previously treated with (eg, is distinguished (characterised) as having had) an immunotherapy (such as one described elsewhere herein) and whose tumour has progressed, in particular whose tumour relapsed, recurred or did not respond. In other particular embodiments of such diagnostic aspects of the invention, the subject (eg, from whom the sample was obtained) had been previously treated with (eg, is distinguished (characterised) as having had) prior radiotherapy, and whose tumour has progressed, in particular whose tumour relapsed, recurred or did not respond.

In other particular embodiments of such diagnostic aspects of the invention, the subject (eg, from whom the sample was obtained) had been previously treated with, or is being treated with, (eg, is distinguished (characterised) by administration of) an anti-TNF agent for an autoimmune disorder (eg rheumatoid arthritis). In particular, the subject may suffer from, or may be at increased risk from suffering from, a malignancy arising during (eg as a consequence) of such treatment with an anti-TNF agent. For example, the subject may suffer from, or may be at increased risk of suffering from, a haematological malignancy arising during (eg as a consequence of) such treatment with an anti-TNF agent, such as a subject suffering from, or at increased risk of suffering from, an iatrogenic immunodeficiency-associated lymphoproliferative disease.

In yet further particular embodiments of such diagnostic aspects of the invention, the subject (eg, from whom the sample was obtained) is being considered for treatment with, (eg, is distinguished (characterised) by being under consideration for administration of) an anti-TNF agent for an autoimmune disorder (eg rheumatoid arthritis). Such an embodiment may be used to determine those subjects suffering from an autoimmune disorder (eg rheumatoid arthritis) who may have an increased risk of developing a malignancy (such as a haematological malignancy eg an iatrogenic immunodeficiency-associated lymphoproliferative disease) during treatment of their autoimmune disease with an anti-TNF agent.

Screening Methods of the Invention:

In an eleventh aspect of the invention is provided, a method for identifying (and/or characterising) a compound, such as a compound suitable for the treatment of a disease, disorder or condition (such as a proliferative disorder) that is characterised by cellular resistance against a cell-mediated immune response and/or one that is characterised by (aberrant) expression or activity of SIK3, the method comprising the steps of:
  bringing into contact a first cell and the candidate compound, wherein the first cell expresses SIK3 (eg, a protein or mRNA of SIK3); and
  determining the expression, activity (eg kinase activity), function and/or stability of the (eg protein or mRNA of) SIK3 (in particular, of phosphorylated SIK3), in the first cell,
  wherein a reduced expression, activity (eg kinase activity) function and/or stability of the (eg protein or mRNA of) SIK3, in said first cell contacted with the candidate compound compared to said first cell not contacted with said candidate compound indicates that the candidate compound is a compound suitable for the treatment of the disease, disorder or condition.

In a related aspect of the invention, a method is provided for identifying (and/or characterising) a compound, such as a compound suitable for the treatment of a disease, disorder or condition (such as a proliferative disorder) that is characterised by cellular resistance against a cell-mediated immune response and/or one that is characterised by (aberrant) expression or activity of SIK3, the method comprising the steps of:
  bringing into contact a first cell and the candidate compound and (components of) a cell-mediated immune response, wherein the first cell expresses SIK3 (eg, a protein or mRNA of SIK3); and
  determining the cytotoxicity of the cell-mediated immune response against the first cell,
  wherein an enhanced cytotoxicity of the cell-mediated immune response against the first cell contacted with the candidate compound compared to the cytotoxicity of the cell-mediated immune response against the first cell not contacted with the candidate compound indicates that the candidate compound is a compound suitable for the treatment of the disease, disorder or condition.

In certain embodiments of such screening aspects of the invention, the activity of the (eg protein or mRNA of) SIK3 in the first cell may be determined directly (eg, by antibody detection of SIK3 protein or by PCR of SIK3 mRNA), or may be determined by determining the presence or an amount of phosphorylated HDAC4 in the first cells, in particular in the cytoplasm of the first cell. For example, a reduction in phosphorylated HDAC4 in the cytoplasm of such first cell would indicate reduced activity of SIK3 in such cell.

In certain embodiments of such aspects, the methods also include the step of providing (such as by obtaining) the first cell and/or the candidate compound and/or (components of) the cell-mediated immune response, in particular where each of such steps is conducted prior to the contacting step.

Typically, the methods of such aspects will be in-vitro (or ex-vivo) methods; that is, typically the methods are those not practiced on the body of a human or animal. For example, one or more of the steps of such methods may be in-vitro steps. Also, typically, such methods are practiced to identify a suitable candidate compound for purposes of further drug development. That is, in typical (but not all) embodiments, such methods are practiced (especially, if an ex-vivo methods) not to determine (eg diagnose) if a compound is a candidate for the treatment of a particular human or animal.

The reduction (or enhancement) of expression, activity function and/or stability or SIK3 (in particular, of phosphorylated SIK3), or the enhancement (or reduction) in cytotoxicity is, preferably, identified by reference to a control method. In one example, the control method may be one practiced in the absence of any candidate compound, or with compound having a known effect on such expression, function, activity and/or stability (such as a positive or negative control), and/or one practiced in the absence of (one or more components of) a cell-mediated immune response.

In certain embodiments of the screening method, the (components of) cell-mediated immune response is a second cell which is a cytotoxic immune cell, for example a cytotoxic T-lymphocyte (CTL), capable of immunologically recognising the first cell. Accordingly, the containing step of such embodiment comprises bringing into contact a first cell and the candidate compound and a second cell, wherein the first cell expresses SIK3 (eg, a protein or mRNA of SIK3) and the second cell is a cytotoxic immune cell, for example a cytotoxic T-lymphocyte (CTL), capable of immunologically recognising the first cell.

In related but alternative embodiments of the screening method, the (components of) cell-mediated immune response is a cell-free medium that has previously contained immunologically stimulated immune cells, for example cytotoxic T-lymphocytes (CTLs). Such immune cells may be stimulated by samples of the first cell and/or by polyclonal stimulants such as CD3-CD28 bead stimulation. Accordingly, the contacting step of such embodiment comprises bringing into contact a first cell and the candidate compound and a cell-free medium, wherein the first cell expresses SIK3 (eg, a protein or mRNA of SIK3) and the cell-free medium had previously contained immunologically stimulated immune cells, for example a cytotoxic T-lymphocyte (CTL), such as those capable of immunologically recognising the first cell.

In other related but alternative embodiments of the screening method, the (components of) cell-mediated immune response is a pro-inflammatory cytokine, such as TNF. Accordingly, the contacting step of such embodiment comprises bringing into contact a first cell and the candidate compound and a pro-inflammatory cytokine, wherein the first cell expresses SIK3 (eg, a protein or mRNA of SIK3).

In particular of such embodiments, the pro-inflammatory cytokine is TNF (such as rHuTNF), optionally brought into contact with the first cell at a concentration of between about 0.01 ng/mL and about 1000 ng/mL. For example, the TNF may be brought into contact with the first cell at a concentration of about 0.05, 0.1, 0.5, 1.0, 5.0, 10, 50, 100, or 500 ng/mL, in particular between about 5 and 50 ng/mL or 50 and 200 ng/mL TNF.

The first cell is preferably a cell involved with a proliferative disorder (such as a tumour), eg a cell derived from a tumour. The tumour or cell thereof, may be one or, or derived from, one of the tumours described elsewhere herein.

In certain embodiments of the screening methods, the first cell expresses a mutant form of a SIK, such as a mutant form of SIK3, and/or a mutant form of SIK2 and/or a mutant form of SIK1. For example, the knock-in SIK mutants as described by Darling et al 2016 (Biochem DOI: 10.1042/BCJ20160646) may be expressed by the first cell. In certain embodiments of the screening methods, the first cell expresses a shRNA, or comprises a siRNA, that inhibit the expression or activity of a SIK (such as SIK3, SIK2 and/or SIK1). Examples of such shRNA or siRNA sequences are described elsewhere herein. Use of recombinant or modified first cells can aid the characterisation of the candidate compound; in particular as to its specificity (or selectivity) towards SIK3 compare to SIK2 and/or SIK1.

The candidate compound used in the screening methods may be one selected from a polypeptide, peptide, glycoprotein, a peptidomimetic, an antibody or antibody-like molecule (such as an intra-body); a nucleic acid such as a DNA or RNA, for example an antisense DNA or RNA, a ribozyme, an RNA or DNA aptamer, siRNA, shRNA and the like, including variants or derivatives thereof such as a peptide nucleic acid (PNA); a genetic construct for targeted gene editing, such as a CRISPR/Cas9 construct and/or guide RNA/DNA (gRNA/gDNA) and/or tracrRNA; a carbohydrate such as a polysaccharide or oligosaccharide and the like, including variants or derivatives thereof; a lipid such as a fatty acid and the like, including variants or derivatives thereof; or a small organic molecules including but not limited to small molecule ligands, or small cell-permeable molecules.

In particular embodiments, the candidate compound is a small molecule, such as one described elsewhere herein.

In further particular embodiments, the candidate compound is a SIK3 inhibitor, such as one described elsewhere herein. For example, in certain of such embodiments, the candidate compound inhibits SIK3 preferentially to inhibiting SIK2 and/or SIK1, in particular the candidate compound inhibits SIK3 in the first cell, for example preferentially to inhibiting SIK2 (and/or SIK3) in the second cell.

Such SIK3 inhibiting candidate compounds, in certain embodiments, may have been identified (or characterised) as a SIK3 inhibitor (such as a SIK3-specific inhibitor, eg a SIK3 selective inhibitor) prior to it being included in a screening method of the invention. For example, a candidate compound may, as a prior step, be subjected to a SIK3 (and/or SIK2 or SIK1) biochemical assay—such as those provided by Promega, ProQuinase or ThermoFisher—to identify or characterise that the candidate compound is a SIK3 inhibitor (such as a SIK3-specific inhibitor, eg a SIK3 selective inhibitor).

In view of the above, it will be appreciated that the present invention also relates to the following numbered items:

Item 1. A method for the treatment of a proliferative disorder in a subject by inhibiting SIK3, the method comprising administering a SIK3 inhibitor to the subject Item 2. A method for the treatment of a proliferative disorder in a subject by sensitising cells involved with the proliferative disorder to a cell-mediated immune response, the method comprising administering a SIK3 inhibitor to the subject.

Item 3. A method for the treatment of a proliferative disorder in a subject, by inhibiting SIK3 and sensitising cells involved with the proliferative disorder to a cell-mediated immune response, the method comprising administering a SIK3 inhibitor to the subject.

Item 4. The method of any one of items 1 to 3, wherein the proliferative disorder is a tumour, in particular a solid tumour.

Item 5. The method of item 2 or 3, wherein the cell-mediated immune response is mediated by a pro-inflammatory cytokine-secreting cell, in particular a lymphocyte, and preferably a cytotoxic T lymphocyte (CTL).

Item 6. The method of any one of items 2, 3 and 5, wherein the cell-mediated immune response induces killing of cells involved with the proliferative disorder.

Item 7. The method of any one of items 2, 3, 5 and 6, wherein the cell-mediated immune response involves at least one immune cell effector molecule, in particular one secretable or secreted by an immune cell.

Item 8. The method of item 7, wherein the effector molecule is a pro-inflammatory cytokine, in particular tumour necrosis factor (TNF).

Item 9. The method of any one of items 1 to 8, wherein the SIK3 inhibitor is administered to the subject to sensitise cells involved with the proliferative disorder to killing induced by TNF.

Item 10. The method of any one of items 1 to 9, wherein the SIK3 inhibitor is administered to the subject to sensitise cells involved with the proliferative disorder to apoptosis mediated by tumour necrosis factor receptor 1 (TNFR1)-signalling.

Item 11. The method of any one of items 1 to 10, wherein the SIK3 inhibitor is administered to the subject to induce a reduced amount of cytotoxicity to cells involved with the proliferative disorder in the absence of the cell-mediated immune response.

Item 12. The method of any one of items 1 to 11, wherein the administration of the SIK3 inhibitor is associated with impairment of NF-kappaB activity in cells involved with the proliferative disorder, in particular by an enhancement or increase in translocation of NF-kappaB out of the nucleus of the cells involved with the proliferative disorder.

Item 13. A method for the sensitisation of cells involved with a proliferative disorder to a cell-mediated immune response, the method comprising exposing the cells involved with the proliferative disorder to a SIK3 inhibitor.

Item 14. A method for the killing of cells involved with a proliferative disorder, the method comprising exposing the cells involved with the proliferative disorder to: (i) TNF, a TNF variant and/or an agonist of TNFR1-signalling; and (ii) a SIK3 inhibitor.

Item 15. The method of item 1 or 14, wherein the effect is mediated by inhibiting SIK3.

Item 16. The method of any one of items 1 to 15, wherein SIK3 in the cells involved with the proliferative disorder is inhibited.

Item 17. The method of any one of items 1 to 16, wherein SIK2 in immune cells is inhibited to a lesser extent than SIK3.

Item 18. The method of any one of items 1 to 17, wherein SIK1 in immune cells is inhibited to a lesser extent than SIK3.

Item 19. The method of any one of items 1 to 18, wherein the effect is not associated with an increase in the production of one or more anti-inflammatory cytokines and/or is not associated with a decrease in the production of one or more pro-inflammatory cytokines.

Item 20. The method of any one of items 1 to 19, wherein cells involved with the proliferative disorder are subject to activated TNFR2-signalling.

Item 21. The method of any one of items 1 to 20, wherein cells involved with the proliferative disorder are exposed to TNF, a TNF variant and/or an agonist of TNFR2-signalling.

Item 22. The method of any one of items 1 to 21, wherein the subject has a plasma concentration of TNF greater than about 2 pg/mL.

Item 23. The method of any one of items 1 to 22, wherein the proliferative disorder is a solid tumour that, in the subject, has an intratumoural concentration of TNF greater than 0.5 pg/mL.

Item 24. A method for the treatment of a proliferative disorder in a subject, the method comprising exposing cells involved with the proliferative disorder in the subject to: (i) TNF, a TNF variant and/or an agonist of TNFR1-signalling; and (ii) a SIK3 inhibitor.

Item 25. The method of item 24, wherein the effect is mediated by inhibiting SIK3, and/or by sensitising the cells involved with the proliferative disorder to the cytotoxic effects of TNFR1- or TNFR2-signalling.

Item 26. The method of item 24 or 25, wherein the SIK3 inhibitor is administered to the subject.

Item 27. The method of any one of items 24 to 26, wherein the TNF, TNF variant or the agonist of TNFR1-signalling is administered to the subject.

Item 28. The method of any one of items 24 to 27, wherein TNF is administered in the subject at a dose of between about 5 and 500 ug/m2/day, in particular between about 20 and 200 ug/m2/day.

Item 29. The method of any one of items 24 to 27, wherein the TNF variant is a variant form of TNF having higher cytotoxic activity and lower systemic toxicity.

Item 30. The method of any one of items 24 to 26, wherein an agent that is capable of inducing or induces the exposure of the cells involved with the proliferative disorder to the TNF, TNF variant or the agonist of TNFR1-signalling, is administered to the subject.

Item 31. The method of item 30, wherein the agent is a virus that is capable of inducing or induces the exposure of the cells involved with the proliferative disorder to the TNF, TNF variant or the agonists of TNFR1-signalling Item 32. The method of item 30, wherein the agent is an immune cell, in particular wherein the immune cell is administered as part of adoptive cell transfer.

Item 33. The method of any one of items 24 to 26, wherein the exposure of the cells involved with the proliferative disorder to TNF is induced by a pharmaceutical, therapeutic or other procedure that increases the amount of TNF in the plasma of the subject and/or in the environment of such cells.

Item 34. The method of item 33, wherein the pharmaceutical, therapeutic or other procedure comprises cancer immunotherapy and/or radiotherapy.

Item 35. A method for the increase of the therapeutic index of treatment with TNF in a subject being treated therewith for a proliferative disorder, the method comprising administering an inhibitor of SIK3 to the subject.

Item 36. A method for the sensitisation of a subject suffering from a proliferative disorder to a therapy involving the administration of TNF to the subject, the method comprising administering an inhibitor of SIK3 to the subject.

Item 37. A method for the reduction in risk of a haematological proliferative disorder in a subject being treated with an anti-TNF agent, the method comprising administering an inhibitor of SIK3 to the subject.

Item 38. The method of any one of items 1 to 37, wherein the SIK3 inhibitor is a SIK3-specific inhibitor.

Item 39. The method of any one of items 1 to 38, wherein the SIK3 inhibitor inhibits SIK3 more potently than it inhibits SIK2.

Item 40. The method of any one of items 1 to 39, wherein the SIK3 inhibitor is selected from a polypeptide, peptide, glycoprotein, a peptidomimetic, an antibody or antibody-like molecule (such as an intra-body); a nucleic acid such as a DNA or RNA, for example an antisense DNA or RNA, a ribozyme, an RNA or DNA aptamer, siRNA, shRNA and the like, including variants or derivatives thereof such as a peptide nucleic acid (PNA); a genetic construct for targeted gene editing, such as a CRISPR/Cas9 construct and/or guide RNA/DNA (gRNA/gDNA) and/or tracrRNA; a hetero-bifunctional compound (such as a PROTAC or a HyT molecule); a carbohydrate such as a polysaccharide or oligosaccharide and the like, including variants or derivatives thereof; a lipid such as a fatty acid and the like, including variants or derivatives thereof; or a small organic molecules including but not limited to small molecule ligands, or small cell-permeable molecules.

Item 41. The method of any one of items 1 to 40, wherein the SIK3 inhibitor is an inhibitory nucleic acid.

Item 42. The method of any one of items 1 to 40, wherein the SIK3 inhibitor is a small molecule, in particular, a small molecule ligand or a small cell-permeable molecule.

Item 43. The method of any one of items 1 to 40, wherein the SIK3 inhibitor is dasatinib or a variant thereof.

Item 44. The method of any one of items 1 to 40, wherein the SIK3 inhibitor is a cyclic compound of the following formula I and salts thereof

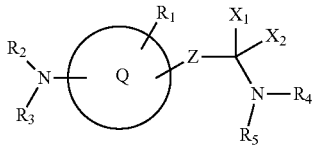

formula I where
Q is:
(1) a 5-membered heteroaryl ring;
(2) a 6-membered heteroaryl ring; or
(3) an aryl ring;
optionally substituted with one or more groups $R_1$;
Z is:
(1) a single bond;
(2) —$R_{16}$C=CH—; or
(3) —(CH$_2$)$_m$—, where m is 1 to 2;
$X_1$ and $X_2$ are each hydrogen, or together form =O or =S;
$R_1$ is:
(1) hydrogen or $R_6$,
    where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$;
(2) —OH or —OR$_6$;
(3) —SH or —SR$_6$;
(4) —C(O)$_2$H, —C(O)$_q$R$_6$, or —O—C(O)$_q$R$_6$, where q is 1 or 2;
(5) —SO$_3$H or —S(O)$_q$R$_6$;
(6) halo;
(7) cyano;
(8) nitro;
(9) —Z$_4$—NR$_7$R$_8$,
(10) —Z$_4$—N(R$_9$)—Z$_5$—NR$_{10}$R$_{11}$;
(11) —Z$_4$—N(R$_{12}$)—Z$_5$—R$_6$;
(12) —P(O)(OR$_6$)$_2$;
$R_2$ and $R_3$ are each independently:
(1) hydrogen or $R_6$;
(2) —Z$_4$—R$_6$; or
(3) —Z$_{13}$—NR$_7$R$_8$;
$R_4$ and $R_5$:
(1) are each independently hydrogen or $R_6$;
(2) —Z$_4$—N(R$_9$)—Z$_5$—NR$_{10}$R$_{11}$;
(3) —N(R$_9$)Z$_4$R$_6$; or
(4) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;
$R_7$, $R_8$, $R_9$, $R_{10}$, $R_{11}$ and $R_{12}$:
(1) are each independently hydrogen or $R_6$;
(2) $R_7$, and $R_8$ may together be alkylene, alkenylene or heteroalkyl, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$ is:
(1) cyano;
(2) nitro;
(3) —NH$_2$;
(4) —NHOalkyl;
(5) —OH;
(6) —NHOaryl;
(7) —NHCOOalkyl;
(8) —NHCOOaryl;
(9) —NHSO$_2$alkyl;
(10) —NHSO$_2$aryl;
(11) aryl;
(12) heteroaryl;
(13) —Oalkyl; or
(14) —Oaryl;
$R_{14}$ is:
(1) —NO$_2$;
(2) —COOalkyl; or
(3) —COOaryl;
$R_{15}$ is:
(1) hydrogen;
(2) alkyl;
(3) aryl;
(4) arylalkyl; or
(5) cycloalkyl;
$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —OZ$_6$;
(3) —SH or —SZ$_6$;
(4) —C(O)$_q$H, —C(O)$_q$Z$_6$, or —O—C(O)$_q$Z$_6$;
(5) —SO$_3$H, —S(O)Z$_6$: or S(O)$_q$N(Z$_9$)Z$_6$;
(6) halo;
(7) cyano;
(8) nitro;
(9) —Z$_4$—NZ$_7$Z$_8$;
(10) —Z$_4$—N(Z$_9$)—Z$_5$—NZ$_7$Z$_8$;
(11) —Z$_4$—N(Z$_{10}$)—Z$_5$—Z$_6$;
(12) —Z$_4$—N(Z$_{10}$)—Z$_5$H;
(13) oxo;
(14) —O—C(O)—Z$_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—(CH$_2$)$_r$—O—, where r is 1 to 5, completing a 4- to 8-membered saturated or unsaturated ring together with the atoms to which they are attached;
$Z_4$ and $Z_5$ are each independently:
(1) a single bond;
(2) —Z$_{11}$—S(O)$_q$—Z$_{12}$—;
(3) —Z$_{11}$—C(O)—Z$_{12}$;
(4) —Z$_{11}$—C(S)—Z$_{12}$—;
(5) —Z$_{11}$—O—Z$_{12}$—;
(6) —Z$_{11}$—S—Z$_{12}$—;
(7) —Z$_{11}$—O—C(O)—Z$_{12}$; or
(8) —Z$_{11}$—C(O)—O—Z$_{12}$—;
$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or (3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$Z_{11}$ and $Z_{12}$ are each independently:
(1) a single bond;
(2) alkylene;
(3) alkenylene; or
(4) alkynylene; and $Z_{13}$ is:
(1) a single bond;
(2) —$Z_{11}$—S(O)$_q$—$Z_{12}$—;
(3) —$Z_{11}$—C(O)—$Z_{12}$—;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—;
(8) —$Z_{11}$—C(O)—O—$Z_{12}$—;
(9) —C(NR$_{13}$)—;
(10) —C(CHR$_{14}$)—; or
(11) —C(C(R$_{14}$)$_2$)—.

Item 45. The method of item 44, wherein such SIK3 inhibitor is a variant of dasatinib.

Item 46. The method of any one of items 1 to 40, wherein the SIK3 inhibitor is selected from the group consisting of:

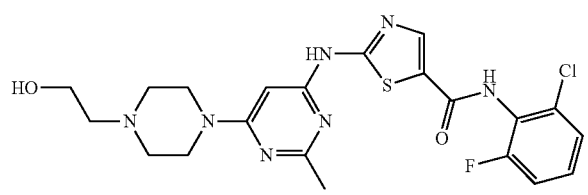

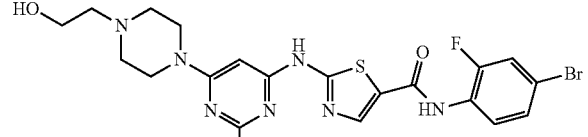

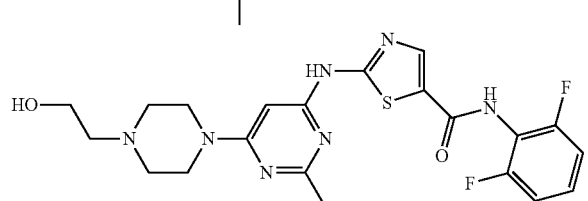

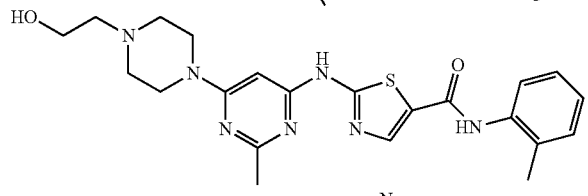

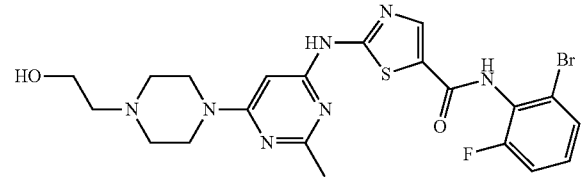

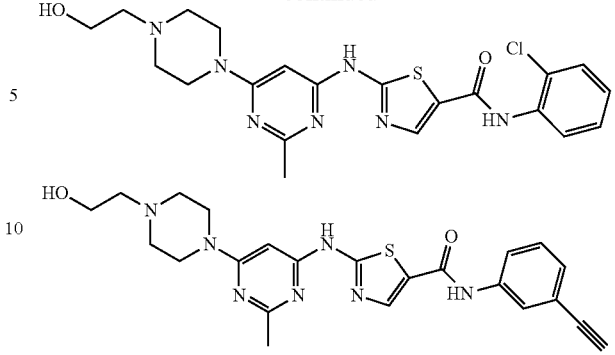

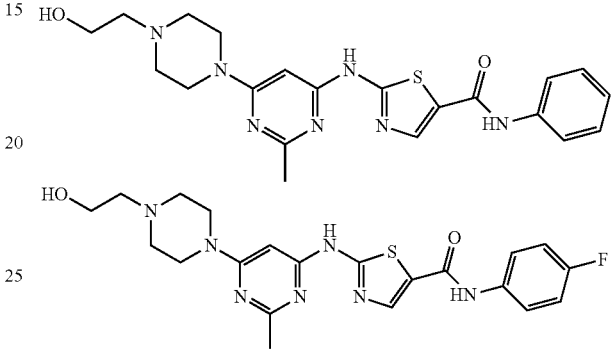

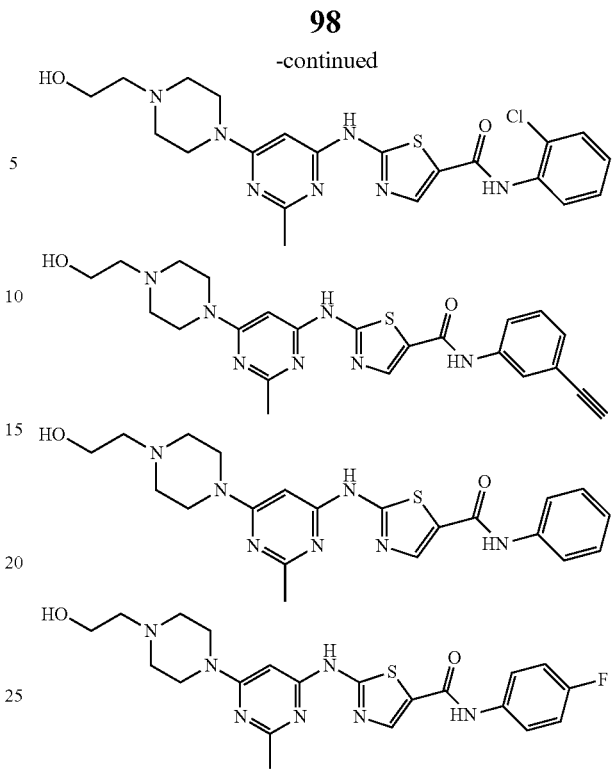

and solvates, salts, complexes, polymorphs, crystalline forms, racemic mixtures, diastereomers, enantiomers, tautomers, isotopically labelled forms, prodrugs, and combinations thereof.

Item 47. The method of any one of items 1 to 46, wherein cells involved in the proliferative disorder are resistant against a cell-mediated immune response.

Item 48. The method of any one of items 1 to 47, wherein cells involved with the proliferative disorder have been subjected to prior immunotherapy, in particular the subject has had prior immunotherapy by administration with an immune checkpoint molecule.

Item 49. The method of any one of items 1 to 48, wherein cells involved in the proliferative disorder are characterised by expression and/or activity of SIK3, in particular such cells express mRNA and/or protein of SIK3, and/or are positive for such SIK3 expression and/or activity.

Item 50. The method of any one of items 1 to 49, wherein the proliferative disorder is a tumour selected from the group consisting of: pancreatic cancer, breast cancer, melanoma, ovarian cancer, oesophageal cancer, sarcomoa and colorectal cancer; or cells involved with the proliferative disorder are those of or derived from one of such tumours.

Item 51. A method for determining whether a subject has, or is at risk of, developing a phenotype that is associated with cellular resistance against a cell-mediated immune response and/or that is associated with expression or activity of SIK3, the method comprising the step of:
  (a) detecting an applicable biomarker in a biological sample from said subject;
  wherein the detection of the applicable biomarker in the sample indicates a phenotype or a risk of developing a phenotype that is associated with cellular resistance against the cell-mediated immune response, and/or that is associated with expression or activity of SIK3, in the subject; and wherein the applicable biomarker is one selected from the group consisting of:
  SIK3, in particular the presence (or an amount) of or expression and/or activity of SIK3, preferably of phosphorylated SIK3;
  TNFR1, in particular the presence (or an amount) of or expression and/or activity of TNFR1; and
  LKB1, in particular the presence (or an amount) of or expression and/or activity of LKB1, preferably of phosphorylated LKB1.

Item 52. The method according to item 51, wherein the detection of the applicable biomarker comprises determining the presence or an amount of SIK3, or activity thereof, in the sample, in particular of phosphorylated SIK3.

Item 53. The method according to items 51 or 52, further comprising a step of determining the presence or amount of TNF in the sample, wherein the presence of or an amount of TNF in the sample indicates a phenotype or a risk of developing a phenotype that is associated with cellular resistance against the cell-mediated immune response, and/or associated with expression or activity of SIK3, in the subject.

Item 54. A method for determining whether a subject has, or has a risk of developing, a disease, disorder or condition that is associated with cellular resistance against a cell-mediated immune response and/or that is associated with expression or activity of SIK3, the method comprising the steps of:
  (a) contacting cells of the subject involved with the disease, disorder or condition with a SIK3 inhibitor in the presence of a cell-mediated immune response being (i) immune cells selected from the group consisting of: lymphocytes, T-cells, CTLs and TILs, or (ii) a pro-inflammatory cytokine in particular TNF; and
  (b) determining the cell-mediated immune response against such cells of the subject,
  wherein an enhancement of the cell-mediated immune response against such cells of the subject indicates that the subject has or has a risk of developing such disease, disorder or condition.

Item 55. A use of an antigen binding protein (ABP) capable of binding specifically to SIK3 in the in-vitro diagnosis of a disease, disorder or condition in a mammalian subject, in particular of a disease, disorder or condition that is associated with cellular resistance against a cell-mediated immune response, and/or that is associated with expression or activity of SIK3.

Item 56. The use according to item 55, wherein the ABP is capable of binding specifically to phosphorylated SIK3.

Item 57. A kit comprising: (a) an ABP or a nucleic acid capable of binding specifically to SIK3; and (b) optionally (i) instructions describing how to use the ABP or a nucleic acid or kit for detecting SIK3 in the sample; and/or (ii) one or more other item, component, reagent or other means useful for the use of the kit or the detection of SIK3 in the sample.

Item 58. The kit according to item 57 comprising an ABP capable of binding specifically to phosphorylated SIK3.

Item 59. A method for identifying and/or characterising a compound suitable for the treatment of a disease, disorder or condition that is characterised by cellular resistance against a cell-mediated immune response and/or one that is characterised by expression or activity of SIK3, the method comprising the steps of:
  (a) bringing into contact a first cell expressing SIK3 and (i) the candidate compound, or (ii) the candidate compound and a cell-mediated immune response; and
  (b) determining (i) the expression, activity, function and/or stability of the (eg protein or mRNA of) SIK3 (in particular, of phosphorylated SIK3), in the first cell; and/or (ii) the cytotoxicity of the cell-mediated immune response against the first cell,
  wherein: (i) a reduced expression, activity function and/or stability of the SIK3, in said first cell contacted with the candidate compound compared to said first cell not contacted with said candidate compound; and/or (ii) an enhanced cytotoxicity of the cell-mediated immune response against the first cell contacted with the candidate compound compared to the cytotoxicity of the cell-mediated immune response against the first cell not contacted with the candidate compound; indicates that the candidate compound is a compound suitable for the treatment of the disease, disorder or condition that is characterised by cellular resistance against a cell-mediated immune response and/or one that is characterised by expression or activity of SIK3.

Item 60. The method according to item 59, wherein the reduction of expression, activity function and/or stability or SIK3 and/or the enhancement in cytotoxicity is identified by reference to a control method selected from a method practiced in the absence of any candidate compound, or a method practised with a compound having a known effect on such expression, function, activity and/or stability, in particular a positive or negative control, and/or a method practiced in the absence of a cell-mediated immune response.

Item 61. The method according to item 59 or 60, wherein the cell-mediated immune response is a pro-inflammatory cytokine, in particular TNF.

Item 62. The method according to any one of items 59 to 61, wherein the first cell is a cell involved with a proliferative disorder, in particular a tumour.

In addition, it will also be appreciated that the present invention also relates to the following additional numbered items:

Item A1. A SIK3 inhibitor for use in the treatment of a proliferative disorder in a subject, by inhibiting SIK3 and sensitising cells involved with the proliferative disorder to a cell-mediated immune response, the treatment comprising administering the SIK3 inhibitor to the subject.

Item A2. The SIK3 inhibitor for use of item A1, wherein: (i) the cell-mediated immune response is mediated by a pro-inflammatory cytokine-secreting cell, in particular a lymphocyte, and preferably a cytotoxic T lymphocyte (CTL)

and/or (ii) wherein the cell-mediated immune response involves at least one immune cell effector molecule that is a pro-inflammatory cytokine, in particular tumour necrosis factor (TNF).

Item A3. The SIK3 inhibitor for use of item A1 or A2, wherein: (i) the subject has a plasma concentration of TNF greater than about 2 pg/mL; and/or (ii) the proliferative disorder is a solid tumour that, in the subject, has an intratumoural concentration of TNF greater than 0.5 pg/mL.

Item A4. A SIK3 inhibitor for use in the treatment of a proliferative disorder in a subject, the treatment comprising exposing cells involved with the proliferative disorder in the subject to: (i) TNF, a TNF variant and/or an agonist of TNFR1-signalling; and (ii) a SIK3 inhibitor, wherein the SIK3 inhibitor is administered to the subject.

Item A5. The SIK3 inhibitor for use of item A4, wherein: (i) the TNF, TNF variant or the agonist of TNFR1-signalling is administered to the subject; (ii) an agent that is capable of inducing or induces the exposure of the cells involved with the proliferative disorder to the TNF, TNF variant or the agonist of TNFR1-signalling, is administered to the subject; or (iii) the exposure of the cells involved with the proliferative disorder to TNF is induced by a pharmaceutical, therapeutic or other procedure that increases the amount of TNF in the plasma of the subject and/or in the environment of such cells.

Item A6. A SIK3 inhibitor for use in a treatment for the reduction in risk of a haematological proliferative disorder in a subject being treated with an anti-TNF agent, the treatment comprising administering the inhibitor of SIK3 to the subject.

Item A7. The SIK3 inhibitor for use of any one of items A1 to A6, wherein the SIK3 inhibitor inhibits SIK3 more potently than it inhibits SIK2.

Item A8. The SIK3 inhibitor for use of any one of items A1 to A7, wherein the SIK3 inhibitor is: (i) an inhibitory nucleic acid; or (ii) a small molecule, in particular, a small molecule ligand or a small cell-permeable molecule.

Item A9. The SIK3 inhibitor for use of any one of items A1 to A8, wherein the SIK3 inhibitor is a cyclic compound of the following formula I and salts thereof

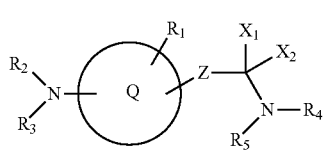

formula I where
Q is:
(1) a 5-membered heteroaryl ring;
(2) a 6-membered heteroaryl ring; or
(3) an aryl ring;
optionally substituted with one or more groups $R_1$;
Z is:
(1) a single bond;
(2) —$R_{16}$C=CH—; or
(3) —(CH)$_m$—, where m is 1 to 2;
$X_1$ and $X_2$ are each hydrogen, or together form =O or =S;
$R_1$ is:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more (preferably, one or two) groups $Z_3$;
(2) —OH or —O$R_6$;
(3) —SH or —S$R_6$;
(4) —C(O)$_2$H, —C(O)$_q R_6$, or —O—C(O)$_q R_6$, where q is 1 or 2;
(5) —SO$_3$H or —S(O)$_q R_6$;
(6) halo;
(7) cyano;
(8) nitro;
(9) —$Z_4$—N$R_7 R_8$;
(10) —$Z_4$—N($R_9$)—$Z_5$—N$R_{10} R_{11}$;
(11) —$Z_4$—N($R_{12}$)—$Z_5$—$R_6$;
(12) —P(O)(O$R_6$)$_2$;
$R_2$ and $R_3$ are each independently:
(1) hydrogen or $R_6$;
(2) —$Z_4$—$R_6$; or
(3) —$Z_3$—N$R_7 R_8$;
$R_4$ and $R_5$:
(1) are each independently hydrogen or $R_6$;
(2) —$Z_4$—N($R_9$)—$Z_5$—N$R_{10} R_{11}$;
(3) —N($R_9$)$Z_4 R_6$; or
(4) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;
$R_7$, $R_8$, $R_9$, $R_{10}$, $R_{11}$ and $R_{12}$:
(1) are each independently hydrogen or $R_6$;
(2) $R_7$, and $R_8$ may together be alkylene, alkenylene or heteroalkyl, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;
$R_{13}$ is:
(1) cyano;
(2) nitro;
(3) —NH$_2$;
(4) —NHOalkyl;
(5) —OH;
(6) —NHOaryl;
(7) —NHCOOalkyl;
(8) —NHCOOaryl;
(9) —NHSO$_2$alkyl;
(10) —NHSO$_2$aryl;
(11) aryl;
(12) heteroaryl;
(13) —Oalkyl; or
(14) —Oaryl;
$R_{14}$ is:
(1) —NO$_2$;
(2) —COOalkyl; or
(3) —COOaryl;
$R_{15}$ is:
(1) hydrogen;
(2) alkyl;
(3) aryl;
(4) arylalkyl; or
(5) cycloalkyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —C(O)$_q$H, —C(O)$_q Z_6$, or —O—C(O)$_q Z_6$;
(5) —$SO_3$H, —S(O)$_q Z_6$; or S(O)$_q$N($Z_9$)$Z_6$;
(6) halo;
(7) cyano;
(8) nitro;
(9) —$Z_4$—$NZ_7 Z_8$;
(10) —$Z_4$—N($Z_9$)—$Z_5$—$NZ_7 Z_8$;
(11) —$Z_4$—N($Z_{10}$)—$Z_5$—$Z_6$;
(12) —$Z_4$—N($Z_{10}$)—$Z_5$H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—(CH$_2$)$_r$—O—, where r is 1 to 5, completing a 4- to 8-membered saturated or unsaturated ring together with the atoms to which they are attached;
$Z_4$ and $Z_5$ are each independently:
(1) a single bond;
(2) —$Z_{11}$—S(O)$_q$—$Z_{12}$—;
(3) —$Z_{11}$—C(O)—$Z_{12}$—;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$; or
(8) —$Z_{11}$—C(O)—O—$Z_{12}$—;
$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;
$Z_{11}$ and $Z_{12}$ are each independently:
(1) a single bond;
(2) alkylene;
(3) alkenylene; or
(4) alkynylene; and
$Z_{13}$ is:
(1) a single bond;
(2) —$Z_{11}$—S(O)$_q$—$Z_{12}$—;
(3) —$Z_{11}$—C(O)—$Z_{12}$;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—;
(8) —$Z_{11}$—C(O)—O—$Z_{12}$—;
(9) —C(N$R_{13}$)—;
(10) —C(CH$R_{14}$)—; or
(11) —C(C($R_{14}$)$_2$)—;

wherein the cyclic compound of formula I has the following formula II:

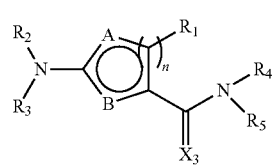

formula II where
n is 1 or 2
A is selected from carbon and nitrogen;
B is selected from nitrogen, oxygen and sulphur;
$X_3$ is oxygen or sulphur; and
$R_1$, $R_2$, $R_3$, $R_4$ and $R_5$ are as described above; and
wherein the $R_2$ of formula II is hydrogen, and $R_3$ of formula II is Rx, wherein Rx has the following formula X:

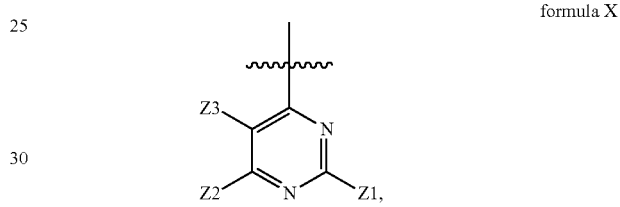

formula X wherein $Z_1$, $Z_2$ and $Z_3$ of formula X are as defined above.

Item A10. The SIK3 inhibitor for use of any one of items A1 to A9, wherein the SIK3 inhibitor is selected from the group consisting of:

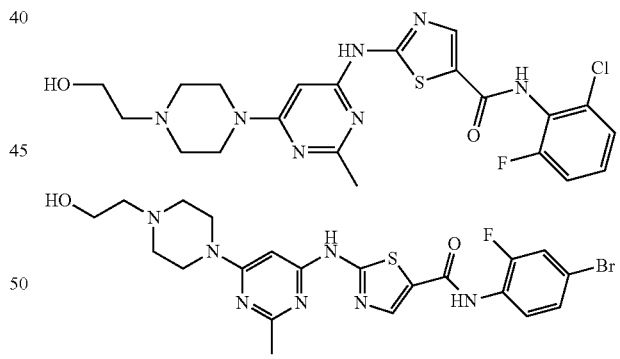

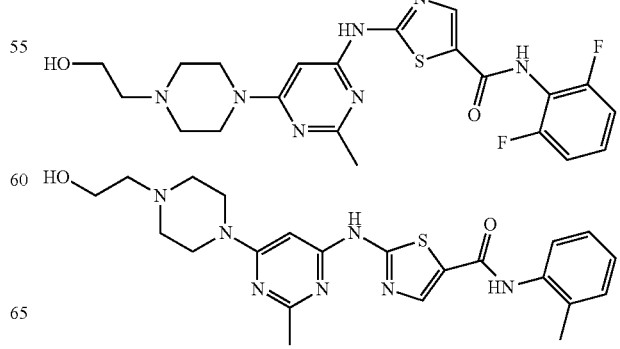

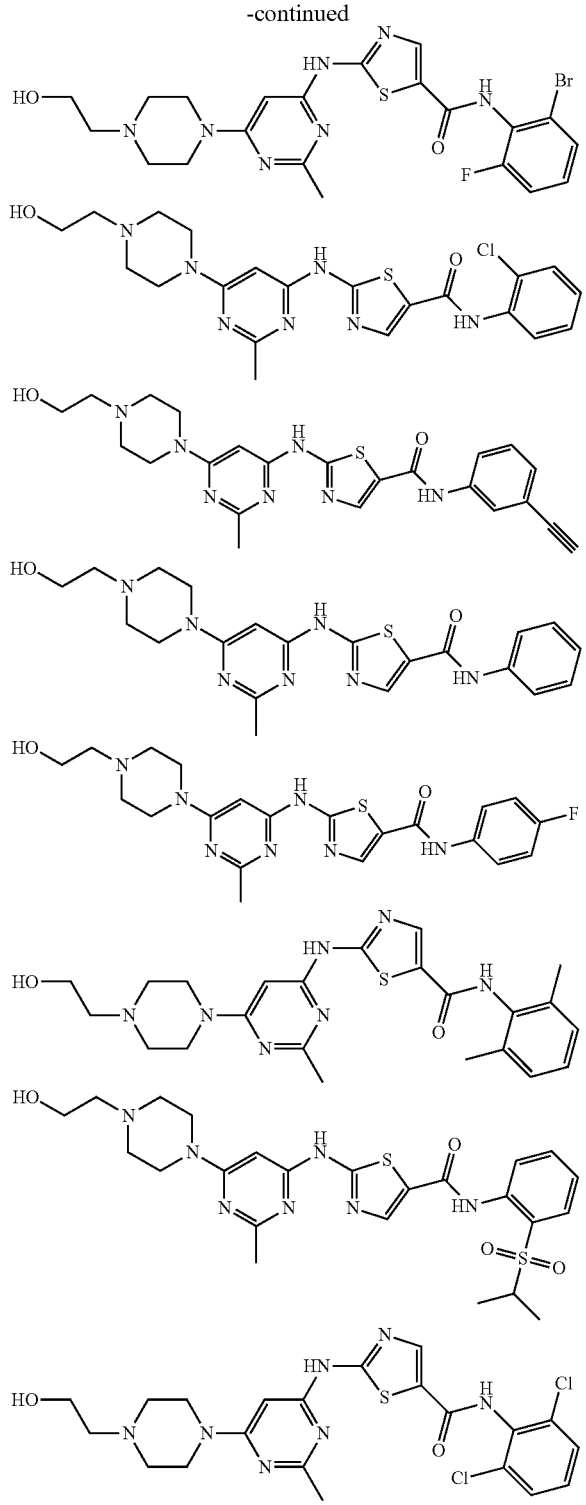

and solvates, salts, complexes, polymorphs, crystalline forms, racemic mixtures, diastereomers, enantiomers, tautomers, isotopically labelled forms, prodrugs, and combinations thereof.

Item A11. The SIK3 inhibitor for use of any one of items A1 to A5 and A7 to A10, wherein cells involved in the proliferative disorder: (i) are resistant against a cell-mediated immune response; and/or (ii) have been subjected to prior immunotherapy, in particular the subject has had prior immunotherapy by administration with an immune checkpoint molecule.

Item A12. The SIK3 inhibitor for use of any one of items A1 to A5 and A7 to A11, wherein cells involved in the proliferative disorder are characterised by expression and/or activity of SIK3, in particular such cells express mRNA and/or protein of SIK3, and/or are positive for such SIK3 expression and/or activity.

Item A13. A method for determining whether a subject has, or is at risk of developing, a proliferative disorder, such as a tumour, that is associated with cellular resistance against a cell-mediated immune response, the method comprising the step of:
(a) detecting an applicable biomarker in a biological sample from said subject;
wherein the detection of the applicable biomarker in the sample indicates a phenotype or a risk of developing a phenotype that is associated with cellular resistance against the cell-mediated immune response, and/or that is associated with expression or activity of SIK3, in the subject; and wherein the applicable biomarker is one selected from the group consisting of:
SIK3, in particular the presence (or an amount) of or expression and/or activity of SIK3, preferably of phosphorylated SIK3;
TNFR1, in particular the presence (or an amount) of or expression and/or activity of TNFR1; and
LKB1, in particular the presence (or an amount) of or expression and/or activity of LKB1, preferably of phosphorylated LKB1.

Item A14. The method according to item A13, further comprising a step of determining the presence or amount of TNF in a biological sample from said subject, wherein the presence of or an amount of TNF in the sample indicates a phenotype or a risk of developing a phenotype that is associated with cellular resistance against the cell-mediated immune response, and/or associated with expression or activity of SIK3, in the subject Item A15. A method for identifying and/or characterising a compound suitable for the treatment of a disease, disorder or condition that is characterised by cellular resistance against a cell-mediated immune response the method comprising the steps of:
(a) bringing into contact a first cell expressing SIK3 and (i) the candidate compound, or (ii) the candidate compound and a cell-mediated immune response; and
(b) determining (i) the expression, activity, function and/or stability of the (eg protein or mRNA of) SIK3 (in particular, of phosphorylated SIK3), in the first cell; and/or (ii) the cytotoxicity of the cell-mediated immune response against the first cell,
wherein: (i) a reduced expression, activity function and/or stability of the SIK3, in said first cell contacted with the candidate compound compared to said first cell not contacted with said candidate compound; and/or (ii) an enhanced cytotoxicity of the cell-mediated immune response against the first cell contacted with the candidate compound compared to the cytotoxicity of the cell-mediated immune response against the first cell not contacted with the candidate compound; indicates that the candidate compound is a compound suitable for the treatment of the disease, disorder or condition that is characterised by cellular resistance against a cell-mediated immune response and/or one that is characterised by expression or activity of SIK3.

Item A16. The method according to item A15, wherein the cell-mediated immune response is: (i) a pro-inflammatory cytokine, in particular TNF; or (ii) a second cell which is a cytotoxic immune cell capable of immunologically recognising the first cell, in particular a CTL.

Item A17. The SIK3 inhibitor for use of any one of items A1 to A5 or A7 to A12, wherein the proliferative disorder is a tumour, in particular a solid tumour.

The terms "of the [present] invention", "in accordance with the invention", "according to the invention" and the like, as used herein are intended to refer to all aspects and embodiments of the invention described and/or claimed herein.

As used herein, the term "comprising" is to be construed as encompassing both "including" and "consisting of", both meanings being specifically intended, and hence individually disclosed embodiments in accordance with the present invention. Where used herein, "and/or" is to be taken as specific disclosure of each of the two specified features or components with or without the other. For example "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by 20%, 15%, 10%, and for example 5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

The examples show:

Example 1: SIK3 Activity in a Cell of a Proliferative Disease Mediates Resistance to an Immune Response The inventors describe herein their surprising finding that SIK3 is a gene involved in tumour cell resistance against a cell-mediated immune response. Such role of SIK3 was first identified by the inventors using a high-throughput screening approach—to identify novel genes involved in mechanisms of tumour resistance towards T cell attack—as adapted and expanded from the screening approach developed and described by Khandelwal et al, 2015 (EMBO Mol Med 7:450). Briefly, using a siRNA library, 2514 genes were individually knocked-down in HLA-A2.1+ luciferase-expressing PANC1 cells (PANC1-luc), a pancreatic adenocarcinoma (PDAC) tumour cell line. Each gene's siRNA-transfected PANC1-luc tumour cells were then co-cultured with magnetically purified CD8+ T cells from an HLA-A2.1+ PDAC-derived tumour infiltrating lymphocyte culture (TIL #1). The impact of siRNA-mediated gene knockdown on TIL-mediated killing of tumour cells was measured using a luciferase-based cytotoxicity assay (cytotoxicity setting). In order to exclude those genes whose knockdown intrinsically affects cell viability, complementary screening was performed without the addition of TIL #1 (viability setting). False positive genes were further excluded using a luciferase-independent viability screen.

The present invention is based on the dramatic impact that inhibition of SIK3 of tumour cells determines a reduction of tumour cell survival after co-culture with a cell-mediated immune response. In the T cell mediated cytotoxicity assay based on the PANC1-luc using the luciferase-based killing assay, inhibition of SIK3 by the SIK3 siRNA sequences set forth in Table A1 (Dharmacon/GE Healthcare) lead to a dramatic reduction of tumour cell survival after co-culture with either TIL #1 or survivin-specific T cell clones (FIG. 2). Surprisingly, SIK3 impairment by siRNA resulted in a stronger increase in tumour killing than siRNA depletion of PD1-L1 (for siRNA sequences, see Table A1). In the absence of T cells, the effect of SIK3 knockdown on tumour cells depended on specific siRNA sequence used, with s1, s2 and s3 showing slight reduction of cell viability, while the pool siRNA moderately increased cell survival. To reliably interpret the intrinsic viability impact of SIK3, a WST-1 viability assay (ie, in the absence of T cells) was performed, and no significant effect in PANC-1 cells was observed after transfection with several SIK3-specific siRNAs (see Example 3 and FIG. 8E).

The PANC1-luc cell line was constructed as follows: PANC-1 cells were acquired from the American Type Cell Culture (ATCC). Tumour cells were transfected with pEGFP-Luc plasmid (kindly provided by Dr Rudolf Haase, LMU Munich), using TransIT-LT1 (Mirus) as transfection reagent. Transfected cells were selected with 1 mg/mL of G418/Geneticin, and 14 days after selection EGFP+ cells were sorted using BD FACSARIA II cell sorter. HLA-A0201-restricted survivin95-104 (clone SK-1) specific CTL clones were generated from PBMC of healthy donors as described (Brackertz et al, 2011). For these experiments, PANC-1-luc cells were transfected either with single (s #) or pooled (pool) siRNA sequences targeting SIK3, with scrambled siRNA used as control (siCtrl), followed by exposure to T cells by a method described briefly as follows: PANC-1-Luc cells were reverse transfected with 25 nM siRNAs in white 96-well plates (Perkin Elmer) using 0.1 uL RNAiMax as transfection reagent for 72 h at 37° C., 5% CO2. Afterwards, TILs, survivin-specific T cells or culture medium (as applicable for the experiment) were added to transfected PANC-1-Luc cells at the desired effector-cell (T cell) to target-cell (tumour) ratio (E:T) and incubated for 24 h at 37° C., 5% CO2. After co-culture, supernatant was removed and the remaining PANC-1-Luc cells were lysed with luciferase cell lysis reagent (0.3% Triton-X in water) for 10 min. After lysis, luciferase assay buffer was added and immediately the luciferase intensity was measured by using the TECAN-Spark microplate reader.

PANC-1 cells express SIK3, and 3 non-overlapping SIK3-specific siRNAs (or the siRNA pool) each induced an efficient SIK3 knockdown at mRNA level as compared to scrambled control siRNA (FIG. 3A). Western blot analysis confirmed knockdown or SIK3 at the protein level using the same SIK3 individual and pool siRNAs (FIG. 3B), using anti-SIK3 Ab (Abcam, Cat No: ab88495) and anti-rabbit IgG-HRP as secondary antibody (Santa Cruz Biotechnology, Cat No: sc2004). Furthermore, the cytotoxic effect observed was specific to SIK3 knockdown, and not from knockdown of other members of the SIK gene family (FIG. 3C). As it can be observed from the separated readouts for such experiments (FIG. 3D), knockdown of SIK3 substantially increased the cytotoxicity in the presence of T cells, without affecting tumour cell viability (No T Cells); SIK1 knockdown did not affect viability in either settings, while SIK2 depletion impaired tumour cell viability per se, and addition of T cells did not synergistically increase tumour cell death.

Tumour infiltrating lymphocytes showed weak cytotoxic activity against tumour cells, even at high E:T ratios, when in the absence of SIK3 knockdown. However, SIK3 downregulation consistently and dramatically increased TIL-mediated killing of tumour cells (FIG. 4A). These data confirm that the observed increase in T cell-mediated cytotoxicity that is dependent on on-target gene silencing of SIK3 is observed across a wide range of E:T ratios. Surprisingly, SIK3 impairment resulted in a stronger increase in lysis than depletion of CEACAM6 by siRNA (Table A1). These data were generated from canonical chromium rerelease assays conducted to directly measure specific lysis of PANC-1 cells after co-culture with TIL #2 using such an assay as described in Khandelwal et al (2015). Western blot analysis demonstrated that CEACAM6, as wells as and PD-L1, are expressed by PANC-1 cells, and their expression can be knocked down by transfection with gene-specific siRNA sequences (FIG. 4B). CEACAM6 and PD-L1 were detected with the following antibodies: anti-CEACAM6 (Abcam, Cat No: ab98109) with anti-rabbit IgG-HRP as secondary antibody (Santa Cruz Biotechnology, Cat No: sc2004); anti-PD-L1 (R&D system; Cat. N. 130021), with secondary antibody: anti-mouse IgG-HRP (Santa Cruz Biotechnology. Cat. N. sc2005).

Data information: FIGS. 2 and 3A show cumulative data of 3 independent experiments, and FIGS. 3B, 3C, 3D and 4 show representative data of at least 2 independent experiments. Error bars represent mean+/−SEM, and P-values were calculated using two-tailed student's t-test: * $p<0.05$, ** $p<0.01$.

Example 2: SIK3 Inhibition Sensitises Tumour Cells from Various Cancer Types to the Anti-Tumour Effects of a Cell-Mediated Immune Response The inventors were able to demonstrate that SIK3 plays a role in the mediation of resistance to an immune response, surprisingly, in other tumour types, and not just the pancreatic cell line used in Example 1; SIK3 knock down in breast (MCF-7) and colorectal (SW480) cancer cell lines and the subsequent challenge with survivin-specific T cells or TIL #1, respectively, resulted in significantly increased tumour cell death in both tumour types (FIGS. 5A and 5B); as measured by real-time live-cell microscopy (Incucye Zoom—Essen Bioscience).

Furthermore, in a primary melanoma co-culture model using luciferase-expressing M579 cells (M579-A2-luc), it was observed that SIK3 knockdown potentiated TIL-mediated cytotoxicity (FIG. 6A); while overexpression of SIK3 dampened the cytotoxic potential of HLA-A2.1+-matched tumour infiltrating lymphocytes (TIL209) (FIG. 6B). Tumour-infiltrating lymphocyte 209 microculture was expanded from an inguinal lymph node of a melanoma patient as described in Dudley et al, 2010 (Clin Cancer Res 16:6122-31). M579-A2-luc, PANC1-luc and MCF7-luc cells were generated as described in Khandelwal et al, 2015.

Data information: FIG. 6B shows cumulative data of 3 independent experiments, and FIGS. 5A, 5B and 6A show representative data of at least 2 independent experiments. Error bars represent mean+/−SEM, and P-values were calculated using two-tailed student's t-test: * $p<0.05$, ** $p<0.01$.

Example 3: SIK3 Mediates Tumour Cell Resistance to an Immune Response by a Mechanism that is Intrinsic to the Tumour Cell The inventors made the surprising finding that SIK3 appears to regulate resistance to anti-tumour T cell response not by regulating T cell activity or function, but is involved in intrinsic mechanisms of tumour resistance. Knockdown of SIK3 in tumour cells did not increase IFN-gamma, granzyme B or perforin production in T cells (data not shown). However, the mere addition of (T cell-free) conditioned medium from T cells previously activated by exposure to tumour cells was sufficient to reduce cell survival (as measured using the luciferase-based killing assay of PANC-1-luc cells described above) in SIK3 knockdown tumour cells (FIG. 8A), while (unconditioned) medium from unstimulated T cells did not alter tumour cell survival after SIK3 siRNA transfection (FIG. 8B). This effect was even more pronounced when exposing the tumour cells to conditioned medium from previously cultured polyclonal T cells activated by CD3/CD28 beads (FIG. 8C). Briefly, 100,000 TILs were cultured and activated with Human Activator CD3/CD28 Dynabeads (Invitrogen) for 24 h according to the manufacturer's protocol. This effect was confirmed using an independent viability assay (WST-1) which recapitulated the decrease in tumour cell viability after SIK3 depletion and stimulation with supernatant of polyclonal activated T cells (FIG. 8D), even compared to PD-L1 knockdown, whose decrease in viability was not seen in the absence of T cells (FIG. 8E). The WST-1 cell proliferation reagent was used according to the manufacture's (Roche) Protocol. Data information: FIGS. 8A, 8B, 8D and 8E show representative data of at least 2 independent experiments. FIG. 8C shows cumulative data of 3 independent experiments, Error bars show mean+/−SEM. P-values were calculated using two-tailed student's t-test. * p<0.05, ** p<0.01.

Example 4: SIK3 Activity Dictates the Fate of TNF-Treated Tumour Cells

The inventors have further made the surprising finding that TNF plays a key role in the cell-mediated immune response that is mediated by such tumour cell's innate resistance. Titration of TNF neutralising antibody (Abcam, Cat No: ab8348) lead to a dramatic, and at higher anti-TNF antibody concentrations complete, rescue from cell death (FIG. 9A). The same treatment in scramble (control) siRNA transfected tumour cells did not alter cell viability in comparison to isotype control (data not shown). Incubation of supernatant from CD3-CD28 bead-stimulated T cells with anti-TRAIL and anti-FASL neutralising antibodies (as per (A)) did not lead to a reduction in cytotoxicity after SIK3 incubation, unlike incubation with the anti-TNF neutralising antibody (FIG. 9C).

Indeed, SIK3 inhibition leads to a dramatic sensitisation of tumour cells to the cytotoxic effects of TNF. Exposure of PANC-1-luc cells to recombinant human TNF (rHuTNF; R&D Systems) leads to a striking change in the effects of TNF but only in those tumour cells transfected with SIK3 siRNA rather than scrambled control (siCtrl) even at low concentrations of rHuTNF (FIG. 10A), and that this effect had a very rapid onset (FIG. 10B).

Data information: FIGS. 9B, 9C, 10A, and 10B show representative data of at least 2 independent experiments. FIG. 9A shows cumulative data of 3 independent experiments. Error bars show mean+/−SEM. P-values were calculated using two-tailed student's t-test. * p<0.05, ** p<0.01.

Example 5: TNF-Signalling Via TNF Receptor 1 Mediates the SIK3 Resistance Mechanism The inventors demonstrated that PANC-1 cells express TNF receptor 1 (TNFR1) by FACS analysis (FIG. 11A). However, while TNF receptor 2 (TNFR2) could be detected on a control cell line TIL412 (FIG. 11B), it could not be detected on PANC-1 (FIG. 11C). Accordingly, the inventors proposed that TNFR1 is the key signalling pathway involved in the observed SIK3/TNF-mediated effect. Tumour-infiltrating lymphocytes 412 microculture was expanded from an inguinal lymph node of a melanoma patient as described in Dudley et al, 2010 (Clin Cancer Res 16:6122-31).

Indeed, blockade of TNFR1 in SIK3 depleted tumour cells after TNF stimulation abrogated TNF induced cytotoxicity (FIG. 11D) compared to isotype antibody control; while TNFR1 blockade in siCtrl-transfected PANC-1 cells did not significantly alter tumour cell survival compared to isotype antibody control (data not shown).

Example 6: Apoptotic-Related Genes are Upregulated in Tumour Cells Upon TNF Exposure and SIK3 Inhibition The inventors demonstrated that the SIK3/TNF-mediated cytotoxicity of tumour cells is mediated through caspases and other pro-apoptotic genes, with Luminex assays detecting apoptosis activation markers in total lysates of PANC-1 cell. Increased cleavage of both caspase 8 and 9 was detected after SIK3 depletion in tumour cells following rHuTNF treatment (FIGS. 12A and 12B). Furthermore, SIK3 depleted cells also showed increased levels of phosphorylated c-Jun N-terminal protein kinase (pJNK) (FIG. 12C).

Example 7: Apoptosis of Tumour Cells Triggered by TNF Stimulation and SIK3 Inhibition is Governed by NF-KB Activation Controlled by HDAC4

Histone deacetylase 4 (HDAC4) is described as a target of SIK3; with SIK3 phosphorylating HDCA4, leading to shuttling of HDAC4 from the nucleus to the cytoplasm (Walkinshaw et al 2013, J Biol Chem 288: 9345). Indeed, siRNA knockdown of both SIK3 and HDAC4 in PANC-1 cells showed decreased cytotoxicity compared to tumour cells transfected with only SIK3-specific siRNA, while HDAC4 depletion alone did not significantly alter tumour cell viability compared to scrambled control siRNA (siCtrl) transfection (FIG. 13A). In the absence of rHuTNF, co-transfection of siSIK3 and siHDAC4 siRNAs, did not show a major impact on tumour cell viability (data not shown).

Although it has been shown that in macrophages, nuclear HDAC4 physically interacts with NF-KB p65 subunit, leading to deacetylation and decreased transactivation of NF-KB (Luan et al 2014, Cell Metab 19:1058), the inventors made the surprising finding that siRNA SIK3 knockdown in tumour cells led to dramatic impairment of NF-KB activation upon rHuTNF stimulation (FIG. 13B). Furthermore, SIK3 overexpression resulted in increased NF-KB nuclear translocation, as detected by ELISA of nuclear lysates of transfected PANC-1 cells (FIG. 13C).

To confirm the involvement of NF-KB transcriptional control in the SIK3/TNF mediated cytotoxicity mechanism, RNA-seq analysis was performed in PANC-1 cells after SIK3 or scrambled control siRNA transfection and rHuTNF or cell culture medium treatment. SIK3 impairment in tumour cells substantially altered gene signature in the absence of TNF stimulation (FIG. 14). Nevertheless, as expected: (i) SIK3 depleted cells showed impairment of NF-KB target genes transcription, after 4 h of rHuTNF treatment; and (ii) the amount of SIK3 mRNA is found to be depleted in those experiments using SIK3 siRNA but not scrambled control siRNA; while, interestingly, amounts of mRNA SIK1 and/or SIK2 are not depleted but show some increase (data not shown).

Example 8: Tumour Resistance to Adoptive T Cell Transfer can be Overcome by SIK3 Inhibition In Vivo The inventors demonstrated that inhibition of SIK3 can be used to overcome resistance of melanoma cells to anti-tumour immune response in an in vivo model. SIK3 was stably knocked down in the primary line using SIK3-specific shRNA (shSIK3) or the control non-targeting shRNA sequence (shCtrl). The shRNA sequences targeting SIK3 are set forth in Table A2, and the transduced cell lines were produced briefly as follows: lentiviral transduction particles expressing an shRNA targeting SIK3 mRNA or control shRNA (Sigma-Aldrich) were used for transduction. $5 \times 10^4$ PANC-1-Luc cells were seeded in a 6 well plate in DMEM 10% FCS 1% P/S. After 24 h, lentiviral particles were added using multiplicity of infection (MOI)=2. 48 h from transduction, cells were put under positive selection using 0.4 pg/ml puromycin. First, the shSIK3 or shCtrl transduced tumour cells were co-cultured with HLA-A2.1+-matched TIL209, and the extent of T cell-mediated killing was monitored using in vitro real-time live-cell microscopy. TIL209 showed increased killing efficacy towards shSIK3 depleted tutor cells compared to shCtrl (FIG. 15A). Second, the shSIK3 and shCtrl transduced tumour cells were subcutaneously injected into the left and the right flank, respectively, of NSG immune deficient mice (FIG. 16A), and adoptive cell transfer of TIL209 or PBS injection was applied i.v. once per week (FIG. 16B Scheme). TIL209 treatment caused retardation of tumour growth in SIK3-impaired tumour cells compared to shCtrl-transduced cells (FIG. 16C). Consistent with the in vitro data (FIG. 15), no difference in the tumour growth kinetic between shCtrl and shSIK3 was observed in PBS-treated mice.

Taken together, these results designate SIK3 as a novel potential immunotherapeutic target, whose blockade sensitizes tumour cells towards immune cell attack by TNF as graphically depicted in FIG. 16D.

Example 9: SIK3 Inhibition by Small Molecule SIK3 Inhibitors Lead to Enhanced Sensitivity of Tumour Cells to the Anti-Tumour Effects of a Cell-Mediated Immune Response The inventors demonstrated that the inhibition of SIK3 in PANC-1 cells by the small molecule SIK3 inhibitors could reproduce the immune-stimulatory effect observed with siRNA-mediated knockdown of SIK3 in tumour cells. As described above, HG-9-91-01 (Clark et al 2012, PNAS 109:16986), bosutinib and dasatinib all inhibit SIK3, amongst other targets. PANC-1 tumour cells upon treatment with such compounds independently showed a remarkable increase in sensitivity to TILs and/or TNF-mediated tumour lysis as indicated by the cytotoxicity to viability ratio in Luc-CTL assay (FIGS. 7A and 7B).

To prove that the immune-stimulatory effect observed with small molecule SIK inhibitors was specific towards SIK3, the inventors treated both SIK3-positive (control siRNA-treated) and SIK3-negative (SIK3 siRNA-treated) PANC-1 tumour cells with titrating doses of dasatinb, in the presence (100 ng/mL) and absence of TNF and measured the tumour cytotoxicity using the luciferase assay. In the absence of TNF treatment, both SIK3-positive and SIK3-negative cells were largely resistant to the drug doses (FIG. 7C). However, upon addition of TNF, SIK3-positive cells showed a striking growth stimulation that became susceptible to tumour lysis upon increasing doses of dasatinib. In SIK3-negative tumour cells, TNF treatment showed significant tumour lysis and interestingly no further response to dasatinib could be observed in these cells. These data suggest that the immune-stimulatory effect of dasatinib occurs via inhibition of SIK3, as SIK3-negative tumours do not respond to such drug (FIG. 7C).

As the immune-stimulatory effect observed with the SIK inhibitors, such as dasatinib (or bosutinib), could possibly also result from inhibiting other SIK family members beyond SIK3, the role of each of the three SIK family members in sensitising the tumours towards immune-mediated cytotoxicity was examined. Firstly, all the three SIK family members were shown to be expressed at varying levels in PANC-1-luc and M579-A2-luc tumour cells, as assessed via qPCR (FIG. 7D). However, knockdown of SIK1 or SIK2 in PANC-1-luc cells failed to induce any T-cell mediated tumour lysis upon addition of TILs (TIL #1) or Flu antigen-specific T cells (generated as described by Trivedi et al 2016, Bio-Protocol 6:e1847); while upon SIK-3 knockdown and addition of T cells, a remarkable increase in tumour lysis was observed (FIG. 3C for TILs and FIG. 7E for Flu antigen-specific T cells). In M579-A2-luc cells, in contrast to SIK3 knockdown, knockdown of SIK1 and SIK2 did not contribute to T cell-mediated tumour lysis by Flu-specific T cells (FIG. 7F). Interestingly, knockdown of SIK1 per se decreased tumour cell viability in both PANC-1-luc and M579-A2-luc tumour cells, whereas SIK2 knockdown increased tumour cell survival, at least in M579-A2-luc cells. Taken together, this proves that amongst the three family members, only SIK3 in tumour cells is involved in mediating resistance to the T cells.

To further strengthen this observation, SIK1 and SIK2-knocked down M579-A2-luc tumour cells were treated with dasatinib, in the presence of TNF (100 ng/mL), to observe if they still respond to the drug. As noted above already, knockdown of SIK1 in these tumour cells per se (without TNF) inhibited tumour growth, while SIK2 knockdown stimulated tumour growth as observed in the Luc CTL assay (FIG. 7F). Upon treatment of these cells with TNF, both the cell types still responded to titrating doses of dasatinib, similar to control siRNA treated cells (comparing the slope of the response curves), beyond their viability effect (FIG. 7G). This was found to be in contrast to SIK3-negative tumour cells as shown in the figure above (FIG. 7C). This highlights that the immune-stimulatory effect of dasatinib in the presence of TNF is orchestrated by inhibiting SIK3 rather than SIK1 or SIK2.

Example 10: Synthesis of Small Molecule Compounds of the General Formula I

Compounds of the general formula I were synthesised according to the procedures described below.
General Synthesis Scheme:

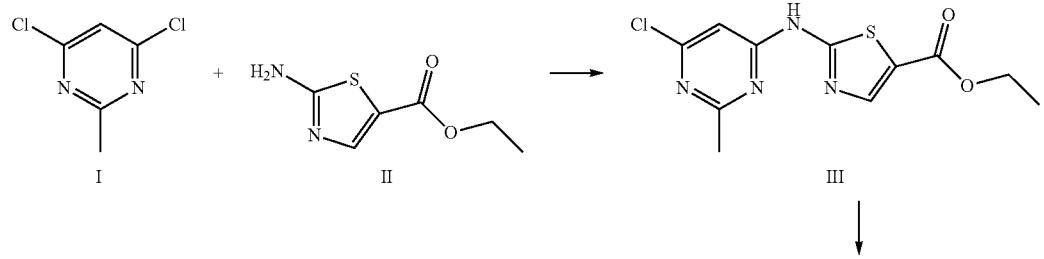

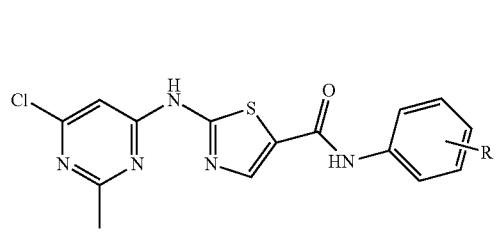
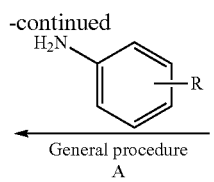
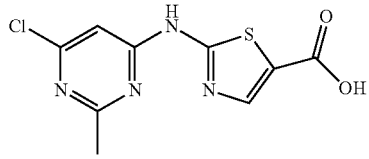
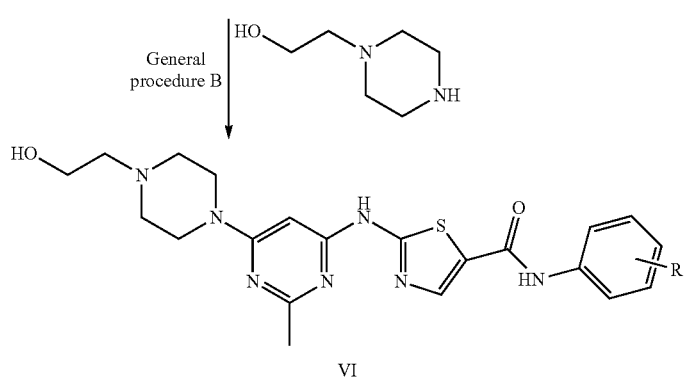

General Methods and Materials:

MPLC purification was performed using a Biotage Isolera Four system, using KP-Sil cartridges with technical grade organic solvents, i.e. dichloromethane and methanol.

$^1$H NMR spectra were recorded on Bruker AVIII 300 MHz or Bruker DPX 400 MHz spectrometers and are reported in ppm with the solvent resonance employed as the internal standard [CDCl$_3$ at 7.26 ppm, DMSO-d$_6$ at 2.50 ppm]. Peaks are reported as (s=singlet, d=doublet, t=triplet, q=quartet, m=multiplet or unresolved, bs=broad signal, coupling constant(s) in Hz, integration).

Reverse phase HPLC was performed on a Shimadzu HPLC system using following system [solvent A: acetonitrile, solvent B: 0.1% formic in water]. Formic acid was used as HPLC grade. All the separations were performed at ambient temperatures. For analytical RP-HPLC analysis [Interchim: Uptisphere Strategy 100 Å, 5 μm, 100×4.6 mm], the flow rate was 1.5 ml min$^{-1}$. For preparative RP-HPLC analysis [Interchim: Uptisphere Strategy 100 Å, 5 μm, 100×21.2 mm] the flow rate was 20 ml min$^{-1}$ Synthesis of Intermediates (III) and (IV)

Ethyl 2-((6-chloro-2-methylpyrimidin-4-yl)amino)thiazole-5-carboxylate(III)

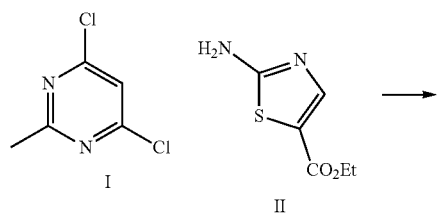

To a solution of 4,6-dichloro-2-methylpyrimidine I (5 g, 30.7 mmol) and ethyl 2-aminothiazole-5-carboxylate II (5.28 g, 30.7 mmol) in DMF (105 ml) at 0° C. under inert atmosphere was added sodium hydride (2.70 g, 67.5 mmol) in portions and the reaction mixture was stirred at 0° C. for 3 h. Excess of the NaH was quenched by addition of saturated solution of ammonium chloride and the reaction mixture was poured on water (2000 ml) and stirred for 1 h at room temperature. Obtained precipitate was filtered off and air dried to get ethyl 2-((6-chloro-2-methylpyrimidin-4-yl)amino)thiazole-5-carboxylate III (8 g, 26.8 mmol, 87% yield) as a light yellow solid. H NMR (300 MHz, CDCl$_3$) δ 1.34-1.51 (t, 3H), 2.75 (s, 3H), 4.41 (q, J=7.1 Hz, 2H), 6.73 (s, 1H), 8.14 (s, 1H). LCMS: m/z=297.1 [M-H]$^-$.

2-((6-chloro-2-methylpyrimidin-4-yl)amino)thiazole-5-carboxylicacid (IV)

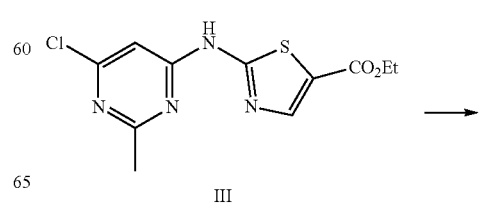

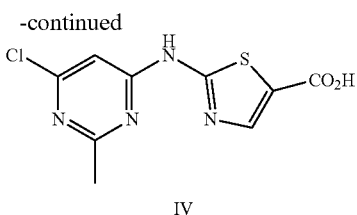

IV

To a suspension of ethyl 2-((6-chloro-2-methylpyrimidin-4-yl)amino)thiazole-5-carboxylate III (8 g, 26.8 mmol) in methanol (65 ml) and water (25 ml) was added sodium hydroxide (8.57 g, 214 mmol) at room temperature and the mixture was stirred at room temperature for 16 h. LCMS analysis showed complete conversion of starting material to product. The reaction mixture was concentrated to remove the methanol and then it was acidified using 6M aqueous hydrochloric acid. Obtained precipitate was filtered off and washed with water, air dried to afford 2-((6-chloro-2-methylpyrimidin-4-yl)amino)thiazole-5-carboxylic acid IV (5.5 g, 20.32 mmol, 76% yield) as a beige coloured powder. H NMR (300 MHz, DMSO-$d_6$) δ 2.57 (s, 3H), 6.93 (s, 1H), 8.04 (s, 1H), 12.46 (bs. 1H). LCMS: m/z=269.0 [M-H]⁻.

General Procedure A:

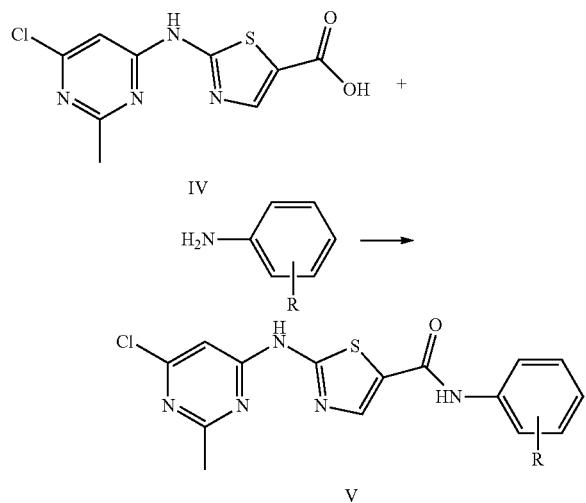

To a mixture of 2-((6-chloro-2-methylpyrimidin-4-yl)amino)thiazole-5-carboxylic acid IV (1.0 equiv.) and aniline (1.1 equiv.) was added $T_3P$ as a 50% solution in ethyl acetate (1.2 equiv.) and N-ethyl-N-isopropylpropan-2-amine (2.0 equiv.) at 25° C. The reaction mixture was stirred at 100° C. for 16 h. After cooling to room temperature, the reaction mixture was poured in water (200 ml) and stirred for minimum 30 min. The resulting precipitate was filtered off, washed with water [5×], air-dried to afford the respective amide as a light to dark brown powder which was directly used in the next step without further purification. All substances were confirmed by LCMS analysis (ESI).

General Procedure B:

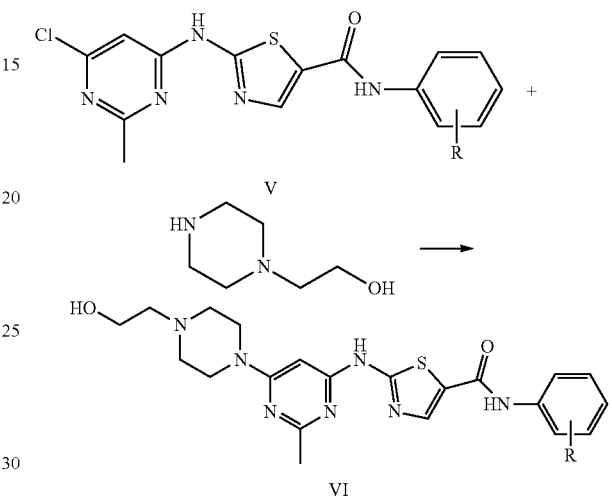

To a suspension of chloropyrimidine derivative V (1.0 equiv.) in n-butanol (2 ml) was added 2-(piperazin-1-yl)ethan-1-ol (5.0 equiv.) and N-ethyl-N-isopropylpropan-2-amine (0.4 equiv.) at 25° C. The tube was sealed and irradiated under microwave conditions (Biotage Initiator+) at 120° C. for 30 min. After cooling to room temperature, the reaction mixture was poured into water (200 ml) and stirred for minimum 30 min. The resulting precipitate was filtered off, washed with water [5×], air-dried to afford to afford the final product VI. If the purity was below 95%, the substance was purified by MPLC (SiO₂, DCM, 10% ammonical methanol) or by preparative reversed-phase HPLC. All substances were confirmed by LCMS analysis (ESI).

General procedures A and B were followed to obtain the compounds of the general formula I shown in Table A3. These compounds were characterised as set forth below in Table 1.

TABLE 1

Synthesis of small molecules of the invention

| Compound Number | Mol. Wt. LCMS: m/z [M − H]− | ¹H NMR |
|---|---|---|
| A1 | 490.3 | (300 MHz, DMSO > d₆) δ 2.41 (m, 9H), 3.44-3.62 (m, 6H), 4.44 (t, J = 5.4 Hz, 1H), 6.05 (s, 1H), 7.26-7.66 (m, 3H), 8.23 (s, 1H), 10.02 (s, 1H), 11.49 (s, 1H). |
| A2 | 474.4 | (300 MHz, DMSO > d₆) δ 2.25-2.48 (m, 9H), 3.53 (m, 6H), 4.44 (t, J = 5.5 Hz, 1H), 6.05 (s, 1H), 7.22 (q, J = 8.5, 5.8 Hz, 2H), 7.40 (t, J = 7.5 Hz, 1H), 8.22 (s, 1H), 9.99 (s, 1H), 11.49 (s, 1H).• |
| A3 | 534.3 | (300 MHz, DMSO > d₆) δ 2.50 (m 9H), 3.53 (m, 6H), 4.44 (t, J = 5.3 Hz, 1H), 6.05 (s, 1H), 7.36 (td, J = 7.6, 6.7, 3.1 Hz, 2H), 7.59 (d, J = 7.5 Hz, 1H), 8.22 (s, 1H), 10.01 (s, 1H), 11.49 (s, 1H).• |
| A4 | 462.4 | (300 MHz, DMSO > d₆) δ 2.42 (m, 9H), 3.52 (m, 6H), 4.20 (s, 1H), 4.46 (s, 1H), 6.04 (s, 1H), 7.19 (d, J = 7.6 Hz, 1H), 7.36 (t, J = 7.9 Hz, 1H), 7.72 (d, J = 8.5 Hz, 1H), 7.86 (s, 1H), 8.24 (s, 1H), 10.14 (s, 1H), 11.50 (s, 1H).• |

TABLE 1-continued

Synthesis of small molecules of the invention

| Compound Number | Mol. Wt. LCMS: m/z [M − H]− | $^1$H NMR |
|---|---|---|
| A5 | 456.3 | (400 MHz, DMSO > $d_6$) δ 2.37-2.50 (m, 9H), 3.52 (q, J = 5.8 Hz, 6H), 4.44 (t, J = 5.3 Hz, 1H), 6.04 (s, 1H), 7.18 (t, J = 8.9 Hz, 2H), 7.64-7.78 (m, 2H), 8.22 (s, 1H), 10.11 (s, 1H), 11.46 (s, 1H). |
| A6 | 544.4 | (300 MHz, DMSO > $d_6$) δ 1.19 (d, J = 6.8 Hz, 6H), 2.43 (m, 9H), 3.52 (m, 7H), 4.44 (t, J = 5.4 Hz, 1H), 6.06 (s, 1H), 7.33-7.51 (m, 1H), 7.72-7.96 (m, 2H), 8.01 (s, 1H), 8.35 (dd, J = 8.4, 1.1 Hz, 1H), 10.27 (s, 1H), 11.66 (s, 1H). |
| A7 | 534.3 | (400 MHz, DMSO > $d_6$) δ 2.38-2.51 (m, 9H), 3.52 (m, 6H), 4.44 (t, J = 5.4 Hz, 1H), 6.05 (s, 1H), 7.43 (dd, J = 8.7, 2.2 Hz, 1H), 7.51-7.73 (m, 2H), 8.24 (s, 1H), 10.02 (s, 1H), 11.49 (s, 1H). |
| A8 | 486.4 | (300 MHz, DMSO > $d_6$) δ 2.23 (s, 3H), 2.44 (m, 9H), 3.38-3.62 (m, 6H), 4.45 (t, J = 5.3 Hz, 1H), 6.04 (s, 1H), 7.23-7.32 (m, 2H), 7.37-7.43 (m, 1H), 8.21 (s, 1H), 9.87 (s, 1H), 11.47 (s, 1H)• |
| A9 | 452.4 | (300 MHz, DMSO > $d_6$) δ 2.23 (s, 3H), 2.41 (m, 9H), 3.51 (m, 6H), 4.46 (t, J = 5.3 Hz, 1H), 6.04 (s, 1H), 7.02-7.45 (m, 4H), 8.18 (s, 1H), 9.71 (s, 1H), 11.44 (s, 1H).• |
| A10 | 472.3 | (400 MHz, DMSO > $d_6$) δ 2.37-2.49 (m, 9H), 3.52 (dt, J = 11.7, 5.9 Hz, 6H), 4.44 (t, J = 5.3 Hz, 1H), 6.05 (s, 1H), 7.28 (td, J = 7.7, 1.7 Hz, 1H), 7.38 (td, J = 7.7, 1.6 Hz, 2H), 8.23 (s, 1H), 9.89 (s, 1H), 11.47 (s, 1H).• |
| A11 | 438.4 | (400 MHz, DMSO > $d_6$) δ 2.42 (m, 9H), 3.53 (m, 6H), 4.44 (t, J = 5.4 Hz, 1H), 6.04 (s, 1H), 7.08 (t, J = 7.4 Hz, 1H), 7.34 (t, J = 7.9 Hz, 2H), 7.69 (d, J = 7.9 Hz, 2H), 8.24 (s, 1H), 10.05 (s, 1H), 11.46 (s, 1H).• |
| A12 | 466.4 | (400 MHz, DMSO > $d_6$) δ 2.19 (s, 6H), 2.36-2.48 (m, 9H), 3.52 (m, 6H), 4.44 (t, J = 5.4 Hz, 1H), 6.05 (s, 1H), 7.12 (s, 3H), 8.19 (s, 1H), 9.60 (s, 1H), 11.42 (s, 1H). |
| A13 | 506.3 | (300 MHz, DMSO > $d_6$) δ 2.41 (m, 9H), 3.53 (m, 6H), 4.45 (t, J = 5.3 Hz, 1H), 6.05 (s, 1H), 7.14-7.53 (m, 1H), 7.59 (d, J = 8.1 Hz, 2H), 8.23 (s, 1H), 10.15 (s, 1H) 11.49 (s, 1H). |

Example 11: Biological Activity and Other Characterisations of Small Molecule Inhibitors of SIK3

Indicative IC50s for compounds synthesised in Table 1 were determined against each of SIK1, SIK2 and SIK3 using a biochemical assay for SIK1, SIK2 or SIK3 activity (Free Choice Kinase Assay provided by ProQinase, Freiburg Germany) and are shown in Table 2A.

TABLE 2A

Biological activity of small molecules of the invention

| Compound Number | SIK1 IC50 rank | SIK2 IC50 rank | SIK3 IC50 rank |
|---|---|---|---|
| A1 | **** | **** | **** |
| A2 | **** | **** | **** |
| A3 | **** | **** | **** |
| A4 | * | *** | * |
| A5 | *** | *** | * |
| A6 | * | *** | * |
| A7 | **** | *** | ** |
| A8 (dasatanib) | **** | **** | **** |
| A9 | **** | **** | **** |
| A10 | **** | **** | *** |
| A11 | *** | *** | * |
| A12 | **** | **** | **** |
| A13 | **** | **** | **** |

**** = <0.1 uM;
*** = >0.1 uM;
** = >0.5 uM;
* = >1.0 uM.

Briefly, a radiometric protein kinase assay (33PanQinase® Activity Assay) was used for measuring the kinase activity of the three protein kinases. All kinase assays were performed in 96-well FlashPlates™ from PerkinElmer (Boston, MA, USA) in a 50 ul reaction volume. The reaction cocktail was pipetted in four steps in the following order:
20 ul of assay buffer (standard buffer)
5 ul of ATP solution (in water)
5 ul of test compound (in 10% DMSO)
20 ul enzyme/substrate mix The assay for all protein kinases contained 70 mM HEPES-NaOH pH7.5, 3 mM MgCl2, 3 mM MnCl2, 3 uM Na-orthovanadate, 1.2 mM DTT, 50 µg/ml PEG20000, ATP (variable concentrations, corresponding to the apparent ATP-Km of the respective kinase, see Table 2B), [gamma-33P]-ATP (approx. 3.5×10^5 cpm per well), protein kinase (variable amount, see Table 2B), and substrate (variable amounts, see Table 2B).

The following amounts of enzyme and a substrate were used per well:

TABLE 2B

Assay parameters for the tested protein kinases.

| Kinase Name | Kinase Conc. (ng/50 ul) | Kinase Conc. (nM*) | ATP Conc. (uM) | Substrate | Substrate Conc. (ug/50 uL) |
|---|---|---|---|---|---|
| SIK1 | 25 | 7.3 | 3.0 | RBER-CHKtide | 2 |
| SIK2 | 2 | 0.7 | 1.0 | RBER-CHKtide | 2 |
| SIK3 | 50 | 15.9 | 1.0 | RBER-CHKtide | 2 |

*Maximal molar enzyme assay concentrations, implying enzyme preparations exclusively containing 100% active enzyme The reaction cocktails were incubated at 30° C. for 60 minutes. The reaction was stopped with 50 ul of 2% (v/v) H3PO4, plates were aspirated and washed two times with 200 ul 0.9% (w/v) NaCl. Incorporation of 33Pi was determined with a microplate scintillation counter (Microbeta, Wallac). All assays were performed with a BeckmanCoulter/SAGIAN™ Core System.

Example 12: Discovery and/or Characterisation of Further Small Molecule Inhibitors of SIK3 that can Sensitise Tumour Cells to the Cytotoxic Effects of TNF Variants of the small molecule SIK3 inhibitor dasatinib, such as those described by the formulae herein, are synthesised according to the applicable scheme described in WO 2000/62778A1. SIK3 inhibition is confirmed using a biochemical screen, such as the SelectScreen as provided by ThermoScientific, the Free Choice Kinase Assay provided by ProQinase or Kinase HotSpot provided by Reaction Biology Inc. Specificity/selectivity to SIK3 (especially compared to SIK1 and/or SIK2) is assessed using biochemical kinase profiling (eg SelectScreen of ThermoScientific, Free Choice Kinase Assay provided by ProQinase and/or KINOMEScan of DiscoverX). Variants or other SIK3 inhibitors (eg as HG-9-91-01 and YKL-05-099) are also synthesised, such as those described by the formulae herein, and such variants are analogously tested in biochemical assays for SIK3 (and other kinase, such as Abl and/or Bcr-Abl) inhibitory potency.

Those variants (eg dasatinib) identified/characterised as being SIK3 inhibitors (in particular, those identified or characterised as being SIK3-specific/selective inhibitors) are tested for their efficacy in cellular assays to sensitise cells of proliferative disease to cell-mediated immune responses (in particular, sensitisation of tumour cells to the cytotoxic effects of TNF). For example, such SIK3 inhibitors are tested in assays analogous to those described for FIG. 7. Such SIK3 inhibitors may be tested in SIK3 (and/or SIK1/SIK2) over expression and/or siRNA knockdown settings to further characterise the in-vivo SIK specificity/selectivity to SIK3, and/or that such inhibition is mediated within the tumour cell rather than an immune cell.

Small molecule SIK3 inhibitors that are particular potent and/or with favourable PK properties are tested in an in-vivo model for overcoming tumour resistance, such as the murine melanoma model described in Example 8.

Example 13: Synthesis and Characterisation of Further Small Molecule Compounds of the General Formula I Except as described below, general procedures A and B of Example 10 were followed to obtain the compounds of general formula I/of the invention shown in Table A4.

For compounds B5, B6 and B7, instead of general procedure B of Example 10, the following modified procedure B' was used:
General Procedure B':

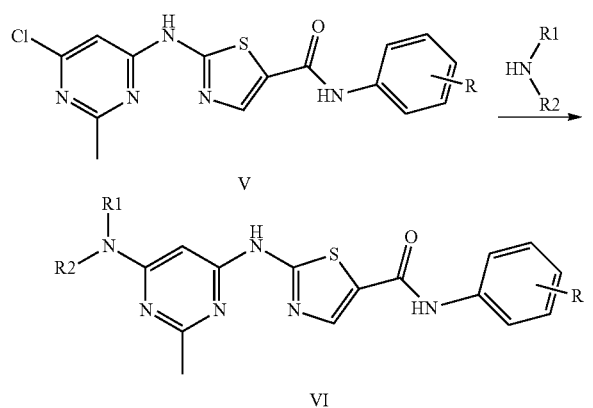

To a suspension of chloropyrimidine derivative V (1.0 equiv.) in n-butanol (2 ml) was added amine HNR1R2 (5.0 equiv.) and N-ethyl-N-isopropylpropan-2-amine (0.4 equiv.) at 25° C. The tube was sealed and irradiated under microwave conditions (Biotage Initiator+) at 120° C. for 30 min. After cooling to room temperature, the reaction mixture was poured into water (200 ml) and stirred for minimum 30 min. The resulting precipitate was filtered off, washed with water [5×], air-dried to afford to afford the final product VI. If the purity was below 95%, the substance was purified by MPLC (SiO$_2$, DCM, 10% ammonical methanol) or by preparative reversed-phase HPLC. All substances were confirmed by LCMS analysis (ESI).

For compound B3, instead of general procedure A of Example 10, the following modified procedure A' was used:
General Procedure A':

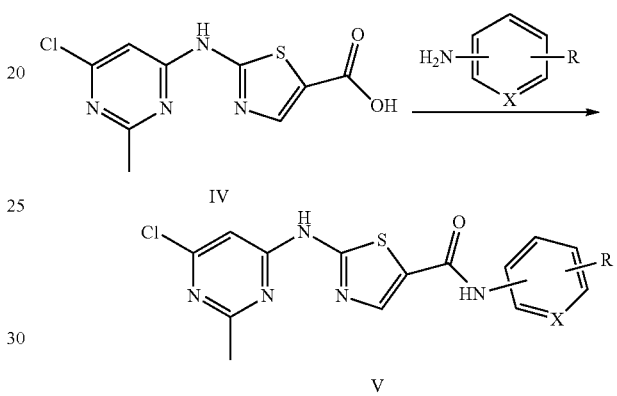

To a mixture of 2-((6-chloro-2-methylpyrimidin-4-yl)amino)thiazole-5-carboxylic acid IV (1.0 equiv.) and aniline/heteroarylamine (1.1 equiv.) was added T$_3$P as a 50% solution in ethyl acetate (1.2 equiv.) and N-ethyl-N-isopropylpropan-2-amine (2.0 equiv.) at 25° C. The reaction mixture was stirred at 100° C. for 16 h. After cooling to room temperature, the reaction mixture was poured in water (200 ml) and stirred for minimum 30 min. The resulting precipitate was filtered off, washed with water [5×], air-dried to afford the respective amide as a light to dark brown powder which was directly used in the next step without further purification. All substances were confirmed by LCMS analysis (ESI).

And, instead of general procedure B of Example 10, the following modified procedure B" was used:
General Procedure B":

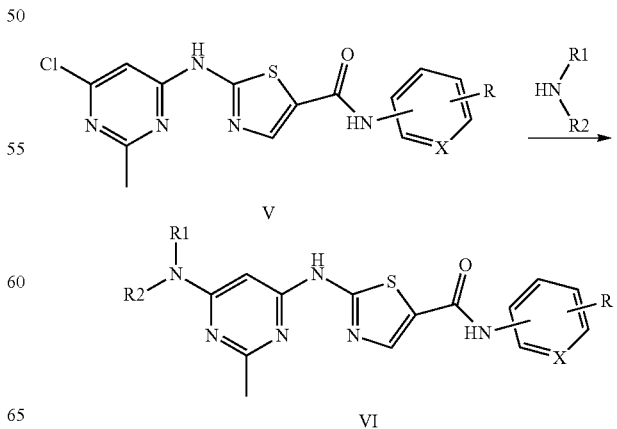

To a suspension of chloropyrimidine derivative V (1.0 equiv.) in n-butanol (2 ml) was added amine HNR1R$_2$ (5.0 equiv.) and N-ethyl-N-isopropylpropan-2-amine (0.4 equiv.) at 25° C. The tube was sealed and irradiated under microwave conditions (Biotage Initiator$^+$) at 120° C. for 30 min. After cooling to room temperature, the reaction mixture was poured into water (200 ml) and stirred for minimum 30 min. The resulting precipitate was filtered off, washed with water [5×], air-dried to afford to afford the final product VI. If the purity was below 95%, the substance was purified by MPLC (SiO$_2$, DCM, 10% ammonical methanol) or by preparative reversed-phase HPLC. All substances were confirmed by LCMS analysis (ESI).

The compounds shown in Table A4 were characterised as set forth below in Table 3.

TABLE 3

Synthesis of further small molecules of formula I/the invention.

| Compound Number | Mol. Wt. LCMS: m/z [M − H]− | NMR (1H or 19F NMR were indicated; or "ND" = not determined) |
|---|---|---|
| B1 | 550.3 | 1H NMR: (300 MHz, DMSO-d6) δ 2.35-2.50 (m, 9H), 3.46-3.60 (m, 6H), 4.45 (t, J = 5.3 Hz, 1H), 6.06 (s, 1H), 7.33 (t, J = 8.1 Hz, 1H), 7.63 (d, J = 8.0 Hz, 1H), 7.74 (d, J = 7.6 Hz, 1H), 8.23 (s, 1H), 10.16 (s, 1H), 11.42 (bs, 1H) |
| B2 | 594.3 | 1H NMR: (300 MHz, DMSO-d6) δ 2.35-2.49 (m, 9H), 3.40-3.66 (m, 6H), 4.43 (d, J = 5.8 Hz, 1H), 6.05 (s, 1H), 7.23 (t, J = 8.1 Hz, 1H), 7.77 (d, J = 8.1 Hz, 2H), 8.22 (s, 1H), 10.19 (s, 1H), 11.48 (s, 1H). |
| B3 | 487.4 | ND |
| B4 | 486.4 | 1H NMR: (300 MHz, DMSO-d6) δ 2.36-2.47 (m, 9H), 3.44-3.62 (m, 6H), 3.88 (d, J = 1.4 Hz, 3H), 4.45 (t, J = 5.3 Hz, 1H), 6.06 (s, 1H), 7.01-7.20 (m, 2H), 7.47-7.61 (m, 1H), 8.25 (s, 1H), 9.61 (s, 1H), 11.50 (s, 1H). 19F NMR: (282 MHz, DMSO-d6) δ −130.45. |
| B5 | 456.3 | ND |
| B6 | 484.4 | ND |
| B7 | 417.2 | 1H NMR (400 MHz, DMSO-d6) δ 11.37 (s, 1H), 9.85 (s, 1H), 8.20 (s, 1H), 7.44-6.91 (m, 4H), 5.89 (s, 1H), 4.74 (s, 1H), 3.50 (s, 4H), 2.36 (s, 3H), 2.24 (s, 3H). |
| B8 | 516.5 | 1H NMR (300 MHz, DMSO-d6) δ 1.27 (t, J = 6.9 Hz, 3H), 2.35-2.50 (m, 9H), 3.41-3.63 (m, 6H), 4.06 (q, J = 6.9 Hz, 2H), 4.45 (t, J = 5.4 Hz, 1H), 6.04 (s, 1H), 7.00-7.22 (m, 2H), 7.29 (t, J = 8.2 Hz, 1H), 8.17 (s, 1H), 9.63 (s, 1H), 11.44 (bs, 1H). |
| B9 | 490.4 | 1H NMR (400 MHz, DMSO-d6) δ 2.46 (s, 3H), 3.11 (d, J = 11.2 Hz, 2H), 3.29 (dd, J = 27.6, 14.6 Hz, 5H), 3.58 (d, J = 12.0 Hz, 2H), 3.76 (t, J = 5.3 Hz, 2H), 4.34 (d, J = 14.0 Hz, 2H), 5.41 (s, 1H), 6.13 (s, 1H), 7.42 (t, J = 9.1 Hz, 1H), 7.63 (ddd, J = 9.0, 4.3, 2.5 Hz, 1H), 7.99 (dd, J = 6.9, 2.6 Hz, 1H), 8.25 (s, 1H), 9.66 (s, 1H), 10.25 (s, 1H), 11.68 (s, 1H). |

Indicative IC50s for compounds synthesised in Table 3 were determined against each of SIK1, SIK2 and SIK3 using a biochemical assay for SIK1, SIK2 or SIK3 activity as described above, as well as against ABL1 and SRC (Free Choice Kinase Assay provided by ProQinase, Freiburg Germany) and are shown in Table 4.

TABLE 4

Biological activity of further small molecules of formula I/the invention.

| Compound Number | SIK1 IC50 rank | SIK2 IC50 rank | SIK3 IC50 rank | ABL1 IC50 rank | SRC IC50 rank |
|---|---|---|---|---|---|
| A8 (dasatanib) | **** | **** | **** | **** | **** |
| B1 | **** | **** | **** | **** | **** |
| B2 | **** | **** | *** | **** | **** |
| B3 | **** | **** | *** | **** | **** |
| B4 | *** | *** | * | **** | **** |
| B5 | **** | **** | **** | **** | **** |
| B6 | **** | **** | **** | **** | **** |
| B7 | **** | **** | **** | **** | **** |
| B8 | * | * | ~ | **** | **** |
| B9 | ~ | ** | ~ | ND | ND |

**** = <0.1 uM;
*** = >0.1 uM;
** = >0.5 uM;
* = >1.0 uM;
~ = >5.0 uM;
ND = not determined Briefly, a radiometric protein kinase assay (33PanQinase® Activity Assay) was used for measuring the kinase activity of the five protein kinases. All kinase assays were performed in 96-well FlashPlates™ from PerkinElmer (Boston, MA, USA) in a 50 ul reaction volume. The reaction cocktail was pipetted in four steps in the following order:

25 ul of assay buffer (standard buffer/[gamma-33P]-ATP)
10 ul of ATP solution (in water)
5 ul of test compound (in 10% DMSO)
20 ul enzyme/substrate mix The assay for all protein kinases contained 70 mM HEPES-NaOH pH7.5, 3 mM MgCl2, 3 mM MnCl2, 3 uM Na-orthovanadate, 1.2 mM DTT, ATP (variable concentrations, corresponding to the apparent ATP-Km of the respective kinase, see Table 5), [gamma-33P]-ATP (approx. 8×10^ cpm per well), protein kinase (variable amount, see Table 5), and substrate (variable amounts, see Table 5).

The following amounts of enzyme and a substrate were used per well:

TABLE 5

Assay parameters for the tested protein kinases.

| Kinase Name | Kinase Conc. (ng/50 ul) | Kinase Conc. (nM*) | ATP Conc. (uM) | Substrate | Substrate Conc. (ug/50 uL) |
| --- | --- | --- | --- | --- | --- |
| ABL1 wt | 5 | 1.3 | 0.3 | Poly(Ala, Glu, Lys, Tyr)6:2:5:1 | 0.125 |
| SIK1 | 50 | 14.6 | 3.0 | RBER-CHKtide | 2 |
| SIK2 | 3 | 1 | 1.0 | RBER-CHKtide | 2 |
| SIK3 | 50 | 15.9 | 1.0 | RBER-CHKtide | 2 |
| SRC (GST-HIS-tag) | 5 | 1.1 | 0.3 | Poly(Glu, Tyr)4:1 | 0.125 |

*Maximal molar enzyme assay concentrations, implying enzyme preparations exclusively containing 100% active enzyme The reaction cocktails were incubated at 30° C. for 60 minutes. The reaction was stopped with 50 ul of 2% (v/v) H3PO4, plates were aspirated and washed two times with 200 ul 0.9% (w/v) NaCl. Incorporation of 33Pi was determined with a microplate scintillation counter (Microbeta, Wallac). All assays were performed with a BeckmanCoulter/SAGIANTM™ Core System.

Example 14: Inhibition of the SIK Family Over Related Kinases is Critical for Achieving Anti-Tumour Immuno-Oncology Effect The inventors were able to demonstrate that the tumour immuno-oncology effect of inhibitors of the invention is mediated by SIK family members, and by SIK3 in particular. Using the luciferase-based tumor cell viability readout described in Example 9 (eg, as used for FIG. 7G), tumour cells show increased cytotoxicity in the presence of TNF (10 ng/mL) and a pan-SIK and ABL1 & SRC inhibitor (compound B1) at a concentration of between about 10 and 100 nM (circles), compared to in the presence of inhibitor alone (squares) (FIG. 17A). In contrast however, compound B8 which is a potent ABL1 & SRC inhibitor but with low inhibitory activity against SIK family members (in particular SIK3), in combination with TNF (circles) fails to exhibit cytotoxicity of M579 A2 cells at such concentration range, compared to inhibitor alone (squares) (FIG. 17B). Indeed, in combination with TNF compound B4 (circles) also fails to exhibit cytotoxicity of M579 A2 cells at such concentration range, compared to inhibitor alone (squares) (FIG. 17C), despite compound B4 being not only a potent inhibitor of ABL1 & SRC but also a strong inhibitor or SIK1 and SIK2, but only a weak inhibitor of SIK3.

Taken together, these data implicate SIK family members, and in particular SIK3, as being the mediator of the anti-tumour immuno-oncology effect and not the other kinase ABL1 or SRC.

Example 15: A SIK1- and SIK2-, but not SIK3-Selective Compound Fails to Show an Anti-Tumour Immuno-Oncology Effect Further analysis of SIK-family member specific/selective compounds by the inventors provides further evidence that the inhibition of SIK3 is critical for achieving an anti-tumour immuno-oncology effect by compounds of formula I, in particular in the concentration range of activity between about of 20 to 100 nM shown in Example 14. In the M579-A2-luc assay described in Example 9, tumour cell survival (increased RLU) remains unaffected at such concentrations by either of (A) compound A11 in combination with 10 ng/mL TNF, a strong SIK1 and SIK2 inhibitor but a weak SIK3 inhibitor; or (B) compound A6 in combination with 10 ng/mL TNF, a strong SIK2 inhibitor but a weak SIK3 and weak SIK 1 inhibitor.

These data, taken together with those shown in Example 14 further implicate that of the SIK family members the anti-tumour immuno-oncology effect of these compounds is mediated by SIK3 inhibition, and not by SIK1 or SIK2.

The sequences show:

```
(SIK3 isoform 1; UniProt identifier: Q9Y2K2-1, Entry version
138 of 15 Mar. 2017):
                                                    SEQ ID NO. 1
         10         20         30         40         50
 MPARIGYYEI DRTIGKGNFA VVKRATHLVT KAKVAIKIID KTQLDEENLK 60         70         80         90        100
 KIFREVQIMK MLCHPHIIRL YQVMETERMI YLVTEYASGG EIFDHLVAHG 110        120        130        140        150
 RMAEKEARRK FKQIVTAVYF CHCRNIVHRD LKAENLLLDA NLNIKIADFG 160        170        180        190        200
 FSNLFTPGQL LKTWCGSPPY AAPELFEGKE YDGPKVDIWS LGVVLYVLVC 210        220        230        240        250
 GALPFDGSTL QNLRARVLSG KFRIPFFMST ECEHLIRHML VLDPNKRLSM 260        270        280        290        300
 EQICKHKWMK LGDADPNFDR LIAECQQLKE ERQVDPLNED VLLAMEDMGL 310        320        330        340        350
 DKEQTLQSLR SDAYDHYSAI YSLLCDRHKR HKTLRLGALP SMPRALAFQA
```

-continued

```
        360        370        380        390        400
PVNIQAEQAG TAMNISVPQV QLINPENQIV EPDGTLNLDS DEGEEPSPEA 410        420        430        440        450
LVRYLSMRRH TVGVADPRTE VMEDLQKLLP GFPGVNPQAP FLQVAPNVNF 460        470        480        490        500
MHNLLPMQNL QPTGQLEYKE QSLLQPPTLQ LLNGMGPLGR RASDGGANIQ 510        520        530        540        550
LHAQQLLKRP RGPSPLVTMT PAVPAVTPVD EESSDGEPDQ EAVQSSTYKD 560        570        580        590        600
SNTLHLPTER FSPVRRFSDG AASIQAFKAH LEKMGNNSSI KQLQQECEQL 610        620        630        640        650
QKMYGGQIDE RTLEKTQQQH MLYQQEQHHQ ILQQQIQDSI CPPQPSPPLQ 660        670        680        690        700
AACENQPALL THQLQRLRIQ PSSPPPNHPN NHLFRQPSNS PPPMSSAMIQ 710        720        730        740        750
PHGAASSSQF QGLPSRSAIF QQQPENCSSP PNVALTCLGM QQPAQSQQVT 760        770        780        790        800
IQVQEPVDML SNMPGTAAGS SGRGISISPS AGQMQMQHRT NLMATLSYGH 810        820        830        840        850
RPLSKQLSAD SAEAHSLNVN RFSPANYDQA HLHPHLFSDQ SRGSPSSYSP 860        870        880        890        900
STGVGFSPTQ ALKVPPLDQF PTFPPSAHQQ PPHYTTSALQ QALLSPTPPD 910        920        930        940        950
YTRHQQVPHI LQGLLSPRHS LTGHSDIRLP PTEFAQLIKR QQQQRQQQQQ 960        970        980        990       1000
QQQQQEYQEL FRHMNQGDAG SLAPSLGGQS MTERQALSYQ NADSYHHHTS 1010       1020       1030       1040       1050
PQHLLQIRAQ ECVSQASSPT PPHGYAHQPA LMHSESMEED CSCEGAKDGF 1060       1070       1080       1090       1100
QDSKSSSTLT KGCHDSPLLL STGGPGDPES LLGTVSHAQE LGIHPYGHQP 1110       1120       1130       1140       1150
TAAFSKNKVP SREPVIGNCM DRSSPGQAVE LPDHNGLGYP ARPSVHEHHR 1160       1170       1180       1190       1200
PRALQRHHTI QNSDDAYVQL DNLPGMSLVA GKALSSARMS DAVLSQSSLM 1210       1220       1230       1240       1250
GSQQFQDGEN EECGASLGGH EHPDLSDGSQ HLNSSCYPST CITDILLSYK

1260
HPEVSFSMEQ AGV (SIK3 isoform 2; UniProt identifier: Q9Y2K2-2, Entry
version 138 of 15 Mar. 2017):
                                               SEQ ID NO. 2
         10         20         30         40         50
MGLRASRPSK LTWKKWATTA ASNSCSRSVS SCRRCTGGRL MKEPWRRPSS 60         70         80         90        100
SICYTSRSST IKFSSNKFKT LSVLLSHLHL FRLHVKISQP SLPISSRGAA 110        120        130        140        150
SSSQFQGLPS RSAIFQQQPE NCSSPPNVAL TCLGMQQPAQ SQQVTIQVQE 160        170        180        190        200
PVDMLSNMPG TAAGSSGRGI SISPSAGQMQ MQHRTNLMAT LSYGHRPLSK 210        220        230        240        250
QLSADSAEAH SAHQQPPHYT TSALQQALLS PTPPDYTRHQ QVPHILQGLL 260        270        280        290        300
SPRHSLTGHS DIRLPPTEFA QLIKRQQQQR QQQQQQQQQQ EYQELFRHMN
```

-continued

```
         310        320        330        340        350
  QGDAGSLAPS LGGQSMTERQ ALSYQNADSY HHHTSPQHLL QIRAQECVSQ 360        370        380        390        400
  ASSPTPPHGY AHQPALMHSE SMEEDCSCEG AKDGFQDSKS SSTLTKGCHD 410        420        430        440        450
  SPLLLSTGGP GDPESLLGTV SHAQELGIHP YGHQPTAAFS KNKVPSREPV 460        470        480        490        500
  IGNCMDRSSP GQAVELPDHN GLGYPARPSV HEHHRPRALQ RHHTIQNSDD 510        520        530        540        550
  AYVQLDNLPG MSLVAGKALS SARMSDAVLS QSSLMGSQQF QDGENEECGA 560        570        580        590
  SLGGHEHPDL SDGSQHLNSS CYPSTCITDI LLSYKHPEVS FSMEQAGV (SIK3 isoform 3; UniProt identifier: Q9Y2K2-3, Entry
version 138 of 15 Mar. 2017):
                                             SEQ ID NO. 3
         10         20         30         40         50
  MPARIGYYEI DRTIGKGNFA VVKRATHLVT KAKVAIKIID KTQLDEENLK 60         70         80         90        100
  KIFREVQIMK MLCHPHIIRL YQVMETERMI YLVTEYASGG EIFDHLVAHG 110        120        130        140        150
  RMAEKEARRK FKQIVTAVYF CHCRNIVHRD LKAENLLLDA NLNIKIADFG 160        170        180        190        200
  FSNLFTPGQL LKTWCGSPPY AAPELFEGKE YDGPKVDIWS LGVVLYVLVC 210        220        230        240        250
  GALPFDGSTL QNLRARVLSG KFRIPFFMST ECEHLIRHML VLDPNKRLSM 260        270        280        290        300
  EQICKHKWMK LGDADPNFDR LIAECQQLKE ERQVDPLNED VLLAMEDMGL 310        320        330        340        350
  DKEQTLQSLR SDAYDHYSAI YSLLCDRHKR HKTLRLGALP SMPRALAFQA 360        370        380        390        400
  PVNIQAEQAG TAMNISVPQV QLINPENQIV EPDGTLNLDS DEGEEPSPEA 410        420        430        440        450
  LVRYLSMRRH TVGVADPRTE VMEDLQKLLP GFPGVNPQAP FLQVAPNVNF 460        470        480        490        500
  MHNLLPMQNL QPTGQLEYKE QSLLQPPTLQ LLNGMGPLGR RASDGGANIQ 510        520        530        540        550
  LHAQQLLKRP RGPSPLVTMT PAVPAVTPVD EESSDGEPDQ EAVQSSTYKD 560        570        580        590        600
  SNTLHLPTER FSPVRRFSDG AASIQAFKAH LEKMGNNSSI KQLQQECEQL 610        620        630        640        650
  QKMYGGQIDE RTLEKTQQQH MLYQQEQHHQ ILQQQIQDSI CPPQPSPPLQ 660        670        680        690        700
  AACENQPALL THQLQRLRIQ PSSPPPNHPN NHLFRQPSNS PPPMSSAMIQ 710        720        730        740        750
  PHGAASSSQF QGLPSRSAIF QQQPENCSSP PNVALTCLGM QQPAQSQQVT 760        770        780        790        800
  IQVQEPVDML SNMPGTAAGS SGRGISISPS AGQMQMQHRT NLMATLSYGH 810        820        830        840        850
  RPLSKQLSAD SAEAHSLNVN RFSPANYDQA HLHPHLFSDQ SRGSPSSYSP 860        870        880        890        900
  STGVGFSPTQ ALKVPPLDQF PTFPPSAHQQ PPHYTTSALQ QALLSPTPPD 910        920        930        940        950
  YTRHQQVPHI LQGLLSPRHS LTGHSDIRLP PTEFAQLIKR QQQQRQQQQQ 960        970        980        990        1000
  QQQQQEYQEL FRHMNQGDAG SLAPSLGGQS MTERQALSYQ NADSYHHHTS
```

```
           1010       1020       1030       1040       1050
     PQHLLQIRAQ ECVSQASSPT PPHGYAHQPA LMHSESMEED CSCEGAKDGF 1060       1070       1080       1090       1100
     QDSKSSSTLT KGCHDSPLLL STGGPGDPES LLGTVSHAQE LGIHPYGHQP 1110       1120
     TAAFSKNKVP SRGKCLLTVE VLGQSALIN (SIK3 isoform 4; UniProt identifier:
     Q9Y2K2-4, Entry version 138 of 15 Mar. 2017):
                                                  SEQ ID NO. 4
             10         20         30         40         50
     MPARIGYYEI DRTIGKGNFA VVKRATHLVT KAKVAIKIID KTQLDEENLK 60         70         80         90        100
     KIFREVQIMK MLCHPHIIRL YQVMETERMI YLVTEYASGG EIFDHLVAHG 110        120        130        140        150
     RMAEKEARRK FKQIVTAVYF CHCRNIVHRD LKAENLLLDA NLNIKIADFG 160        170        180        190        200
     FSNLFTPGQL LKTWCGSPPY AAPELFEGKE YDGPKVDIWS LGVVLYVLVC 210        220        230        240        250
     GALPFDGSTL QNLRARVLSG KFRIPFFMST ECEHLIRHML VLDPNKRLSM 260        270        280        290        300
     EQICKHKWMK LGDADPNFDR LIAECQQLKE ERQVDPLNED VLLAMEDMGL 310        320        330        340        350
     DKEQTLQAEQ AGTAMNISVP QVQLINPENQ IVEPDGTLNL DSDEGEEPSP 360        370        380        390        400
     EALVRYLSMR RHTVGVADPR TEVMEDLQKL LPGFPGVNPQ APFLQVAPNV 410        420        430        440        450
     NFMHNLLPMQ NLQPTGQLEY KEQSLLQPPT LQLLNGMGPL GRRASDGGAN 460        470        480        490        500
     IQLHAQQLLK RPRGPSPLVT MTPAVPAVTP VDEESSDGEP DQEAVQRYLA 510        520        530        540        550
     NRSKRHTLAM TNPTAEIPPD LQRQLGQQPF RSRVWPPHLV PDQHRSTYKD 560        570        580        590        600
     SNTLHLPTER FSPVRRFSDG AASIQAFKAH LEKMGNNSSI KQLQQECEQL 610        620        630        640        650
     QKMYGGQIDE RTLEKTQQQH MLYQQEQHHQ ILQQQIQDSI CPPQPSPPLQ 660        670        680        690        700
     AACENQPALL THQLQRLRIQ PSSPPPNHPN NHLFRQPSNS PPPMSSAMIQ 710        720        730        740        750
     PHGAASSSQF QGLPSRSAIF QQQPENCSSP PNVALTCLGM QQPAQSQQVT 760        770        780        790        800
     IQVQEPVDML SNMPGTAAGS SGRGISISPS AGQMQMQHRT NLMATLSYGH 810        820        830        840        850
     RPLSKQLSAD SAEAHSAHQQ PPHYTTSALQ QALLSPTPPD YTRHQQVPHI 860        870        880        890        900
     LQGLLSPRHS LTGHSDIRLP PTEFAQLIKR QQQRQQQQQ QQQQQEYQEL 910        920        930        940        950
     FRHMNQGDAG SLAPSLGGQS MTERQALSYQ NADSYHHHTS PQHLLQIRAQ 960        970        980        990       1000
     ECVSQASSPT PPHGYAHQPA LMHSESMEED CSCEGAKDGF QDSKSSSTLT 1010       1020       1030       1040       1050
     KGCHDSPLLL STGGPGDPES LLGTVSHAQE LGIHPYGHQP TAAFSKNKVP 1060       1070       1080       1090       1100
     SREPVIGNCM DRSSPGQAVE LPDHNGLGYP ARPSVHEHHR PRALQRHHTI 1110       1120       1130       1140       1150
     QNSDDAYVQL DNLPGMSLVA GKALSSARMS DAVLSQSSLM GSQQFQDGEN
```

-continued

```
              1160       1170       1180       1190       1200
         EECGASLGGH EHPDLSDGSQ HLNSSCYPST CITDILLSYK HPEVSFSMEQ

AGV (SIK1; UniProt identifier: P57059-1):
                                                      SEQ ID NO. 5
               10         20         30         40         50
         MVIMSEFSAD PAGQGQGQQK PLRVGFYDIE RTLGKGNFAV VKLARHRVTK 60         70         80         90        100
         TQVAIKIIDK TRLDSSNLEK IYREVQLMKL LNHPHIIKLY QVMETKDMLY 110        120        130        140        150
         IVTEFAKNGE MFDYLTSNGH LSENEARKKF WQILSAVEYC HDHHIVHRDL 160        170        180        190        200
         KTENLLLDGN MDIKLADFGF GNFYKSGEPL STWCGSPPYA APEVFEGKEY 210        220        230        240        250
         EGPQLDIWSL GVVLYVLVCG SLPFDGPNLP TLRQRVLEGR FRIPFFMSQD 260        270        280        290        300
         CESLIRRMLV VDPARRITIA QIRQHRWMRA EPCLPGPACP AFSAHSYTSN 310        320        330        340        350
         LGDYDEQALG IMQTLGVDRQ RTVESLQNSS YNHFAAIYYL LLERLKEYRN 360        370        380        390        400
         AQCARPGPAR QPRPRSSDLS GLEVPQEGLS TDPFRPALLC PQPQTLVQSV 410        420        430        440        450
         LQAEMDCELQ SSLQWPLFFP VDASCSGVFR PRPVSPSSLL DTAISEEARQ 460        470        480        490        500
         GPGLEEEQDT QESLPSSTGR RHTLAEVSTR LSPLTAPCIV VSPSTTASPA 510        520        530        540        550
         EGTSSDSCLT FSASKSPAGL SGTPATQGLL GACSPVRLAS PFLGSQSATP 560        570        580        590        600
         VLQAQGGLGG AVLLPVSFQE GRRASDTSLT QGLKAFRQQL RKTTRTKGFL 610        620        630        640        650
         GLNKIKGLAR QVCQAPASRA SRGGLSPFHA PAQSPGLHGG AAGSREGWSL 660        670        680        690        700
         LEEVLEQQRL LQLQHHPAAA PGCSQAPQPA PAPFVIAPCD GPGAAPLPST 710        720        730        740        750
         LLTSGLPLLP PPLLQTGASP VASAAQLLDT HLHIGTGPTA LPAVPPPRLA 760        770        780
         RLAPGCEPLG LLQGDCEMED LMPCSLGTFV LVQ (SIK2; UniProt identifier: Q9H0K1-1):
                                                      SEQ ID NO. 6
               10         20         30         40         50
         MVMADGPRHL QRGPVRVGFY DIEGTLGKGN FAVVKLGRHR ITKTEVAIKI 60         70         80         90        100
         IDKSQLDAVN LEKIYREVQI MKMLDHPHII KLYQVMETKS MLYLVTEYAK 110        120        130        140        150
         NGEIFDYLAN HGRLNESEAR RKFWQILSAV DYCHGRKIVH RDLKAENLLL 160        170        180        190        200
         DNNMNIKIAD FGFGNFFKSG ELLATWCGSP PYAAPEVFEG QQYEGPQLDI 210        220        230        240        250
         WSMGVVLYVL VCGALPFDGP TLPILRQRVL EGRFRIPYFM SEDCEHLIRR 260        270        280        290        300
         MLVLDPSKRL TIAQIKEHKW MLIEVPVQRP VLYPQEQENE PSIGEFNEQV 310        320        330        340        350
         LRLMHSLGID QQKTIESLQN KSYNHFAAIY FLLVERLKSH RSSFPVEQRL 360        370        380        390        400
         DGRQRRPSTI AEQTVAKAQT VGLPVTMHSP NMRLLRSALL PQASNVEAFS
```

```
            410        420        430        440        450
FPASGCQAEA AFMEEECVDT PKVNGCLLDP VPPVLRKGC QSLPSNMMET 460        470        480        490        500
SIDEGLETEG EAEEDPAHAF EAFQSTRSGQ RRHTLSEVTN QLVVMPGAGK 510        520        530        540        550
IFSMNDSPSL DSVDSEYDMG SVQRDLNFLE DNPSLKDIML ANQPSPRMTS 560        570        580        590        600
PFISLRPTNP AMQALSSQKR EVHNRSPVSF REGRRASDTS LTQGIVAFRQ 610        620        630        640        650
HLQNLARTKG ILELNKVQLL YEQIGPEADP NLAPAAPQLQ DLASSCPQEE 660        670        680        690        700
VSQQQESVST LPASVHPQLS PRQSLETQYL QHRLQKPSLL SKAQNTCQLY 710        720        730        740        750
CKEPPRSLEQ QLQEHRLQQK RLFLQKQSQL QAYFNQMQIA ESSYPQPSQQ 760        770        780        790        800
LPLPRQETPP PSQQAPPFSL TQPLSPVLEP SSEQMQYSPF LSQYQEMQLQ 810        820        830        840        850
PLPSTSGPRA APPLPTQLQQ QQPPPPPPPP PPRQPGAAPA PLQFSYQTCE 860        870        880        890        900
LPSAASPAPD YPTPCQYPVD GAQQSDLTGP DCPRSPGLQE APSSYDPLAL 910        920
SELPGLFDCE MLDAVDPQHN GYVLVN (SIK3 siRNA S1):
                                                 SEQ ID NO. 7
            10
GCGCCAGGCU UUAUCUUAU (SIK3 siRNA s2):
                                                 SEQ ID NO. 8
            10
GAACAGCGAC GAUGCUUAU (SIK3 siRNA s3):
                                                 SEQ ID NO. 9
            10
GCACUAACCU GCUUGGGUA (SIK3 siRNA s4):
                                                SEQ ID NO. 10
            10
GGAGCAGGCA GGCGUGUAA (SIK3 shRNA shSIK3):
                                                SEQ ID NO. 11
            10         20         30         40         50
CCGGGCCAGG CTTTATCTTA TCAAACTCGA GTTTGATAAG ATAAAGCCTG

GCTTTTTG
(Control shRNA shCtrl):
                                                SEQ ID NO. 12
            10         20         30         40         50
CCGGGCGCGA TAGCGCTAAT AATTTCTCGA GAAATTATTA GCGCTATCGC

GCTTTTT (SIK3 canonical sequence/Isoform 1; UniProt identifier:
Q9Y2K2-5, Entry version 144 of 28 Mar. 2018):
                                                SEQ ID NO. 13
            10         20         30         40         50
MAAAAASGAG GAAGAGTGGA GPAGRLLPPP APGSPAAPAA VSPAAGQPRP 60         70         80         90        100
PAPASRGPMP ARIGYYEIDR TIGKGNFAVV KRATHLVTKA KVAIKIIDKT 110        120        130        140        150
QLDEENLKKI FREVQIMKML CHPHIIRLYQ VMETERMIYL VTEYASGGEI 160        170        180        190        200
FDHLVAHGRM AEKEARRKFK QIVTAVYFCH CRNIVHRDLK AENLLLDANL
```

-continued

```
          210        220        230        240        250
NIKIADFGFS NLFTPGQLLK TWCGSPPYAA PELFEGKEYD GPKVDIWSLG 260        270        280        290        300
VVLYVLVCGA LPFDGSTLQN LRARVLSGKF RIPFFMSTEC EHLIRHMLVL 310        320        330        340        350
DPNKRLSMEQ ICKHKWMKLG DADPNFDRLI AECQQLKEER QVDPLNEDVL 360        370        380        390        400
LAMEDMGLDK EQTLQSLRSD AYDHYSAIYS LLCDRHKRHK TLRLGALPSM 410        420        430        440        450
PRALAFQAPV NIQAEQAGTA MNISVPQVQL INPENQIVEP DGTLNLDSDE 460        470        480        490        500
GEEPSPEALV RYLSMRRHTV GVADPRTEVM EDLQKLLPGF PGVNPQAPFL 510        520        530        540        550
QVAPNVNFMH NLLPMQNLQP TGQLEYKEQS LLQPPTLQLL NGMGPLGRRA 560        570        580        590        600
SDGGANIQLH AQQLLKRPRG PSPLVTMTPA VPAVTPVDEE SSDGEPDQEA 610        620        630        640        650
VQSSTYKDSN TLHLPTERFS PVRRFSDGAA SIQAFKAHLE KMGNNSSIKQ 660        670        680        690        700
LQQECEQLQK MYGGQIDERT LEKTQQQHML YQQEQHHQIL QQQIQDSICP 710        720        730        740        750
PQPSPPLQAA CENQPALLTH QLQRLRIQPS SPPPNHPNNH LFRQPSNSPP 760        770        780        790        800
PMSSAMIQPH GAASSSQFQG LPSRSAIFQQ QPENCSSPPN VALTCLGMQQ 810        820        830        840        850
PAQSQQVTIQ VQEPVDMLSN MPGTAAGSSG RGISISPSAG QMQMQHRTNL 860        870        880        890        900
MATLSYGHRP LSKQLSADSA EAHSLNVNRF SPANYDQAHL HPHLFSDQSR 910        920        930        940        950
GSPSSYSPST GVGFSPTQAL KVPPLDQFPT FPPSAHQQPP HYTTSALQQA 960        970        980        990       1000
LLSPTPPDYT RHQQVPHILQ GLLSPRHSLT GHSDIRLPPT EFAQLIKRQQ 1010       1020       1030       1040       1050
QQRQQQQQQQ QQQEYQELFR HMNQGDAGSL APSLGGQSMT ERQALSYQNA 1060       1070       1080       1090       1100
DSYHHHTSPQ HLLQIRAQEC VSQASSPTPP HGYAHQPALM HSESMEEDCS 1110       1120       1130       1140       1150
CEGAKDGFQD SKSSSTLTKG CHDSPLLLST GGPGDPESLL GTVSHAQELG 1160       1170       1180        190       1200
IHPYGHQPTA AFSKNKVPSR EPVIGNCMDR SSPGQAVELP DHNGLGYPAR 1210       1220       1230       1240       1250
PSVHEHHRPR ALQRHHTIQN SDDAYVQLDN LPGMSLVAGK ALSSARMSDA 1260       1270       1280       1290       1300
VLSQSSLMGS QQFQDGENEE CGASLGGHEH PDLSDGSQHL NSSCYPSTCI 1310       1320
TDILLSYKHP EVSFSMEQAG V (SIK3 Isoform 2; UniProt identifier: Q9Y2K2-6, Entry version
144 of 28 Mar. 2018):
                                            SEQ ID NO. 14
           10         20         30         40         50
MACSTPHGSN RRLPRKCHFS LPTRTPTLCT SLRSVSPLCA GSQMGLRASR 60         70         80         90        100
PSKLTWKKWA TTAASNSCSR SVSSCRRCTG GRLMKEPWRR PSSSICYTSR 110        120        130        140        150
SSTIKFSSNK FKTLSVLLSH LHLFRLHVKI SQPSLPISSR GAASSSQFQG
```

```
        160         170         180         190         200
LPSRSAIFQQ QPENCSSPPN VALTCLGMQQ PAQSQQVTIQ VQEPVDMLSN 210         220         230         240         250
MPGTAAGSSG RGISISPSAG QMQMQHRTNL MATLSYGHRP LSKQLSADSA 260         270         280         290         300
EAHSAHQQPP HYTTSALQQA LLSPTPPDYT RHQQVPHILQ GLLSPRHSLT 310         320         330         340         350
GHSDIRLPPT EFAQLIKRQQ QQRQQQQQQQ QQQEYQELFR HMNQGDAGSL 360         370         380         390         400
APSLGGQSMT ERQALSYQNA DSYHHHTSPQ HLLQIRAQEC VSQASSPTPP 410         420         430         440         450
HGYAHQPALM HSESMEEDCS CEGAKDGFQD SKSSSTLTKG CHDSPLLLST 460         470         480         490         500
GGPGDPESLL GTVSHAQELG IHPYGHQPTA AFSKNKVPSR EPVIGNCMDR 510         520         530         540         550
SSPGQAVELP DHNGLGYPAR PSVHEHHRPR ALQRHHTIQN SDDAYVQLDN 560         570         580         590         600
LPGMSLVAGK ALSSARMSDA VLSQSSLMGS QQFQDGENEE CGASLGGHEH 610         620         630         640
PDLSDGSQHL NSSCYPSTCI TDILLSYKHP EVSFSMEQAG V (SIK3 Isoform 3; UniProt identifier: Q9Y2K2-7, Entry version
144 of 28 Mar. 2018):
                                                SEQ ID NO. 15
         10         20         30         40         50
MAAAAASGAG GAAGAGTGGA GPAGRLLPPP APGSPAAPAA VSPAAGQPRP 60         70         80         90         100
PAPASRGPMP ARIGYYEIDR TIGKGNFAVV KRATHLVTKA KVAIKIIDKT 110         120         130         140         150
QLDEENLKKI FREVQIMKML CHPHIIRLYQ VMETERMIYL VTEYASGGEI 160         170         180         190         200
FDHLVAHGRM AEKEARRKFK QIVTAVYFCH CRNIVHRDLK AENLLLDANL 210         220         230         240         250
NIKIADFGFS NLFTPGQLLK TWCGSPPYAA PELFEGKEYD GPKVDIWSLG 260         270         280         290         300
VVLYVLVCGA LPFDGSTLQN LRARVLSGKF RIPFFMSTEC EHLIRHMLVL 310         320         330         340         350
DPNKRLSMEQ ICKHKWMKLG DADPNFDRLI AECQQLKEER QVDPLNEDVL 360         370         380         390         400
LAMEDMGLDK EQTLQSLRSD AYDHYSAIYS LLCDRHKRHK TLRLGALPSM 410         420         430         440         450
PRALAFQAPV NIQAEQAGTA MNISVPQVQL INPENQIVEP DGTLNLDSDE 460         470         480         490         500
GEEPSPEALV RYLSMRRHTV GVADPRTEVM EDLQKLLPGF PGVNPQAPFL 510         520         530         540         550
QVAPNVNFMH NLLPMQNLQP TGQLEYKEQS LLQPPTLQLL NGMGPLGRRA 560         570         580         590         600
SDGGANIQLH AQQLLKRPRG PSPLVTMTPA VPAVTPVDEE SSDGEPDQEA 610         620         630         640         650
VQSSTYKDSN TLHLPTERFS PVRRFSDGAA SIQAFKAHLE KMGNNSSIKQ 660         670         680         690         700
LQQECEQLQK MYGGQIDERT LEKTQQQHML YQQEQHHQIL QQQIQDSICP 710         720         730         740         750
PQPSPPLQAA CENQPALLTH QLQRLRIQPS SPPPNHPNNH LFRQPSNSPP 760         770         780         790         800
PMSSAMIQPH GAASSSQFQG LPSRSAIFQQ QPENCSSPPN VALTCLGMQQ
```

-continued

```
           810        820        830        840        850
    PAQSQQVTIQ VQEPVDMLSN MPGTAAGSSG RGISISPSAG QMQMQHRTNL 860        870        880        890        900
    MATLSYGHRP LSKQLSADSA EAHSLNVNRF SPANYDQAHL HPHLFSDQSR 910        920        930        940        950
    GSPSSYSPST GVGFSPTQAL KVPPLDQFPT FPPSAHQQPP HYTTSALQQA 960        970        980        990       1000
    LLSPTPPDYT RHQQVPHILQ GLLSPRHSLT GHSDIRLPPT EFAQLIKRQQ 1010       1020       1030       1040       1050
    QQRQQQQQQQ QQQEYQELFR HMNQGDAGSL APSLGGQSMT ERQALSYQNA 1060       1070       1080       1090       1100
    DSYHHHTSPQ HLLQIRAQEC VSQASSPTPP HGYAHQPALM HSESMEEDCS 1110       1120       1130       1140 v1150
    CEGAKDGFQD SKSSSTLTKG CHDSPLLLST GGPGDPESLL GTVSHAQELG 1160       1170       1180
    IHPYGHQPTA AFSKNKVPSR GKCLLTVEVL GQSALIN (SIK3 Isoform 4; UniProt identifier: Q9Y2K2-8, Entry version
    144 of 28 Mar. 2018):
                                                   SEQ ID NO. 16
            10         20         30         40         50
    MAAAAASGAG GAAGAGTGGA GPAGRLLPPP APGSPAAPAA VSPAAGQPRP 60         70         80         90        100
    PAPASRGPMP ARIGYYEIDR TIGKGNFAVV KRATHLVTKA KVAIKIIDKT 110        120        130        140        150
    QLDEENLKKI FREVQIMKML CHPHIIRLYQ VMETERMIYL VTEYASGGEI 160        170        180        190        200
    FDHLVAHGRM AEKEARRKFK QIVTAVYFCH CRNIVHRDLK AENLLLDANL 210        220        230        240        250
    NIKIADFGFS NLFTPGQLLK TWCGSPPYAA PELFEGKEYD GPKVDIWSLG 260        270        280        290        300
    VVLYVLVCGA LPFDGSTLQN LRARVLSGKF RIPFFMSTEC EHLIRHMLVL 310        320        330        340        350
    DPNKRLSMEQ ICKHKWMKLG DADPNFDRLI AECQQLKEER QVDPLNEDVL 360        370        380        390        400
    LAMEDMGLDK EQTLQAEQAG TAMNISVPQV QLINPENQIV EPDGTLNLDS 410        420        430        440        450
    DEGEEPSPEA LVRYLSMRRH TVGVADPRTE VMEDLQKLLP GFPGVNPQAP 460        470        480        490        500
    FLQVAPNVNF MHNLLPMQNL QPTGQLEYKE QSLLQPPTLQ LLNGMGPLGR 510        520        530        540        550
    RASDGGANIQ LHAQQLLKRP RGPSPLVTMT PAVPAVTPVD EESSDGEPDQ 560        570        580        590        600
    EAVQRYLANR SKRHTLAMTN PTAEIPPDLQ RQLGQQPFRS RVWPPHLVPD 610        620        630        640        650
    QHRSTYKDSN TLHLPTERFS PVRRFSDGAA SIQAFKAHLE KMGNNSSIKQ 660        670        680        690        700
    LQQECEQLQK MYGGQIDERT LEKTQQQHML YQQEQHHQIL QQQIQDSICP 710        720        730        740        750
    PQPSPPLQAA CENQPALLTH QLQRLRIQPS SPPPNHPNNH LFRQPSNSPP 760        770        780        790        800
    PMSSAMIQPH GAASSSQFQG LPSRSAIFQQ QPENCSSPPN VALTCLGMQQ 810        820        830        840        850
    PAQSQQVTIQ VQEPVDMLSN MPGTAAGSSG RGISISPSAG QMQMQHRTNL 860        870        880        890        900
    MATLSYGHRP LSKQLSADSA EAHSAHQQPP HYTTSALQQA LLSPTPPDYT
```

-continued

```
         910        920        930        940        950
RHQQVPHILQ GLLSPRHSLT GHSDIRLPPT EFAQLIKRQQ QQRQQQQQQQ 960        970        980        990       1000
QQQEYQELFR HMNQGDAGSL APSLGGQSMT ERQALSYQNA DSYHHHTSPQ 1010       1020       1030       1040       1050
HLLQIRAQEC VSQASSPTPP HGYAHQPALM HSESMEEDCS CEGAKDGFQD 1060       1070       1080       1090       1100
SKSSSTLTKG CHDSPLLLST GGPGDPESLL GTVSHAQELG IHPYGHQPTA 1110       1120       1130       1140       1150
AFSKNKVPSR EPVIGNCMDR SSPGQAVELP DHNGLGYPAR PSVHEHHRPR 1160       1170       1180       1190       1200
ALQRHHTIQN SDDAYVQLDN LPGMSLVAGK ALSSARMSDA VLSQSSLMGS 1210       1220       1230       1240       1250
QQFQDGENEE CGASLGGHEH PDLSDGSQHL NSSCYPSTCI TDILLSYKHP

1260
EVSFSMEQAG V
```

---

The invention claimed is:

1. A method of treating cancer in a subject, the treatment comprising exposing cancer cells in a solid tumor within the subject to Tumor Necrosis Factor (TNF) and/or an agonist of TNFR1-signalling and inhibiting SIK3 in the solid tumor cancer cells, wherein the cancer cells express SIK3 and are resistant to an anti-tumor immune response and wherein inhibiting SIK3 in the solid tumor cancer cells comprises:

(i) administering a therapeutically effective amount of a SIK3 inhibitor effective to directly inhibit the SIK3 in the cancer cells, wherein the SIK3 inhibitor comprises an inhibitory nucleic acid that specifically targets a nucleic acid encoding SIK3 or is complementary to a SIK3 mRNA or (ii) administering a therapeutically effective amount of a SIK3 inhibitor effective to inhibit the SIK3 in the cancer cells, wherein the SIK3 inhibitor is a small molecule, and wherein the small molecule comprises a cyclic compound of the following formula I, and salts, prodrugs, solvates, complexes, polymorphs, crystalline forms, tautomers, isotopically labelled forms or combinations thereof, and stereoisomers thereof:

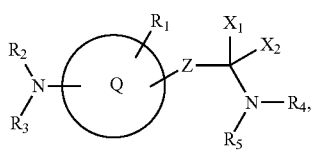

formula I where Q is:
(1) a 5-membered heteroaryl ring;
(2) a 6-membered heteroaryl ring; or
(3) an aryl ring;
optionally substituted with one or more groups R1;
Z is:
(1) a single bond;
(2) —$R_{16}$C═CH—; or
(3) —$(CH_2)_m$—, where m is 1 to 2;
$X_1$ and $X_2$ are each hydrogen, or together form ═O or ═S;

$R_1$ is:
(1) hydrogen or $R_6$,
where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
(2) —OH or —$OR_6$;
(3) —SH or —$SR_6$;
(4) —$C(O)_2H$, —$C(O)_qR_6$, or —O—$C(O)_qR_6$, where q is 1 or 2;
(5) —$SO_3H$ or —$S(O)_qR_6$;
(6) halo;
(7) cyano;
(8) nitro;
(9) —$Z_4$—$NR_7R_8$;
(10) —$Z_4$—$N(R_9)$—$Z_5$—$NR_{10}R_{11}$;
(11) —$Z_4$—$N(R_{12})$—$Z_5$—$R_6$;
(12) —$P(O)(OR_6)_2$;
$R_2$ and $R_3$ are each independently:
(1) hydrogen or $R_6$;
(2) —$Z_4$—$R_6$; or
(3) —$Z_{13}$—$NR_7R_8$;
$R_4$ and $R_5$:
(1) are each independently hydrogen or $R_6$;
(2) —$Z_4$—$N(R_9)$—$Z_5$—$NR_{10}R_{11}$;
(3) —$N(R_9)$ $Z_4R_6$; or
(4) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;
$R_7$, $R_8$, $R_9$, $R_{10}$, $R_{11}$ and $R_{12}$:
(1) are each independently hydrogen or $R_6$;
(2) $R_7$, and $R_8$ may together be alkylene, alkenylene or heteroalkyl, completing a 3- to 8-membered saturated or unsaturated ring with the nitrogen atom to which they are attached, which ring is unsubstituted or substituted with $Z_1$, $Z_2$ and $Z_3$; or
(3) any two of $R_9$, $R_{10}$ and $R_{11}$ may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$R_{13}$ is:
(1) cyano;
(2) nitro;
(3) —$NH_2$;
(4) —NHOalkyl;
(5) —OH;
(6) —NHOaryl;
(7) —NHCOOalkyl;
(8) —NHCOOaryl;
(9) —$NHSO_2$alkyl;
(10) —$NHSO_2$aryl;
(11) aryl;
(12) heteroaryl;
(13) —Oalkyl; or
(14) —Oaryl;

$R_{14}$ is:
(1) —$NO_2$;
(2) —COOalkyl; or
(3) —COOaryl;

$R_{15}$ is:
(1) hydrogen;
(2) alkyl;
(3) aryl;
(4) arylalkyl; or
(5) cycloalkyl;

$Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_qH$, —$C(O)_qZ_6$, or —O—$C(O)_qZ_6$;
(5) —$SO_3H$, —$S(O)_qZ_6$; or $S(O)_qN(Z_9)Z_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$—$Z_6$;
(12) —$Z_4$—$N(Z_{10})$—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_r$—O—, where r is 1 to 5, completing a 4- to 8-membered saturated or unsaturated ring together with the atoms to which they are attached;

$Z_4$ and $Z_5$ are each independently:
(1) a single bond;
(2) —$Z_{11}$—$S(O)_q$—$Z_{12}$—;
(3) —$Z_{11}$—C(O)—$Z_{12}$—;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—; or
(8) —$Z_{11}$—C(O)—O—$Z_{12}$—;

$Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$Z_{11}$ and $Z_{12}$ are each independently:
(1) a single bond;
(2) alkylene;
(3) alkenylene; or
(4) alkynylene; and $Z_{13}$ is:
(1) a single bond;
(2) —$Z_{11}$—$S(O)_q$—$Z_{12}$—;
(3) —$Z_{11}$—C(O)—$Z_{12}$;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$—;
(8) —$Z_{11}$—C(O)—O—$Z_{12}$—;
(9) —$C(NR_{13})$—;
(10) —$C(CHR_{14})$—; or
(11) —$C(C(R_{14})_2)$—;

wherein:
Q is thiazole;
Z is a single bond;
$R_1$ is hydrogen;
$X_1$ and $X_2$ together form-O;
$R_2$ is hydrogen;
$R_3$ is —$Z_4$—$R_6$, wherein $Z_4$ is a single bond and $R_6$ is aryl or heteroaryl which is unsubstituted or substituted with $Z_1$, $Z_2$ and one, two or more groups $Z_3$; and
$R_4$ is hydrogen,
wherein, the cyclic compound of formula I has the following formula II:

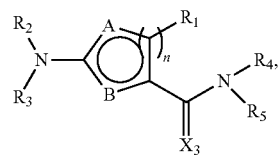

formula II where n is 1;
A is nitrogen;
B is sulphur;
$X_3$ is oxygen;
$R_1$ is hydrogen;
$R_2$ is hydrogen;
$R_4$ is hydrogen; and $R_3$ is $R_x$, where $R_x$ has the following formula X:

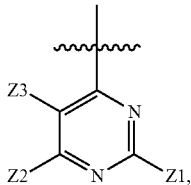

formula X wherein $Z_1$, $Z_2$ and $Z_3$ of formula X are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_qH$, —$C(O)_qZ_6$, or —O—$C(O)_qZ_6$;
(5) —$SO_3H$, —$S(O)_qZ_6$; or $S(O)_qN(Z_9)Z_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$-$Z_6$;
(12) —$Z_4$—$N(Z_{10})$—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_r$—O—, where r is 1 to 5, completing a 4- to 8-membered saturated or unsaturated ring together with the atoms to which they are attached.

2. The method of claim 1, wherein the amount of TNF exposed to the cancer cells in the subject is increased.

3. The method of claim 1, wherein: (i) TNF or an agonist of TNFR1-signalling is administered to the subject; (ii) an agent that is capable of inducing or induces the exposure of the cancer cells to TNF or an agonist of TNFR1-signalling, is administered to the subject; or (iii) the exposure of the cancer cells to TNF is induced by a pharmaceutical or therapeutic procedure that increases the amount of TNF in the plasma of the subject and/or in the environment of the cells.

4. The method of claim 3, wherein the agent that is capable of inducing or induces the exposure of the cancer cells to TNF or an agonist of TNFR1-signalling is a T-cell modified to alter the specificity of a T-cell receptor, or is a T-cell modified to introduce an antibody-like recognition in a chimeric antigen receptor.

5. The method of claim 1, wherein, in formula X:
$Z_1$ is methyl;
$Z_2$ is —$Z_4$—$NZ_7Z_8$, —$Z_4$—$N(Z_9)$—$Z_5$—$NZ_7Z_8$ or $Z_4$—$N(Z_{10})$—$Z_5$—H;

wherein $Z_4$ and $Z_5$ are each independently:
(1) a single bond;
(2) —$Z_{11}$—$S(O)_q$—$Z_{12}$—;
(3) —$Z_{11}$—C(O)—$Z_{12}$;
(4) —$Z_{11}$—C(S)—$Z_{12}$—;
(5) —$Z_{11}$—O—$Z_{12}$—;
(6) —$Z_{11}$—S—$Z_{12}$—;
(7) —$Z_{11}$—O—C(O)—$Z_{12}$; or
(8) —$Z_{11}$—C(O)—O—$Z_{12}$—,
in particular where $Z_4$ is a single bond;
wherein $Z_7$, $Z_8$, $Z_9$ and $Z_{10}$:
(1) are each independently hydrogen or $Z_6$;
(2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$, or
(3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$; and
$Z_3$ is hydrogen.

6. The method of claim 1, wherein: $Z_2$ in formula X is a substituent selected from the group consisting of:

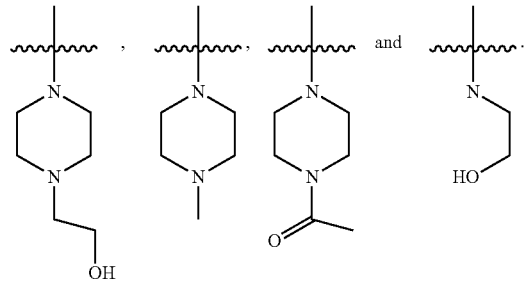

7. The method of claim 1, wherein $R_4$ of formula II is hydrogen and $R_5$ of formula II is $R_6$, where $R_6$ is alkyl, alkenyl, alkynyl, cycloalkyl, cycloalkylalkyl, cycloalkenyl, cycloalkenylalkyl, aryl, aralkyl, heterocyclo, heteroaryl or heterocycloalkyl, each of which is unsubstituted or substituted with $Z_1$, $Z_2$ and one, two or more groups $Z_3$; wherein $Z_1$, $Z_2$ and $Z_3$ are
each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_qH$, —$C(O)_qZ_6$, or —O—$C(O)_qZ_6$;
(5) —$SO_3H$, —$S(O)_qZ_6$; or $S(O)_qN(Z_9)Z_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$-$Z_6$;
(12) —$Z_4$—$N(Z_{10})$—$Z_5$—H;
(13) oxo;

(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_r$—O—, where r is 1 to 5, completing a 4- to 8-membered saturated or unsaturated ring together with the atoms to which they are attached.

8. The method of claim 7, wherein $R_6$ is aryl or heteroaryl, each of which is unsubstituted or substituted with $Z_1$, $Z_2$ and one, two or more groups $Z_3$; wherein $Z_1$, $Z_2$ and $Z_3$ are each independently:
(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
(2) —OH or —$OZ_6$;
(3) —SH or —$SZ_6$;
(4) —$C(O)_qH$, —$C(O)_qZ_6$, or —O—$C(O)_qZ_6$;
(5) —$SO_3H$, —$S(O)_qZ_6$; or $S(O)_qN(Z_9)Z_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$-$Z_6$;
(12) —$Z_4$—$N(Z_{10})$—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_r$—O—, where r is 1 to 5, completing a 4- to 8-membered saturated or unsaturated ring together with the atoms to which they are attached,
and wherein $R_6$ is a monocyclic aryl or heteroaryl substituted with one, two or three Zx, with at least one Zx at an ortho-position on the monocyclic aryl or heteroaryl; wherein each Zx may be, independently: (i) Zy, where Zy is a $C_1$, $C_2$ or $C_3$ alkyl, alkenyl or alkynyl; (ii) —OH or —OZy; (iii) —SH or —SZy; (iv) halo; or (v) —$SO_2$-Zy or —$SO_2$—N—(Zy) (Zy).

9. The method of claim 8, wherein $R_6$ is phenyl, optionally substituted with one, two or three Zx; in particular where one Zx is substituted at the ortho position of the phenyl; and/or in particular where each Zx is independently selected from the group consisting of: —Cl, —F, —Br, —Me, —OMe, —OEt and —CN.

10. The method of claim 8, wherein the $R_6$ is a monocyclic heteroaryl.

11. The method of claim 10, wherein the monocyclic heteroaryl $R_6$ is a pyridinyl, where the monocyclic heteroaryl is optionally substituted with one, two or three Zx; in particular where one Zx is substituted at the ortho position of the pyridinyl; and/or in particular where each Zx is independently selected from the group consisting of: —Cl, —F, —Br, —Me, —OMe, —OEt and —CN.

12. The method of claim 10, wherein the cyclic compound comprises a compound selected from solvates, salts, stereoisomers, complexes, polymorphs, crystalline forms, tautomers, isotopically labelled forms, prodrugs, or combinations thereof.

13. The method of claim 12, wherein the stereoisomer is a racemic mixture, a diastereomer, or an enantiomer.

14. The method of claim 1, wherein when, in general formula II, n is 1, A is nitrogen, B is sulphur, $X_3$ is oxygen, $R_1$ is hydrogen, $R_2$ is hydrogen, $R_4$ is hydrogen, $R_5$ is $R_6$ and $R_6$ is:
a phenyl substituted at an ortho position with a —Cl, then either (x) the other ortho position is hydrogen, or a Zx that is not methyl, in particular a Zx that is —Cl, —F, —Br, —OMe, —OEt, or —CN, and at least one of the meta or the para positions is substituted with Zx that is —Cl, —F, —Br, —OMe, —OEt, or —CN; or (y) the other ortho position is methyl and at least two of the meta or para positions are substituted with Zx; or (z) $R_3$ is not formula Y, wherein formula Y is as follows:

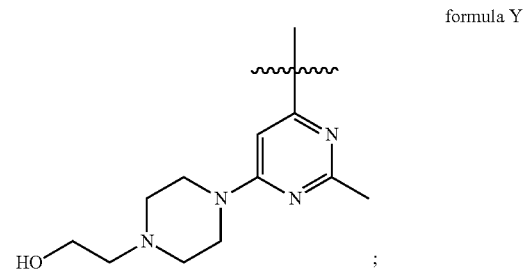 [SMILES: *c1cc(N2CCN(CCO)CC2)nc(C)n1]

formula Y or
a phenyl substituted at an ortho position with a methyl, then either (x) the other ortho position is hydrogen, or a Zx that is not —Cl, in particular a Zx that is —F, —Br, —Me, —OMe, —OEt or —CN, and at least one of the meta or the para positions is substituted with Zx that is —Cl, —F, —Br, —OMe, —OEt, or —CN; or (y) the other ortho position is —Cl and at least two of the meta or para positions are substituted with Zx; or (z) R3 is not formula Y, wherein formula Y is as follows:

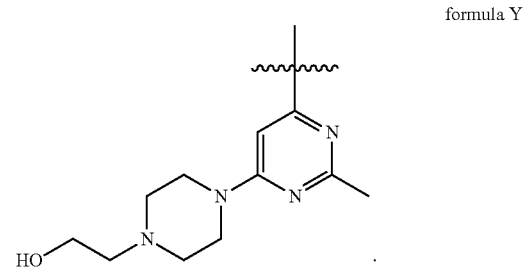 [SMILES: *c1cc(N2CCN(CCO)CC2)nc(C)n1]

formula Y

15. The method of claim 1, wherein the SIK3 inhibitor is the small molecule and the small molecule comprises a cyclic compound selected from the group consisting of:

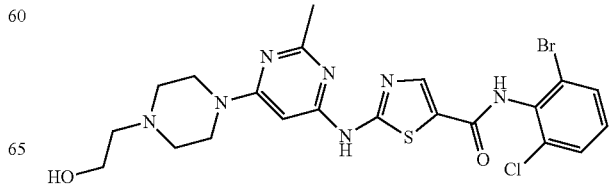

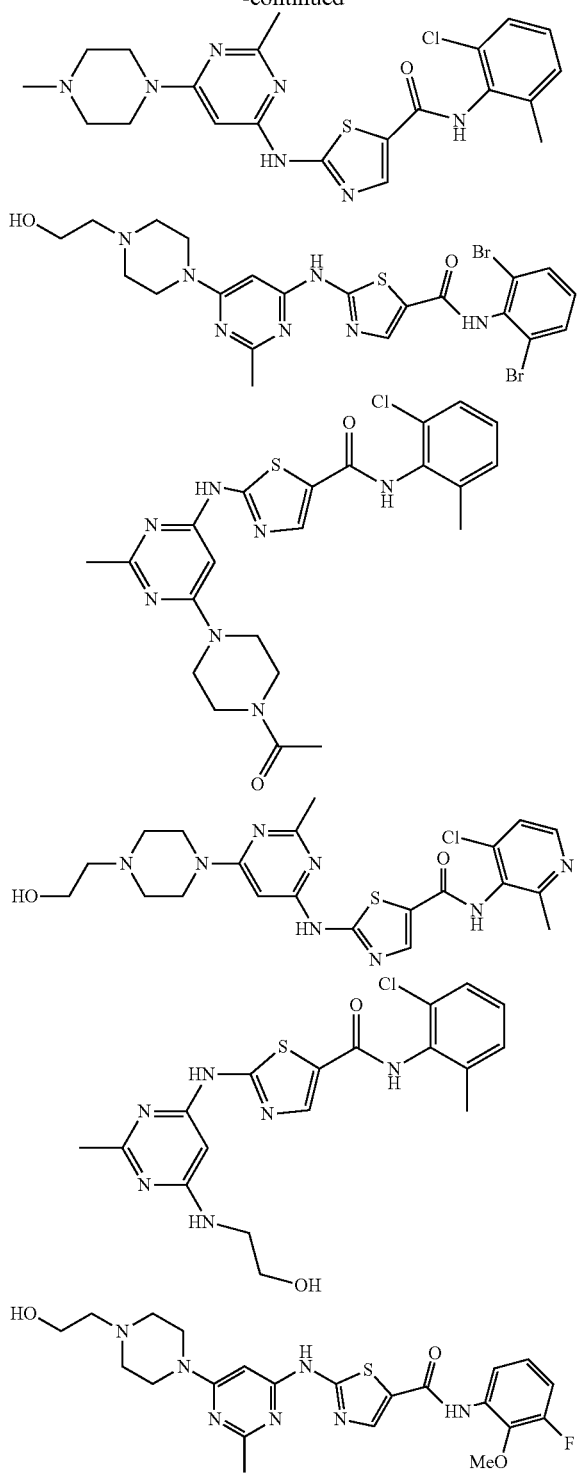

and solvates, salts, complexes, stereoisomers, polymorphs, crystalline forms tautomers, isotopically labelled forms, prodrugs, and combinations thereof.

16. The method of claim 15, wherein the stereoisomer is a racemic mixture, a diastereomer, or an enantiomer.

17. The method of claim 1, wherein the SIK3 inhibitor is the small molecule and the small molecule comprises the cyclic compound:

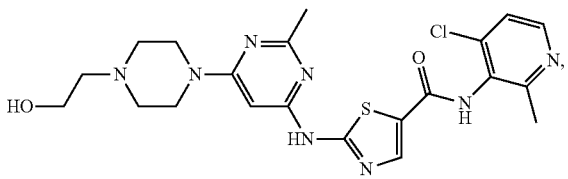

and solvates, salts, stereoisomers, complexes, polymorphs, crystalline forms tautomers, isotopically labelled forms, prodrugs, and combinations thereof;
or
wherein the SIK3 inhibitor is the small molecule and the small molecule comprises a cyclic compound:

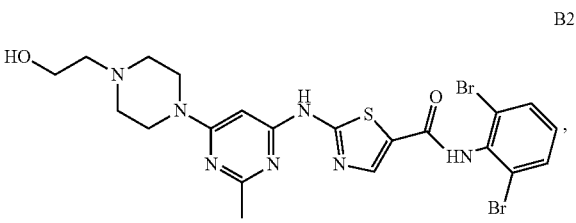 [SMILES: Cc1nc(Nc2ncc(C(=O)Nc3c(Br)cccc3Br)s2)cc(N2CCN(CCO)CC2)n1]

and solvates, salts, stereoisomers, complexes, polymorphs, crystalline forms, tautomers, isotopically labelled forms, prodrugs, and combinations thereof;
or
wherein the SIK3 inhibitor is the small molecule and the small molecule comprises a cyclic compound:

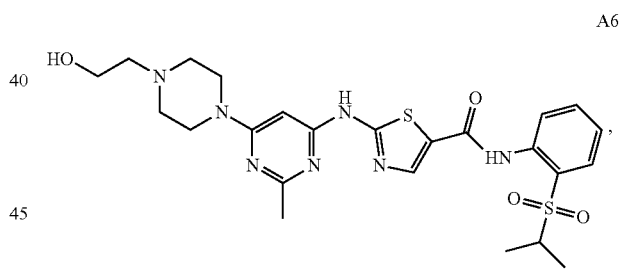

and solvates, salts, stereoisomers, complexes, polymorphs, crystalline forms, tautomers, isotopically labelled forms, prodrugs, and combinations thereof.

18. The method of claim 17, wherein the stereoisomer is a racemic mixture, a diastereomer, or an enantiomer.

19. The method of claim 17, wherein the SIK3 inhibitor inhibits SIK2 more potently than SIK3 and inhibits SIK3 more potently than SIK1.

20. The method of claim 1, wherein the cancer is a pancreatic cancer, a colorectal cancer or a breast cancer.

21. The method of claim 1, wherein the SIK3 inhibitor comprises an inhibitory nucleic acid that specifically targets a nucleic acid encoding SIK3 or is complementary to a SIK3 mRNA.

22. The method of claim 21, wherein the SIK3 inhibitor comprises an siRNA, an shRNA or an antisense molecule.

23. The method of claim 1, wherein the exposure of the cancer cells to TNF is induced by a pharmaceutical or therapeutic procedure that increases the amount of TNF in the plasma of the subject and/or in the environment of the cells.

24. The method of claim 23, wherein the pharmaceutical or therapeutic procedure comprises immunotherapy.

25. The method of claim 23, wherein the pharmaceutical or therapeutic procedure comprises radiotherapy.

26. The method of claim 1, wherein an agent that is capable of inducing or induces the exposure of the cancer cells to TNF or an agonist of TNFR1-signalling, is administered to the subject.

27. The method of claim 26, wherein the agent is a virus that is capable of inducing or induces the exposure of the cancer cells to the TNF or the agonist of TNFR1-signalling.

28. The method of claim 26, wherein the agent is an immune cell.

29. The method of claim 28, wherein the immune cell is administered as part of adoptive cell transfer.

30. The method of claim 1, wherein: $Z_2$ in formula X is the substituent:

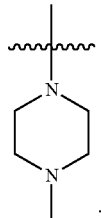

31. The method of claim 1, wherein $R_4$ of formula II is hydrogen and $R_5$ of formula II is $R_6$, where $R_6$ is a monocyclic heteroaryl which is unsubstituted or substituted with $Z_1$, $Z_2$ and one, two or more groups $Z_3$; wherein $Z_1$, $Z_2$ and $Z_3$ are each independently:

(1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;

(2) —OH or —$OZ_6$;
(3) —SH or —$SZ_6$;
(4) —$C(O)_qH$, —$C(O)_qZ_6$, or —O—$C(O)_qZ_6$;
(5) —$SO_3H$, —$S(O)_qZ_6$; or $S(O)_qN(Z_9)Z_6$;
(6) halo;
(7) cyano;
(8) nitro;
(9) —$Z_4$—$NZ_7Z_8$;
(10) —$Z_4$—$N(Z_9)$—$Z_5$—$NZ_7Z_8$;
(11) —$Z_4$—$N(Z_{10})$—$Z_5$-$Z_6$;
(12) —$Z_4$—$N(Z_{10})$—$Z_5$—H;
(13) oxo;
(14) —O—C(O)—$Z_6$;
(15) any two of $Z_1$, $Z_2$, and $Z_3$ may together be alkylene or alkenylene completing a 3- to 8-membered saturated or unsaturated ring together with the atoms to which they are attached; or
(16) any two of $Z_1$, $Z_2$, and $Z_3$ may together be —O—$(CH_2)_r$—O—, where r is 1 to 5, completing a 4- to 8-membered saturated or unsaturated ring together with the atoms to which they are attached.

32. The method of claim 31, wherein $R_6$ is a monocyclic heteroaryl, wherein each of $Z_1$ and $Z_2$ is hydrogen, and wherein the monocyclic heteroaryl is substituted with two $Z_3$, wherein at least one $Z_3$ is Cl substituted at an ortho position on the monocyclic heteroaryl.

33. A method of treating cancer in a subject, the treatment comprising exposing cancer cells in a solid tumor within the subject to Tumor Necrosis Factor (TNF) and/or an agonist of TNFR1-signalling and inhibiting SIK3 in the solid tumor cancer cells, wherein the cancer cells express SIK3 and are resistant to an anti-tumor immune response and wherein inhibiting SIK3 in the solid tumor cancer cells comprises:
(i) administering a therapeutically effective amount of a SIK3 inhibitor effective to directly inhibit the SIK3 in the cancer cells, wherein the SIK3 inhibitor comprises an inhibitory nucleic acid that specifically targets expression of a nucleic acid encoding SIK3 or is complementary to a SIK3 mRNA.

* * * * *

SEQUENCE LISTING

<160> NUMBER OF SEQ ID NOS: 16

<210> SEQ ID NO 1
<211> LENGTH: 1263
<212> TYPE: PRT
<213> ORGANISM: Homo sapiens

<400> SEQUENCE: 1

```
Met Pro Ala Arg Ile Gly Tyr Tyr Glu Ile Asp Arg Thr Ile Gly Lys
1               5                   10                  15

Gly Asn Phe Ala Val Val Lys Arg Ala Thr His Leu Val Thr Lys Ala
            20                  25                  30

Lys Val Ala Ile Lys Ile Ile Asp Lys Thr Gln Leu Asp Glu Glu Asn
        35                  40                  45

Leu Lys Lys Ile Phe Arg Glu Val Gln Ile Met Lys Met Leu Cys His
    50                  55                  60

Pro His Ile Ile Arg Leu Tyr Gln Val Met Glu Thr Glu Arg Met Ile
65                  70                  75                  80

Tyr Leu Val Thr Glu Tyr Ala Ser Gly Gly Glu Ile Phe Asp His Leu
                85                  90                  95

Val Ala His Gly Arg Met Ala Glu Lys Glu Ala Arg Arg Lys Phe Lys
            100                 105                 110

Gln Ile Val Thr Ala Val Tyr Phe Cys His Cys Arg Asn Ile Val His
        115                 120                 125

Arg Asp Leu Lys Ala Glu Asn Leu Leu Leu Asp Ala Asn Leu Asn Ile
    130                 135                 140

Lys Ile Ala Asp Phe Gly Phe Ser Asn Leu Phe Thr Pro Gly Gln Leu
145                 150                 155                 160

Leu Lys Thr Trp Cys Gly Ser Pro Pro Tyr Ala Ala Pro Glu Leu Phe
                165                 170                 175

Glu Gly Lys Glu Tyr Asp Gly Pro Lys Val Asp Ile Trp Ser Leu Gly
            180                 185                 190

Val Val Leu Tyr Val Leu Val Cys Gly Ala Leu Pro Phe Asp Gly Ser
        195                 200                 205

Thr Leu Gln Asn Leu Arg Ala Arg Val Leu Ser Gly Lys Phe Arg Ile
    210                 215                 220
```

-continued

```
Pro Phe Phe Met Ser Thr Glu Cys Glu His Leu Ile Arg His Met Leu
225                 230                 235                 240

Val Leu Asp Pro Asn Lys Arg Leu Ser Met Glu Gln Ile Cys Lys His
            245                 250                 255

Lys Trp Met Lys Leu Gly Asp Ala Asp Pro Asn Phe Asp Arg Leu Ile
        260                 265                 270

Ala Glu Cys Gln Gln Leu Lys Glu Glu Arg Gln Val Asp Pro Leu Asn
    275                 280                 285

Glu Asp Val Leu Leu Ala Met Glu Asp Met Gly Leu Asp Lys Glu Gln
290                 295                 300

Thr Leu Gln Ser Leu Arg Ser Asp Ala Tyr Asp His Tyr Ser Ala Ile
305                 310                 315                 320

Tyr Ser Leu Leu Cys Asp Arg His Lys Arg His Lys Thr Leu Arg Leu
            325                 330                 335

Gly Ala Leu Pro Ser Met Pro Arg Ala Leu Ala Phe Gln Ala Pro Val
        340                 345                 350

Asn Ile Gln Ala Glu Gln Ala Gly Thr Ala Met Asn Ile Ser Val Pro
    355                 360                 365

Gln Val Gln Leu Ile Asn Pro Glu Asn Gln Ile Val Glu Pro Asp Gly
370                 375                 380

Thr Leu Asn Leu Asp Ser Asp Glu Gly Glu Glu Pro Ser Pro Glu Ala
385                 390                 395                 400

Leu Val Arg Tyr Leu Ser Met Arg Arg His Thr Val Gly Val Ala Asp
            405                 410                 415

Pro Arg Thr Glu Val Met Glu Asp Leu Gln Lys Leu Leu Pro Gly Phe
        420                 425                 430

Pro Gly Val Asn Pro Gln Ala Pro Phe Leu Gln Val Ala Pro Asn Val
    435                 440                 445

Asn Phe Met His Asn Leu Leu Pro Met Gln Asn Leu Gln Pro Thr Gly
450                 455                 460

Gln Leu Glu Tyr Lys Glu Gln Ser Leu Leu Gln Pro Pro Thr Leu Gln
465                 470                 475                 480

Leu Leu Asn Gly Met Gly Pro Leu Gly Arg Arg Ala Ser Asp Gly Gly
            485                 490                 495

Ala Asn Ile Gln Leu His Ala Gln Gln Leu Leu Lys Arg Pro Arg Gly
        500                 505                 510

Pro Ser Pro Leu Val Thr Met Thr Pro Ala Val Pro Ala Val Thr Pro
    515                 520                 525

Val Asp Glu Glu Ser Ser Asp Gly Glu Pro Asp Gln Glu Ala Val Gln
530                 535                 540

Ser Ser Thr Tyr Lys Asp Ser Asn Thr Leu His Leu Pro Thr Glu Arg
545                 550                 555                 560

Phe Ser Pro Val Arg Arg Phe Ser Asp Gly Ala Ala Ser Ile Gln Ala
            565                 570                 575

Phe Lys Ala His Leu Glu Lys Met Gly Asn Asn Ser Ser Ile Lys Gln
        580                 585                 590

Leu Gln Gln Glu Cys Glu Gln Leu Gln Lys Met Tyr Gly Gly Gln Ile
    595                 600                 605

Asp Glu Arg Thr Leu Glu Lys Thr Gln Gln His Met Leu Tyr Gln
610                 615                 620

Gln Glu Gln His His Gln Ile Leu Gln Gln Ile Gln Asp Ser Ile
625                 630                 635                 640
```

-continued

```
Cys Pro Pro Gln Pro Ser Pro Leu Gln Ala Ala Cys Glu Asn Gln
            645                 650                 655

Pro Ala Leu Leu Thr His Gln Leu Gln Arg Leu Arg Ile Gln Pro Ser
        660                 665                 670

Ser Pro Pro Asn His Pro Asn Asn His Leu Phe Arg Gln Pro Ser
    675                 680                 685

Asn Ser Pro Pro Pro Met Ser Ser Ala Met Ile Gln Pro His Gly Ala
690                 695                 700

Ala Ser Ser Ser Gln Phe Gln Gly Leu Pro Ser Arg Ser Ala Ile Phe
705                 710                 715                 720

Gln Gln Gln Pro Glu Asn Cys Ser Ser Pro Pro Asn Val Ala Leu Thr
                725                 730                 735

Cys Leu Gly Met Gln Gln Pro Ala Gln Ser Gln Gln Val Thr Ile Gln
            740                 745                 750

Val Gln Glu Pro Val Asp Met Leu Ser Asn Met Pro Gly Thr Ala Ala
        755                 760                 765

Gly Ser Ser Gly Arg Gly Ile Ser Ile Ser Pro Ser Ala Gly Gln Met
    770                 775                 780

Gln Met Gln His Arg Thr Asn Leu Met Ala Thr Leu Ser Tyr Gly His
785                 790                 795                 800

Arg Pro Leu Ser Lys Gln Leu Ser Ala Asp Ser Ala Glu Ala His Ser
                805                 810                 815

Leu Asn Val Asn Arg Phe Ser Pro Ala Asn Tyr Asp Gln Ala His Leu
            820                 825                 830

His Pro His Leu Phe Ser Asp Gln Ser Arg Gly Ser Pro Ser Ser Tyr
        835                 840                 845

Ser Pro Ser Thr Gly Val Gly Phe Ser Pro Thr Gln Ala Leu Lys Val
    850                 855                 860

Pro Pro Leu Asp Gln Phe Pro Thr Phe Pro Ser Ala His Gln Gln
865                 870                 875                 880

Pro Pro His Tyr Thr Thr Ser Ala Leu Gln Gln Ala Leu Leu Ser Pro
                885                 890                 895

Thr Pro Pro Asp Tyr Thr Arg His Gln Gln Val Pro His Ile Leu Gln
            900                 905                 910

Gly Leu Leu Ser Pro Arg His Ser Leu Thr Gly His Ser Asp Ile Arg
        915                 920                 925

Leu Pro Pro Thr Glu Phe Ala Gln Leu Ile Lys Arg Gln Gln Gln Gln
    930                 935                 940

Arg Gln Gln Gln Gln Gln Gln Gln Gln Gln Glu Tyr Gln Glu Leu
945                 950                 955                 960

Phe Arg His Met Asn Gln Gly Asp Ala Gly Ser Leu Ala Pro Ser Leu
                965                 970                 975

Gly Gly Gln Ser Met Thr Glu Arg Gln Ala Leu Ser Tyr Gln Asn Ala
            980                 985                 990

Asp Ser Tyr His His His Thr Ser  Pro Gln His Leu Leu  Gln Ile Arg
        995                 1000                1005

Ala Gln  Glu Cys Val Ser Gln  Ala Ser Pro Thr  Pro Pro His
        1010                1015                1020

Gly Tyr  Ala His Gln Pro Ala  Leu Met His Ser Glu  Ser Met Glu
        1025                1030                1035

Glu Asp  Cys Ser Cys Glu Gly  Ala Lys Asp Gly Phe  Gln Asp Ser
        1040                1045                1050
```

```
Lys Ser Ser Ser Thr Leu Thr Lys Gly Cys His Asp Ser Pro Leu
    1055                1060                1065

Leu Leu Ser Thr Gly Gly Pro Gly Asp Pro Glu Ser Leu Leu Gly
    1070                1075                1080

Thr Val Ser His Ala Gln Glu Leu Gly Ile His Pro Tyr Gly His
    1085                1090                1095

Gln Pro Thr Ala Ala Phe Ser Lys Asn Lys Val Pro Ser Arg Glu
    1100                1105                1110

Pro Val Ile Gly Asn Cys Met Asp Arg Ser Ser Pro Gly Gln Ala
    1115                1120                1125

Val Glu Leu Pro Asp His Asn Gly Leu Gly Tyr Pro Ala Arg Pro
    1130                1135                1140

Ser Val His Glu His His Arg Pro Arg Ala Leu Gln Arg His His
    1145                1150                1155

Thr Ile Gln Asn Ser Asp Asp Ala Tyr Val Gln Leu Asp Asn Leu
    1160                1165                1170

Pro Gly Met Ser Leu Val Ala Gly Lys Ala Leu Ser Ser Ala Arg
    1175                1180                1185

Met Ser Asp Ala Val Leu Ser Gln Ser Ser Leu Met Gly Ser Gln
    1190                1195                1200

Gln Phe Gln Asp Gly Glu Asn Glu Glu Cys Gly Ala Ser Leu Gly
    1205                1210                1215

Gly His Glu His Pro Asp Leu Ser Asp Gly Ser Gln His Leu Asn
    1220                1225                1230

Ser Ser Cys Tyr Pro Ser Thr Cys Ile Thr Asp Ile Leu Leu Ser
    1235                1240                1245

Tyr Lys His Pro Glu Val Ser Phe Ser Met Glu Gln Ala Gly Val
    1250                1255                1260

<210> SEQ ID NO 2
<211> LENGTH: 598
<212> TYPE: PRT
<213> ORGANISM: Homo sapiens

<400> SEQUENCE: 2

Met Gly Leu Arg Ala Ser Arg Pro Ser Lys Leu Thr Trp Lys Lys Trp
1               5                   10                  15

Ala Thr Thr Ala Ala Ser Asn Ser Cys Ser Arg Ser Val Ser Ser Cys
                20                  25                  30

Arg Arg Cys Thr Gly Gly Arg Leu Met Lys Glu Pro Trp Arg Arg Pro
            35                  40                  45

Ser Ser Ser Ile Cys Tyr Thr Ser Arg Ser Ser Thr Ile Lys Phe Ser
        50                  55                  60

Ser Asn Lys Phe Lys Thr Leu Ser Val Leu Leu Ser His Leu His Leu
65                  70                  75                  80

Phe Arg Leu His Val Lys Ile Ser Gln Pro Ser Leu Pro Ile Ser Ser
                85                  90                  95

Arg Gly Ala Ala Ser Ser Ser Gln Phe Gln Gly Leu Pro Ser Arg Ser
            100                 105                 110

Ala Ile Phe Gln Gln Gln Pro Glu Asn Cys Ser Ser Pro Pro Asn Val
        115                 120                 125

Ala Leu Thr Cys Leu Gly Met Gln Gln Pro Ala Gln Ser Gln Gln Val
    130                 135                 140
```

```
Thr Ile Gln Val Gln Glu Pro Val Asp Met Leu Ser Asn Met Pro Gly
145                 150                 155                 160

Thr Ala Ala Gly Ser Ser Gly Arg Gly Ile Ser Ile Ser Pro Ser Ala
            165                 170                 175

Gly Gln Met Gln Met Gln His Arg Thr Asn Leu Met Ala Thr Leu Ser
        180                 185                 190

Tyr Gly His Arg Pro Leu Ser Lys Gln Leu Ser Ala Asp Ser Ala Glu
    195                 200                 205

Ala His Ser Ala His Gln Gln Pro His Tyr Thr Thr Ser Ala Leu
210                 215                 220

Gln Gln Ala Leu Leu Ser Pro Thr Pro Asp Tyr Thr Arg His Gln
225                 230                 235                 240

Gln Val Pro His Ile Leu Gln Gly Leu Leu Ser Pro Arg His Ser Leu
            245                 250                 255

Thr Gly His Ser Asp Ile Arg Leu Pro Pro Thr Glu Phe Ala Gln Leu
            260                 265                 270

Ile Lys Arg Gln Gln Gln Gln Arg Gln Gln Gln Gln Gln Gln Gln Gln
        275                 280                 285

Gln Gln Glu Tyr Gln Glu Leu Phe Arg His Met Asn Gln Gly Asp Ala
290                 295                 300

Gly Ser Leu Ala Pro Ser Leu Gly Gly Gln Ser Met Thr Glu Arg Gln
305                 310                 315                 320

Ala Leu Ser Tyr Gln Asn Ala Asp Ser Tyr His His His Thr Ser Pro
            325                 330                 335

Gln His Leu Leu Gln Ile Arg Ala Gln Glu Cys Val Ser Gln Ala Ser
            340                 345                 350

Ser Pro Thr Pro Pro His Gly Tyr Ala His Gln Pro Ala Leu Met His
            355                 360                 365

Ser Glu Ser Met Glu Glu Asp Cys Ser Cys Glu Gly Ala Lys Asp Gly
        370                 375                 380

Phe Gln Asp Ser Lys Ser Ser Thr Leu Thr Lys Gly Cys His Asp
385                 390                 395                 400

Ser Pro Leu Leu Leu Ser Thr Gly Gly Pro Gly Asp Pro Glu Ser Leu
            405                 410                 415

Leu Gly Thr Val Ser His Ala Gln Glu Leu Gly Ile His Pro Tyr Gly
            420                 425                 430

His Gln Pro Thr Ala Ala Phe Ser Lys Asn Lys Val Pro Ser Arg Glu
        435                 440                 445

Pro Val Ile Gly Asn Cys Met Asp Arg Ser Ser Pro Gly Gln Ala Val
        450                 455                 460

Glu Leu Pro Asp His Asn Gly Leu Gly Tyr Pro Ala Arg Pro Ser Val
465                 470                 475                 480

His Glu His His Arg Pro Arg Ala Leu Gln Arg His His Thr Ile Gln
            485                 490                 495

Asn Ser Asp Asp Ala Tyr Val Gln Leu Asp Asn Leu Pro Gly Met Ser
            500                 505                 510

Leu Val Ala Gly Lys Ala Leu Ser Ser Ala Arg Met Ser Asp Ala Val
            515                 520                 525

Leu Ser Gln Ser Ser Leu Met Gly Ser Gln Gln Phe Gln Asp Gly Glu
            530                 535                 540

Asn Glu Glu Cys Gly Ala Ser Leu Gly Gly His Glu His Pro Asp Leu
545                 550                 555                 560
```

```
Ser Asp Gly Ser Gln His Leu Asn Ser Ser Cys Tyr Pro Ser Thr Cys
                565                 570                 575

Ile Thr Asp Ile Leu Leu Ser Tyr Lys His Pro Glu Val Ser Phe Ser
            580                 585                 590

Met Glu Gln Ala Gly Val
        595

<210> SEQ ID NO 3
<211> LENGTH: 1129
<212> TYPE: PRT
<213> ORGANISM: Homo sapiens

<400> SEQUENCE: 3

Met Pro Ala Arg Ile Gly Tyr Tyr Glu Ile Asp Arg Thr Ile Gly Lys
1               5                   10                  15

Gly Asn Phe Ala Val Val Lys Arg Ala Thr His Leu Val Thr Lys Ala
            20                  25                  30

Lys Val Ala Ile Lys Ile Ile Asp Lys Thr Gln Leu Asp Glu Glu Asn
        35                  40                  45

Leu Lys Lys Ile Phe Arg Glu Val Gln Ile Met Lys Met Leu Cys His
    50                  55                  60

Pro His Ile Ile Arg Leu Tyr Gln Val Met Glu Thr Glu Arg Met Ile
65                  70                  75                  80

Tyr Leu Val Thr Glu Tyr Ala Ser Gly Gly Glu Ile Phe Asp His Leu
                85                  90                  95

Val Ala His Gly Arg Met Ala Glu Lys Glu Ala Arg Arg Lys Phe Lys
            100                 105                 110

Gln Ile Val Thr Ala Val Tyr Phe Cys His Cys Arg Asn Ile Val His
        115                 120                 125

Arg Asp Leu Lys Ala Glu Asn Leu Leu Leu Asp Ala Asn Leu Asn Ile
    130                 135                 140

Lys Ile Ala Asp Phe Gly Phe Ser Asn Leu Phe Thr Pro Gly Gln Leu
145                 150                 155                 160

Leu Lys Thr Trp Cys Gly Ser Pro Pro Tyr Ala Ala Pro Glu Leu Phe
                165                 170                 175

Glu Gly Lys Glu Tyr Asp Gly Pro Lys Val Asp Ile Trp Ser Leu Gly
            180                 185                 190

Val Val Leu Tyr Val Leu Val Cys Gly Ala Leu Pro Phe Asp Gly Ser
        195                 200                 205

Thr Leu Gln Asn Leu Arg Ala Arg Val Leu Ser Gly Lys Phe Arg Ile
    210                 215                 220

Pro Phe Phe Met Ser Thr Glu Cys Glu His Leu Ile Arg His Met Leu
225                 230                 235                 240

Val Leu Asp Pro Asn Lys Arg Leu Ser Met Glu Gln Ile Cys Lys His
                245                 250                 255

Lys Trp Met Lys Leu Gly Asp Ala Asp Pro Asn Phe Asp Arg Leu Ile
            260                 265                 270

Ala Glu Cys Gln Gln Leu Lys Glu Glu Arg Gln Val Asp Pro Leu Asn
        275                 280                 285

Glu Asp Val Leu Leu Ala Met Glu Asp Met Gly Leu Asp Lys Glu Gln
    290                 295                 300

Thr Leu Gln Ser Leu Arg Ser Asp Ala Tyr Asp His Tyr Ser Ala Ile
305                 310                 315                 320

Tyr Ser Leu Leu Cys Asp Arg His Lys Arg His Lys Thr Leu Arg Leu
                325                 330                 335
```

Gly Ala Leu Pro Ser Met Pro Arg Ala Leu Ala Phe Gln Ala Pro Val
            340                 345                 350

Asn Ile Gln Ala Glu Gln Ala Gly Thr Ala Met Asn Ile Ser Val Pro
        355                 360                 365

Gln Val Gln Leu Ile Asn Pro Glu Asn Gln Ile Val Glu Pro Asp Gly
370                 375                 380

Thr Leu Asn Leu Asp Ser Asp Glu Gly Glu Glu Pro Ser Pro Glu Ala
385                 390                 395                 400

Leu Val Arg Tyr Leu Ser Met Arg Arg His Thr Val Gly Val Ala Asp
                405                 410                 415

Pro Arg Thr Glu Val Met Glu Asp Leu Gln Lys Leu Leu Pro Gly Phe
            420                 425                 430

Pro Gly Val Asn Pro Gln Ala Pro Phe Leu Gln Val Ala Pro Asn Val
        435                 440                 445

Asn Phe Met His Asn Leu Leu Pro Met Gln Asn Leu Gln Pro Thr Gly
    450                 455                 460

Gln Leu Glu Tyr Lys Glu Gln Ser Leu Leu Gln Pro Pro Thr Leu Gln
465                 470                 475                 480

Leu Leu Asn Gly Met Gly Pro Leu Gly Arg Arg Ala Ser Asp Gly Gly
                485                 490                 495

Ala Asn Ile Gln Leu His Ala Gln Gln Leu Leu Lys Arg Pro Arg Gly
            500                 505                 510

Pro Ser Pro Leu Val Thr Met Thr Pro Ala Val Pro Ala Val Thr Pro
        515                 520                 525

Val Asp Glu Glu Ser Ser Asp Gly Glu Pro Asp Gln Glu Ala Val Gln
    530                 535                 540

Ser Ser Thr Tyr Lys Asp Ser Asn Thr Leu His Leu Pro Thr Glu Arg
545                 550                 555                 560

Phe Ser Pro Val Arg Arg Phe Ser Asp Gly Ala Ala Ser Ile Gln Ala
                565                 570                 575

Phe Lys Ala His Leu Glu Lys Met Gly Asn Asn Ser Ser Ile Lys Gln
            580                 585                 590

Leu Gln Gln Glu Cys Glu Gln Leu Gln Lys Met Tyr Gly Gly Gln Ile
        595                 600                 605

Asp Glu Arg Thr Leu Glu Lys Thr Gln Gln His Met Leu Tyr Gln
    610                 615                 620

Gln Glu Gln His His Gln Ile Leu Gln Gln Gln Ile Gln Asp Ser Ile
625                 630                 635                 640

Cys Pro Pro Gln Pro Ser Pro Leu Gln Ala Ala Cys Glu Asn Gln
                645                 650                 655

Pro Ala Leu Leu Thr His Gln Leu Gln Arg Leu Arg Ile Gln Pro Ser
            660                 665                 670

Ser Pro Pro Asn His Pro Asn Asn His Leu Phe Arg Gln Pro Ser
        675                 680                 685

Asn Ser Pro Pro Met Ser Ser Ala Met Ile Gln Pro His Gly Ala
    690                 695                 700

Ala Ser Ser Ser Gln Phe Gln Gly Leu Pro Ser Arg Ser Ala Ile Phe
705                 710                 715                 720

Gln Gln Gln Pro Glu Asn Cys Ser Ser Pro Asn Val Ala Leu Thr
                725                 730                 735

Cys Leu Gly Met Gln Gln Pro Ala Gln Ser Gln Val Thr Ile Gln
            740                 745                 750

-continued

Val Gln Glu Pro Val Asp Met Leu Ser Asn Met Pro Gly Thr Ala Ala
              755                 760                 765

Gly Ser Ser Gly Arg Gly Ile Ser Ile Ser Pro Ser Ala Gly Gln Met
    770                 775                 780

Gln Met Gln His Arg Thr Asn Leu Met Ala Thr Leu Ser Tyr Gly His
785                 790                 795                 800

Arg Pro Leu Ser Lys Gln Leu Ser Ala Asp Ser Ala Glu Ala His Ser
                805                 810                 815

Leu Asn Val Asn Arg Phe Ser Pro Ala Asn Tyr Asp Gln Ala His Leu
            820                 825                 830

His Pro His Leu Phe Ser Asp Gln Ser Arg Gly Ser Pro Ser Ser Tyr
        835                 840                 845

Ser Pro Ser Thr Gly Val Gly Phe Ser Pro Thr Gln Ala Leu Lys Val
    850                 855                 860

Pro Pro Leu Asp Gln Phe Pro Thr Phe Pro Ser Ala His Gln Gln
865                 870                 875                 880

Pro Pro His Tyr Thr Thr Ser Ala Leu Gln Gln Ala Leu Leu Ser Pro
                885                 890                 895

Thr Pro Pro Asp Tyr Thr Arg His Gln Gln Val Pro His Ile Leu Gln
            900                 905                 910

Gly Leu Leu Ser Pro Arg His Ser Leu Thr Gly His Ser Asp Ile Arg
        915                 920                 925

Leu Pro Pro Thr Glu Phe Ala Gln Leu Ile Lys Arg Gln Gln Gln Gln
    930                 935                 940

Arg Gln Gln Gln Gln Gln Gln Gln Gln Gln Glu Tyr Gln Glu Leu
945                 950                 955                 960

Phe Arg His Met Asn Gln Gly Asp Ala Gly Ser Leu Ala Pro Ser Leu
                965                 970                 975

Gly Gly Gln Ser Met Thr Glu Arg Gln Ala Leu Ser Tyr Gln Asn Ala
            980                 985                 990

Asp Ser Tyr His His His Thr Ser Pro Gln His Leu Leu Gln Ile Arg
        995                 1000                1005

Ala Gln Glu Cys Val Ser Gln Ala Ser Ser Pro Thr Pro Pro His
    1010                1015                1020

Gly Tyr Ala His Gln Pro Ala Leu Met His Ser Glu Ser Met Glu
    1025                1030                1035

Glu Asp Cys Ser Cys Glu Gly Ala Lys Asp Gly Phe Gln Asp Ser
    1040                1045                1050

Lys Ser Ser Ser Thr Leu Thr Lys Gly Cys His Asp Ser Pro Leu
    1055                1060                1065

Leu Leu Ser Thr Gly Gly Pro Gly Asp Pro Glu Ser Leu Leu Gly
    1070                1075                1080

Thr Val Ser His Ala Gln Glu Leu Gly Ile His Pro Tyr Gly His
    1085                1090                1095

Gln Pro Thr Ala Ala Phe Ser Lys Asn Lys Val Pro Ser Arg Gly
    1100                1105                1110

Lys Cys Leu Leu Thr Val Glu Val Leu Gly Gln Ser Ala Leu Ile
    1115                1120                1125

Asn

<210> SEQ ID NO 4
<211> LENGTH: 1203
<212> TYPE: PRT
<213> ORGANISM: Homo sapiens

<400> SEQUENCE: 4

| | | | | | | | | | | | | | | |
|---|---|---|---|---|---|---|---|---|---|---|---|---|---|---|
| Met | Pro | Ala | Arg | Ile | Gly | Tyr | Tyr | Glu | Ile | Asp | Arg | Thr | Ile | Gly | Lys |
| 1 | | | | 5 | | | | | 10 | | | | | 15 | |
| Gly | Asn | Phe | Ala | Val | Val | Lys | Arg | Ala | Thr | His | Leu | Val | Thr | Lys | Ala |
| | | | 20 | | | | | 25 | | | | | 30 | | |
| Lys | Val | Ala | Ile | Lys | Ile | Ile | Asp | Lys | Thr | Gln | Leu | Asp | Glu | Glu | Asn |
| | | | 35 | | | | 40 | | | | | 45 | | | |
| Leu | Lys | Lys | Ile | Phe | Arg | Glu | Val | Gln | Ile | Met | Lys | Met | Leu | Cys | His |
| | 50 | | | | | 55 | | | | | 60 | | | | |
| Pro | His | Ile | Ile | Arg | Leu | Tyr | Gln | Val | Met | Glu | Thr | Glu | Arg | Met | Ile |
| 65 | | | | | 70 | | | | | 75 | | | | | 80 |
| Tyr | Leu | Val | Thr | Glu | Tyr | Ala | Ser | Gly | Gly | Glu | Ile | Phe | Asp | His | Leu |
| | | | | 85 | | | | | 90 | | | | | 95 | |
| Val | Ala | His | Gly | Arg | Met | Ala | Glu | Lys | Glu | Ala | Arg | Arg | Lys | Phe | Lys |
| | | | 100 | | | | | 105 | | | | | 110 | | |
| Gln | Ile | Val | Thr | Ala | Val | Tyr | Phe | Cys | His | Cys | Arg | Asn | Ile | Val | His |
| | | | 115 | | | | | 120 | | | | | 125 | | |
| Arg | Asp | Leu | Lys | Ala | Glu | Asn | Leu | Leu | Leu | Asp | Ala | Asn | Leu | Asn | Ile |
| | 130 | | | | | 135 | | | | | 140 | | | | |
| Lys | Ile | Ala | Asp | Phe | Gly | Phe | Ser | Asn | Leu | Phe | Thr | Pro | Gly | Gln | Leu |
| 145 | | | | | 150 | | | | | 155 | | | | | 160 |
| Leu | Lys | Thr | Trp | Cys | Gly | Ser | Pro | Pro | Tyr | Ala | Ala | Pro | Glu | Leu | Phe |
| | | | | 165 | | | | | 170 | | | | | 175 | |
| Glu | Gly | Lys | Glu | Tyr | Asp | Gly | Pro | Lys | Val | Asp | Ile | Trp | Ser | Leu | Gly |
| | | | 180 | | | | | 185 | | | | | 190 | | |
| Val | Val | Leu | Tyr | Val | Leu | Val | Cys | Gly | Ala | Leu | Pro | Phe | Asp | Gly | Ser |
| | | | | 195 | | | | | 200 | | | | | 205 | |
| Thr | Leu | Gln | Asn | Leu | Arg | Ala | Arg | Val | Leu | Ser | Gly | Lys | Phe | Arg | Ile |
| | 210 | | | | | 215 | | | | | 220 | | | | |
| Pro | Phe | Phe | Met | Ser | Thr | Glu | Cys | Glu | His | Leu | Ile | Arg | His | Met | Leu |
| 225 | | | | | 230 | | | | | 235 | | | | | 240 |
| Val | Leu | Asp | Pro | Asn | Lys | Arg | Leu | Ser | Met | Glu | Gln | Ile | Cys | Lys | His |
| | | | | 245 | | | | | 250 | | | | | 255 | |
| Lys | Trp | Met | Lys | Leu | Gly | Asp | Ala | Asp | Pro | Asn | Phe | Asp | Arg | Leu | Ile |
| | | | 260 | | | | | 265 | | | | | 270 | | |
| Ala | Glu | Cys | Gln | Gln | Leu | Lys | Glu | Glu | Arg | Gln | Val | Asp | Pro | Leu | Asn |
| | | 275 | | | | | 280 | | | | | 285 | | | |
| Glu | Asp | Val | Leu | Leu | Ala | Met | Glu | Asp | Met | Gly | Leu | Asp | Lys | Glu | Gln |
| | 290 | | | | | 295 | | | | | 300 | | | | |
| Thr | Leu | Gln | Ala | Glu | Gln | Ala | Gly | Thr | Ala | Met | Asn | Ile | Ser | Val | Pro |
| 305 | | | | | 310 | | | | | 315 | | | | | 320 |
| Gln | Val | Gln | Leu | Ile | Asn | Pro | Glu | Asn | Gln | Ile | Val | Glu | Pro | Asp | Gly |
| | | | | 325 | | | | | 330 | | | | | 335 | |
| Thr | Leu | Asn | Leu | Asp | Ser | Asp | Glu | Gly | Glu | Glu | Pro | Ser | Pro | Glu | Ala |
| | | | 340 | | | | | 345 | | | | | 350 | | |
| Leu | Val | Arg | Tyr | Leu | Ser | Met | Arg | Arg | His | Thr | Val | Gly | Val | Ala | Asp |
| | | | | 355 | | | | | 360 | | | | | 365 | |
| Pro | Arg | Thr | Glu | Val | Met | Glu | Asp | Leu | Gln | Lys | Leu | Leu | Pro | Gly | Phe |
| | 370 | | | | | 375 | | | | | 380 | | | | |
| Pro | Gly | Val | Asn | Pro | Gln | Ala | Pro | Phe | Leu | Gln | Val | Ala | Pro | Asn | Val |
| 385 | | | | | 390 | | | | | 395 | | | | | 400 |

```
Asn Phe Met His Asn Leu Leu Pro Met Gln Asn Leu Gln Pro Thr Gly
            405                 410                 415

Gln Leu Glu Tyr Lys Glu Gln Ser Leu Leu Gln Pro Pro Thr Leu Gln
            420                 425                 430

Leu Leu Asn Gly Met Gly Pro Leu Gly Arg Arg Ala Ser Asp Gly Gly
            435                 440                 445

Ala Asn Ile Gln Leu His Ala Gln Gln Leu Leu Lys Arg Pro Arg Gly
            450                 455                 460

Pro Ser Pro Leu Val Thr Met Thr Pro Ala Val Pro Ala Val Thr Pro
465                 470                 475                 480

Val Asp Glu Glu Ser Ser Asp Gly Glu Pro Asp Gln Glu Ala Val Gln
            485                 490                 495

Arg Tyr Leu Ala Asn Arg Ser Lys Arg His Thr Leu Ala Met Thr Asn
            500                 505                 510

Pro Thr Ala Glu Ile Pro Pro Asp Leu Gln Arg Gln Leu Gly Gln Gln
            515                 520                 525

Pro Phe Arg Ser Arg Val Trp Pro Pro His Leu Val Pro Asp Gln His
            530                 535                 540

Arg Ser Thr Tyr Lys Asp Ser Asn Thr Leu His Leu Pro Thr Glu Arg
545                 550                 555                 560

Phe Ser Pro Val Arg Arg Phe Ser Asp Gly Ala Ala Ser Ile Gln Ala
            565                 570                 575

Phe Lys Ala His Leu Glu Lys Met Gly Asn Asn Ser Ser Ile Lys Gln
            580                 585                 590

Leu Gln Gln Glu Cys Glu Gln Leu Gln Lys Met Tyr Gly Gly Gln Ile
            595                 600                 605

Asp Glu Arg Thr Leu Glu Lys Thr Gln Gln His Met Leu Tyr Gln
            610                 615                 620

Gln Glu Gln His His Gln Ile Leu Gln Gln Gln Ile Gln Asp Ser Ile
625                 630                 635                 640

Cys Pro Pro Gln Pro Ser Pro Leu Gln Ala Ala Cys Glu Asn Gln
            645                 650                 655

Pro Ala Leu Leu Thr His Gln Leu Gln Arg Leu Arg Ile Gln Pro Ser
            660                 665                 670

Ser Pro Pro Asn His Pro Asn Asn His Leu Phe Arg Gln Pro Ser
            675                 680                 685

Asn Ser Pro Pro Met Ser Ser Ala Met Ile Gln Pro His Gly Ala
690                 695                 700

Ala Ser Ser Ser Gln Phe Gln Gly Leu Pro Ser Arg Ser Ala Ile Phe
705                 710                 715                 720

Gln Gln Gln Pro Glu Asn Cys Ser Ser Pro Asn Val Ala Leu Thr
            725                 730                 735

Cys Leu Gly Met Gln Gln Pro Ala Gln Ser Gln Val Thr Ile Gln
            740                 745                 750

Val Gln Glu Pro Val Asp Met Leu Ser Asn Met Pro Gly Thr Ala Ala
            755                 760                 765

Gly Ser Ser Gly Arg Gly Ile Ser Ile Ser Pro Ser Ala Gly Gln Met
            770                 775                 780

Gln Met Gln His Arg Thr Asn Leu Met Ala Thr Leu Ser Tyr Gly His
785                 790                 795                 800

Arg Pro Leu Ser Lys Gln Leu Ser Ala Asp Ser Ala Glu Ala His Ser
            805                 810                 815
```

```
Ala His Gln Gln Pro Pro His Tyr Thr Thr Ser Ala Leu Gln Gln Ala
                820                 825                 830

Leu Leu Ser Pro Thr Pro Pro Asp Tyr Thr Arg His Gln Gln Val Pro
            835                 840                 845

His Ile Leu Gln Gly Leu Leu Ser Pro Arg His Ser Leu Thr Gly His
850                 855                 860

Ser Asp Ile Arg Leu Pro Pro Thr Glu Phe Ala Gln Leu Ile Lys Arg
865                 870                 875                 880

Gln Gln Gln Gln Arg Gln Gln Gln Gln Gln Gln Gln Gln Gln Gln Glu
                885                 890                 895

Tyr Gln Glu Leu Phe Arg His Met Asn Gln Gly Asp Ala Gly Ser Leu
                900                 905                 910

Ala Pro Ser Leu Gly Gly Gln Ser Met Thr Glu Arg Gln Ala Leu Ser
            915                 920                 925

Tyr Gln Asn Ala Asp Ser Tyr His His His Thr Ser Pro Gln His Leu
            930                 935                 940

Leu Gln Ile Arg Ala Gln Glu Cys Val Ser Gln Ala Ser Ser Pro Thr
945                 950                 955                 960

Pro Pro His Gly Tyr Ala His Gln Pro Ala Leu Met His Ser Glu Ser
                965                 970                 975

Met Glu Glu Asp Cys Ser Cys Glu Gly Ala Lys Asp Gly Phe Gln Asp
                980                 985                 990

Ser Lys Ser Ser Ser Thr Leu Thr Lys Gly Cys His Asp Ser Pro Leu
            995                 1000                1005

Leu Leu Ser Thr Gly Gly Pro Gly Asp Pro Glu Ser Leu Leu Gly
    1010                1015                1020

Thr Val Ser His Ala Gln Glu Leu Gly Ile His Pro Tyr Gly His
    1025                1030                1035

Gln Pro Thr Ala Ala Phe Ser Lys Asn Lys Val Pro Ser Arg Glu
    1040                1045                1050

Pro Val Ile Gly Asn Cys Met Asp Arg Ser Ser Pro Gly Gln Ala
    1055                1060                1065

Val Glu Leu Pro Asp His Asn Gly Leu Gly Tyr Pro Ala Arg Pro
    1070                1075                1080

Ser Val His Glu His His Arg Pro Arg Ala Leu Gln Arg His His
    1085                1090                1095

Thr Ile Gln Asn Ser Asp Asp Ala Tyr Val Gln Leu Asp Asn Leu
    1100                1105                1110

Pro Gly Met Ser Leu Val Ala Gly Lys Ala Leu Ser Ser Ala Arg
    1115                1120                1125

Met Ser Asp Ala Val Leu Ser Gln Ser Ser Leu Met Gly Ser Gln
    1130                1135                1140

Gln Phe Gln Asp Gly Glu Asn Glu Glu Cys Gly Ala Ser Leu Gly
    1145                1150                1155

Gly His Glu His Pro Asp Leu Ser Asp Gly Ser Gln His Leu Asn
    1160                1165                1170

Ser Ser Cys Tyr Pro Ser Thr Cys Ile Thr Asp Ile Leu Leu Ser
    1175                1180                1185

Tyr Lys His Pro Glu Val Ser Phe Ser Met Glu Gln Ala Gly Val
    1190                1195                1200

<210> SEQ ID NO 5
<211> LENGTH: 783
<212> TYPE: PRT
```

<213> ORGANISM: Homo sapiens

<400> SEQUENCE: 5

| | | | | | | | | | | | | | | |
|---|---|---|---|---|---|---|---|---|---|---|---|---|---|---|
| Met | Val | Ile | Met | Ser | Glu | Phe | Ser | Ala | Asp | Pro | Ala | Gly | Gln | Gly | Gln |
| 1 | | | | 5 | | | | | 10 | | | | | 15 | |
| Gly | Gln | Gln | Lys | Pro | Leu | Arg | Val | Gly | Phe | Tyr | Asp | Ile | Glu | Arg | Thr |
| | | | 20 | | | | | 25 | | | | | 30 | | |
| Leu | Gly | Lys | Gly | Asn | Phe | Ala | Val | Val | Lys | Leu | Ala | Arg | His | Arg | Val |
| | | 35 | | | | | 40 | | | | | 45 | | | |
| Thr | Lys | Thr | Gln | Val | Ala | Ile | Lys | Ile | Ile | Asp | Lys | Thr | Arg | Leu | Asp |
| | 50 | | | | | 55 | | | | | 60 | | | | |
| Ser | Ser | Asn | Leu | Glu | Lys | Ile | Tyr | Arg | Glu | Val | Gln | Leu | Met | Lys | Leu |
| 65 | | | | | 70 | | | | | 75 | | | | | 80 |
| Leu | Asn | His | Pro | His | Ile | Ile | Lys | Leu | Tyr | Gln | Val | Met | Glu | Thr | Lys |
| | | | | 85 | | | | | 90 | | | | | 95 | |
| Asp | Met | Leu | Tyr | Ile | Val | Thr | Glu | Phe | Ala | Lys | Asn | Gly | Glu | Met | Phe |
| | | | 100 | | | | | 105 | | | | | 110 | | |
| Asp | Tyr | Leu | Thr | Ser | Asn | Gly | His | Leu | Ser | Glu | Asn | Glu | Ala | Arg | Lys |
| | | 115 | | | | | 120 | | | | | 125 | | | |
| Lys | Phe | Trp | Gln | Ile | Leu | Ser | Ala | Val | Glu | Tyr | Cys | His | Asp | His | His |
| | 130 | | | | | 135 | | | | | 140 | | | | |
| Ile | Val | His | Arg | Asp | Leu | Lys | Thr | Glu | Asn | Leu | Leu | Leu | Asp | Gly | Asn |
| 145 | | | | | 150 | | | | | 155 | | | | | 160 |
| Met | Asp | Ile | Lys | Leu | Ala | Asp | Phe | Gly | Phe | Gly | Asn | Phe | Tyr | Lys | Ser |
| | | | | 165 | | | | | 170 | | | | | 175 | |
| Gly | Glu | Pro | Leu | Ser | Thr | Trp | Cys | Gly | Ser | Pro | Pro | Tyr | Ala | Ala | Pro |
| | | | 180 | | | | | 185 | | | | | 190 | | |
| Glu | Val | Phe | Glu | Gly | Lys | Glu | Tyr | Glu | Gly | Pro | Gln | Leu | Asp | Ile | Trp |
| | | 195 | | | | | 200 | | | | | 205 | | | |
| Ser | Leu | Gly | Val | Val | Leu | Tyr | Val | Leu | Val | Cys | Gly | Ser | Leu | Pro | Phe |
| | 210 | | | | | 215 | | | | | 220 | | | | |
| Asp | Gly | Pro | Asn | Leu | Pro | Thr | Leu | Arg | Gln | Arg | Val | Leu | Glu | Gly | Arg |
| 225 | | | | | 230 | | | | | 235 | | | | | 240 |
| Phe | Arg | Ile | Pro | Phe | Phe | Met | Ser | Gln | Asp | Cys | Glu | Ser | Leu | Ile | Arg |
| | | | | 245 | | | | | 250 | | | | | 255 | |
| Arg | Met | Leu | Val | Val | Asp | Pro | Ala | Arg | Arg | Ile | Thr | Ile | Ala | Gln | Ile |
| | | | 260 | | | | | 265 | | | | | 270 | | |
| Arg | Gln | His | Arg | Trp | Met | Arg | Ala | Glu | Pro | Cys | Leu | Pro | Gly | Pro | Ala |
| | | 275 | | | | | 280 | | | | | 285 | | | |
| Cys | Pro | Ala | Phe | Ser | Ala | His | Ser | Tyr | Thr | Ser | Asn | Leu | Gly | Asp | Tyr |
| | 290 | | | | | 295 | | | | | 300 | | | | |
| Asp | Glu | Gln | Ala | Leu | Gly | Ile | Met | Gln | Thr | Leu | Gly | Val | Asp | Arg | Gln |
| 305 | | | | | 310 | | | | | 315 | | | | | 320 |
| Arg | Thr | Val | Glu | Ser | Leu | Gln | Asn | Ser | Ser | Tyr | Asn | His | Phe | Ala | Ala |
| | | | | 325 | | | | | 330 | | | | | 335 | |
| Ile | Tyr | Tyr | Leu | Leu | Leu | Glu | Arg | Leu | Lys | Glu | Tyr | Arg | Asn | Ala | Gln |
| | | | 340 | | | | | 345 | | | | | 350 | | |
| Cys | Ala | Arg | Pro | Gly | Pro | Ala | Arg | Gln | Pro | Arg | Pro | Arg | Ser | Ser | Asp |
| | | 355 | | | | | 360 | | | | | 365 | | | |
| Leu | Ser | Gly | Leu | Glu | Val | Pro | Gln | Glu | Gly | Leu | Ser | Thr | Asp | Pro | Phe |
| | 370 | | | | | 375 | | | | | 380 | | | | |
| Arg | Pro | Ala | Leu | Leu | Cys | Pro | Gln | Pro | Gln | Thr | Leu | Val | Gln | Ser | Val |
| 385 | | | | | 390 | | | | | 395 | | | | | 400 |

-continued

| | | | | | | | | | | | |
|---|---|---|---|---|---|---|---|---|---|---|---|
|Leu|Gln|Ala|Glu|Met|Asp|Cys|Glu|Leu|Gln|Ser|Ser|Leu|Gln|Trp|Pro|
| | | | |405| | | |410| | | |415| |

Leu Phe Phe Pro Val Asp Ala Ser Cys Ser Gly Val Phe Arg Pro Arg
                420                        425                        430

Pro Val Ser Pro Ser Ser Leu Leu Asp Thr Ala Ile Ser Glu Glu Ala
                435                        440                        445

Arg Gln Gly Pro Gly Leu Glu Glu Gln Asp Thr Gln Glu Ser Leu
450                        455                        460

Pro Ser Ser Thr Gly Arg Arg His Thr Leu Ala Glu Val Ser Thr Arg
465                        470                        475                        480

Leu Ser Pro Leu Thr Ala Pro Cys Ile Val Val Ser Pro Ser Thr Thr
                485                        490                        495

Ala Ser Pro Ala Glu Gly Thr Ser Ser Asp Ser Cys Leu Thr Phe Ser
                500                        505                        510

Ala Ser Lys Ser Pro Ala Gly Leu Ser Gly Thr Pro Ala Thr Gln Gly
                515                        520                        525

Leu Leu Gly Ala Cys Ser Pro Val Arg Leu Ala Ser Pro Phe Leu Gly
                530                        535                        540

Ser Gln Ser Ala Thr Pro Val Leu Gln Ala Gln Gly Gly Leu Gly Gly
545                        550                        555                        560

Ala Val Leu Leu Pro Val Ser Phe Gln Glu Gly Arg Arg Ala Ser Asp
                565                        570                        575

Thr Ser Leu Thr Gln Gly Leu Lys Ala Phe Arg Gln Gln Leu Arg Lys
                580                        585                        590

Thr Thr Arg Thr Lys Gly Phe Leu Gly Leu Asn Lys Ile Lys Gly Leu
                595                        600                        605

Ala Arg Gln Val Cys Gln Ala Pro Ala Ser Arg Ala Ser Arg Gly Gly
                610                        615                        620

Leu Ser Pro Phe His Ala Pro Ala Gln Ser Pro Gly Leu His Gly Gly
625                        630                        635                        640

Ala Ala Gly Ser Arg Glu Gly Trp Ser Leu Leu Glu Glu Val Leu Glu
                645                        650                        655

Gln Gln Arg Leu Leu Gln Leu Gln His His Pro Ala Ala Ala Pro Gly
                660                        665                        670

Cys Ser Gln Ala Pro Gln Pro Ala Pro Ala Pro Phe Val Ile Ala Pro
                675                        680                        685

Cys Asp Gly Pro Gly Ala Ala Pro Leu Pro Ser Thr Leu Leu Thr Ser
                690                        695                        700

Gly Leu Pro Leu Leu Pro Pro Pro Leu Leu Gln Thr Gly Ala Ser Pro
705                        710                        715                        720

Val Ala Ser Ala Ala Gln Leu Leu Asp Thr His Leu His Ile Gly Thr
                725                        730                        735

Gly Pro Thr Ala Leu Pro Ala Val Pro Pro Arg Leu Ala Arg Leu
                740                        745                        750

Ala Pro Gly Cys Glu Pro Leu Gly Leu Leu Gln Gly Asp Cys Glu Met
                755                        760                        765

Glu Asp Leu Met Pro Cys Ser Leu Gly Thr Phe Val Leu Val Gln
        770                        775                        780

<210> SEQ ID NO 6
<211> LENGTH: 926
<212> TYPE: PRT
<213> ORGANISM: Homo sapiens

<400> SEQUENCE: 6

```
Met Val Met Ala Asp Gly Pro Arg His Leu Gln Arg Gly Pro Val Arg
1               5                   10                  15

Val Gly Phe Tyr Asp Ile Glu Gly Thr Leu Gly Lys Gly Asn Phe Ala
            20                  25                  30

Val Val Lys Leu Gly Arg His Arg Ile Thr Lys Thr Glu Val Ala Ile
            35                  40                  45

Lys Ile Ile Asp Lys Ser Gln Leu Asp Ala Val Asn Leu Glu Lys Ile
50                  55                  60

Tyr Arg Glu Val Gln Ile Met Lys Met Leu Asp His Pro His Ile Ile
65                  70                  75                  80

Lys Leu Tyr Gln Val Met Glu Thr Lys Ser Met Leu Tyr Leu Val Thr
                85                  90                  95

Glu Tyr Ala Lys Asn Gly Glu Ile Phe Asp Tyr Leu Ala Asn His Gly
                100                 105                 110

Arg Leu Asn Glu Ser Glu Ala Arg Arg Lys Phe Trp Gln Ile Leu Ser
                115                 120                 125

Ala Val Asp Tyr Cys His Gly Arg Lys Ile Val His Arg Asp Leu Lys
130                 135                 140

Ala Glu Asn Leu Leu Leu Asp Asn Asn Met Asn Ile Lys Ile Ala Asp
145                 150                 155                 160

Phe Gly Phe Gly Asn Phe Phe Lys Ser Gly Glu Leu Leu Ala Thr Trp
                165                 170                 175

Cys Gly Ser Pro Pro Tyr Ala Ala Pro Glu Val Phe Glu Gly Gln Gln
                180                 185                 190

Tyr Glu Gly Pro Gln Leu Asp Ile Trp Ser Met Gly Val Val Leu Tyr
                195                 200                 205

Val Leu Val Cys Gly Ala Leu Pro Phe Asp Gly Pro Thr Leu Pro Ile
210                 215                 220

Leu Arg Gln Arg Val Leu Glu Gly Arg Phe Arg Ile Pro Tyr Phe Met
225                 230                 235                 240

Ser Glu Asp Cys Glu His Leu Ile Arg Arg Met Leu Val Leu Asp Pro
                245                 250                 255

Ser Lys Arg Leu Thr Ile Ala Gln Ile Lys Glu His Lys Trp Met Leu
                260                 265                 270

Ile Glu Val Pro Val Gln Arg Pro Val Leu Tyr Pro Gln Glu Gln Glu
                275                 280                 285

Asn Glu Pro Ser Ile Gly Glu Phe Asn Glu Gln Val Leu Arg Leu Met
                290                 295                 300

His Ser Leu Gly Ile Asp Gln Gln Lys Thr Ile Glu Ser Leu Gln Asn
305                 310                 315                 320

Lys Ser Tyr Asn His Phe Ala Ala Ile Tyr Phe Leu Leu Val Glu Arg
                325                 330                 335

Leu Lys Ser His Arg Ser Ser Phe Pro Val Glu Gln Arg Leu Asp Gly
                340                 345                 350

Arg Gln Arg Arg Pro Ser Thr Ile Ala Glu Gln Thr Val Ala Lys Ala
                355                 360                 365

Gln Thr Val Gly Leu Pro Val Thr Met His Ser Pro Asn Met Arg Leu
                370                 375                 380

Leu Arg Ser Ala Leu Leu Pro Gln Ala Ser Asn Val Glu Ala Phe Ser
385                 390                 395                 400
```

```
Phe Pro Ala Ser Gly Cys Gln Ala Glu Ala Ala Phe Met Glu Glu Glu
            405                 410                 415
Cys Val Asp Thr Pro Lys Val Asn Gly Cys Leu Leu Asp Pro Val Pro
            420                 425                 430
Pro Val Leu Val Arg Lys Gly Cys Gln Ser Leu Pro Ser Asn Met Met
            435                 440                 445
Glu Thr Ser Ile Asp Glu Gly Leu Glu Thr Glu Gly Glu Ala Glu Glu
            450                 455                 460
Asp Pro Ala His Ala Phe Glu Ala Phe Gln Ser Thr Arg Ser Gly Gln
465                 470                 475                 480
Arg Arg His Thr Leu Ser Glu Val Thr Asn Gln Leu Val Val Met Pro
            485                 490                 495
Gly Ala Gly Lys Ile Phe Ser Met Asn Asp Ser Pro Ser Leu Asp Ser
            500                 505                 510
Val Asp Ser Glu Tyr Asp Met Gly Ser Val Gln Arg Asp Leu Asn Phe
            515                 520                 525
Leu Glu Asp Asn Pro Ser Leu Lys Asp Ile Met Leu Ala Asn Gln Pro
            530                 535                 540
Ser Pro Arg Met Thr Ser Pro Phe Ile Ser Leu Arg Pro Thr Asn Pro
545                 550                 555                 560
Ala Met Gln Ala Leu Ser Ser Gln Lys Arg Glu Val His Asn Arg Ser
            565                 570                 575
Pro Val Ser Phe Arg Glu Gly Arg Arg Ala Ser Asp Thr Ser Leu Thr
            580                 585                 590
Gln Gly Ile Val Ala Phe Arg Gln His Leu Gln Asn Leu Ala Arg Thr
            595                 600                 605
Lys Gly Ile Leu Glu Leu Asn Lys Val Gln Leu Leu Tyr Glu Gln Ile
            610                 615                 620
Gly Pro Glu Ala Asp Pro Asn Leu Ala Pro Ala Pro Gln Leu Gln
625                 630                 635                 640
Asp Leu Ala Ser Ser Cys Pro Gln Glu Glu Val Ser Gln Gln Gln Glu
            645                 650                 655
Ser Val Ser Thr Leu Pro Ala Ser Val His Pro Gln Leu Ser Pro Arg
            660                 665                 670
Gln Ser Leu Glu Thr Gln Tyr Leu Gln His Arg Leu Gln Lys Pro Ser
            675                 680                 685
Leu Leu Ser Lys Ala Gln Asn Thr Cys Gln Leu Tyr Cys Lys Glu Pro
            690                 695                 700
Pro Arg Ser Leu Glu Gln Gln Leu Gln Glu His Arg Leu Gln Gln Lys
705                 710                 715                 720
Arg Leu Phe Leu Gln Lys Gln Ser Gln Leu Gln Ala Tyr Phe Asn Gln
            725                 730                 735
Met Gln Ile Ala Glu Ser Ser Tyr Pro Gln Pro Ser Gln Gln Leu Pro
            740                 745                 750
Leu Pro Arg Gln Glu Thr Pro Pro Ser Gln Gln Ala Pro Pro Phe
            755                 760                 765
Ser Leu Thr Gln Pro Leu Ser Pro Val Leu Glu Pro Ser Ser Glu Gln
            770                 775                 780
Met Gln Tyr Ser Pro Phe Leu Ser Gln Tyr Gln Glu Met Gln Leu Gln
785                 790                 795                 800
Pro Leu Pro Ser Thr Ser Gly Pro Arg Ala Ala Pro Pro Leu Pro Thr
            805                 810                 815
```

```
Gln Leu Gln Gln Gln Gln Pro Pro Pro Pro Pro Pro Pro Pro
            820                 825                 830

Arg Gln Pro Gly Ala Ala Pro Ala Pro Leu Gln Phe Ser Tyr Gln Thr
        835                 840                 845

Cys Glu Leu Pro Ser Ala Ala Ser Pro Ala Pro Asp Tyr Pro Thr Pro
    850                 855                 860

Cys Gln Tyr Pro Val Asp Gly Ala Gln Gln Ser Asp Leu Thr Gly Pro
865                 870                 875                 880

Asp Cys Pro Arg Ser Pro Gly Leu Gln Glu Ala Pro Ser Ser Tyr Asp
                885                 890                 895

Pro Leu Ala Leu Ser Glu Leu Pro Gly Leu Phe Asp Cys Glu Met Leu
            900                 905                 910

Asp Ala Val Asp Pro Gln His Asn Gly Tyr Val Leu Val Asn
            915                 920                 925

<210> SEQ ID NO 7
<211> LENGTH: 19
<212> TYPE: RNA
<213> ORGANISM: Artificial
<220> FEATURE:
<223> OTHER INFORMATION: SIK3 siRNA s1

<400> SEQUENCE: 7
gcgccaggcu uuaucuuau                                               19

<210> SEQ ID NO 8
<211> LENGTH: 19
<212> TYPE: RNA
<213> ORGANISM: artificial
<220> FEATURE:
<223> OTHER INFORMATION: SIK3 siRNA s2

<400> SEQUENCE: 8
gaacagcgac gaugcuuau                                               19

<210> SEQ ID NO 9
<211> LENGTH: 19
<212> TYPE: RNA
<213> ORGANISM: artificial
<220> FEATURE:
<223> OTHER INFORMATION: SIK3 siRNA s3

<400> SEQUENCE: 9
gcacuaaccu gcuugggua                                               19

<210> SEQ ID NO 10
<211> LENGTH: 19
<212> TYPE: RNA
<213> ORGANISM: artificial
<220> FEATURE:
<223> OTHER INFORMATION: SIK3 siRNA s4

<400> SEQUENCE: 10
ggagcaggca ggcguguaa                                               19

<210> SEQ ID NO 11
<211> LENGTH: 58
<212> TYPE: DNA
<213> ORGANISM: artificial
<220> FEATURE:
<223> OTHER INFORMATION: SIK3 shRNA shSIK3
```

-continued

<400> SEQUENCE: 11
ccgggccagg ctttatctta tcaaactcga gtttgataag ataaagcctg gcttttg        58

<210> SEQ ID NO 12
<211> LENGTH: 57
<212> TYPE: DNA
<213> ORGANISM: artificial
<220> FEATURE:
<223> OTHER INFORMATION: shCtrl

<400> SEQUENCE: 12
ccgggcgcga tagcgctaat aatttctcga gaaattatta gcgctatcgc gctttt         57

<210> SEQ ID NO 13
<211> LENGTH: 1321
<212> TYPE: PRT
<213> ORGANISM: Homo sapiens

<400> SEQUENCE: 13

```
Met Ala Ala Ala Ala Ser Gly Ala Gly Ala Ala Gly Ala Gly
1               5                   10                  15

Thr Gly Gly Ala Gly Pro Ala Gly Arg Leu Leu Pro Pro Ala Pro
                20                  25                  30

Gly Ser Pro Ala Ala Pro Ala Ala Val Ser Pro Ala Ala Gly Gln Pro
                35                  40                  45

Arg Pro Pro Ala Pro Ala Ser Arg Gly Pro Met Pro Ala Arg Ile Gly
        50                  55                  60

Tyr Tyr Glu Ile Asp Arg Thr Ile Gly Lys Gly Asn Phe Ala Val Val
65                  70                  75                  80

Lys Arg Ala Thr His Leu Val Thr Lys Ala Lys Val Ala Ile Lys Ile
                85                  90                  95

Ile Asp Lys Thr Gln Leu Asp Glu Glu Asn Leu Lys Lys Ile Phe Arg
                100                 105                 110

Glu Val Gln Ile Met Lys Met Leu Cys His Pro His Ile Ile Arg Leu
                115                 120                 125

Tyr Gln Val Met Glu Thr Glu Arg Met Ile Tyr Leu Val Thr Glu Tyr
        130                 135                 140

Ala Ser Gly Gly Glu Ile Phe Asp His Leu Val Ala His Gly Arg Met
145                 150                 155                 160

Ala Glu Lys Glu Ala Arg Arg Lys Phe Lys Gln Ile Val Thr Ala Val
                165                 170                 175

Tyr Phe Cys His Cys Arg Asn Ile Val His Arg Asp Leu Lys Ala Glu
                180                 185                 190

Asn Leu Leu Leu Asp Ala Asn Leu Asn Ile Lys Ile Ala Asp Phe Gly
        195                 200                 205

Phe Ser Asn Leu Phe Thr Pro Gly Gln Leu Leu Lys Thr Trp Cys Gly
        210                 215                 220

Ser Pro Pro Tyr Ala Ala Pro Glu Leu Phe Glu Gly Lys Glu Tyr Asp
225                 230                 235                 240

Gly Pro Lys Val Asp Ile Trp Ser Leu Gly Val Val Leu Tyr Val Leu
                245                 250                 255

Val Cys Gly Ala Leu Pro Phe Asp Gly Ser Thr Leu Gln Asn Leu Arg
                260                 265                 270

Ala Arg Val Leu Ser Gly Lys Phe Arg Ile Pro Phe Phe Met Ser Thr
        275                 280                 285
```

-continued

| | | | | | | | | | | | | | | |
|---|---|---|---|---|---|---|---|---|---|---|---|---|---|---|
|Glu|Cys|Glu|His|Leu|Ile|Arg|His|Met|Leu|Val|Leu|Asp|Pro|Asn|Lys
290| | | | |295| | | | |300| | | | |

Arg Leu Ser Met Glu Gln Ile Cys Lys His Lys Trp Met Lys Leu Gly
305                 310                 315                 320

Asp Ala Asp Pro Asn Phe Asp Arg Leu Ile Ala Glu Cys Gln Gln Leu
            325                 330                 335

Lys Glu Glu Arg Gln Val Asp Pro Leu Asn Glu Asp Val Leu Leu Ala
        340                 345                 350

Met Glu Asp Met Gly Leu Asp Lys Glu Gln Thr Leu Gln Ser Leu Arg
    355                 360                 365

Ser Asp Ala Tyr Asp His Tyr Ser Ala Ile Tyr Ser Leu Leu Cys Asp
370                 375                 380

Arg His Lys Arg His Lys Thr Leu Arg Leu Gly Ala Leu Pro Ser Met
385                 390                 395                 400

Pro Arg Ala Leu Ala Phe Gln Ala Pro Val Asn Ile Gln Ala Glu Gln
            405                 410                 415

Ala Gly Thr Ala Met Asn Ile Ser Val Pro Gln Val Gln Leu Ile Asn
        420                 425                 430

Pro Glu Asn Gln Ile Val Glu Pro Asp Gly Thr Leu Asn Leu Asp Ser
    435                 440                 445

Asp Glu Gly Glu Glu Pro Ser Pro Glu Ala Leu Val Arg Tyr Leu Ser
450                 455                 460

Met Arg Arg His Thr Val Gly Val Ala Asp Pro Arg Thr Glu Val Met
465                 470                 475                 480

Glu Asp Leu Gln Lys Leu Leu Pro Gly Phe Pro Gly Val Asn Pro Gln
            485                 490                 495

Ala Pro Phe Leu Gln Val Ala Pro Asn Val Asn Phe Met His Asn Leu
        500                 505                 510

Leu Pro Met Gln Asn Leu Gln Pro Thr Gly Gln Leu Glu Tyr Lys Glu
    515                 520                 525

Gln Ser Leu Leu Gln Pro Pro Thr Leu Gln Leu Leu Asn Gly Met Gly
530                 535                 540

Pro Leu Gly Arg Arg Ala Ser Asp Gly Gly Ala Asn Ile Gln Leu His
545                 550                 555                 560

Ala Gln Gln Leu Leu Lys Arg Pro Arg Gly Pro Ser Pro Leu Val Thr
            565                 570                 575

Met Thr Pro Ala Val Pro Ala Val Thr Pro Val Asp Glu Glu Ser Ser
        580                 585                 590

Asp Gly Glu Pro Asp Gln Glu Ala Val Gln Ser Ser Thr Tyr Lys Asp
    595                 600                 605

Ser Asn Thr Leu His Leu Pro Thr Glu Arg Phe Ser Pro Val Arg Arg
610                 615                 620

Phe Ser Asp Gly Ala Ala Ser Ile Gln Ala Phe Lys Ala His Leu Glu
625                 630                 635                 640

Lys Met Gly Asn Asn Ser Ser Ile Lys Gln Leu Gln Gln Glu Cys Glu
            645                 650                 655

Gln Leu Gln Lys Met Tyr Gly Gly Gln Ile Asp Glu Arg Thr Leu Glu
        660                 665                 670

Lys Thr Gln Gln Gln His Met Leu Tyr Gln Glu Gln His His Gln
    675                 680                 685

Ile Leu Gln Gln Gln Ile Gln Asp Ser Ile Cys Pro Pro Gln Pro Ser
690                 695                 700

```
Pro Pro Leu Gln Ala Ala Cys Glu Asn Gln Pro Ala Leu Leu Thr His
705                 710                 715                 720

Gln Leu Gln Arg Leu Arg Ile Gln Pro Ser Ser Pro Pro Asn His
            725                 730                 735

Pro Asn Asn His Leu Phe Arg Gln Pro Ser Asn Ser Pro Pro Met
            740                 745                 750

Ser Ser Ala Met Ile Gln Pro His Gly Ala Ala Ser Ser Gln Phe
            755                 760                 765

Gln Gly Leu Pro Ser Arg Ser Ala Ile Phe Gln Gln Pro Glu Asn
            770                 775                 780

Cys Ser Ser Pro Pro Asn Val Ala Leu Thr Cys Leu Gly Met Gln Gln
785                 790                 795                 800

Pro Ala Gln Ser Gln Gln Val Thr Ile Gln Val Gln Glu Pro Val Asp
                    805                 810                 815

Met Leu Ser Asn Met Pro Gly Thr Ala Ala Gly Ser Ser Gly Arg Gly
                    820                 825                 830

Ile Ser Ile Ser Pro Ser Ala Gly Gln Met Gln Met Gln His Arg Thr
                    835                 840                 845

Asn Leu Met Ala Thr Leu Ser Tyr Gly His Arg Pro Leu Ser Lys Gln
                    850                 855                 860

Leu Ser Ala Asp Ser Ala Glu Ala His Ser Leu Asn Val Asn Arg Phe
865                 870                 875                 880

Ser Pro Ala Asn Tyr Asp Gln Ala His Leu His Pro His Leu Phe Ser
                    885                 890                 895

Asp Gln Ser Arg Gly Ser Pro Ser Ser Tyr Ser Pro Ser Thr Gly Val
                    900                 905                 910

Gly Phe Ser Pro Thr Gln Ala Leu Lys Val Pro Pro Leu Asp Gln Phe
            915                 920                 925

Pro Thr Phe Pro Pro Ser Ala His Gln Gln Pro Pro His Tyr Thr Thr
            930                 935                 940

Ser Ala Leu Gln Gln Ala Leu Leu Ser Pro Thr Pro Pro Asp Tyr Thr
945                 950                 955                 960

Arg His Gln Gln Val Pro His Ile Leu Gln Gly Leu Leu Ser Pro Arg
                    965                 970                 975

His Ser Leu Thr Gly His Ser Asp Ile Arg Leu Pro Pro Thr Glu Phe
                    980                 985                 990

Ala Gln Leu Ile Lys Arg Gln Gln Gln Arg Gln Gln Gln Gln Gln
            995                 1000                1005

Gln Gln Gln Gln Gln Glu Tyr Gln Glu Leu Phe Arg His Met Asn
            1010                1015                1020

Gln Gly Asp Ala Gly Ser Leu Ala Pro Ser Leu Gly Gly Gln Ser
            1025                1030                1035

Met Thr Glu Arg Gln Ala Leu Ser Tyr Gln Asn Ala Asp Ser Tyr
            1040                1045                1050

His His His Thr Ser Pro Gln His Leu Leu Gln Ile Arg Ala Gln
            1055                1060                1065

Glu Cys Val Ser Gln Ala Ser Ser Pro Thr Pro His Gly Tyr
            1070                1075                1080

Ala His Gln Pro Ala Leu Met His Ser Glu Ser Met Glu Glu Asp
            1085                1090                1095

Cys Ser Cys Glu Gly Ala Lys Asp Gly Phe Gln Asp Ser Lys Ser
            1100                1105                1110
```

-continued

```
Ser Ser Thr Leu Thr Lys Gly Cys His Asp Ser Pro Leu Leu Leu
    1115                1120                1125

Ser Thr Gly Gly Pro Gly Asp Pro Glu Ser Leu Leu Gly Thr Val
    1130                1135                1140

Ser His Ala Gln Glu Leu Gly Ile His Pro Tyr Gly His Gln Pro
    1145                1150                1155

Thr Ala Ala Phe Ser Lys Asn Lys Val Pro Ser Arg Glu Pro Val
    1160                1165                1170

Ile Gly Asn Cys Met Asp Arg Ser Ser Pro Gly Gln Ala Val Glu
    1175                1180                1185

Leu Pro Asp His Asn Gly Leu Gly Tyr Pro Ala Arg Pro Ser Val
    1190                1195                1200

His Glu His His Arg Pro Arg Ala Leu Gln Arg His His Thr Ile
    1205                1210                1215

Gln Asn Ser Asp Asp Ala Tyr Val Gln Leu Asp Asn Leu Pro Gly
    1220                1225                1230

Met Ser Leu Val Ala Gly Lys Ala Leu Ser Ser Ala Arg Met Ser
    1235                1240                1245

Asp Ala Val Leu Ser Gln Ser Ser Leu Met Gly Ser Gln Gln Phe
    1250                1255                1260

Gln Asp Gly Glu Asn Glu Glu Cys Gly Ala Ser Leu Gly Gly His
    1265                1270                1275

Glu His Pro Asp Leu Ser Asp Gly Ser Gln His Leu Asn Ser Ser
    1280                1285                1290

Cys Tyr Pro Ser Thr Cys Ile Thr Asp Ile Leu Leu Ser Tyr Lys
    1295                1300                1305

His Pro Glu Val Ser Phe Ser Met Glu Gln Ala Gly Val
    1310                1315                1320

<210> SEQ ID NO 14
<211> LENGTH: 641
<212> TYPE: PRT
<213> ORGANISM: Homo sapiens

<400> SEQUENCE: 14

Met Ala Cys Ser Thr Pro His Gly Ser Asn Arg Arg Leu Pro Arg Lys
1               5                   10                  15

Cys His Phe Ser Leu Pro Thr Arg Thr Pro Thr Leu Cys Thr Ser Leu
                20                  25                  30

Arg Ser Val Ser Pro Leu Cys Ala Gly Ser Gln Met Gly Leu Arg Ala
            35                  40                  45

Ser Arg Pro Ser Lys Leu Thr Trp Lys Lys Trp Ala Thr Thr Ala Ala
        50                  55                  60

Ser Asn Ser Cys Ser Arg Ser Val Ser Ser Cys Arg Arg Cys Thr Gly
65                  70                  75                  80

Gly Arg Leu Met Lys Glu Pro Trp Arg Arg Pro Ser Ser Ser Ile Cys
                85                  90                  95

Tyr Thr Ser Arg Ser Ser Thr Ile Lys Phe Ser Ser Asn Lys Phe Lys
                100                 105                 110

Thr Leu Ser Val Leu Leu Ser His Leu His Leu Phe Arg Leu His Val
            115                 120                 125

Lys Ile Ser Gln Pro Ser Leu Pro Ile Ser Ser Arg Gly Ala Ala Ser
        130                 135                 140

Ser Ser Gln Phe Gln Gly Leu Pro Ser Arg Ser Ala Ile Phe Gln Gln
145                 150                 155                 160
```

-continued

```
Gln Pro Glu Asn Cys Ser Ser Pro Asn Val Ala Leu Thr Cys Leu
                165                 170                 175

Gly Met Gln Gln Pro Ala Gln Ser Gln Gln Val Thr Ile Gln Val Gln
            180                 185                 190

Glu Pro Val Asp Met Leu Ser Asn Met Pro Gly Thr Ala Ala Gly Ser
        195                 200                 205

Ser Gly Arg Gly Ile Ser Ile Ser Pro Ser Ala Gly Gln Met Gln Met
    210                 215                 220

Gln His Arg Thr Asn Leu Met Ala Thr Leu Ser Tyr Gly His Arg Pro
225                 230                 235                 240

Leu Ser Lys Gln Leu Ser Ala Asp Ser Ala Glu Ala His Ser Ala His
                245                 250                 255

Gln Gln Pro Pro His Tyr Thr Thr Ser Ala Leu Gln Gln Ala Leu Leu
            260                 265                 270

Ser Pro Thr Pro Pro Asp Tyr Thr Arg His Gln Gln Val Pro His Ile
        275                 280                 285

Leu Gln Gly Leu Leu Ser Pro Arg His Ser Leu Thr Gly His Ser Asp
    290                 295                 300

Ile Arg Leu Pro Pro Thr Glu Phe Ala Gln Leu Ile Lys Arg Gln Gln
305                 310                 315                 320

Gln Gln Arg Gln Gln Gln Gln Gln Gln Gln Gln Gln Glu Tyr Gln
                325                 330                 335

Glu Leu Phe Arg His Met Asn Gln Gly Asp Ala Gly Ser Leu Ala Pro
            340                 345                 350

Ser Leu Gly Gly Gln Ser Met Thr Glu Arg Gln Ala Leu Ser Tyr Gln
        355                 360                 365

Asn Ala Asp Ser Tyr His His His Thr Ser Pro Gln His Leu Leu Gln
    370                 375                 380

Ile Arg Ala Gln Glu Cys Val Ser Gln Ala Ser Ser Pro Thr Pro Pro
385                 390                 395                 400

His Gly Tyr Ala His Gln Pro Ala Leu Met His Ser Glu Ser Met Glu
                405                 410                 415

Glu Asp Cys Ser Cys Glu Gly Ala Lys Asp Gly Phe Gln Asp Ser Lys
            420                 425                 430

Ser Ser Ser Thr Leu Thr Lys Gly Cys His Asp Ser Pro Leu Leu Leu
        435                 440                 445

Ser Thr Gly Gly Pro Gly Asp Pro Glu Ser Leu Leu Gly Thr Val Ser
    450                 455                 460

His Ala Gln Glu Leu Gly Ile His Pro Tyr Gly His Gln Pro Thr Ala
465                 470                 475                 480

Ala Phe Ser Lys Asn Lys Val Pro Ser Arg Glu Pro Val Ile Gly Asn
                485                 490                 495

Cys Met Asp Arg Ser Ser Pro Gly Gln Ala Val Glu Leu Pro Asp His
            500                 505                 510

Asn Gly Leu Gly Tyr Pro Ala Arg Pro Ser Val His Glu His His Arg
        515                 520                 525

Pro Arg Ala Leu Gln Arg His His Thr Ile Gln Asn Ser Asp Asp Ala
    530                 535                 540

Tyr Val Gln Leu Asp Asn Leu Pro Gly Met Ser Leu Val Ala Gly Lys
545                 550                 555                 560

Ala Leu Ser Ser Ala Arg Met Ser Asp Ala Val Leu Ser Gln Ser Ser
                565                 570                 575
```

-continued

```
Leu Met Gly Ser Gln Gln Phe Gln Asp Gly Glu Asn Glu Cys Gly
        580                 585                 590

Ala Ser Leu Gly Gly His Glu His Pro Asp Leu Ser Asp Gly Ser Gln
        595                 600                 605

His Leu Asn Ser Ser Cys Tyr Pro Ser Thr Cys Ile Thr Asp Ile Leu
        610                 615                 620

Leu Ser Tyr Lys His Pro Glu Val Ser Phe Ser Met Glu Gln Ala Gly
625                 630                 635                 640

Val

<210> SEQ ID NO 15
<211> LENGTH: 1187
<212> TYPE: PRT
<213> ORGANISM: Homo sapiens

<400> SEQUENCE: 15

Met Ala Ala Ala Ala Ser Gly Ala Gly Ala Ala Gly Ala Gly
1               5                   10                  15

Thr Gly Gly Ala Gly Pro Ala Gly Arg Leu Leu Pro Pro Ala Pro
                20                  25                  30

Gly Ser Pro Ala Ala Pro Ala Ala Val Ser Pro Ala Ala Gly Gln Pro
                35                  40                  45

Arg Pro Pro Ala Pro Ala Ser Arg Gly Pro Met Pro Ala Arg Ile Gly
50                  55                  60

Tyr Tyr Glu Ile Asp Arg Thr Ile Gly Lys Gly Asn Phe Ala Val Val
65                  70                  75                  80

Lys Arg Ala Thr His Leu Val Thr Lys Ala Lys Val Ala Ile Lys Ile
                85                  90                  95

Ile Asp Lys Thr Gln Leu Asp Glu Glu Asn Leu Lys Lys Ile Phe Arg
                100                 105                 110

Glu Val Gln Ile Met Lys Met Leu Cys His Pro His Ile Ile Arg Leu
                115                 120                 125

Tyr Gln Val Met Glu Thr Glu Arg Met Ile Tyr Leu Val Thr Glu Tyr
            130                 135                 140

Ala Ser Gly Gly Glu Ile Phe Asp His Leu Val Ala His Gly Arg Met
145                 150                 155                 160

Ala Glu Lys Glu Ala Arg Arg Lys Phe Lys Gln Ile Val Thr Ala Val
                165                 170                 175

Tyr Phe Cys His Cys Arg Asn Ile Val His Arg Asp Leu Lys Ala Glu
                180                 185                 190

Asn Leu Leu Leu Asp Ala Asn Leu Asn Ile Lys Ile Ala Asp Phe Gly
            195                 200                 205

Phe Ser Asn Leu Phe Thr Pro Gly Gln Leu Leu Lys Thr Trp Cys Gly
        210                 215                 220

Ser Pro Pro Tyr Ala Ala Pro Glu Leu Phe Glu Gly Lys Glu Tyr Asp
225                 230                 235                 240

Gly Pro Lys Val Asp Ile Trp Ser Leu Gly Val Val Leu Tyr Val Leu
                245                 250                 255

Val Cys Gly Ala Leu Pro Phe Asp Gly Ser Thr Leu Gln Asn Leu Arg
                260                 265                 270

Ala Arg Val Leu Ser Gly Lys Phe Arg Ile Pro Phe Phe Met Ser Thr
            275                 280                 285

Glu Cys Glu His Leu Ile Arg His Met Leu Val Leu Asp Pro Asn Lys
        290                 295                 300
```

```
Arg Leu Ser Met Glu Gln Ile Cys Lys His Lys Trp Met Lys Leu Gly
305                 310                 315                 320

Asp Ala Asp Pro Asn Phe Asp Arg Leu Ile Ala Glu Cys Gln Gln Leu
                325                 330                 335

Lys Glu Glu Arg Gln Val Asp Pro Leu Asn Glu Asp Val Leu Leu Ala
            340                 345                 350

Met Glu Asp Met Gly Leu Asp Lys Glu Gln Thr Leu Gln Ser Leu Arg
        355                 360                 365

Ser Asp Ala Tyr Asp His Tyr Ser Ala Ile Tyr Ser Leu Leu Cys Asp
370                 375                 380

Arg His Lys Arg His Lys Thr Leu Arg Leu Gly Ala Leu Pro Ser Met
385                 390                 395                 400

Pro Arg Ala Leu Ala Phe Gln Ala Pro Val Asn Ile Gln Ala Glu Gln
                405                 410                 415

Ala Gly Thr Ala Met Asn Ile Ser Val Pro Gln Val Gln Leu Ile Asn
            420                 425                 430

Pro Glu Asn Gln Ile Val Glu Pro Asp Gly Thr Leu Asn Leu Asp Ser
        435                 440                 445

Asp Glu Gly Glu Glu Pro Ser Pro Glu Ala Leu Val Arg Tyr Leu Ser
450                 455                 460

Met Arg Arg His Thr Val Gly Val Ala Asp Pro Arg Thr Glu Val Met
465                 470                 475                 480

Glu Asp Leu Gln Lys Leu Leu Pro Gly Phe Pro Gly Val Asn Pro Gln
                485                 490                 495

Ala Pro Phe Leu Gln Val Ala Pro Asn Val Asn Phe Met His Asn Leu
            500                 505                 510

Leu Pro Met Gln Asn Leu Gln Pro Thr Gly Gln Leu Glu Tyr Lys Glu
        515                 520                 525

Gln Ser Leu Leu Gln Pro Pro Thr Leu Gln Leu Leu Asn Gly Met Gly
530                 535                 540

Pro Leu Gly Arg Arg Ala Ser Asp Gly Gly Ala Asn Ile Gln Leu His
545                 550                 555                 560

Ala Gln Gln Leu Leu Lys Arg Pro Arg Gly Pro Ser Pro Leu Val Thr
                565                 570                 575

Met Thr Pro Ala Val Pro Ala Val Thr Pro Val Asp Glu Glu Ser Ser
            580                 585                 590

Asp Gly Glu Pro Asp Gln Glu Ala Val Gln Ser Ser Thr Tyr Lys Asp
        595                 600                 605

Ser Asn Thr Leu His Leu Pro Thr Glu Arg Phe Ser Pro Val Arg Arg
610                 615                 620

Phe Ser Asp Gly Ala Ala Ser Ile Gln Ala Phe Lys Ala His Leu Glu
625                 630                 635                 640

Lys Met Gly Asn Asn Ser Ser Ile Lys Gln Leu Gln Gln Glu Cys Glu
                645                 650                 655

Gln Leu Gln Lys Met Tyr Gly Gly Gln Ile Asp Glu Arg Thr Leu Glu
            660                 665                 670

Lys Thr Gln Gln Gln His Met Leu Tyr Gln Glu Gln His His Gln
        675                 680                 685

Ile Leu Gln Gln Gln Ile Gln Asp Ser Ile Cys Pro Pro Gln Pro Ser
690                 695                 700

Pro Pro Leu Gln Ala Ala Cys Glu Asn Gln Pro Ala Leu Leu Thr His
705                 710                 715                 720
```

-continued

```
Gln Leu Gln Arg Leu Arg Ile Gln Pro Ser Ser Pro Pro Asn His
            725                 730                 735

Pro Asn Asn His Leu Phe Arg Gln Pro Ser Asn Ser Pro Pro Met
            740                 745                 750

Ser Ser Ala Met Ile Gln Pro His Gly Ala Ala Ser Ser Gln Phe
            755                 760                 765

Gln Gly Leu Pro Ser Arg Ser Ala Ile Phe Gln Gln Pro Glu Asn
            770                 775             780

Cys Ser Ser Pro Pro Asn Val Ala Leu Thr Cys Leu Gly Met Gln Gln
785                 790                 795                 800

Pro Ala Gln Ser Gln Gln Val Thr Ile Gln Val Gln Glu Pro Val Asp
                    805                 810                 815

Met Leu Ser Asn Met Pro Gly Thr Ala Ala Gly Ser Ser Gly Arg Gly
                    820                 825                 830

Ile Ser Ile Ser Pro Ser Ala Gly Gln Met Gln Met Gln His Arg Thr
                    835                 840                 845

Asn Leu Met Ala Thr Leu Ser Tyr Gly His Arg Pro Leu Ser Lys Gln
            850                 855                 860

Leu Ser Ala Asp Ser Ala Glu Ala His Ser Leu Asn Val Asn Arg Phe
865                 870                 875                 880

Ser Pro Ala Asn Tyr Asp Gln Ala His Leu His Pro His Leu Phe Ser
                    885                 890                 895

Asp Gln Ser Arg Gly Ser Pro Ser Ser Tyr Ser Pro Ser Thr Gly Val
                    900                 905                 910

Gly Phe Ser Pro Thr Gln Ala Leu Lys Val Pro Pro Leu Asp Gln Phe
                    915                 920                 925

Pro Thr Phe Pro Pro Ser Ala His Gln Gln Pro Pro His Tyr Thr Thr
            930                 935                 940

Ser Ala Leu Gln Gln Ala Leu Leu Ser Pro Thr Pro Pro Asp Tyr Thr
945                 950                 955                 960

Arg His Gln Gln Val Pro His Ile Leu Gln Gly Leu Leu Ser Pro Arg
                    965                 970                 975

His Ser Leu Thr Gly His Ser Asp Ile Arg Leu Pro Pro Thr Glu Phe
                    980                 985                 990

Ala Gln Leu Ile Lys Arg Gln Gln  Gln Gln Arg Gln Gln  Gln Gln Gln
            995                1000                1005

Gln Gln  Gln Gln Gln Glu Tyr  Gln Glu Leu Phe Arg  His Met Asn
   1010                1015                1020

Gln Gly  Asp Ala Gly Ser Leu  Ala Pro Ser Leu Gly  Gly Gln Ser
   1025                1030                1035

Met Thr  Glu Arg Gln Ala Leu  Ser Tyr Gln Asn Ala  Asp Ser Tyr
   1040                1045                1050

His His  His Thr Ser Pro Gln  His Leu Leu Gln Ile  Arg Ala Gln
   1055                1060                1065

Glu Cys  Val Ser Gln Ala Ser  Ser Pro Thr Pro Pro  His Gly Tyr
   1070                1075                1080

Ala His  Gln Pro Ala Leu Met  His Ser Glu Ser Met  Glu Glu Asp
   1085                1090                1095

Cys Ser  Cys Glu Gly Ala Lys  Asp Gly Phe Gln Asp  Ser Lys Ser
   1100                1105                1110

Ser Ser  Thr Leu Thr Lys Gly  Cys His Asp Ser Pro  Leu Leu Leu
   1115                1120                1125
```

-continued

```
Ser Thr Gly Gly Pro Gly Asp Pro Glu Ser Leu Leu Gly Thr Val
1130                1135                1140

Ser His Ala Gln Glu Leu Gly Ile His Pro Tyr Gly His Gln Pro
1145                1150                1155

Thr Ala Ala Phe Ser Lys Asn Lys Val Pro Ser Arg Gly Lys Cys
1160                1165                1170

Leu Leu Thr Val Glu Val Leu Gly Gln Ser Ala Leu Ile Asn
1175                1180                1185

<210> SEQ ID NO 16
<211> LENGTH: 1261
<212> TYPE: PRT
<213> ORGANISM: Homo sapiens

<400> SEQUENCE: 16

Met Ala Ala Ala Ala Ser Gly Ala Gly Ala Ala Gly Ala Gly
1               5                   10                  15

Thr Gly Gly Ala Gly Pro Ala Gly Arg Leu Leu Pro Pro Ala Pro
                20                  25                  30

Gly Ser Pro Ala Ala Pro Ala Val Ser Pro Ala Ala Gly Gln Pro
            35                  40                  45

Arg Pro Pro Ala Pro Ala Ser Arg Gly Pro Met Pro Ala Arg Ile Gly
    50                  55                  60

Tyr Tyr Glu Ile Asp Arg Thr Ile Gly Lys Gly Asn Phe Ala Val Val
65                  70                  75                  80

Lys Arg Ala Thr His Leu Val Thr Lys Ala Lys Val Ala Ile Lys Ile
                85                  90                  95

Ile Asp Lys Thr Gln Leu Asp Glu Glu Asn Leu Lys Lys Ile Phe Arg
                100                 105                 110

Glu Val Gln Ile Met Lys Met Leu Cys His Pro His Ile Ile Arg Leu
            115                 120                 125

Tyr Gln Val Met Glu Thr Glu Arg Met Ile Tyr Leu Val Thr Glu Tyr
    130                 135                 140

Ala Ser Gly Gly Glu Ile Phe Asp His Leu Val Ala His Gly Arg Met
145                 150                 155                 160

Ala Glu Lys Glu Ala Arg Arg Lys Phe Lys Gln Ile Val Thr Ala Val
                165                 170                 175

Tyr Phe Cys His Cys Arg Asn Ile Val His Arg Asp Leu Lys Ala Glu
                180                 185                 190

Asn Leu Leu Leu Asp Ala Asn Leu Asn Ile Lys Ile Ala Asp Phe Gly
            195                 200                 205

Phe Ser Asn Leu Phe Thr Pro Gly Gln Leu Leu Lys Thr Trp Cys Gly
    210                 215                 220

Ser Pro Pro Tyr Ala Ala Pro Glu Leu Phe Glu Gly Lys Glu Tyr Asp
225                 230                 235                 240

Gly Pro Lys Val Asp Ile Trp Ser Leu Gly Val Val Leu Tyr Val Leu
                245                 250                 255

Val Cys Gly Ala Leu Pro Phe Asp Gly Ser Thr Leu Gln Asn Leu Arg
                260                 265                 270

Ala Arg Val Leu Ser Gly Lys Phe Arg Ile Pro Phe Phe Met Ser Thr
            275                 280                 285

Glu Cys Glu His Leu Ile Arg His Met Leu Val Leu Asp Pro Asn Lys
    290                 295                 300

Arg Leu Ser Met Glu Gln Ile Cys Lys His Lys Trp Met Lys Leu Gly
305                 310                 315                 320
```

```
Asp Ala Asp Pro Asn Phe Asp Arg Leu Ile Ala Glu Cys Gln Gln Leu
                325                 330                 335

Lys Glu Glu Arg Gln Val Asp Pro Leu Asn Glu Asp Val Leu Leu Ala
            340                 345                 350

Met Glu Asp Met Gly Leu Asp Lys Glu Gln Thr Leu Gln Ala Glu Gln
        355                 360                 365

Ala Gly Thr Ala Met Asn Ile Ser Val Pro Gln Val Gln Leu Ile Asn
    370                 375                 380

Pro Glu Asn Gln Ile Val Glu Pro Asp Gly Thr Leu Asn Leu Asp Ser
385                 390                 395                 400

Asp Glu Gly Glu Glu Pro Ser Pro Glu Ala Leu Val Arg Tyr Leu Ser
                405                 410                 415

Met Arg Arg His Thr Val Gly Val Ala Asp Pro Arg Thr Glu Val Met
            420                 425                 430

Glu Asp Leu Gln Lys Leu Leu Pro Gly Phe Pro Gly Val Asn Pro Gln
        435                 440                 445

Ala Pro Phe Leu Gln Val Ala Pro Asn Val Asn Phe Met His Asn Leu
    450                 455                 460

Leu Pro Met Gln Asn Leu Gln Pro Thr Gly Gln Leu Glu Tyr Lys Glu
465                 470                 475                 480

Gln Ser Leu Leu Gln Pro Pro Thr Leu Gln Leu Leu Asn Gly Met Gly
                485                 490                 495

Pro Leu Gly Arg Arg Ala Ser Asp Gly Gly Ala Asn Ile Gln Leu His
            500                 505                 510

Ala Gln Gln Leu Leu Lys Arg Pro Arg Gly Pro Ser Pro Leu Val Thr
        515                 520                 525

Met Thr Pro Ala Val Pro Ala Val Thr Pro Val Asp Glu Glu Ser Ser
    530                 535                 540

Asp Gly Glu Pro Asp Gln Glu Ala Val Gln Arg Tyr Leu Ala Asn Arg
545                 550                 555                 560

Ser Lys Arg His Thr Leu Ala Met Thr Asn Pro Thr Ala Glu Ile Pro
                565                 570                 575

Pro Asp Leu Gln Arg Gln Leu Gly Gln Gln Pro Phe Arg Ser Arg Val
            580                 585                 590

Trp Pro His Leu Val Pro Asp Gln His Arg Ser Thr Tyr Lys Asp
        595                 600                 605

Ser Asn Thr Leu His Leu Pro Thr Glu Arg Phe Ser Pro Val Arg Arg
    610                 615                 620

Phe Ser Asp Gly Ala Ala Ser Ile Gln Ala Phe Lys Ala His Leu Glu
625                 630                 635                 640

Lys Met Gly Asn Asn Ser Ser Ile Lys Gln Leu Gln Gln Glu Cys Glu
                645                 650                 655

Gln Leu Gln Lys Met Tyr Gly Gly Gln Ile Asp Glu Arg Thr Leu Glu
            660                 665                 670

Lys Thr Gln Gln Gln His Met Leu Tyr Gln Gln Glu Gln His His Gln
        675                 680                 685

Ile Leu Gln Gln Gln Ile Gln Asp Ser Ile Cys Pro Pro Gln Pro Ser
    690                 695                 700

Pro Pro Leu Gln Ala Ala Cys Glu Asn Gln Pro Ala Leu Leu Thr His
705                 710                 715                 720

Gln Leu Gln Arg Leu Arg Ile Gln Pro Ser Ser Pro Pro Pro Asn His
                725                 730                 735
```

```
Pro Asn Asn His Leu Phe Arg Gln Pro Ser Asn Ser Pro Pro Met
            740                 745                 750

Ser Ser Ala Met Ile Gln Pro His Gly Ala Ala Ser Ser Ser Gln Phe
        755                 760                 765

Gln Gly Leu Pro Ser Arg Ser Ala Ile Phe Gln Gln Gln Pro Glu Asn
    770                 775                 780

Cys Ser Ser Pro Pro Asn Val Ala Leu Thr Cys Leu Gly Met Gln Gln
785                 790                 795                 800

Pro Ala Gln Ser Gln Gln Val Thr Ile Gln Val Gln Glu Pro Val Asp
                805                 810                 815

Met Leu Ser Asn Met Pro Gly Thr Ala Ala Gly Ser Ser Gly Arg Gly
            820                 825                 830

Ile Ser Ile Ser Pro Ser Ala Gly Gln Met Gln Met Gln His Arg Thr
        835                 840                 845

Asn Leu Met Ala Thr Leu Ser Tyr Gly His Arg Pro Leu Ser Lys Gln
    850                 855                 860

Leu Ser Ala Asp Ser Ala Glu Ala His Ser Ala His Gln Gln Pro Pro
865                 870                 875                 880

His Tyr Thr Thr Ser Ala Leu Gln Gln Ala Leu Leu Ser Pro Thr Pro
                885                 890                 895

Pro Asp Tyr Thr Arg His Gln Gln Val Pro His Ile Leu Gln Gly Leu
            900                 905                 910

Leu Ser Pro Arg His Ser Leu Thr Gly His Ser Asp Ile Arg Leu Pro
        915                 920                 925

Pro Thr Glu Phe Ala Gln Leu Ile Lys Arg Gln Gln Gln Gln Arg Gln
    930                 935                 940

Gln Gln Gln Gln Gln Gln Gln Gln Glu Tyr Gln Glu Leu Phe Arg
945                 950                 955                 960

His Met Asn Gln Gly Asp Ala Gly Ser Leu Ala Pro Ser Leu Gly Gly
                965                 970                 975

Gln Ser Met Thr Glu Arg Gln Ala Leu Ser Tyr Gln Asn Ala Asp Ser
            980                 985                 990

Tyr His His His Thr Ser Pro Gln His Leu Leu Gln Ile Arg Ala Gln
        995                 1000                1005

Glu Cys Val Ser Gln Ala Ser Ser Pro Thr Pro Pro His Gly Tyr
    1010                1015                1020

Ala His Gln Pro Ala Leu Met His Ser Glu Ser Met Glu Glu Asp
    1025                1030                1035

Cys Ser Cys Glu Gly Ala Lys Asp Gly Phe Gln Asp Ser Lys Ser
    1040                1045                1050

Ser Ser Thr Leu Thr Lys Gly Cys His Asp Ser Pro Leu Leu Leu
    1055                1060                1065

Ser Thr Gly Gly Pro Gly Asp Pro Glu Ser Leu Leu Gly Thr Val
    1070                1075                1080

Ser His Ala Gln Glu Leu Gly Ile His Pro Tyr Gly His Gln Pro
    1085                1090                1095

Thr Ala Ala Phe Ser Lys Asn Lys Val Pro Ser Arg Glu Pro Val
    1100                1105                1110

Ile Gly Asn Cys Met Asp Arg Ser Ser Pro Gly Gln Ala Val Glu
    1115                1120                1125

Leu Pro Asp His Asn Gly Leu Gly Tyr Pro Ala Arg Pro Ser Val
    1130                1135                1140
```

-continued

```
His Glu His His Arg Pro Arg Ala Leu Gln Arg His His Thr Ile
    1145            1150            1155

Gln Asn Ser Asp Asp Ala Tyr Val Gln Leu Asp Asn Leu Pro Gly
    1160            1165            1170

Met Ser Leu Val Ala Gly Lys Ala Leu Ser Ser Ala Arg Met Ser
    1175            1180            1185

Asp Ala Val Leu Ser Gln Ser Ser Leu Met Gly Ser Gln Gln Phe
    1190            1195            1200

Gln Asp Gly Glu Asn Glu Glu Cys Gly Ala Ser Leu Gly Gly His
    1205            1210            1215

Glu His Pro Asp Leu Ser Asp Gly Ser Gln His Leu Asn Ser Ser
    1220            1225            1230

Cys Tyr Pro Ser Thr Cys Ile Thr Asp Ile Leu Leu Ser Tyr Lys
    1235            1240            1245

His Pro Glu Val Ser Phe Ser Met Glu Gln Ala Gly Val
    1250            1255            1260
```